United States Patent
Christensen et al.

(10) Patent No.: US 12,024,713 B2
(45) Date of Patent: Jul. 2, 2024

(54) NUCLEOTIDE SEQUENCES AND POLYPEPTIDES ENCODED THEREBY USEFUL FOR MODIFYING PLANT CHARACTERISTICS IN RESPONSE TO COLD

(71) Applicant: CERES, INC., Thousand Oaks, CA (US)

(72) Inventors: Cory Christensen, Zionsville, IN (US); Bonnie Hund, Pueblo, CO (US)

(73) Assignee: Ceres, Inc., Thousand Oaks, CA (US)

( * ) Notice: Subject to any disclaimer, the term of this patent is extended or adjusted under 35 U.S.C. 154(b) by 0 days.

(21) Appl. No.: 18/049,501

(22) Filed: Oct. 25, 2022

(65) Prior Publication Data

US 2023/0242933 A1    Aug. 3, 2023

Related U.S. Application Data

(60) Division of application No. 16/829,740, filed on Mar. 25, 2020, now Pat. No. 11,542,521, which is a division of application No. 14/273,492, filed on May 8, 2014, now Pat. No. 10,689,661, which is a continuation of application No. 12/863,773, filed as application No. PCT/US2009/031609 on Jan. 21, 2009, now abandoned.

(60) Provisional application No. 61/022,786, filed on Jan. 22, 2008.

(51) Int. Cl.
*A01H 5/00* (2018.01)
*A01H 1/00* (2006.01)
*C07K 14/415* (2006.01)
*C12N 15/82* (2006.01)

(52) U.S. Cl.
CPC ........... *C12N 15/8273* (2013.01); *A01H 1/00* (2013.01); *A01H 1/12* (2021.01); *A01H 1/1245* (2021.01); *A01H 5/00* (2013.01); *C07K 14/415* (2013.01)

(58) Field of Classification Search
None
See application file for complete search history.

(56) References Cited

U.S. PATENT DOCUMENTS

| | | | |
|---|---|---|---|
| 11,542,521 B2 | 1/2023 | Christensen | |
| 11,761,013 B2 | 9/2023 | Christensen et al. | |
| 2006/0057724 A1 | 3/2006 | Alexandrov et al. | |
| 2006/0150283 A1 | 7/2006 | Alexandrov et al. | |
| 2007/0039067 A1* | 2/2007 | Feldmann | C07K 14/415 536/23.6 |
| 2007/0214517 A1 | 9/2007 | Alexandrov et al. | |
| 2010/0192237 A1 | 7/2010 | Ren et al. | |
| 2013/0042367 A1 | 2/2013 | Nadzan et al. | |
| 2020/0239904 A1 | 7/2020 | Christensen et al. | |

FOREIGN PATENT DOCUMENTS

| | | |
|---|---|---|
| EP | 1033405 | 9/2000 |
| WO | 2007044988 | 4/2007 |

OTHER PUBLICATIONS

Feldmann et al., Published Applications Database, US Publication No. 20070039067, Feb. 15, 2007, Seq ID No. 56571.*
USPTO: Non-Final Office Action regarding U.S. Appl. No. 16/829,755, dated Feb. 7, 2023.
Dissmeyer et al, "T-Loop Phosphorylation of *Arabidopsis* CDKA; 1 is required for its function and can be partially substituted by an aspartate residue,". The Plant Cell vol. 19:972-985; Mar. 2007.
Friedberg, "Automated protein function prediction- the genomic challenge," Briefings in Bioinformatics; vol. 7. No. 3. 225-242; Jan. 2006.
Guerois et al., "Predicting changes in the stability of proteins and protein complexes: A study of more than 1000 mutations", J. Mol. Biol.; 320; 369-287; 2002.
Kumar et al., "Predicting the effects of coding non-synonymous variants on protein function using the SIFT algorithm," www.nature.com/natureprotocols; Nature Protocols; vol. 4 No. 8; 2009.
Ng et al., Predicting the effects of amino acid substitutions on protein function, Annual Review Genom. Hum. Genet; 7:61-80; 2006.
Reva et al., Predicting the functional impact of protein mutations: application to cancergenomics,: Nucleic Acids Research; vol. 39. No 17.; e118; Jul. 2011.
Rivera et al., Genomic evidence for two functionally distinct gene classes, Proc. Natl. Acad. Sci.; vol. 95; 6239-6244; May 1998.
Sandhya et al., "CUSP: an algorithm to distinguish structurally conserved and unconserved regions in protein domain alignments and its application in the study of large length variations," BMC Structural Biol: 8:28; May 2008.
Churchman, et al., SIAMESE, A plant-specific cell cycle regulator, controls endoreplication onset in *Arabidopsis thaliana*, The Plant Cell, 2006, 18(11):3145-3157.
Gong, et al., "RNA helicase-like protein as an early regulator of transcription factor for plant chilling and freezing tolerance", PNAS, vol. 99, No. 17, Aug. 20, 2002, pp. 11507-11512.
Low, et al., Conformational switch upon phosphorylation: human CDK inhibitor p19INK4d between the native and partially folded state, ACS Chemical Biology, 2008, 4(1):53-63.
NCBI GenBank Acession AAM6430, 5, Jan. 27, 2006.
Salaita, et al., "Identification and characterization of mutants capable of seed germination at 10° C. from activation-tagged lines of *Arabidopsis thaliana*", Journal of Experimental Botany, vol. 56, No. 418, Aug. 2005, pp. 2059-2069.

(Continued)

*Primary Examiner* — Phuong T Bui
(74) *Attorney, Agent, or Firm* — Dentons US LLP

(57) ABSTRACT

Methods and materials for modulating cold tolerance levels in plants are disclosed. For example, nucleic acids encoding cold tolerance-modulating polypeptides are disclosed as well as methods for using such nucleic acids to transform plant cells. Also disclosed are plants having increased cold tolerance levels and plant products produced from plants having increased cold tolerance levels.

6 Claims, 18 Drawing Sheets

Specification includes a Sequence Listing.

(56) References Cited

OTHER PUBLICATIONS

Yi, et al., "The pepper transcription factor CaPF1 confers pathogen and freezing tolerance in *Arabidopsis*", Plant Physiology, vol. 136, No. 1, Sep. 3, 2004, pp. 2862-2874.

Churchman et al. SIAMESE, a plant-specific cell cycle regulator, controls endoreplication onset in *Arabidopsis thaliana*. The Plant Cell. 2006. 18:3145-3157.

Peres et al. Novel plant-specific cyclin-dependent kinase inhibitors induced by biotic and abiotic stresses. Journal of Biological Chemistry. 2007. 282(35):25588-25596.

GenBank Accession No. Q9LZ60. SIAMESE-related 3. published Feb. 17, 2016. pp. 1-3.

GenBank Accession No. BX833341. published Feb. 6, 2004. pp 1-2.

* cited by examiner

FIGURE 1

|  |  |  |  |  |  |
|---|---|---|---|---|---|
| SEQ-ID-NO-15 | —MN⎡DL⎤I———— | ———————— | ———————— | ———————— | QD⎡LPM⎤L⎡KFPS⎤—P | 17 |
| SEQ-ID-NO-17 | MDDL⎡ELL⎤———— | ———————— | ———————— | ———————— | QD⎡LSQ⎤F⎡NFPA⎤—T | 18 |
| SEQ-ID-NO-2  | MAEI⎡CCV⎤———— | ———————— | ———————— | ———KEI⎡QEED⎤ | ⎡VEKI⎤R⎡L⎤⎡PTRP⎤ | 24 |
| SEQ-ID-NO-8  | —MEF⎡DIL⎤KRP | —LPVKCQT | TTSS———— | SFSPGKQKE | EGEI NVKAAG | 40 |
| SEQ-ID-NO-10 | —MEF⎡NFL⎤VRS | ALELGDDCEI | VPQDLHQEKE | VLEKEEKQED | ECEI SVPT⎡LK⎤ | 49 |

|  |  |  |  |  |  |
|---|---|---|---|---|---|
| SEQ-ID-NO-15 | ——KI PS⎡——⎤—N | ⎡NT⎤NRD⎡DD⎤GSS | GG——C⎡ITPTS⎤ | ⎡SD⎤HKI PP⎡STA⎤ | TTPPPPPPQKR | 61 |
| SEQ-ID-NO-17 | ——KI PS⎡KT⎤SK | ⎡DN⎤KD⎡GD⎤⎡GND⎤ | ⎡EGF⎤S⎡CS⎤⎡TPTS⎤ | ⎡QE⎤HKI P—⎡SVH⎤ | DSPPPPPRKP | 66 |
| SEQ-ID-NO-2  | EL⎡DI⎤ PV——⎤—S | ⎡DH⎤EDPTVNEE | ⎡EG⎤——C⎡KTPTS⎤ | ⎡SD⎤HKI PEVKY | TLCPPAPRKP | 69 |
| SEQ-ID-NO-8  | EGKEEKKEK—— | ⎡NSKE⎤I⎡DDDD⎤ | DG——F⎡KTPTS⎤ | ⎡TD⎤SKI P—⎡AEP⎤ | KQCPPAPRKP | 86 |
| SEQ-ID-NO-10 | —⎡KLPS⎤⎡VEAF⎤ | QI⎡EDDK⎤⎡DDD⎤ | DG——F⎡KTPTS⎤ | ⎡LD⎤RKI P—⎡VIE⎤ | —QCPPAPRKP | 94 |

|  |  |  |  |  |  |
|---|---|---|---|---|---|
| SEQ-ID-NO-15 | ⎡RP⎤———P—⎡PS⎤ | ⎡PS⎤⎡CFI⎤ ⎡RS⎤⎡CKR⎤ | KLL⎡T⎤PSKVEI | I VNK⎡DEI⎤ ⎡ERF⎤ | ⎡F⎤SSVY⎡N⎤HSTT | 106 |
| SEQ-ID-NO-17 | ⎡R⎤ALPSKPSP⎡IT⎤ | ⎡AA⎤LVI ⎡RS⎤⎡CKR⎤ | KL⎡LV⎤⎡S⎤AP—EI | I MNK⎡EEI⎤ DRF | ⎡F⎤SSVY⎡S⎤DTST | 115 |
| SEQ-ID-NO-2  | KPNRSSG—⎡TK⎤ | RKLTPVNVLN | ⎡RIPI⎤⎡DLS⎤— | ———⎡REI⎤ ⎡EMF⎤ | ⎡F⎤E———— | 103 |
| SEQ-ID-NO-8  | KPNKRKA—⎡SS⎤ | ⎡PT⎤NGSTA⎡VRN⎤ | ⎡PL⎤⎡I⎤⎡LDLS⎤— | ———⎡EE⎤⎡LESL⎤ | SH———— | 120 |
| SEQ-ID-NO-10 | ⎡K⎤———⎡SL⎤ | ⎡PS⎤AKRKSPQR | ⎡RVLLDLS⎤— | ———⎡NEI⎤ ⎡ESL⎤ | ⎡F⎤PPAL⎡A⎤GDLG | 130 |

|  |  |  |  |
|---|---|---|---|
| SEQ-ID-NO-15 | SSPTTTTTKK | ALAVV⎡RRRR⎤S | ⎡FR⎤⎡SCS⎤⎡RR⎤ | 133 |
| SEQ-ID-NO-17 | TA———— | ———⎡KRRR⎤R | YLYCARR | 129 |
| SEQ-ID-NO-2  | ———— | ———⎡DL⎤⎡DRR⎤ | I ⎡KKS⎤RKQ | 115 |
| SEQ-ID-NO-8  | ———— | ———⎡KV⎤KKK | TRT QEQQ | 132 |
| SEQ-ID-NO-10 | G——— | ———⎡KI⎤ KK⎡V⎤ | RQGND⎡T⎤K | 143 |

| | | | | | | |
|---|---|---|---|---|---|---|
| SEQ-ID-NO-20 | RFAKRT | | | FLSHVYASAA | HA | | 350 |
| SEQ-ID-NO-32 | RFAKRT | | ETEND-D | VERLYSPGP | AV | QY-----G | 369 |
| SEQ-ID-NO-28 | RFAKRT | | EIDSD | MDTLYNSPS | SV | MLDTPY---G | 379 |
| SEQ-ID-NO-22 | RFAKRN | | EMESD | VDHMYNSAS | PF | LADTHY---G | 363 |
| SEQ-ID-NO-40 | RFAKRA | | ETDNE | DDAEAEAE | SAATA--AAF | MYDNQY---G | 359 |
| SEQ-ID-NO-44 | RFAKRT | KGGA | DHDGDADA | EDEEMYSSAA | AAVPM--SY | VLDFGY---G | 326 |
| SEQ-ID-NO-58 | RFAKRT | | GADADADG | ERDGPFSPAS | AAVAALMAPG | GSDADY GVDG | 315 |
| SEQ-ID-NO-71 | RFAKR | CSAEA | -AEDD-AL | EEGACFSPAV | HL | ASDGDY--- G |  |
| | | EDED EALLEH | | SA | ASD |  | 328 |

| | |
|---|---|
| SEQ-ID-NO-20 | VVPTF | 355 |
| SEQ-ID-NO-32 | VVPSF | 374 |
| SEQ-ID-NO-28 | VVPSF | 384 |
| SEQ-ID-NO-22 | IVPSF | 368 |
| SEQ-ID-NO-40 | VVPSF | 364 |
| SEQ-ID-NO-44 | VVPTF | 331 |
| SEQ-ID-NO-58 | VVPSF | 320 |
| SEQ-ID-NO-71 | VVPSFC | 334 |

FIGURE 3

| SEQ-ID-NO | | | | | | |
|---|---|---|---|---|---|---|
| SEQ-ID-NO:79 | | | | MA | SAT RN | 8 |
| SEQ-ID-NO:88 | | | | MD | YSSTKEL PL | 20 |
| SEQ-ID-NO:81 | | | RERREERRRE | | VTLLRAV PYE | 43 |
| SEQ-ID-NO:82 | MGKKGKAAA | | RERREQRRRE | | VTLLRAV PYE | 49 |
| SEQ-ID-NO:83 | MGKKGKEAA | | RERREQRRRE | PAGAMWSR | VTLLRAV PYE | 48 |
| SEQ-ID-NO:90 | MTNK EKA | | RERRE KRMQE | PHQRWWDGLA | SLLRTI PYS | 37 |
| SEQ-ID-NO:86 | MGHK ERN | | KSRKDKRLQE | PHQRWWDGLA | SLLRTI PYS | 35 |
| SEQ-ID-NO:74 | MSCKK | | KEKREKRLQE | PHQRWWSC | SLLRTI PYS | 38 |
| SEQ-ID-NO:85 | MGSK EPA | | KEKREKRL QE | DHQRWWSK | SLLRTI PYS | 37 |
| | | | | DHQRWWSQ | | |
| | | | | DHQRWWSS | | |

| SEQ-ID-NO | | | | | | |
|---|---|---|---|---|---|---|
| SEQ-ID-NO:79 | AVVTGANKG | GFGI CKQLV | SNGI TVVLTA | RDEKRGLEAV | EKL KEF | 53 |
| SEQ-ID-NO:88 | VAVVTGANRG | GHAL AARLA | EHGLTVVLTA | RDGARGEAA | APL RAR | 66 |
| SEQ-ID-NO:81 | VAVVTGASRG | GYEI SRQLA | RHGLHVVLAS | RDAARGRDAA | EGI LREE | 90 |
| SEQ-ID-NO:82 | VAVVTGANRG | GYEA ARQLA | THGLHVVLTS | RDAARGRDAA | EQI RAAAGKP | 99 |
| SEQ-ID-NO:83 | VAVVTGANRG | GYEA ARQLA | THGLHVVLTS | RDAARGRDAT | EQI RAAAGKP | 98 |
| SEQ-ID-NO:90 | VAVVTGSNRG | GFEI SRQLA | VHGLTVVLTA | RNVNA GLEAV | KSL R HQEE | 85 |
| SEQ-ID-NO:86 | AVVTGANRG | GFEI ARQLA | DHGVTVVLTS | RDASVGVESI | KVL QEG | 81 |
| SEQ-ID-NO:74 | VAVVTGANRG | GFEI ARQLA | HGLTVI LTS | RN SVGI EAT | KAL REL | 84 |
| SEQ-ID-NO:85 | VAVVTGNRG | GFEI ARQLA | DHGLSVI LTS | RESSAGLEAA | NVL | 83 |

| SEQ-ID-NO | | | | | | |
|---|---|---|---|---|---|---|
| SEQ-ID-NO:79 | GVSDQV VFHQ | LDVTDPKSI E | SLANFI KTQF | GKLDI LVNNA | GI HGAYVDRD | 103 |
| SEQ-ID-NO:88 | GLA VAFRR | LDVSDAASVE | AFAAWLRDAV | GGLDI VNNA | A | 105 |
| SEQ-ID-NO:81 | GTS AEWRQ | LDVADAASVE | AFAAWI ARTH | GGI HV INNA | G | 129 |
| SEQ-ID-NO:82 | GVS VEWRQ | LDVTDAASVE | GFATWERTH | GGVHVLVNNA | G | 138 |
| SEQ-ID-NO:83 | GVS VEWRQ | LDVTDAASVE | GFATWVERTH | GGLDI LVNNA | G | 137 |
| SEQ-ID-NO:90 | GLK VYFHQ | LDVTDSSSI R | EFGCWLKQTF | GGLDI LVNNA | G | 124 |
| SEQ-ID-NO:86 | GLD VHCHQ | LDI DSSSVN | EFAEWLKEEY | GGLDI LVNNA | G | 120 |
| SEQ-ID-NO:74 | GFS YDVHQ | LDI LDGESI S | AFVEWI KQKY | GGI DI LVNNA | G | 123 |
| SEQ-ID-NO:85 | GLS VDFHQ | LDVLDSLSIK | TFAEWI QQTY | GGLDVLVNNA | G | 122 |

| SEQ-ID-NO | | | | | | |
|---|---|---|---|---|---|---|
| SEQ-ID-NO:79 | ALAAAGEKVA | NVDWRKI STE | NFEAAEAGI R | TNYYGVKLMC | EALI PLLEIS | 153 |
| SEQ-ID-NO:88 | | VSFNEL CTN | SVEHAETVLR | TNFYGAKMLT | EALLPLPLKPS | 144 |
| SEQ-ID-NO:81 | | VNFNRGADN | SVEFAEQVI E | TNYFGTRRMI | EAMLPLLKPS | 168 |
| SEQ-ID-NO:82 | | VNFNRGADN | SVEFAEQVTE | TNYFGTKRMI | EAMMPLMI TS | 177 |
| SEQ-ID-NO:83 | | VNFNRGADN | SVEFAEQVI E | TNYFGTKRMI | EAMMPLMI TS | 176 |
| SEQ-ID-NO:90 | | VNYNLGSDN | TVEFAETVI S | TNYQGTKRMI | KAMI PLMRPS | 163 |
| SEQ-ID-NO:86 | | VNSNMGSDN | SVENARKCI | TNYYGTKRMI | EAMI PLMKPS | 159 |
| SEQ-ID-NO:74 | | VNFNL GFDN | SVEFARQVVD | TNYYGTKNMI | KAMI PVMKPS | 162 |
| SEQ-ID-NO:85 | | VNYNMGSON | SVENAKNVVD | TNYYGI KNVT | EALI PLMRPS | 161 |

FIGURE 3 (Continued)

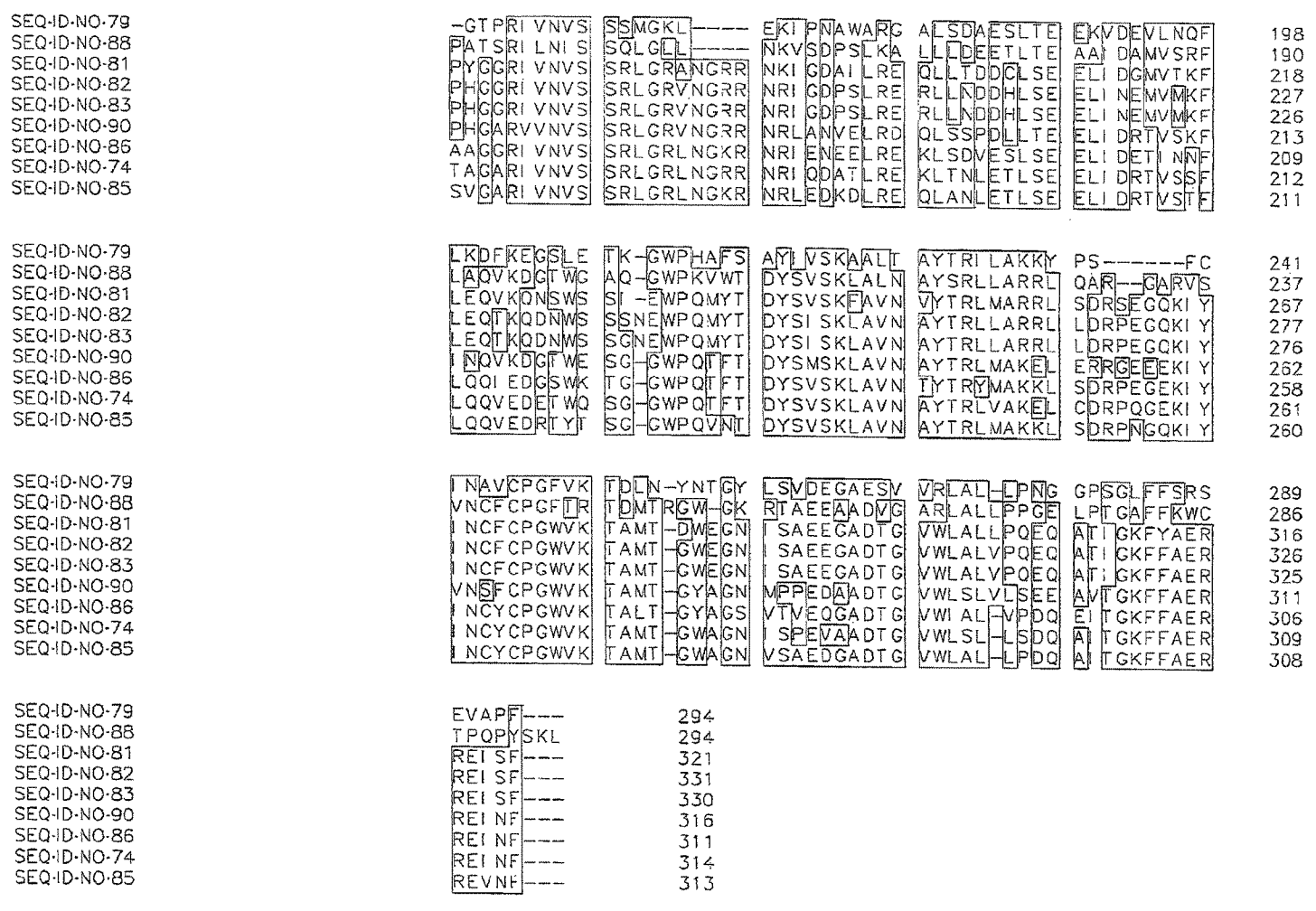

[Sequence alignment figure showing multiple protein sequences labeled SEQ-ID-NO:79, SEQ-ID-NO:88, SEQ-ID-NO:81, SEQ-ID-NO:82, SEQ-ID-NO:83, SEQ-ID-NO:90, SEQ-ID-NO:86, SEQ-ID-NO:74, and SEQ-ID-NO:85 in four blocks with position numbers on the right side.]

FIGURE 4

| | | | | | | |
|---|---|---|---|---|---|---|
| SEQ-ID-NO-104 | —MCEALI PLL | ELS—GT PRI V | NVSSS—MGKL— | ———EKI PNAW | ARGA SDA ES | 44 |
| SEQ-ID-NO-95 | MLTEALLPLF | RQSPATSRI L | NI SSQLGLL— | ———NKVSDPS | LKALL DEET | 46 |
| SEQ-ID-NO-98 | —MI KAMI PVM | KPSTAGARI V | NVSSR-GRLN | GRRNRI QDAT | LREKLT NLET | 49 |
| SEQ-ID-NO-107 | —MI EAMMPLM | ITSPHGGRI V | NVSSRLGRVN | GRRNRI GDPS | LRERLL NDDH | 49 |
| SEQ-ID-NO-93 | —MI EAMLPLL | KPSPYGGRI V | NVSSRLGRAN | GRRNKI GDA | LREQLL TDDC | 49 |
| SEQ-ID-NO-106 | —MI EAMLPLL | KPSPYGGRI V | NVSSRLGRAN | GRRNKI GDA | LREQLL TDDC | 49 |

| | | | | | | |
|---|---|---|---|---|---|---|
| SEQ-ID-NO-104 | LTEEKVDEVL | NQFLKDFKEG | SL—ET KGWPH | AFSAM VSKA | ALTAYTRI LA | 93 |
| SEQ-ID-NO-95 | LTEAAI DAMV | SRFLAQVKDG | TW—GAQGWPK | VWTDYSVSKL | ALNAYSRLLA | 95 |
| SEQ-ID-NO-98 | LSEELI DRTV | SSFLQQVEDE | TW—QSGGWPQ | TFTDYSVSKL | AVNAYTRLLA | 98 |
| SEQ-ID-NO-107 | LSEELI NEMV | MKFLEQT KQD | NWS SNEWPQ | MYTDYSI SKL | AVNAYTRLLA | 99 |
| SEQ-ID-NO-93 | LSEELI GGI V | TKFLEQVKQN | SW—SSI EWPQ | MYTDYSI SKL | AVNVYTRLMA | 98 |
| SEQ-ID-NO-106 | LSEELI DGMV | TKFLEQVKQN | SW—SSI EWPQ | MYTDYSVSKF | AVNVYTRLMA | 98 |

| | | | | | | |
|---|---|---|---|---|---|---|
| SEQ-ID-NO-104 | KKYPS————— | —FCI NAVCPG | FVKT DLN—YN | TGYLS VDEGA | ESM VRLALL P | 136 |
| SEQ-ID-NO-95 | RRLQAR——GA | RVSVNCFCPG | FT RT DMT RGW | —CKRT AEEAA | DV GARLALL P | 142 |
| SEQ-ID-NO-98 | KELCDRPQGE | KI YI NCYCPG | MVKTAMT —GW | AGNI SPEVAA | DTGVWLSLLS | 147 |
| SEQ-ID-NO-107 | RRLLDRPEGQ | KI YI NCFCPG | MVKTAMT —GW | EGNI SAEEGA | DTGVWLALVP | 148 |
| SEQ-ID-NO-93 | KRLADRSEGQ | KI YI NCFCPG | MVKTAMT —DW | EGNI SAEEGA | DTGVWLALLP | 147 |
| SEQ-ID-NO-106 | RRLSDRSEGQ | KI YI NCFCPG | MVKTAMT —DW | EGNI SAEEGA | DTGVWLALLP | 147 |

| | | | |
|---|---|---|---|
| SEQ-ID-NO-104 | NG—GPS GLFF | SRSEVAPF —— | 153 |
| SEQ-ID-NO-95 | PGELPT GAFF | KWCTPQPYSK | L 163 |
| SEQ-ID-NO-98 | DQ AL T GKFF | AERREI NF —— | 164 |
| SEQ-ID-NO-107 | QEQATI GKFF | AERREI SF —— | 166 |
| SEQ-ID-NO-93 | QAQATI GKFY | AERREI SF —— | 165 |
| SEQ-ID-NO-106 | QEQATI GKFY | AERREI SF —— | 165 |

| SEQ ID NO | Sequence | Position |
|---|---|---|
| SEQ-ID-NO-143 | ESDVPQS DSD N SAPVSADKD | 676 |
| SEQ-ID-NO-123 | — | 808 |
| SEQ-ID-NO-121 | CL ST SSLNSE NC — | 857 |
| SEQ-ID-NO-120 | CL ST SSLNSE NC — | 853 |
| SEQ-ID-NO-124 | CL ST SSLNSE NC — | 836 |
| SEQ-ID-NO-125 | CL ST SSLNSE NC — | 852 |
| SEQ-ID-NO-126 | CL ST SSLNSE NC — | 853 |
| SEQ-ID-NO-114 | LPLPSACSPM NC — | 845 |
| SEQ-ID-NO-116 | LPLPSACSPM — — | 852 |
| SEQ-ID-NO-119 | ASNPSL SSAG NS — | 848 |
| SEQ-ID-NO-118 | ASNPSL SSAG NS — | 859 |
| SEQ-ID-NO-112 | ASNPSL SSAG NS — | 859 |
| SEQ-ID-NO-117 | ASNPSL SSAG NS — | 859 |
| SEQ-ID-NO-134 | LCAAPLGI — — | 660 |
| SEQ-ID-NO-136 | LCAAPLGI — — | 680 |
| SEQ-ID-NO-131 | MRDMLLDI AL — | 608 |
| SEQ-ID-NO-132 | MRDMLLDI AL — | 608 |
| SEQ-ID-NO-128 | MRDMLLDI AL — | 608 |
| SEQ-ID-NO-127 | LDVGVGALIM — | 719 |
| SEQ-ID-NO-138 | LDVGVGALIM — | 719 |

FIGURE 5 (Continued)

| | | | | | |
|---|---|---|---|---|---|
| SEQ-ID-NO-15 | ---MNLDLI | --------- | -------- | -------QD | LPMLKFPS-P | 17 |
| SEQ-ID-NO-17 | MDDLELL-- | --------- | -------- | -------QD | LSQFNFPA-T | 18 |
| SEQ-ID-NO-2 | MAEI CCV-- | --------- | -------- | ---------- | VEKIRLPTRP | 24 |
| SEQ-ID-NO-8 | MEFDILKRP | ---LPVKCQT | TTSS----- | ---KEIQEED | EGEINVKAAG | 40 |
| SEQ-ID-NO-10 | MEFNFLVRS | ALELGDDCEI | VPQDLHQEKE | SFSPGKQQKE | ECEISVPTLK | 49 |

| | | | | | |
|---|---|---|---|---|---|
| SEQ-ID-NO-15 | -KIPS----N | NTNRDDDGSS | GG--CTPTS | SDHKIPPSTA | TTPPPPPQKR | 61 |
| SEQ-ID-NO-17 | -KIPSKTSK | DNKDGDGND | EGFSCSTPTS | QEHKIP-SVH | DSPPPPRKP | 66 |
| SEQ-ID-NO-2 | ELDLPV---S | DHEDPTVNEE | EG---CKTPTS | SDHKIPEVKY | TLCPPAPRKP | 69 |
| SEQ-ID-NO-8 | EGKEEKKEK | NSKEIDDDD | DG--FKTPTS | TDSKIP-AEP | KQCPPAPRKP | 86 |
| SEQ-ID-NO-10 | KLPSVEAF | QIEDDKDDDD | DG--FKTPTS | LDRKIP-VIE | -QCPPAPRKP | 94 |

| | | | | | |
|---|---|---|---|---|---|
| SEQ-ID-NO-15 | RPI----P-PS | PSCFIRSCKR | KLLTPSKVEI | VNKDETERF | FSSVYNHSTT | 106 |
| SEQ-ID-NO-17 | RALPSKPSPT | AALVIRSCKR | KLLVSAP-EI | MNKEEIDRF | FSSVYSDTST | 115 |
| SEQ-ID-NO-2 | KPNRSSG-TK | RKLTPVNVLN | RIPIDLS--- | REIEMF--- | FE-------- | 103 |
| SEQ-ID-NO-8 | KPNKRRKA-SS | PTNGSTAVRN | PLLLDLS--- | EELESL--- | SH-------- | 120 |
| SEQ-ID-NO-10 | K-------SL | PSAKRKSPQR | RVLLDLS--- | NEIESL--- | EPPALAGDLG | 130 |

| | | | |
|---|---|---|---|
| SEQ-ID-NO-15 | SSPTTTTKK | ALAVVRRRS | FRSCSRR | 133 |
| SEQ-ID-NO-17 | TA------- | ------KRRR | YLYCARR | 129 |
| SEQ-ID-NO-2 | --------- | -------DLDRR | IKKSRKQ | 115 |
| SEQ-ID-NO-8 | --------- | ------KVKKK | TRTQEQQ | 132 |
| SEQ-ID-NO-10 | G-------- | ------KIKKV | RQGNDTK | 143 |

SEQUENCE LISTING

```
Sequence total quantity: 260
SEQ ID NO: 1              moltype = DNA   length = 621
FEATURE                   Location/Qualifiers
misc_feature              1..621
                          note = Ceres SEEDLINE ID no.ME00327
misc_feature              1..621
                          note = Inplanta Sequence
misc_feature              1..621
                          note = Encodes the peptide sequence at SEQ ID NO. 2
source                    1..621
                          mol_type = other DNA
                          organism = Arabidopsis thaliana
SEQUENCE: 1
actagttagt tgaaatggag gctttcaagc ttcggatcca acgcacgtaa tctctctctc   60
tctctctctt ctctcttttt tctttctctc ttctttctct ctgtaaaact tgtctaatgg  120
cagagatctg ctgcgtcaaa gagatccaag aagaagacgt ggagaagatc cgattaccga  180
cccgacccga attagacatt cctgtctctg atcacgaaga tccaacggtc aacgaagaag  240
aagggtgcaa gactccaaca tcgtccgatc acaagattcc ggaggtgaag tatacgttat  300
gtccaccggc tccgagaaaa ccaaaaccga atcgatcttc cggtacgaaa cggaaattaa  360
cgccggttaa tgttcttaac cgcataccga ttgatctgag ccgtgagatc gagatgttct  420
tcgaggattt ggaccgtagg atcaagaagt cacggaaaca ataagaagat tattgcctta  480
attggtaatg atcgttcatt tctaattcat gactgtgtgg tggtaatttg atcctttgaa  540
ttttcttca ttttttttt ctttttttt tcgtttctg tataattaat tagctaataa  600
caataagaaa atttatgtac c                                           621

SEQ ID NO: 2              moltype = AA   length = 115
FEATURE                   Location/Qualifiers
REGION                    1..115
                          note = misc_feature - Ceres SEEDLINE ID no.ME00327
REGION                    1..115
                          note = misc_feature - Bit score of 224.6 for hmm based on
                            sequences of FIGURE 1.
source                    1..115
                          mol_type = protein
                          organism = Arabidopsis thaliana
SEQUENCE: 2
MAEICCVKEI QEEDVEKIRL PTRPELDIPV SDHEDPTVNE EEGCKTPTSS DHKIPEVKYT   60
LCPPAPRKPK PNRSSGTKRK LTPVNVLNRI PIDLSREIEM FFEDLDRRIK KSRKQ       115

SEQ ID NO: 3              moltype = DNA   length = 992
FEATURE                   Location/Qualifiers
misc_feature              1..992
                          note = Ceres CLONE ID no.1897908
misc_feature              1..992
                          note = Encodes the peptide sequence at SEQ ID NO 4
```

-continued

```
source                  1..992
                        mol_type = other DNA
                        organism = Gossypium hirsutum
SEQUENCE: 3
gggttgtcaa agccttttct ctgtctctca tctttgcctt ctctttctca tttcgcagct    60
aaattccaaa ctaaaatcca agatagaaaa agaaattcag agaacaatca aggaagatgg   120
tgatgtgatg aattaaaaaa aagaaaaacc ctctggcatt ttcgtttcct atatatcaaa   180
taccaagctt cttctctttg ttttttctagg ctttttttc ctgctggtac ttgtactgtc   240
ttttccttca tttgcttgca attttcataa tttgatccct ctctctaatc tttaaattct   300
ttgtcttcat catttcttca tatcctaggt tgattttgga cttccatgta ctcaaaatta   360
aaaccagttc cattcatggg tgtctcaact accatggaac tcagtttctt ggttaggcct   420
cctctagaat tcaatgaaga ttgtggaact gcaactaatg ttaaacaaga agaagaagaa   480
gagaagagca agttggtgat gatgggtaca tctgaatctg aggtggttgc tgctgctaat   540
gatgatcaag atgaaaacga caacgatggg ttcaagactc ctacttcgtt cgaccataaa   600
atcccagccg ccaccatcct caagtgccca cctgcaccaa ggaaaccaaa tccctcccc    660
attatatcgt caccagcaaa acgaaaatcg cttcgcagga gaatcctact tgatttgacg   720
aaagagatcg agtctttgtt ccctccagct cttattgcag atctagggaa caagattaag   780
aaagtcagac aaggaagtga cttcaaatga tatgatatat atatacatat atacatacaa   840
atataactat atatgtatca tgtatttatt tgaagaattt taattatgtt atttgttttc   900
atcatccaag accatcacat ctatgttcag tttcattgat gtgttttta tttggtgttt   960
ctatcagatc taaaaccata taaagacttt gc                                 992

SEQ ID NO: 4             moltype = AA   length = 154
FEATURE                  Location/Qualifiers
REGION                   1..154
                         note = misc_feature - Ceres CLONE ID no.1897908
REGION                   1..154
                         note = misc_feature - Bit score of 132.4 for hmm based on
                           sequences of FIGURE 1.
REGION                   1..154
                         note = misc_feature - Functional Homolog Of Ceres SEEDLINE
                           ID no. ME00327 at SEQ ID NO. 2
source                   1..154
                         mol_type = protein
                         organism = Gossypium hirsutum
SEQUENCE: 4
MYSKLKPVPF MGVSTTMELS FLVRPPLEFN EDCGTATNVK QEEEEEKSKL VMMGTSESEV    60
VAAANDDQDE NDNDGFKTPT SFDHKIPAAT ILKCPPAPRK PKSLPIISSP AKRKSLRRRI   120
LLDLTKEIES LFPPALIADL GNKIKKVRQG SDFK                               154

SEQ ID NO: 5             moltype = DNA   length = 1175
FEATURE                  Location/Qualifiers
misc_feature             1..1175
                         note = Ceres CLONE ID no.1938030
misc_feature             1..1175
                         note = Encodes the peptide sequence at SEQ ID NO 6
source                   1..1175
                         mol_type = other DNA
                         organism = Gossypium hirsutum
SEQUENCE: 5
aaaagtgggt tgtcaaagcc ttttctctgt ctctcatctt tgctttctct ttctcatttc    60
gcagctaaat tccaaactaa aatccaagat agaaaagaa attcagagag caatcaagga   120
agatggtgat gtgatgaatt aaaaaaaaaa actttggcat tttcgtttac tatatatcaa   180
ataacaagct tcttctcttt gttttttctag gctttttttc tcctgctggt acttgaactgc   240
tcttttcctt catttgcttg caattttcat aagttgatcc ctctctctca tctttaaatt   300
ctttgtcctt caccatttct tcatatccta ggttgatttt ggacttccat gtactcaaaa   360
ttaaaaccag ttccattcat gggtgtctca agtaccatgg aactcagttt cttggttagg   420
cctcctctag aattcaatga agattgtgga actgcaacta atgttaaaca ggaagaagaa   480
gaagagaaga gcaagttggt gacgatgggt acatctgaat ctgaggtggt tgctgctgct   540
aatgattatc aagatgaaaa cgacaacgat gggttcaaga ccaacgatgg gttcaagact   600
cctacttcat tggaccataa aatcccagcc gccgccatcc tcaagtgccc acctgcacca   660
aggaaaccaa aatccctccc cattatatcg tcaccagcaa aacgaaaatc tcttcgcagg   720
agaatcctgc ttgatttgac gaaagagatc gagtctttgt ccctccagc tcttattgca   780
gatctaggga acaagattaa gaaagtcaga caaggaagtg acttcaaatg acatgataca   840
tatacatata tacatacata caaatataac tatatatgtg tcatgtattt atttgaagaa   900
ttttaattat gttatttgtt tcatcatcc tagaccatca cttctatgtt cagtttcatt   960
ggtgtgtttt tatttggtg tttctatcag atctaaaacc atacaaagac tttgcaaaat  1020
ggatcaaagc aagtacaaag tgagtgatgt gattcatgga tttagcatt gggttctta   1080
ctttctttt cttttggctg cactcttaac ctagctaaaa gatgaacttt tgaggtttga  1140
tttaaattt aattagagct acatataatt atacg                             1175

SEQ ID NO: 6             moltype = AA   length = 160
FEATURE                  Location/Qualifiers
REGION                   1..160
                         note = misc_feature - Ceres CLONE ID no.1938030
REGION                   1..160
                         note = misc_feature - Bit score of 131.1 for hmm based on
                           sequences of FIGURE 1.
REGION                   1..160
```

|  | note = misc_feature - Functional Homolog Of Ceres SEEDLINE ID no. ME00327 at SEQ ID NO. 2 |
|---|---|
| source | 1..160<br>mol_type = protein<br>organism = Gossypium hirsutum |

SEQUENCE: 6

```
MYSKLKPVPF MGVSSTMELS FLVRPPLEFN EDCGTATNVK QEEEEEKSKL VTMGTSESEV    60
VAAANDYQDE NDNDGFKTND GFKTPTSLDH KIPAAAILKC PPAPRKPKSL PIISSPAKRK   120
SLRRRILLDL TKEIESLFPP ALIADLGNKI KKVRQGSDFK                        160
```

| SEQ ID NO: 7 | moltype = DNA length = 781 |
|---|---|
| FEATURE | Location/Qualifiers |
| misc_feature | 1..781<br>note = Ceres CLONE ID no.1915941 |
| misc_feature | 1..781<br>note = Encodes the peptide sequence at SEQ ID NO 8 |
| source | 1..781<br>mol_type = other DNA<br>organism = Gossypium hirsutum |

SEQUENCE: 7

```
tcgctcgctc gctgggttaa aactgtttcg tcctattttc tctcttaact gtagaaacaa    60
agtctggaat tgtacaactc caccaggggg aaggatgtg atttgatgat ttaccatatt    120
gctttatgtt atacattctc atcgcttttt atctgtttgc actaatgtat gtagaattgc    180
ggctgcctgc aggtttccct tgtcggtatc tcgagttcag agacggccgt agtcaaaggt    240
ggtgaagaag gaatggaatt cgacattctg aaacgacccc taccggtgaa gtgccaaact    300
acaacctctt cttctttttc acccggtaaa caacaaaaag aagaaggaga aatcaacgtt    360
aaagcagctg gtgaggggaa ggaagagaag aaagaaaaga attccaagga aatagatgat    420
gatgatgatg atgggtttaa aactccaaca tctacggatt ccaaaatccc agctgagccg    480
aaacaatgcc cgcctgcacc tagaaaaccc aagccaaata aagaaaagc atcatcgcct     540
accatggttc aaccgcagt caggaatccg ctactgctgg atctttcgga agagctcagt    600
tccttgagtc acaaggtcaa gaaaaaaact cgaacacaag agcagcaata attttattc    660
attgttagcg gtattaagta cacacccatc aaacattaat aacttaattc tttatttgta    720
tttatgggag ttcattgttt ttgctgacgg tgaagatcat gatgatattg aagcttatga    780
c                                                                 781
```

| SEQ ID NO: 8 | moltype = AA length = 132 |
|---|---|
| FEATURE | Location/Qualifiers |
| REGION | 1..132<br>note = misc_feature - Ceres CLONE ID no.1915941 |
| REGION | 1..132<br>note = misc_feature - Bit score of 254.1 for hmm based on sequences of FIGURE 1. |
| REGION | 1..132<br>note = misc_feature - Functional Homolog Of Ceres SEEDLINE ID no. ME00327 at SEQ ID NO. 2 |
| source | 1..132<br>mol_type = protein<br>organism = Gossypium hirsutum |

SEQUENCE: 8

```
MEFDILKRPL PVKCQTTTSS SFSPGKQQKE EGEINVKAAG EGKEEKKEKN SKEIDDDDDD    60
GFKTPTSTDS KIPAEPKQCP PAPRKPKPNK RKASSPTNGS TAVRNPLLLD LSEELESLSH   120
KVKKKTRTQE QQ                                                     132
```

| SEQ ID NO: 9 | moltype = DNA length = 483 |
|---|---|
| FEATURE | Location/Qualifiers |
| misc_feature | 1..483<br>note = Ceres ANNOT ID no.1461830 |
| misc_feature | 1..483<br>note = Encodes the peptide sequence at SEQ ID NO 10 |
| source | 1..483<br>mol_type = other DNA<br>organism = Populus balsamifera<br>sub_species = trichocarpa |

SEQUENCE: 9

```
atggggtttt ccaactctga gatgttttc tctgagaaag atctgaatcc catggaattc     60
aatttccttg tgagatctgc attagaactt ggagatgact gtgaaattgt accccaagat    120
cttcatcagg aaaagaagt acttgaaaaa gaagaaaagc aagaagacga atgcgagata    180
tcggtgccta ctttgaagat aaaactgccg tctgtagaag cattccaaat tgaagatgat    240
aaagatgacg atgatgtgg gttcaagact ccaacttctt tggatcgcaa aattcctgtc    300
attttttcaat gtccgcccgc acccagaaaa cctaaatcac tcccatcagc caaacgaaaa    360
tcgcctcaac ggagagtctt acttgatctg tccaatgaga tcgaatcctt gtttcctcca    420
gctcttgctg gggatcttgg tggcaagatt aagaaagtta gacaaggcaa tgacaccaag    480
taa                                                                 483
```

| SEQ ID NO: 10 | moltype = AA length = 143 |
|---|---|
| FEATURE | Location/Qualifiers |
| REGION | 1..143<br>note = misc_feature - Ceres ANNOT ID no.1461830 |
| REGION | 1..143 |

|  |  |
|---|---|
|  | note = misc_feature - Bit score of 305.4 for hmm based on sequences of FIGURE 1. |
| REGION | 1..143 |
|  | note = misc_feature - Functional Homolog Of Ceres SEEDLINE ID no. ME00327 at SEQ ID NO. 2 |
| source | 1..143 |
|  | mol_type = protein |
|  | note = subspecies = trichocarpa |
|  | organism = Populus balsamifera |
| SEQUENCE: 10 | |

```
MEFNFLVRSA LELGDDCEIV PQDLHQEKEV LEKEEKQEDE CEISVPTLKI KLPSVEAFQI   60
EDDKDDDDDG FKTPTSLDRK IPVIFQCPPA PRKPKSLPSA KRKSPQRRVL LDLSNEIESL  120
FPPALAGDLG GKIKKVRQGN DTK                                         143
```

| | |
|---|---|
| SEQ ID NO: 11 | moltype = DNA length = 561 |
| FEATURE | Location/Qualifiers |
| misc_feature | 1..561 |
|  | note = Ceres ANNOT ID no.1439985 |
| misc_feature | 1..561 |
|  | note = Encodes the peptide sequence at SEQ ID NO 12 |
| source | 1..561 |
|  | mol_type = other DNA |
|  | organism = Populus balsamifera |
|  | sub_species = trichocarpa |
| SEQUENCE: 11 | |

```
atggctgacc cgataaagag tgaacctcat tctcaaagcg aaggttttc tgccatgttc   60
tcggaatcga aaccattttc gttaacgggg ttgcctaact ctcagatttt tttctctgag  120
aaagatccga atcctaagga attcaatttc cttgtgagac ccacgttaga acttggagat  180
gacggtgaaa ctgtacctca agagcttcat caggaaaaag aagttgaaga agaaggaaag  240
caagaagata aatgcgagat ctcggtacct actttgaaga taaaattccc atctttagga  300
gctttccaaa ttgaagatag tgatcatggt gatggttcga agactccaac ttcttcggat  360
tgcaaaatcc ctgtcatttt tcaatgtccg cctgcaccta aaaacctaa atcacttcca  420
tcaaccaaac gaaaatcgcc tcgacggaga gtcttacttg atctgtccaa cgaggttgaa  480
actttgtttc ccccagctct tgctgcaaat cttggtggca agattaagaa agttagacaa  540
ggcaacgaca gtaccaaata a                                           561
```

| | |
|---|---|
| SEQ ID NO: 12 | moltype = AA length = 168 |
| FEATURE | Location/Qualifiers |
| REGION | 1..168 |
|  | note = misc_feature - Ceres ANNOT ID no.1439985 |
| REGION | 1..168 |
|  | note = misc_feature - Bit score of 220.9 for hmm based on sequences of FIGURE 1. |
| REGION | 1..168 |
|  | note = misc_feature - Functional Homolog Of Ceres SEEDLINE ID no. ME00327 at SEQ ID NO. 2 |
| source | 1..168 |
|  | mol_type = protein |
|  | note = subspecies = trichocarpa |
|  | organism = Populus balsamifera |
| SEQUENCE: 12 | |

```
MFSESKPFSL TGLPNSQIFF SEKDPNPKEF NFLVRPTLEL GDDGETVPQE LHQEKEVEEE   60
GKQEDKCEIS VPTLKIKFPS LGAFQIEDSD HGDSKTPTS SDCKIPVIFQ CPPAPIKPKS  120
LPSTKRKSPR RRVLLDLSNE VETLFPPALA ANLGGKIKKV RQGNDSTK              168
```

| | |
|---|---|
| SEQ ID NO: 13 | moltype = AA length = 115 |
| FEATURE | Location/Qualifiers |
| REGION | 1..115 |
|  | note = misc_feature - Public GI ID no.15241794 |
| REGION | 1..115 |
|  | note = misc_feature - Bit score of 218.0 for hmm based on sequences of FIGURE 1. |
| REGION | 1..115 |
|  | note = misc_feature - Functional Homolog Of Ceres SEEDLINE ID no. ME00327 at SEQ ID NO. 2 |
| source | 1..115 |
|  | mol_type = protein |
|  | organism = Arabidopsis thaliana |
| SEQUENCE: 13 | |

```
MAEICCVKEI QEEDVEKIRL PTRPELDIPD SDHEDPTVNE EEGCKTPTSS DHKIPEVKYT   60
LCPPAPRKPK PNRSSGTKRK LTPVNVVNRI PIDLSREIEM FFEDLDRRIK KSRKQ       115
```

| | |
|---|---|
| SEQ ID NO: 14 | moltype = DNA length = 678 |
| FEATURE | Location/Qualifiers |
| misc_feature | 1..678 |
|  | note = Ceres CLONE ID no.1080942 |
| misc_feature | 1..678 |
|  | note = Encodes the peptide sequence at SEQ ID NO 15 |
| source | 1..678 |

```
                        mol_type = other DNA
                        organism = Brassica napus
SEQUENCE: 14
ctaagaagat ttgttcagtg cacacgacaa aacacaaaaa caaaaccttc aagaacaact    60
ccatttaaat atctataaag aaatgaatct tgatttaata caagatctgc ccatgctgaa   120
gttcccatca cccatcaaga tcccatccaa caacaccaac agagatgatg acggcagcag   180
cggcggctgc accactccca cttcctccga ccacaagatt cctccctcca ccgccactac   240
tcctcctcct ccgcctcaga aacgccgccc acctccgtcg ccatcatgtt tcatcagatc   300
ttgcaagagg aagcttttga cgccatcaaa ggttgagatc atcgtcaaca aagatgagat   360
cgaacggttc tttctcctct gtttacaatca ctcaacgacg tcatccccca caacaaccac   420
caccaaaaag gctctcgcgg tggttaggcg acggagaagt ttccgttctt gttcacgaag   480
atgatcaata attggagtta accacaataa agttaaaggt tccttcattt cggtaacttt   540
ttatttattt tatgtaacga ttctcaactt tacacgtcga cccactctat aaatatacat   600
gtgctatcga tcgttggaat ctttcttttc ttaatagctt catgaattat gtaaatgttc   660
aataaattta tatttgct                                                 678

SEQ ID NO: 15          moltype = AA   length = 133
FEATURE                Location/Qualifiers
REGION                 1..133
                       note = misc_feature - Ceres CLONE ID no.1080942
REGION                 1..133
                       note = misc_feature - Bit score of 274.7 for hmm based on
                         sequences of FIGURE 1.
REGION                 1..133
                       note = misc_feature - Functional Homolog Of Ceres SEEDLINE
                         ID no. ME00327 at SEQ ID NO. 2
source                 1..133
                       mol_type = protein
                       organism = Brassica napus
SEQUENCE: 15
MNLDLIQDLP MLKFPSPIKI PSNNTNRDDD GSSGGCTTPT SSDHKIPPST ATTPPPPPQK     60
RRPPPSPSCF IRSCKRKLLT PSKVEIIVNK DEIERFFSSV YNHSTTSSPT TTTTKKALAV   120
VRRRRSFRSC SRR                                                      133

SEQ ID NO: 16          moltype = DNA   length = 623
FEATURE                Location/Qualifiers
misc_feature           1..623
                       note = Ceres CLONE ID no.1073190
misc_feature           1..623
                       note = Encodes the peptide sequence at SEQ ID NO 17
source                 1..623
                       mol_type = other DNA
                       organism = Glycine max
SEQUENCE: 16
aacaagtttt ctacatccac acaaaaaagg ttttccaaac ataagcacac atttacagac    60
atggatgatc ttgagttatt acaagatctg tcccaattca acttcccagc aaccatcaag   120
atcccatcta aaacctctaa agacaacaaa gacggcgatg gtgataacga cgagggcttt   180
agctgcagca cacccacatc tcaagaacac aagattcctt ctgtccacga ttctccacct   240
ccccccgccga gaaaacctcg tgcactgcct tcaaaaccgt cgcctacggc ggctctggtg   300
ataagatcgt gtaagaggaa gctcttagtg tcggctcctg agattatcat gaacaaggaa   360
gagattgacc gtttcttctc ctctgtctat agtgacacgt caacgacggc taaacgacgg   420
agacgttatc tttattgtgc gcgaagatga gcctttagtt caagatttac attttctaca   480
gttttactgg aaatatataa attaaaaacc ttattataag tatttttaatt ttcaaaatgg   540
atggataatt ttctgtagcc gcatattaat tccgcatgga ggggtcgttg ttgtaaattc   600
cgtaataaat gaaatttaat tcc                                           623

SEQ ID NO: 17          moltype = AA   length = 129
FEATURE                Location/Qualifiers
REGION                 1..129
                       note = misc_feature - Ceres CLONE ID no.1073190
REGION                 1..129
                       note = misc_feature - Bit score of 272.3 for hmm based on
                         sequences of FIGURE 1.
REGION                 1..129
                       note = misc_feature - Functional Homolog Of Ceres SEEDLINE
                         ID no. ME00327 at SEQ ID NO. 2
source                 1..129
                       mol_type = protein
                       organism = Glycine max
SEQUENCE: 17
MDDLELLQDL SQFNFPATIK IPSKTSKDNK DGDGDNDEGF SCSTPTSQEH KIPSVHDSPP     60
PPPRKPRALP SKPSPTAALV IRSCKRKLLV SAPEIIMNKE EIDRFFSSVY SDTSTTAKRR   120
RRYLYCARR                                                           129

SEQ ID NO: 18          moltype = DNA   length = 1377
FEATURE                Location/Qualifiers
misc_feature           1..1377
                       note = Ceres SEEDLINE ID no.ME04315
misc_feature           1..1377
```

```
                        note = Expected Sequence
misc_feature            1..1377
                        note = Encodes the peptide sequence at SEQ ID NO. 20
source                  1..1377
                        mol_type = other DNA
                        organism = Arabidopsis thaliana
SEQUENCE: 18
aaaaaacttc aaagagagag agagagagag ttttgtgaac tcaagaaaat aaaaaaagtt    60
atagttaatg ggattcggct tagagagtat caaatcaatc tccggcggat ggggcgcggc   120
ggcgcgttcc tgtgacgctt gtaaatcagt taccgccgcc gtgttctgtc gagttgactc   180
agcttcctta tgcatagcat gtgacacaag aatccattcc ttcactcgcc acgagcgcgt   240
gtgggtttgt gaagtttgtg aacaagctcc cgccgccgtc acttgcaaag ccgacgccgc   300
cgctctttgc gtcacttgtg atgccgatat tcactctgct aatcctctcg ctagccgtca   360
cgaacgtgtc cccgtcgaaa cttttcttcga ctcagccgaa accgccgtcg ccaaaatctc   420
agcttcttcg acttttggta tccttggctc atccaccacc gttgatttaa ccgctgttcc   480
ggttatggct gatgatctcg gtttatgtcc gtggttactt cctaatgatt caacgaacc    540
ggctaaaatc gaaatcggaa ctgaaaacat gaaaggttct tctgactta tgttttctga   600
tttcgatcgg cttattgatt tcgagtttcc gaattcgttc aatcatcatc aaaacaacgc   660
cggaggagat agtcttgttc cggttcagac gaaaacagag cctctcccgt taactaacaa   720
tgatcattgc ttcgatattg atttctgcag atcaaagctc tctgctttca cttacccttc   780
tcaatcagtc agccacagtg tttcgacttc ttcattgaa tacggtgtag ttcctgacgg   840
aaacacaaac aactctgtta accggagcac gatcactagc tcgacgactg gtggtgatca   900
tcaagcgagc tctatggata gagaagctag ggttttgagg tacagagaga agagaaagaa   960
caggaaattt gagaagacga ttcgttacgc ttcgaggaaa gcttatgcag agtcacggcc  1020
aaggatcaaa ggccggtttg cgaaaagaac agagacagaa aacgacgaca tttttcctag  1080
tcatgtttat gcttcagcag cacacgcaca gtacggtgtc gtaccaacgt tctgattcga  1140
atctacggtg gataaacaat caacctgaag acttcatatc ttccaccgtt gatttacagt  1200
cggtgtataa taagtatagt gagtcttacc gtagacaaac atcttatcct ctttaccgtt  1260
ttaattactt tttttttacg cgctctcact gccactgtaa ctctttttt ttcttccta   1320
tatatgtatg cttattttta tttagaaaat gttatgaaat catataattt ggtaatc     1377

SEQ ID NO: 19           moltype = DNA  length = 1377
FEATURE                 Location/Qualifiers
misc_feature            1..1377
                        note = Ceres SEEDLINE ID no.ME04315
misc_feature            1..1377
                        note = Inplanta Sequence
misc_feature            1..1377
                        note = Encodes the peptide sequence at SEQ ID NO. 20
source                  1..1377
                        mol_type = other DNA
                        organism = Arabidopsis thaliana
SEQUENCE: 19
aaaaaacttc aaagagagag agagagagag ttttgtgaac tcaagaaaat aaaaaaagtt    60
atagttaatg ggattcggct tagagagtat caaatcaatc tccggcggat ggggcgcggc   120
ggcgcgttcc tgtgacgctt gtaaatcagt taccgccgcc gtgttctgtc gagttgactc   180
agcttcctta tgcatagcat gtgacacaag aatccattcc ttcactcgcc acgagcgcgt   240
gtgggtttgt gaagtttgtg aacaagctcc cgccgccgtc acttgcaaag ccgacgccgc   300
cgctctttgc gtcacttgtg atgccgatat tcactctgct aatcctctcg ctagccgtca   360
cgaacgtgtc cccgtcgaaa cttttcttcga ctcagccgaa accgccgtcg ccaaaatctc   420
agcttcttcg acttttggta tccttggctc atccaccacc gttgatttaa ccgctgttcc   480
ggttatggct gatgatctcg gtttatgtcc gtggttactt cctaatgatt caacgaacc    540
ggctaaaatc gaaatcggaa ctgaaaacat gaaaggttct tctgactta tgttttctga   600
tttcgatcgg cttattgatt tcgagtttcc gaattcgttc aatcatcatc aaaacaacgc   660
cggaggagat agtcttgttc cggttcagac gaaaacagag cctctcccgt taactaacaa   720
tgatcattgc ttcgatattg atttctgcag atcaaagctc tctgctttca cttacccttc   780
tcaatcagtc agccacagtg tttcgacttc ttcattgaa tacggtgtag ttcctgacgg   840
aaacacaaac aactctgtta accggagcac gatcactagc tcgacgactg gtggtgatca   900
tcaagcgagc tctatggata gagaagctag ggttttgagg tacagagaga agagaaagaa   960
caggaaattt gagaagacga ttcgttacgc ttcgaggaaa gcttatgcag agtcacggcc  1020
aaggatcaaa ggccggtttg cgaaaagaac agagacagaa aacgacgaca tttttcctag  1080
tcatgtttat gcttcagcag cacacgcaca gtacggtgtc gtaccaacgt tctgattcga  1140
atctacggtg gataaacaat caacctgaag acttcatatc ttccaccgtt gatttacagt  1200
cggtgtataa taagtatagt gagtcttacc gtagacaaac atcttatcct ctttaccgtt  1260
ttaattactt tttttttacg cgctctcact gccactgtaa ctctttttt ttcttccta   1320
tatatgtatg cttattttta tttaaaaaat gttatgaaat catataattt ggtaatc     1377

SEQ ID NO: 20           moltype = AA  length = 355
FEATURE                 Location/Qualifiers
REGION                  1..355
                        note = misc_feature - Ceres SEEDLINE ID no.ME04315
REGION                  1..355
                        note = misc_feature - Bit score of 860.9 for hmm based on
                         sequences of FIGURE 2.
REGION                  285..329
                        note = misc_feature - Pfam Name: CCT Pfam Description: CCT
                         motif
REGION                  56..103
                        note = misc_feature - Pfam Name: zf-B_box Pfam Description:
```

|  |  |
|---|---|
|  | B-box zinc finger |
| source | 1..355 |
|  | mol_type = protein |
|  | organism = Arabidopsis thaliana |
| SEQUENCE: 20 | |

```
MGFGLESIKS ISGGWGAAAR SCDACKSVTA AVFCRVDSAF LCIACDTRIH SFTRHERVWV    60
CEVCEQAPAA VTCKADAAAL CVTCDADIHS ANPLASRHER VPVETFFDSA ETAVAKISAS   120
STFGILGSST TVDLTAVPVM ADDLGLCPWL LPNDFNEPAK IEIGTENMKG SSDFMFSDFD   180
RLIDFEFPNS FNHHQNNAGG DSLVPVQTKT EPLPLTNNDH CFDIDFCRSK LSAFTYPSQS   240
VSHSVSTSSI EYGVVPDGNT NNSVNRSTIT SSTTGGDHQA SSMDREARVL RYREKRKNRK   300
FEKTIRYASR KAYAESRPRI KGRFAKRTET ENDDIFLSHV YASAAHAQYG VVPTF        355
```

| SEQ ID NO: 21 | moltype = DNA  length = 1541 |
|---|---|
| FEATURE | Location/Qualifiers |
| misc_feature | 1..1541 |
|  | note = Ceres CLONE ID no.1842825 |
| misc_feature | 1..1541 |
|  | note = Encodes the peptide sequence at SEQ ID NO 22 |
| source | 1..1541 |
|  | mol_type = other DNA |
|  | organism = Gossypium hirsutum |
| SEQUENCE: 21 | |

```
aagagcaaac tgtggcacta ctccatgtat actcccaaaa tctctaaaaa gggaaatact    60
agtcctttcg agggcaactg aaagaggaga aaaaaaaatc tattggtttt gatttgtgag   120
gatggtaatc gatacaacca acgtcaaggg acttacggga cgctgggggca tggcagcaaa   180
gacatggcgac acatgtaaat cagcggcagc ggctattttc tgtcgttctg attccgcttt   240
tatgtgcctc agctgcgatt ccaggatcca ctctgctaat gacaagcttg tttcttgtcg   300
tcacgagagg gtgtggatgt gtgaggtgtg cgagcaggcc ccagctgccg tcacttgcaa   360
ggccgacgcc gctgcccttt gcgtcgcctg cgattccgac atccactctg ctaatccttt   420
ggctcgtcgc cacgagcgtg tccctgtcca gcctttcttt gactctgctg attccatcgt   480
caaatcttct tctttcagct tccttgtgcc gactgatcct aatactggtt ctaattgtca   540
acaagaagat gtagagacag gttcttggct gttgcccaat cccaaactca ccatggaaac   600
taaccaagtc aaaacagggg attttttctt ctccgacatg gatccgttta ttgatttga   660
gtaccaggat tcgtttcaac agcatgacgg agctatggac agcgtagttc cagttcagac   720
caaaccagct acaatttcaa tgatcaacaa tgaaaattgt ttcgatgttg atttctgtcg   780
atccaagttc cctactttca gctaccagac aaagtctcaa agccatgtg tttcatcatc   840
gtcgctcgag gtaggagtag ttccagatgg gaactccgtg tcggatatct catatacttt   900
gggacggacc atgggtgacc caagcgcacc aatctgggca gctacagcca ataaccaagc   960
accacctcag gcccaagtcg gtggaatgga tcgagaagct agagttctaa ggtacagaga  1020
gaagagaaag aacagaaaat tgagaaaac aatccgctac gcttcgagaa aggcatacgc  1080
cgagtcaagg ccaaggatca aaggccgttt cgccaaaaga aatgaaccg acaacgaagt  1140
tgaccacatg tataactcgg cttcttccgc tgctaccgca gcagctttca tgtacgataa  1200
ccagtacggc atcgtcccat cctttgagg atgtcatgaa tgaatctgat tcagatggaa  1260
acaagaattg ttggcgtgtaa tattcaactg tgatatatat atccagcaag tagaatcaac  1320
tacccctaagg aaaacaaatg atgtagcttt taattatggt tattgatgta aaaatagtgt  1380
atccatgagc tattgatttg cagggattca ttcaagttga ttaactgcag aataagatgg  1440
aaaagtcctg caaaatctga aacaaagccc ttccactttt tctctagagg gcttcttctg  1500
tgattctgtt atctagaagt aaaagttttt cttggttttt c                       1541
```

| SEQ ID NO: 22 | moltype = AA  length = 368 |
|---|---|
| FEATURE | Location/Qualifiers |
| REGION | 1..368 |
|  | note = misc_feature - Ceres CLONE ID no.1842825 |
| REGION | 1..368 |
|  | note = misc_feature - Bit score of 932.9 for hmm based on sequences of FIGURE 2. |
| REGION | 291..335 |
|  | note = misc_feature - Pfam Name: CCT Pfam Description: CCT motif |
| REGION | 62..109 |
|  | note = misc_feature - Pfam Name: zf-B_box Pfam Description: B-box zinc finger |
| REGION | 1..368 |
|  | note = misc_feature - Functional Homolog Of Ceres SEEDLINE ID no. ME04315 at SEQ ID NO. 20 |
| source | 1..368 |
|  | mol_type = protein |
|  | organism = Gossypium hirsutum |
| SEQUENCE: 22 | |

```
MVIDTTNVKG LTGRWGMAAK TCDTCKSAAA AIFCRSDSAF MCLSCDSRIH SANDKLVSCR    60
HERVWMCEVC EQAPAAVTCK ADAAALCVAC DSDIHSANPL ARRHERVPVQ PFFDSADSIV   120
KSSSFSFLVP TDPNTGSNCQ QEDVETGSWL LPNPKLTMET NQVKTGDFFF SDMDPFIDFE   180
YQDSFQQHDG AMDSVVPVQT KPATISMINN ENCFDVDFCR SKFPTFSYQT KSQSHSVSSS   240
SLEVGVVPDG NSVSDISYTL GRTMGDPSAP IWAATANNQA PPQAQVGGMD REARVLRYRE   300
KRKNRKFEKT IRYASRKAYA ESRPRIKGRF AKRNETDNEV DHMYNSASSA ATAAAFMYDN   360
QYGIVPSF                                                           368
```

| SEQ ID NO: 23 | moltype = DNA  length = 1332 |
|---|---|
| FEATURE | Location/Qualifiers |

```
misc_feature            1..1332
                        note = Ceres CLONE ID no.1834027
misc_feature            1..1332
                        note = Encodes the peptide sequence at SEQ ID NO 24
source                  1..1332
                        mol_type = other DNA
                        organism = Gossypium hirsutum
SEQUENCE: 23
ttaaaatcaa taacaaacac ttcaaaccct ccacgtttga tccaaacata atatttttt      60
atttccattg ctttgatttg attcgcgatt atgggaatcg aaataagcgg cggcacgatc    120
attccaggag gttgggggc cgccgccatg gctgtcgcgg ctaagacatg cgacgcatgt    180
aaatcatcg cggcagctat cttttgtcgt actgattggg tcttttatg cttgaattgt     240
gattccaatt tccattccgg tcacgaaagg gtgtctatgt gtgaagtttg cgaacaagct    300
ccggcggctg tcacttgtaa agccgacgcg gcggctcttt gtgtcacttg cgacgccgat    360
atccattcag cgaacccact ggctcgccgt cacgaacgtg tacccatcga acctttctac    420
gactccgctg attccatcgt caaatcttcc cctttagct tccttgtgcc gacgacggat     480
cataatggta ctaattgtaa acaagaaatt gaatctaaca aaggggattt ttttttcaca    540
gaaatggatc ggtttatcga tttcgggtac ccgaattcat ctcaacatct tcatgatgcc    600
gccatggata gcgttgttcc agttcaaact ccaaaaccag tcattccact gatcaacgat    660
ggaagctgtt tcgatacttt cagctatcaa actcaatcat ctctcagtca tagcgtttca    720
tcatcgtcgc ttgaagtaga aacagttcca gatgggaatt accacgcaac acaagtgggt    780
ggttcaatcg atcgagaagc tagggtttta aggtacaaag agaagagaaa gaacaggaaa    840
ttcgagaaga caatacgata cgcttcaaga aaggcttacg ctgaatcaag accaagaatc    900
aaaggtcgat ttgctaaaag aacagaaacc cacaacgatg atgttgatca catgttcaat    960
aactcttctt tcgctgttgg tcctgctggt ttcatggcgg aaacagacta tggtgtcgtt   1020
ccatcgtttt gaatgttgat gttttatgtt tggtttaatc tgtaatgtat taaattattt   1080
aatccaattt ccagcaaagt agaaataacc ttatggccat tgaaaatcaa ggaagaaaga   1140
tgcttagttc tttgattaat cattaaagtt tctgatgtat aaaaaacagt gtatcggtgg   1200
agttcgtcgt atgttcgcca tggttgattt gcaggattcc tgcaagggag atatattagt   1260
tttcataaaa atgtttattt caatctctga ataaaaccag atatatggta agtaaatgct   1320
tcaatttagt tc                                                        1332

SEQ ID NO: 24           moltype = AA   length = 313
FEATURE                 Location/Qualifiers
REGION                  1..313
                        note = misc_feature - Ceres CLONE ID no.1834027
REGION                  1..313
                        note = misc_feature - Bit score of 543.8 for hmm based on
                          sequences of FIGURE 2.
REGION                  235..279
                        note = misc_feature - Pfam Name: CCT Pfam Description: CCT
                          motif
REGION                  64..106
                        note = misc_feature - Pfam Name: zf-B_box Pfam Description:
                          B-box zinc finger
REGION                  1..313
                        note = misc_feature - Functional Homolog Of Ceres SEEDLINE
                          ID no. ME04315 at SEQ ID NO. 20
source                  1..313
                        mol_type = protein
                        organism = Gossypium hirsutum
SEQUENCE: 24
MGIEISGGTI IPGGWGAAAM AVAAKTCDAC KSSAAAIFCR TDWVFLCLNC DSNFHSGHER     60
VSMCEVCEQA PAAVTCKADA AALCVTCDAD IHSANPLARR HERVPIEPFY DSADSIVKSS    120
PFSFLVPTTD HNGTNCKQEI ESNKGDFFFT EMDRFIDFGY PNSSQHLHDA AMDSVVPVQT    180
PKPVIPLIND GSCFDTFSYQ TQSSLSHSVS SSSLEVETVP DGNYHATQVG GSIDREARVL    240
RYKEKRKNRK FEKTIRYASR KAYAESRPRI KGRFAKRTET HNDDVDHMFN NSSFAVGPAG    300
FMAETDYGVV PSF                                                       313

SEQ ID NO: 25           moltype = DNA   length = 1226
FEATURE                 Location/Qualifiers
misc_feature            1..1226
                        note = Ceres CLONE ID no.1837064
misc_feature            1..1226
                        note = Encodes the peptide sequence at SEQ ID NO 26
source                  1..1226
                        mol_type = other DNA
                        organism = Gossypium hirsutum
SEQUENCE: 25
gattccaaag atctcacccc atcaactgaa atggctgcaa agcattcgga cgcctgtaaa     60
ccaacagcta ccgatccaga tttttatgtgc ctgagttatg attcttccac cgccatccat   120
ggctgcattg gagggtgtt gatgtgcgac gtttgcgagc aagttccggc tgcgttcact    180
tgcaaagccg atgccgccgc gctttgtgtc gcttgtgatg ccgatattca ctccgctaat    240
cattcgtcgc gtcgtcacta ccgtgtcccg atcgaccctt ttcttggtcg acaaaaagag    300
gatgtagtag tgatgggttc ttggtctttg ttacctggtt tcaatcataa actggttgaa    360
acagaggatt tggggatttc agaaatggat ccatttattg atttggagta ccaggatgga    420
tatcatgttt tacagcatca taattaggt atggaaagct tagttccagt tcagatcgaa    480
ccggcaacaa cagttccagt ggtcaaccct attcacttct gccaatctca gtctctcagc    540
catagtgtat cgtcatcctc ggttgagtta ggtgatggga attctttatc agatatctca    600
```

```
tgcccattaa gaggtaccac aactgatcca agcatactca tatgcaacaa ccaagtagac    660
caagttggtt caatggatcg agtggctcgg gttttgaggt acagagaaaa gagaaagaag    720
agaaaatttg agaaaacagt tcgttacgct tcacgaaaag cctacgctga atcaagaccg    780
agaatcaaag gtcgtttcgt taaagaact caaatccata accgagttga ccatctctgt    840
aactcggcaa catcaccatc atcatcaaca acgacatccc acacgcatta ctacggtatc    900
gtcccatctt ttttatgaaa gggaaacgtg gaaaatgaa accaaaaaat ttaattttag    960
tgatgatatt gtaaaattcc actagtttat gtagcaagta gaataataat cccaagtcca   1020
ttaagattga ggaagatatt atgtaaccca ataacggtg atgttttgg tagccgttga    1080
tatttggggc ttttagggtt atacgcaagc agatgttaga gttctaagaa ctgatatttt   1140
gcttgcagtt ctgaaaaaaa tgaagcccct ttcaccattt ttattgagag gggcttcttt   1200
tgtttttatg ttactaaagt ttgacc                                       1226

SEQ ID NO: 26           moltype = AA  length = 295
FEATURE                 Location/Qualifiers
REGION                  1..295
                        note = misc_feature - Ceres CLONE ID no.1837064
REGION                  1..295
                        note = misc_feature - Bit score of 317.3 for hmm based on
                          sequences of FIGURE 2.
REGION                  217..261
                        note = misc_feature - Pfam Name: CCT Pfam Description: CCT
                          motif
REGION                  34..81
                        note = misc_feature - Pfam Name: zf-B_box Pfam Description:
                          B-box zinc finger
REGION                  1..295
                        note = misc_feature - Functional Homolog Of Ceres SEEDLINE
                          ID no. ME04315 at SEQ ID NO. 20
source                  1..295
                        mol_type = protein
                        organism = Gossypium hirsutum
SEQUENCE: 26
MAAKHSDACK PTATDPDFMC LSYDSSTAIH GCIGRVLMCD VCEQVPAAFT CKADAAALCV    60
ACDADIHSAN HLARRHYRVP IDPFLGPQKE DVVVMGSWSL LPGFNHKLVE TEDLGISEMD   120
PFIDLEYQDG YHVLQHHNLG MESLVPVQIE PATTVPVVNP IHFCQSQSLS HSVSSSSVEL   180
GDGNSLSDIS CPLRGTTTDP SILICNNQVD QVGSMDRVAR VLRYREKRKK RKFEKTVRYA   240
SRKAYAESRP RIKGRFVKRT QIHNRVDHLC NSATSPSSST TTSHTHYYGI VPSFL        295

SEQ ID NO: 27           moltype = DNA  length = 1155
FEATURE                 Location/Qualifiers
misc_feature            1..1155
                        note = Ceres ANNOT ID no.1482536
misc_feature            1..1155
                        note = Encodes the peptide sequence at SEQ ID NO 28
source                  1..1155
                        mol_type = other DNA
                        organism = Populus balsamifera
                        sub_species = trichocarpa
SEQUENCE: 27
atgggaattg aagttgagag cttaaagaac ttgaccggag gatggagtgt tgcggctaaa     60
cgttgcgact cgtgcaaaac ggcagctgca gctgcgtttt gccgggcgga ctctgctttt   120
ttgtgtctga attgtgacac caagattcac catagtgggg tgaacagcaa gatcatgtca   180
aggcacgagc gtgtgtggat gtgtgaggtt tgcgagcaag cacccgctgc ggttacctgt   240
aaggctgatg cagctgctct ttgtgttact tgtgatgctg acatccactc tgctaaccct   300
cttgctcgcc gtcatgaacg agtccccgtg gagccttttt atgactctgc tgaatcaatt   360
gttaagactt cctcggcgtt taattttcta gtgcctggtg atcaaaatgg tgtgtctgca   420
tatgatcata acgatgagat cgagggtgtt tcgtggttgt tgcacggtaa tcacacaaca   480
catgacctta ataccaagat caacatcgag aatcctgttg tcaagactgg agatatgttt   540
ttctgtgaaa tggatccctt tcttgatttt gagtatcaga attcgatgga tgggaggtac   600
aagcagagtc atggtggggg tggtgctgga gctgatcacg ttgtgcctgt gcaaaacaaa   660
ccagctccgc ttcccgtgat cgatcataaa aactgctttg atattgattt ctgtagatcg   720
aaactcacct ctttcagcag ctaccctctc cagtccctta gccacagcgt ttcttcgtct   780
tccctcgatg ttggtgttgt tcctgatggg aattctatgt ccgatatttc gtatcccttc   840
ggccgaagca tgaatactta taccgatcca agcatgccca tctcaggttc cactacaaat   900
caagcagcag ctcagttagc tgggattgac cgcgaagcta gagttttgag gtacagagag   960
aaaagaaaga accgtaaatt cgaaaaaacc atacggtatg cttcacgtaa agcttacgca  1020
gaaaccaggc caagaatcaa aggccgattc gcgaagcgaa ccgaaatgga atccgatatg  1080
gacaccctat ataactctcc gagctctgtc cctttcctgg ccgatactca ttacggtgtc  1140
gttccctcgt tttga                                                   1155

SEQ ID NO: 28           moltype = AA  length = 384
FEATURE                 Location/Qualifiers
REGION                  1..384
                        note = misc_feature - Ceres ANNOT ID no.1482536
REGION                  1..384
                        note = misc_feature - Bit score of 969.7 for hmm based on
                          sequences of FIGURE 2.
REGION                  311..355
                        note = misc_feature - Pfam Name: CCT Pfam Description: CCT
```

|   |   |
|---|---|
|   | motif |
| REGION | 63..110 |
|   | note = misc_feature - Pfam Name: zf-B_box Pfam Description: B-box zinc finger |
| REGION | 1..384 |
|   | note = misc_feature - Functional Homolog Of Ceres SEEDLINE ID no. ME04315 at SEQ ID NO. 20 |
| source | 1..384 |
|   | mol_type = protein |
|   | note = subspecies = trichocarpa |
|   | organism = Populus balsamifera |

SEQUENCE: 28

```
MGIEVESLKN LTGGWSVAAK RCDSCKTAAA AAFCRADSAF LCLNCDTKIH HSGVNSKIMS   60
RHERVWMCEV CEQAPAAVTC KADAAALCVT CDADIHSANP LARRHERVPV EPFYDSAESI  120
VKTSSAFNFL VPGDQNGVSA YDHNDEIEGV SWLLHGNHTT HDLNTKINIE NPVVKTGDMF  180
FCEMDPFLDF EYQNSMDGRY KQSHGGGGAG ADSVVPVQNK PAPLPVIDHK NCFDIDFCRS  240
KLTSFSSYPS QSLSHSVSSS SLDVGVVPDG NSMSDISYPF GRSMNTYTDP SMPISGSTTN  300
QAAAQLAGID REARVLRYRE KRKNRKFEKT IRYASRKAYA ETRPRIKGRF AKRTEMESDM  360
DTLYNSPSSV PFLADTHYGV VPSF                                        384
```

|   |   |
|---|---|
| SEQ ID NO: 29 | moltype = AA  length = 355 |
| FEATURE | Location/Qualifiers |
| REGION | 1..355 |
|   | note = misc_feature - Public GI ID no.18424009 |
| REGION | 1..355 |
|   | note = misc_feature - Bit score of 856.7 for hmm based on sequences of FIGURE 2. |
| REGION | 285..329 |
|   | note = misc_feature - Pfam Name: CCT Pfam Description: CCT motif |
| REGION | 56..103 |
|   | note = misc_feature - Pfam Name: zf-B_box Pfam Description: B-box zinc finger |
| REGION | 1..355 |
|   | note = misc_feature - Functional Homolog Of Ceres SEEDLINE ID no. ME04315 at SEQ ID NO. 20 |
| source | 1..355 |
|   | mol_type = protein |
|   | organism = Arabidopsis thaliana |

SEQUENCE: 29

```
MGFGLESIKS ISGGWGAAAR SCDACKSVTA AVFCRVDSAF LCIACDTRIH SFTRHERVWV   60
CEVCEQAPAA VTCKADAAAL CVSCDADIHS ANPLASRHER VPVETFFDSA ETAVAKISAS  120
STFGILGSST TVDLTAVPVM ADDLGLCPWL LPNDFNEPAK IEIGTENMKG SSDFMFSDFD  180
RLIDFEFPNS FNHHQNNAGG DSLVPVQTKT EPLPLTNNDH CFDIDFCRSK LSAFTYPSQS  240
VSHSVSTSSI EYGVVPDGNT NNSVNRSTIT SSTTGGDHQA SSMDREARVL RYREKRKNRK  300
FEKTIRYASR KAYAESRPRI KGRFAKRTET ENDDIFLSHV YASAAHAQYG VVPTF       355
```

|   |   |
|---|---|
| SEQ ID NO: 30 | moltype = AA  length = 351 |
| FEATURE | Location/Qualifiers |
| REGION | 1..351 |
|   | note = misc_feature - Public GI ID no.9759262 |
| REGION | 1..351 |
|   | note = misc_feature - Bit score of 833.0 for hmm based on sequences of FIGURE 2. |
| REGION | 281..325 |
|   | note = misc_feature - Pfam Name: CCT Pfam Description: CCT motif |
| REGION | 56..103 |
|   | note = misc_feature - Pfam Name: zf-B_box Pfam Description: B-box zinc finger |
| REGION | 1..351 |
|   | note = misc_feature - Functional Homolog Of Ceres SEEDLINE ID no. ME04315 at SEQ ID NO. 20 |
| source | 1..351 |
|   | mol_type = protein |
|   | organism = Arabidopsis thaliana |

SEQUENCE: 30

```
MGFGLESIKS ISGGWGAAAR SCDACKSVTA AVFCRVDSAF LCIACDTRIH SFTRHERVWV   60
CEVCEQAPAA VTCKADAAAL CVSCDADIHS ANPLASRHER VPVETFFDSA ETAVAKISAS  120
STFGILGSST TVDLTAVPVM ADDLGLCPWL LPNDFNEPAK IEIGTENMKG SSDFMFSDFD  180
RLIDFEFPNS FNHHQNNAGG DSLVPVQTKT EPLPLTNNDH CFDIDFCRSK LSAFTYPSQS  240
VSTSSIEYGV VPDGNTNNSV NRSTITSSTT GGDHQASSMD REARVLRYRE KRKNRKFEKT  300
IRYASRKAYA ESRPRIKGRF AKRTETENDD IFLSHVYASA AHAQYGVVPT F           351
```

|   |   |
|---|---|
| SEQ ID NO: 31 | moltype = DNA  length = 1428 |
| FEATURE | Location/Qualifiers |
| misc_feature | 1..1428 |
|   | note = Ceres CLONE ID no.463157 |
| misc_feature | 1..1428 |

```
                        note = Encodes the peptide sequence at SEQ ID NO 32
source                  1..1428
                        mol_type = other DNA
                        organism = Glycine max
SEQUENCE: 31
aactcactca ctcattcaag tcgctaatcc tagttccttc aactcctcgc tggcaacaac    60
agcagtacta ccattagccg cgttttttcaa aagtgatttt cgagaattag cgatgggaat   120
tgaaagagga ggcttcaagg gattcaggag cgcctggagc gtgccgccca agccgtgcga   180
ttcctgcaag ctggcctcgg cggcgctttt ctgccgcccc gattccgcgt ttctctgcat   240
cgcctgcgat tccaacattc actgctcgaa caaactcgcg tcgcgccacg agcgcgtgtg   300
gatgtgtgag gtgtgcgagc aggcaccccg tgctgtcacg tgcaaggccg acgccgccgc   360
cctctgcgtc acgtgtgact ccgacatcca ctccgcgaac ccctcgcgc aacgccacga   420
gcgcgtcccc gtggaacctt tctttgactc cgctgagtcc atagtgaaag cctctgctgc   480
cgccacctcc gggttcattg tcccatccga cgacggcggc gcctccgacg ctttcgccc   540
cgatgactcc gacgccgcg cgtggctcat cccgaaccct aatttcgggt ccaagctcat   600
ggacgccccc gaaatcaagt ccaaggagat tcttctct gaaatggacc ccttcctcga   660
ttttgattac tcaaactcct tccaaaacaa caacagcgcc ggaaacgaca cgtcgttcc   720
agttcaaaaa ccctctctcg cccctcccct aatcaataat caccaccacc accaatcga   780
aacttgcttc gacgtcgatt tttgtcgctc gaagctctcc tcctttaact accccttccaa  840
ttctcttagc caaagcgttt cgtcgtcgtc gcttgatgtt ggagtggtgc cggacgggaa   900
cacggtgtca gacatgtcgt attctttttgg tcggaacagt tcggattcga gtgggattgt   960
tgttgtgtca ggaaatagtg tggggcaagg tgcgacgcag ttgtgtggaa tggatcggga  1020
agcgagggta ctgcgataca gagagaaaag gaagaaccga aaattcgaga agacaattcg  1080
atacgcatcg cgaaaagcat atgcggaaac ccggcccagg ataaaaggcc gcttcgccaa  1140
acgaacagaa attgactcgg atgtggagcg tctctatagc cctggccctg cggtgctcat  1200
gctggacact ccatacggcg tcgtaccatc gttttagtta atttcaaaat gaagaaacga  1260
tggagtgcat gaatcttaga ataatgatta gcgattctgt gggattgtta ggggaaaaag  1320
gtgaagaatc gaatcggtac gaacgtgatt cttagctgga gcgcgatggg ggaagattat  1380
tgtgaagatt tgtctcgatc gaccagaaaa gcccgtttac tttttatg               1428

SEQ ID NO: 32           moltype = AA   length = 374
FEATURE                 Location/Qualifiers
REGION                  1..374
                        note = misc_feature - Ceres CLONE ID no.463157
REGION                  1..374
                        note = misc_feature - Bit score of 912.7 for hmm based on
                         sequences of FIGURE 2.
REGION                  302..346
                        note = misc_feature - Pfam Name: CCT Pfam Description: CCT
                         motif
REGION                  60..107
                        note = misc_feature - Pfam Name: zf-B_box Pfam Description:
                         B-box zinc finger
REGION                  1..374
                        note = misc_feature - Functional Homolog Of Ceres SEEDLINE
                         ID no. ME04315 at SEQ ID NO. 20
source                  1..374
                        mol_type = protein
                        organism = Glycine max
SEQUENCE: 32
MGIERGGFKG FRSAWSVPPK PCDSCKLASA ALFCRPDSAF LCIACDSNIH CSNKLASRHE    60
RVWMCEVCEQ APAAVTCKAD AAALCVTCDS DIHSANPLAQ RHERVPVEPF FDSAESIVKA   120
SAAATFGFIV PSDDGASDA FAPDDSDAAA WLIPNPNFGS KLMDAPEIKS KEIFFSEMDP    180
FLDFDYSNSF QNNNSAGNDS VVPVQKPSLA PPLINNHHHH QSETCFDVDF CRSKLSSFNY   240
PSNSLSQSVS SSSLDVGVVP DGNTVSDMSY SFGRNSSDSS GIVVVSGNSV GQGATQLCGM   300
DREARVLRYR EKRKNRKFEK TIRYASRKAY AETRPRIKGR FAKRTEIDSD VERLYSPGPA   360
VLMLDTPYGV VPSF                                                    374

SEQ ID NO: 33           moltype = DNA   length = 1556
FEATURE                 Location/Qualifiers
misc_feature            1..1556
                        note = Ceres CLONE ID no.685991
misc_feature            1..1556
                        note = Encodes the peptide sequence at SEQ ID NO 34
source                  1..1556
                        mol_type = other DNA
                        organism = Triticum aestivum
SEQUENCE: 33
aactttgct tcgccgtgga aaggatcgtc gtagctggct tagccttgctg ctttgcttcc    60
aagtgttgct gctggtggtg ctgtggtagt gtggtgtgag gtgtgatgga gctgcagggg   120
ctggggaggt actgggcgt gggcggcagg aggtgcgggt cgtgccgggg gtcgccggcg   180
gcggtgcact gccggacgtg cgatggggc agtggggacg gggcgtacct gtgcgcgggc   240
tgtgcgagg gcacgcgcg gcggggcac gagagggtgt gggtctgcga ggtgtgcgag   300
ctcgcgcg ccgcggtcac ctgcaaggcc gacgccgcg cctctgcgg tcgcctgcat   360
gccgacatcc accacgccaa cccgctcgcg cgccgccacg agcgcgtccc cgtgcagccc   420
atcgggtcct cgtcacccga ggggcaggag caggagcagg atgcgttcgt gatgtcgttc   480
ggcggctcgg tcgacgggga gaagcagcag aaccccgtgg tgaacctgaa cgacgctctg   540
gaggccggcc ccgcgggaa ggagaacgtg aagctggact tcctgttcgc ggacatgatg   600
gacccttttct tcggctccga gctccgcgc ttcccgcacg ccgacagcgt tgtccccagc   660
```

```
ggcggcgcgg tggagctgga cttcggtggc gtcgccgccc cgtcgtcgt ctccaacccg    720
tcctacagct cctacacggc ggcgtcgctc ggtggaagtg gctcgtcgtc ggaggtcggc    780
ttggtgccgg acgcgatctg tggccgaggc ggcggcatca tcgagctgga cttcgcacag    840
tccaaggccg cgtacctgcc ctacaccccc acaccaagcc acagtaccgt ctcctcggtg    900
gatgttgggt cggtgccgga gcggagcgac agcgccgtcg cggcggcgac gccggcgacg    960
gggagggga gggaggcgcg tctgatgcgg taccgcgaga agcgcaagaa ccggcggttc   1020
gagaagacca tccggtacgc gtcccggaag gcctacgccg agagcaggcc gcgcgtcaag   1080
ggccgcttcg ccaagcgcgc cgacgacgcg gacaccgacg ccgtcgcggc ggccacgatc   1140
accacgccgg ggccatgcgt gctcgacttc ggcagctacg gcgtcgtgcc caccttctga   1200
ggcgcgcct gatttcgtgt ccatttcctc cggcgagcgt gccggctggg tgcctaatta   1260
aatccggcac cgccatggcc ggcacgagcg cgccgacgtg catgcgtcgt gttccctctt   1320
gtataattgc atgtaatgtt tttcgagctg gctgatcgct ggctggcgtg tagtatactg   1380
taatcaacat gcacgcacgc acgcacgcat gttttgctag aactagaata atacagatag   1440
ttctagttga ctagtctact accctgtacc ctttccctgg gctagtttga tgccaaatta   1500
ggctagggca atgtaacgtg tttgctggaa cagcttagtt ctagttttgg atccgc        1556

SEQ ID NO: 34           moltype = AA  length = 364
FEATURE                 Location/Qualifiers
REGION                  1..364
                        note = misc_feature - Ceres CLONE ID no.685991
REGION                  1..364
                        note = misc_feature - Bit score of 464.6 for hmm based on
                          sequences of FIGURE 2.
REGION                  289..333
                        note = misc_feature - Pfam Name: CCT Pfam Description: CCT
                          motif
REGION                  56..103
                        note = misc_feature - Pfam Name: zf-B_box Pfam Description:
                          B-box zinc finger
REGION                  1..364
                        note = misc_feature - Functional Homolog Of Ceres SEEDLINE
                          ID no. ME04315 at SEQ ID NO. 20
source                  1..364
                        mol_type = protein
                        organism = Triticum aestivum
SEQUENCE: 34
MELQGLGRYW GVGGRRCGSC RGSPAAVHCR TCDGGSGDGA YLCAGCGEGH ARAGHERVWV    60
CEVCELAPAA VTCKADAAAL CAACDADIHH ANPLARRHER VPVQPIGSSS PEGQEQEQDA   120
FVMSFGGSVD GEKQQNPVVN LNDALEAGAG GKENVKLDPL FADMMDPFFG SELPRFPHAD   180
SVVPSGGAVE LDFGGVAAPV VVSNPSYSSY TAASLGGSGS SSEVGLVPDA ICGRGGGIIE   240
LDFAQSKAAY LPYTPTPSHS TVSSVDVGSV PERSDSAVAA ATPATGEGRE ARLMRYREKR   300
KNRRFEKTIR YASRKAYAES RPRVKGRFAK RADDADTDAV AAATITTGPG CVLDFGSYGV   360
VPTF                                                               364

SEQ ID NO: 35           moltype = DNA  length = 1442
FEATURE                 Location/Qualifiers
misc_feature            1..1442
                        note = Ceres CLONE ID no.702632
misc_feature            1..1442
                        note = Encodes the peptide sequence at SEQ ID NO 36
source                  1..1442
                        mol_type = other DNA
                        organism = Triticum aestivum
SEQUENCE: 35
acctcagatc aatcactctt ccctcccact actcccaccg cgttcacccg ccattgcctg     60
tcgaagctac gagattagtt actagtatga tggagctgcg caagtactgg ggcgtggggg    120
ggaggaggtg cggggcgtgc gaggggcgg cgccggcggc ggtgcactgc cgggattgcg    180
ccgggtacct gtgcacgggg tgcgacgcg ggccggcgca cgcgcgggct ggccacgagc    240
gcgtctgggt gtgcgaggtc tgcgaggtca gccccgcggc cgtgacgtgc aaggccgacg    300
ccgccgtgct ctgcgccgtg tgcgacgcca acatccacca cgcccaaccg ctcgccgagc    360
gccacgtgcg cgtgcccatc gcgcccatct gctccccga ggccgccgcg gtggcggccg    420
aggccatgat gttctgtggc gccggtgacg gcgaggcgcg ggcggatcag gacgacgtgc    480
ccgagcagct gcaccaacac gggggatgc tgaaacctca acgtggaggc cggcaaggag    540
ggccggaaga tggactacct cttctccgac tcgtcgcaca cctacctcgc tgtcgacttc    600
acgcgcttcg cccacgctga cagcgtcgtg cccagcggcc tcgccaccgg cgccgtaccc    660
gccgtcgtgg acctggactt cgcgtgcggg atcggcgcca agccgccggc gacctacagc    720
tcctcgtaca cggccaacgc ctccggcgcg cacagcggct cttcatcgga ggtcagcgtg    780
gtgccggagg ccatctgcgg cggcgtcggg agcttcgaga tcgacttcac ccggcccaag    840
ccgcagccgt acatgcccgc gtacaccgcg gcaccgccgca gccatgggggt gagcgcgag    900
caggcgtggc cggtggacat gggggtacttg acggtgccgg agcgtccggt ggcggtgacc    960
ggggagggca gggtggcgag gctgatgcgg taccggagga gaggaagaa ccgccggttc   1020
gagaagacca tccggtacgc gtccaggaag gcctacgccg agtcgcggcc gcgcgtcaag   1080
ggccgcttcg ccaagcgcac cgaccaggac gccgacggca cgacgtggac gcggaggcc   1140
catgccgtcg cgtcttccac gtcctacttg tcgactttg gctacggcgt cgtgccgtgc   1200
ttctgatccg ccggcccggc gccccggccg gcggccttgt acttgtacca ttgatgcatg   1260
tacagtagta cgtagggac tagtaatcca tccatgtact cctcctgagc tagttcgatc   1320
gcgctttga tgtactagta atactgtaaa ctgtaacagt agtagtactt tggccaatat   1380
gctcgtttat ttttggatgg ccgaaactag tagcccaaac atttggatca tcaatcatta   1440
tt                                                                 1442
```

```
SEQ ID NO: 36          moltype = AA  length = 372
FEATURE                Location/Qualifiers
REGION                 1..372
                       note = misc_feature - Ceres CLONE ID no.702632
REGION                 1..372
                       note = misc_feature - Bit score of 497.8 for hmm based on
                         sequences of FIGURE 2.
REGION                 295..339
                       note = misc_feature - Pfam Name: CCT Pfam Description: CCT
                         motif
REGION                 51..98
                       note = misc_feature - Pfam Name: zf-B_box Pfam Description:
                         B-box zinc finger
REGION                 1..372
                       note = misc_feature - Functional Homolog Of Ceres SEEDLINE
                         ID no. ME04315 at SEQ ID NO. 20
source                 1..372
                       mol_type = protein
                       organism = Triticum aestivum
SEQUENCE: 36
MMELRKYWGV GGRRCGACEG AAPAAVHCRD CAGYLCTGCD ARPAHARAGH ERVWVCEVCE   60
VSPAAVTCKA DAAVLCAVCD ADIHHANPLA ERHVRVPIAP ICSPEAAAVA AEAMMFCGAG  120
DGEARADQDD VPEQLHQHGG MLNLNVEAGK EGRKMDYLFS DLVDPYLAVD FTRFAHADSV  180
VPSGVATGAV PAVVDLDFAC GIGAKPPATY SSSYTANASG AHSGSSSEVS VVPEAICGGV  240
GSFEIDFTRP KPQPYMPAYT AAPPSHGVSA QQAWPVDMGY LTVPERPVAV TGEGRVARLM  300
RYREKRKNRR FEKTIRYASR KAYAESRPRV KGRFAKRTDQ DADGDDVDAE AHAVPSSTSY  360
LLDFGYGVVP SF                                                     372

SEQ ID NO: 37          moltype = DNA  length = 1345
FEATURE                Location/Qualifiers
misc_feature           1..1345
                       note = Ceres CLONE ID no.1559496
misc_feature           1..1345
                       note = Encodes the peptide sequence at SEQ ID NO 38
source                 1..1345
                       mol_type = other DNA
                       organism = Zea mays
SEQUENCE: 37
ctgacacccg tggcatccct ctcgtgactc ccggagcgga ggcatggaca ccgcggcgga     60
gctggagctg gggctggagt tggagcagaa gccggcggcg gggtactgga gcgtggtggg    120
cgcgcgccct tgcgacgcgt gcgccgcgga gccggcgcgg ctgcactgcc gcgcggacgg    180
cgcgttcctg tgccccggct gcgacgcccg ggcgcacgtc gccggtcgc gccacgtcgc    240
cgtctggctg tgcgaggtct gcgagcacgc ccccgccgtc gtcacctgcc gcgccgacgc    300
cgccgcgctc tgcgccgcct gcgacgccga catccactcg gccaacccgc tcgcgcgccc    360
ccacgagcgc ctccccatcg cccctctctt cggcgcgctc gcggacgcgc cgcagcccct    420
ccgtcccccg gccctcgctg ccgccgcggg ggccgaggcc cccgcccga ccccggtca    480
gggtgaagcg gtggcggaag actacggag cagcgaggcc gaggcggcgt cgtggttgct    540
ccccgagccc gacaacagcc acgaggacag cgccgccgac acgttcttcg cggagtcgga    600
cgcgtacctc ggcgccgacc tcgacttcgc ccggtgcatg gacggcgtca aggccatcgg    660
cgtgccggtc gcgccgcccg agctggacat cggtgccggc agcttttgct acccccgaaca    720
ctccatgaac cacatttttgt cgtcatcctc ggaggtggcg gtggtaccgg acgcgcaggc    780
ggccggtctg ccggtggtgg tggtggtgag cagaggggag gagcgggagg cgcggctgat    840
gcggtaccgt gagaagcgca agaaccgccg gttcgacaag accatccgct acgcgtcccg    900
caaggcgtac gccgagacgc ggccgcgcat caagggctgc ttcgccaagc gccgttcgc    960
ggagggcgag gacgaggcgc tggagcacga ggaaggggcg tgcttctcgc ccgcggggtc   1020
ggcgccccgc cgtcggacg gcgtcgtccc gtccttgtgt tgaggggaga agacgacgac   1080
gaccccggca gacggctgct taactttgcc agctctgtcg accctgaacc ttttttttttt   1140
ccctccccca ccttctctct tttgatcgag gggttgccag ctctggatct gaaactctga   1200
acgcatggga cgcgagctgt gtgtagcatg aataactgcg tagtttgttg gatggacgaa   1260
ctcaatcgcg ctcgcatgga atggaactct tgtaatccac cctttgtaca ttaccatcta   1320
gagttgctcc ttttttccat gagcc                                        1345

SEQ ID NO: 38          moltype = AA  length = 339
FEATURE                Location/Qualifiers
REGION                 1..339
                       note = misc_feature - Ceres CLONE ID no.1559496
REGION                 1..339
                       note = misc_feature - Bit score of 612.0 for hmm based on
                         sequences of FIGURE 2.
REGION                 261..305
                       note = misc_feature - Pfam Name: CCT Pfam Description: CCT
                         motif
REGION                 70..112
                       note = misc_feature - Pfam Name: zf-B_box Pfam Description:
                         B-box zinc finger
REGION                 1..339
                       note = misc_feature - Functional Homolog Of Ceres SEEDLINE
                         ID no. ME04315 at SEQ ID NO. 20
```

```
source                          1..339
                                mol_type = protein
                                organism = Zea mays
SEQUENCE: 38
MDTAAELELG LELEQKPAAG YWSVVGARPC DACAAEPARL HCRADGAFLC PGCDARAHGA    60
GSRHARVWLC EVCEHAPAVV TCRADAAALC AACDADIHSA NPLARRHERL PIAPLFGALA   120
DAPQPFPSPA LAAAAGAEAP APTPAQGEAV AEDYGSSEAE AASWLLPEPD NSHEDSAADT   180
FFAESDAYLG ADLDFARCMD GVKAIGVPVA PPELDIGAGS FCYPEHSMNH ILSSSSEVAV   240
VPDAQAAGLP VVVVVSRGEE REARLMRYRE KRKNRRFDKT IRYASRKAYA ETRPRIKGRF   300
AKRRSAEGED EALEHEEGAC FSPAGSAPAA SDGVVPSLC                          339

SEQ ID NO: 39                   moltype = DNA   length = 1490
FEATURE                         Location/Qualifiers
misc_feature                    1..1490
                                note = Ceres CLONE ID no.1674443
misc_feature                    1..1490
                                note = Encodes the peptide sequence at SEQ ID NO 40
source                          1..1490
                                mol_type = other DNA
                                organism = Zea mays
SEQUENCE: 39
gctgcgctgc ctccctccac tactacgcca gccactctgc cttccctccc ccaccaccac    60
aagaaccgct tcaccattgc cgcgccgcgt ccagctgagc ctcctcttag ccgcgccagc   120
caggagaagg cgcgcgcgca cacctgctgc ttggtgaccg cgttcgatgg agctgcacaa   180
gtactggggc gtgggggggcc ggcggtgcgg cagctgcgag ggggcccggg cggcggtgca   240
ctgccgcacg tgcgttggtg gatccttcct ctgcacgacg tgcgacgcgc gccccgcacg   300
cgcgcgcctg ggccacgagc gcgtgtggat gtgcgaggtc tgcgagctgg ccccccgccg   360
cgtcacgtgc aaggccgacg ccgccgtgct ctgcgccgct tgcgactccg acatcccacga   420
cgccaacccg ctggccccggc gccacgcgcg ggtccccgtc gcccccatcg ctccgaggcc   480
cgccgcgcg gccgtggagg ccatgctgtt cgggaccggc gaggcggcca cttccgatgga   540
cgacgagcag cacgcggcgg ccgagcacgc gcacgcgcac gcgctgaacc tcaacgtgga   600
ggccaaggac atgaagctgg actacctctt ctctgaactg gatccctacc tcagcgtcga   660
gatcccgcgc ttccagcacg ctgacagcgt cgtcccaaac ggcgccggcg ctgccgtcga   720
gctggactc acgtgcggca tcggcgttaa gcactcctcc tacagctcct acacggccac    780
ctccctcgct catagcggct cctcgtcgga ggttggcgtg gtgcagagg ccttcggcgg    840
cagcggcagc ggcggcggga gctttgagct cgacttcaca aggcccaagc tcaggccta    900
catgccatac accgggactc cccagagcca cagcgtgcca tccgcggacg tggaggtggt    960
gccggagcgg ggagacttgg ctgcggtgag gccggtgccg ctgatggggg agagcaggga  1020
ggcgcgccgtg atgcggtacc gtgagaaaag gaagaaccgg cgcttcgaga agaccatccg  1080
gtacgcgtcc cggaaggcct acgccgagac gcggccgcga atcaagggcc ggtttgccaa  1140
gcgtgctgac cacgacgggg acgccgacgc cgacgcggct gaggccgagg ccgaggccga  1200
ggccgccgtg ccgatgtcat atgtgctcga cttcggctac ggcgtcgtac cgagcttttg  1260
atgtgcccgg gcccaacacg cgcgcacatg gccggccggg ccttgaacc ggcatggcac  1320
gccgctgcgc gcgcgcccttg tacttgtatc gatcgatgta tagggaggag tagtaatccc  1380
atgtactctc tttttgagca agtcttgcg taaactagtg atgtataatt tgtactacta  1440
gtaagaaact gcagtagccg ctgctaatgg atcaccaatc tataccgcgc              1490

SEQ ID NO: 40                   moltype = AA   length = 364
FEATURE                         Location/Qualifiers
REGION                          1..364
                                note = misc_feature - Ceres CLONE ID no.1674443
REGION                          1..364
                                note = misc_feature - Bit score of 815.7 for hmm based on
                                 sequences of FIGURE 2.
REGION                          284..328
                                note = misc_feature - Pfam Name: CCT Pfam Description: CCT
                                 motif
REGION                          51..98
                                note = misc_feature - Pfam Name: zf-B_box Pfam Description:
                                 B-box zinc finger
REGION                          1..364
                                note = misc_feature - Functional Homolog Of Ceres SEEDLINE
                                 ID no. ME04315 at SEQ ID NO: 20
source                          1..364
                                mol_type = protein
                                organism = Zea mays
SEQUENCE: 40
MELHKYWGVG GRRCGSCEGA PAAVHCRTCV GGSFLCTTCD ARPAHARLGH ERVWMCEVCE    60
LAPAAVTCKA DAAVLCAACD SDIHDANPLA RRHARVPVAP IGSEAAAAAV EAMLFGTGEA   120
AASEADEQHA AAEHAHAHAL NLNVEAKDMK LDYLFSELDP YLSVEIPRFQ HADSVVPNGA   180
GAAVELDFTC GIGVKHSSYS SYTATSLAHS GSSSEVGVVP EAFGGSGSGG GSFELDFTRP   240
KPQAYMPYTG TPQSHSVPSA DVEVVPERGD LAAVRPVPLM GESREARLMR YREKRKNRRF   300
EKTIRYASRK AYAETRPRIK GRFAKRADHD GDADADDEAE AEAEAAVPM SYVLDFGYGV   360
VPSF                                                                 364

SEQ ID NO: 41                   moltype = DNA   length = 1449
FEATURE                         Location/Qualifiers
misc_feature                    1..1449
                                note = Ceres CLONE ID no.1828897
```

|     |     |     |
| --- | --- | --- |
| misc_feature | 1..1449 | |
| | note = Encodes the peptide sequence at SEQ ID NO 42 | |
| source | 1..1449 | |
| | mol_type = other DNA | |
| | organism = Panicum virgatum | |

SEQUENCE: 41

```
gcgcgcgctc cctccctcc cctcctccca ccagcccacc accaccacaa gcaccgcgtc    60
gtccacacca cctgccattg ccgcgccgag ctcagcctct agctgcgcca ggagggcgcc   120
cgcctccctc cctgccgacg ccggtgtgat ggagctgcac aagtactggg gcgtggggggg  180
ccgccggtgc ggcggctgcg aggcggcccc ggcggcggtg cactgccgct cgtgccccgc   240
cggggggcgcg ttcctctgca cggcgtgcga cgccgcgccg gggcacgcgc atctgggcca   300
cgagcgcgtg tggatgtgcg aggtctgcga gctggcgccc ccgccgtca cgtgcaaggc    360
cgacgccgcc gtgctctgcg ccgcctgcga cgccgacatc cacgacgcca acccgctggc   420
gcgccgccac gcacgcgtcc ccgtcgccgc catcggctcg gaggccgcgg ccgccgccgt   480
ggaggccatg ctgttcggga ccggcgagcc ggccgcgtcc gaggccgagg agccgcagaa   540
cgcggcggcc gggcacaacc accagcacgc gctgaacctc aacgtggagg ccaaggacat   600
gaagctggac tacctctttt ccgacctgga ccccctacctc agcgtcgata tcccgcgctt   660
ccagcacgcc gacagcgtcg tcccagcgg cgtcggcgcc ggagcagccg cgccgtcga    720
gctggacttc acgtgcggca tcggcgtcga gccctccggg ggggggggg gggggggggac   780
atccctcgcc cacagcggct cctcttctga ggtcggcgtg gtgccagagg ccttctgcgg   840
cgggggggg agcttcgagc tcgacttcac aaggcccaag cctcaagcct acatgccgta    900
caccgcgact cctcagagtc acagcgtgtc gtcggtggac gtggaggtgg tgccggacgg   960
gggggacatg atggcggcgg cgaggccggt gccgctggtg ggggagagcc gggaggcgcg  1020
gctgatgcgc taccgggaga gcggaaggaa ccggcggttc gagaagacca tccggtacgc  1080
gtcccggaag gcctacgccg agatgcggcc gcggatcaag ggccggttcg ccaagcgcgc  1140
cgaccacgac gccgacgccg acgacgccga ggaggccgcc tgccgtgcca               1200
ggcgtcgtac gtgctcgact cggctacgg cgtcgtgccc agcttctgat cgacgacgat   1260
cgtctcgctc gttccacgcg cggcgcgctt gacccggcac cggcgcgcgc gccttgtact  1320
tgtatcgatg catgtatagg ggaggaatag taatcccatg tactctcgtc ttggagctgc   1380
gctagccctg cgtacgtacg ctagtgatgt ataatttgta caacccagta ttttgccctg  1440
tacccgctc                                                           1449
```

|     |     |     |
| --- | --- | --- |
| SEQ ID NO: 42 | moltype = AA  length = 366 | |
| FEATURE | Location/Qualifiers | |
| REGION | 1..366 | |
| | note = misc_feature - Ceres CLONE ID no.1828897 | |
| REGION | 1..366 | |
| | note = misc_feature - Bit score of 667.9 for hmm based on sequences of FIGURE 2. | |
| REGION | 288..332 | |
| | note = misc_feature - Pfam Name: CCT Pfam Description: CCT motif | |
| REGION | 52..99 | |
| | note = misc_feature - Pfam Name: zf-B_box Pfam Description: B-box zinc finger | |
| REGION | 1..366 | |
| | note = misc_feature - Functional Homolog Of Ceres SEEDLINE ID no. ME04315 at SEQ ID NO. 20 | |
| source | 1..366 | |
| | mol_type = protein | |
| | organism = Panicum virgatum | |

SEQUENCE: 42

```
MELHKYWGVG GRRCGGCEAA PAAVHCRSCP AGGAFLCTAC DARPGHAHLG HERVWMCEVC    60
ELAPAAVTCK ADAAVLCAAC DADIHDANPL ARRHARVPVA PIGSEAAAAA VEAMLFGTGE   120
PAASEAEEPQ NAAAGHNHQH ALNLNVEAKD MKLDYLFSDL DPYLSVDIPR FQHADSVVPS   180
GVGAGAAGAV ELDFTCGIGV EPSGGGGGGG TSLAHSGSSS EVGVVPEAFC GGGGSFELDF   240
TRPKPQAYMP YTATPQSHSV SSVDVEVVPE RGDMMAAARP VPLVGESREA RLMRYREKRK   300
NRRFEKTIRY ASRKAYAEMR PRIKGRFAKR ADHDADADDA EAEAEAAVPS PASYVLDFGY   360
GVVPSF                                                              366
```

|     |     |     |
| --- | --- | --- |
| SEQ ID NO: 43 | moltype = AA  length = 332 | |
| FEATURE | Location/Qualifiers | |
| REGION | 1..332 | |
| | note = misc_feature - Public GI ID no.125540249 | |
| REGION | 1..332 | |
| | note = misc_feature - Bit score of 624.0 for hmm based on sequences of FIGURE 2. | |
| REGION | 261..305 | |
| | note = misc_feature - Pfam Name: CCT Pfam Description: CCT motif | |
| REGION | 72..114 | |
| | note = misc_feature - Pfam Name: zf-B_box Pfam Description: B-box zinc finger | |
| REGION | 1..332 | |
| | note = misc_feature - Functional Homolog Of Ceres SEEDLINE ID no. ME04315 at SEQ ID NO. 20 | |
| source | 1..332 | |
| | mol_type = protein | |
| | note = subspecies = indica | |

```
                        organism = Oryza sativa
SEQUENCE: 43
MEAVEDKAMV  GVGGAVAAGY  SSSSWGLGTR  ACDSCGGEAA  RLYCRADGAF  LCARCDARAH    60
GAGSRHARVW  LCEVCEHAPA  AVTCRADAAA  LCAACDADIH  SANPLARRHE  RLPVAPFFGP   120
LADAPQPFTF  SQAAADAAGA  REEDADDDRS  NEAEAASWLL  PEPDDNSHED  SAAAADAFFA   180
DTGAYLGVDL  DFARSMDGIK  AIGVPVAPPE  LDLTAGSLFY  PEHSMAHSLS  SSEVAIVPDA   240
LSAGAAAPPM  VVVVASKGKE  REARLMRYRE  KRKNRRFDKT  IRYASRKAYA  ETRPRIKGRF   300
AKRTADADDD  DEAPCSPAFS  ALAASDGVVP  SF                                  332

SEQ ID NO: 44           moltype = AA   length = 331
FEATURE                 Location/Qualifiers
REGION                  1..331
                        note = misc_feature - Public GI ID no.116310719
REGION                  1..331
                        note = misc_feature - Bit score of 733.5 for hmm based on
                          sequences of FIGURE 2.
REGION                  239..283
                        note = misc_feature - Pfam Name: CCT Pfam Description: CCT
                          motif
REGION                  62..104
                        note = misc_feature - Pfam Name: zf-B_box Pfam Description:
                          B-box zinc finger
REGION                  1..331
                        note = misc_feature - Functional Homolog Of Ceres SEEDLINE
                          ID no. ME04315 at SEQ ID NO. 20
source                  1..331
                        mol_type = protein
                        note = subspecies = indica
                        organism = Oryza sativa
SEQUENCE: 44
MEGDDKSAVV  GGAYWGLAAR  ACDACGGEAA  RLFCRADAAF  LCAGCDARAH  GPGSRHARVW    60
LCEVCEHAPA  AVTCRADAAA  LCAACDADIH  SANPLARRHE  RLPVAPFFGA  LADAPKPGSG   120
AHGGDAAAAD  DDGSNDAEAA  SWLLPEPDHG  QKDGAVGATD  ELYADSDPYL  DLDFARSMDD   180
IKAIGVQNGP  PELDITGGKL  FYSDHSMNHS  VSSSEAAVVP  DAAAGGGAPM  PVVSRGRERE   240
ARLMRYREKR  KSRRFEKTIR  YASRKAYAET  RPRIKGRFAK  RTKGGAGADA  DADADGEDEE   300
MYSSAAAAVA  ALMAPGGSDA  DYGVDGVVPT  F                                   331

SEQ ID NO: 45           moltype = AA   length = 370
FEATURE                 Location/Qualifiers
REGION                  1..370
                        note = misc_feature - Public GI ID no.125556324
REGION                  1..370
                        note = misc_feature - Bit score of 608.3 for hmm based on
                          sequences of FIGURE 2.
REGION                  294..338
                        note = misc_feature - Pfam Name: CCT Pfam Description: CCT
                          motif
REGION                  50..97
                        note = misc_feature - Pfam Name: zf-B_box Pfam Description:
                          B-box zinc finger
REGION                  1..370
                        note = misc_feature - Functional Homolog Of Ceres SEEDLINE
                          ID no. ME04315 at SEQ ID NO. 20
source                  1..370
                        mol_type = protein
                        note = subspecies = indica
                        organism = Oryza sativa
SEQUENCE: 45
MELRKYWGVG  GRRCGACEAS  PAAVHCRGCG  GVYLCTACDA  RPGHARAAHE  RVWVCEVCEV    60
APAAVTCKAD  AAVLCAACDA  DIHDANPLAR  RHARVPVAPI  GSAAAAAVAA  EAMLFGVAAA   120
GAEAEAVEEK  AAAEHHHHQQ  RQQHGALNLN  VEAKDMKLDY  LFSDLDPYLN  VEFARFPHAD   180
SVVPNGAGAG  AAIELDFTCG  LGVGVGGAKQ  SYSSYTATDL  AHSGSSSEVG  VVPEAMCGGG   240
GAIDLDFTRP  KPQPYMPYTA  TPPPSHSVVS  AQMSSSVVDV  GVVPERAAAM  GEGREARLMR   300
YREKRKNRRF  EKTIRYASRK  AYAETRPRIK  GRFAKRADHD  ADDADADADD  PAAVPSSYML   360
DFGYGVVPSF                                                              370

SEQ ID NO: 46           moltype = AA   length = 347
FEATURE                 Location/Qualifiers
REGION                  1..347
                        note = misc_feature - Public GI ID no.125538317
REGION                  1..347
                        note = misc_feature - Bit score of 444.3 for hmm based on
                          sequences of FIGURE 2.
REGION                  279..323
                        note = misc_feature - Pfam Name: CCT Pfam Description: CCT
                          motif
REGION                  55..102
                        note = misc_feature - Pfam Name: zf-B_box Pfam Description:
                          B-box zinc finger
```

| | | |
|---|---|---|
| REGION | 1..347 | |
| | note = misc_feature - Functional Homolog Of Ceres SEEDLINE ID no. ME04315 at SEQ ID NO. 20 | |
| source | 1..347 | |
| | mol_type = protein | |
| | note = subspecies = indica | |
| | organism = Oryza sativa | |

SEQUENCE: 46
```
MELGLGRYWG VGGRRCGACA VAPAAVHCRT CDGGGGGGGY LCAGCDAEHG RAGHERVWVC    60
EVCELAPAAV TCKADAAALC AACDSDIHDA NPLARRHERV PGHPIGSSAA PPPDALLLGG   120
ENDAAAAVDG GGGGKEVKLD FLFADFMDPY LGGSPELARF PHADSVVPNH NGSAGPAMEL   180
GFAGGGGAAV KPSYSSYTAA SLGNSGSSSE VGLVPDAICG GGGGIIELD FAQSKAAYLP    240
YASTPSHSMS SSMDMGVAAP EMSDGAAAAA GRAYAAEGRA ARLMRYREKR KNRRFEKTIR   300
YASRKAYAET RPRVKGRFAK RADDHDAAAP PPQIMLDFAG YGVVPTF                347
```

| | | |
|---|---|---|
| SEQ ID NO: 47 | moltype = AA  length = 332 | |
| FEATURE | Location/Qualifiers | |
| REGION | 1..332 | |
| | note = misc_feature - Public GI ID no.115447239 | |
| REGION | 1..332 | |
| | note = misc_feature - Bit score of 623.8 for hmm based on sequences of FIGURE 2. | |
| REGION | 261..305 | |
| | note = misc_feature - Pfam Name: CCT Pfam Description: CCT motif | |
| REGION | 72..114 | |
| | note = misc_feature - Pfam Name: zf-B_box Pfam Description: B-box zinc finger | |
| REGION | 1..332 | |
| | note = misc_feature - Functional Homolog Of Ceres SEEDLINE ID no. ME04315 at SEQ ID NO. 20 | |
| source | 1..332 | |
| | mol_type = protein | |
| | note = subspecies = japonica | |
| | organism = Oryza sativa | |

SEQUENCE: 47
```
MEAVEDKAMV GVGGAVAAGY SSSSWGLGTR ACDSCGGEAA RLYCRADGAF LCARCDARAH    60
GAGSRHARVW LCEVCEHAPA AVTCRADAAA LCAACDADIH SANPLARRHE RLPVAPFFGP   120
LADAPQPFPF SQAAADAAAA REEDADDDRS NEAEAASWLL PEPDDNSHED SAAAADAFFA   180
DTGAYLGVDL DFARSMDGIK AIGVPVAPPE LDLTAGSLFY PEHSMAHSLS SSEVAIVPDA   240
LSAGSAAPPM VVVVASKGKE REARLMRYRE KRKNRRFDKT IRYASRKAYA ETRPRIKGRF   300
AKRTADADDD DEAPCSPAFS ALAASDGVVP SF                                332
```

| | | |
|---|---|---|
| SEQ ID NO: 48 | moltype = AA  length = 333 | |
| FEATURE | Location/Qualifiers | |
| REGION | 1..333 | |
| | note = misc_feature - Public GI ID no.115459216 | |
| REGION | 1..333 | |
| | note = misc_feature - Bit score of 726.7 for hmm based on sequences of FIGURE 2. | |
| REGION | 239..283 | |
| | note = misc_feature - Pfam Name: CCT Pfam Description: CCT motif | |
| REGION | 62..104 | |
| | note = misc_feature - Pfam Name: zf-B_box Pfam Description: B-box zinc finger | |
| REGION | 1..333 | |
| | note = misc_feature - Functional Homolog Of Ceres SEEDLINE ID no. ME04315 at SEQ ID NO. 20 | |
| source | 1..333 | |
| | mol_type = protein | |
| | note = subspecies = japonica | |
| | organism = Oryza sativa | |

SEQUENCE: 48
```
MEGDDKSAVV GGAYWGLAAR ACDACGGEAA RLFCRADAAF LCAGCDARAH GPGSRHARVW    60
LCEVCEHAPA AVTCRADAAA LCAACDADIH SANPLARRHE RLPVAPFFGA LADAPKPGSG   120
AHGGDAAAAD DDGSNDAEAA SWLLPEPDHG QKDGAVGATD ELYADSDPYL DLDFARSMDD   180
IKAIGVQNGP PELDITGGKL FYSDHSMNHS VSSSEAAVVP DAAAGGGAPM PVVSRGRERE   240
ARLMRYREKR KSRRFEKTIR YASRKAYAET RPRIKGRFAK RTKGGAGADA DADADADGED   300
EEMYSSAAAA VAALMAPGGS DADYGVDGVV PTF                                333
```

| | | |
|---|---|---|
| SEQ ID NO: 49 | moltype = AA  length = 370 | |
| FEATURE | Location/Qualifiers | |
| REGION | 1..370 | |
| | note = misc_feature - Public GI ID no.115469296 | |
| REGION | 1..370 | |
| | note = misc_feature - Bit score of 607.4 for hmm based on sequences of FIGURE 2. | |
| REGION | 294..338 | |

```
                         note = misc_feature - Pfam Name: CCT Pfam Description: CCT
                            motif
REGION                   50..97
                         note = misc_feature - Pfam Name: zf-B_box Pfam Description:
                            B-box zinc finger
REGION                   1..370
                         note = misc_feature - Functional Homolog Of Ceres SEEDLINE
                            ID no. ME04315 at SEQ ID NO. 20
source                   1..370
                         mol_type = protein
                         note = subspecies = japonica
                         organism = Oryza sativa
SEQUENCE: 49
MELRKYWGVG GRRCGACEAS PAAVHCRGCG GVYLCTACDA RPGHARAAHE RVWVCEVCEV    60
APAAVTCKAD AAVLCAACDA DIHDANPLAR RHARVPVAPI GSAAAAAVAA EAMLFGVAAA   120
GAEAEAVEDK AAAEHHHHQQ RQQHGALNLN VEAKDMKLDY LFSDLDPYLN VEFARFPHAD   180
SVVPNGAGAG AAIELDFTCG LGVGVGGAKQ SYSSYTATDL AHSGSSSEVG VVPEAMCGGG   240
GAIDLDFTRP KPQPYMPYTA TPPPSHSVVS AQMSSSVVDV GVVPERAAAM GEGREARLMR   300
YREKRKNRRF EKTIRYASRK AYAETRPRIK GRFAKRADHD ADDADADADD PAAVPSSYML   360
DFGYGVVPSF                                                         370

SEQ ID NO: 50            moltype = AA  length = 332
FEATURE                  Location/Qualifiers
REGION                   1..332
                         note = misc_feature - Public GI ID no.125582846
REGION                   1..332
                         note = misc_feature - Bit score of 505.9 for hmm based on
                            sequences of FIGURE 2.
REGION                   261..305
                         note = misc_feature - Pfam Name: CCT Pfam Description: CCT
                            motif
REGION                   27..71
                         note = misc_feature - Pfam Name: zf-B_box Pfam Description:
                            B-box zinc finger
REGION                   1..332
                         note = misc_feature - Functional Homolog Of Ceres SEEDLINE
                            ID no. ME04315 at SEQ ID NO. 20
source                   1..332
                         mol_type = protein
                         note = subspecies = japonica
                         organism = Oryza sativa
SEQUENCE: 50
MEAVEDKAMV GVGGAVAAGY SSSSWGLGTR ACDSCGGEAA RLYCRADGAF LCARCDARAH    60
GAGSRHARVW LCEVCEHAPA RRHVPGGRRG AVRRLRRRHH SANPLARRHE RLPVAPFFGP   120
LADAPQPFPF SQAAADAAAA REEDADDDRS NEAEAASWLL PEPDDNSHED SAAAADAFFA   180
DTGAYLGVDL DFARSMDGIK AIGVPVAPPE LDLTAGSLFY PEHSMAHSLS SSEVAIVPDA   240
LSAGSAAPPM VVVVASKGKE REARLMRYRE KRKNRRFDKT IRYASRKAYA ETRPRIKGRF   300
AKRTADADDD DEAPCSPAFS ALAASDGVVP SF                                332

SEQ ID NO: 51            moltype = AA  length = 375
FEATURE                  Location/Qualifiers
REGION                   1..375
                         note = misc_feature - Public GI ID no.92875402
REGION                   1..375
                         note = misc_feature - Bit score of 812.8 for hmm based on
                            sequences of FIGURE 2.
REGION                   298..342
                         note = misc_feature - Pfam Name: CCT Pfam Description: CCT
                            motif
REGION                   60..107
                         note = misc_feature - Pfam Name: zf-B_box Pfam Description:
                            B-box zinc finger
REGION                   1..375
                         note = misc_feature - Functional Homolog Of Ceres SEEDLINE
                            ID no. ME04315 at SEQ ID NO. 20
source                   1..375
                         mol_type = protein
                         organism = Medicago truncatula
SEQUENCE: 51
MGIERGGLKS LRGGWSVPPK LCDSCKLTPA ALFCRSDSAF LCINCDSTIH SANKLSSRHE    60
RVWMCEVCEQ APASVTCKAD AAALCVTCDS DIHSANPLAR RHERVPVPEF FDSAESVVKS   120
SSAAAAAAAS FNFVVPTDDG YGQDDAEAAA WLIPNPNFGS KLNETQDIKT REMFFSDMDP   180
FLDFDYSNNF QNNNCSNAMN DSVVPVQTKP TPAPMMNHNS EGCFDIDFCR SKLSSFNYPS   240
HSISHSVSSS SLDVGVVPDG NTVSEISYNF GSESMVSGGV NSSNQGVQGA TQLCGMDREA   300
RVMRYREKRK NRKFEKTIRY ASRKAYAETR PRIKGRFAKR TEIDSDVDRL YNPADPLSVP   360
SSMLMDCPYG VVPTF                                                   375

SEQ ID NO: 52            moltype = AA  length = 307
FEATURE                  Location/Qualifiers
```

```
REGION                  1..307
                        note = misc_feature - Public GI ID no.3341723
REGION                  1..307
                        note = misc_feature - Bit score of 395.2 for hmm based on
                          sequences of FIGURE 2.
REGION                  1..48
                        note = misc_feature - Pfam Name: zf-B_box Pfam Description:
                          B-box zinc finger
REGION                  241..285
                        note = misc_feature - Pfam Name: CCT Pfam Description: CCT
                          motif
REGION                  1..307
                        note = misc_feature - Functional Homolog Of Ceres SEEDLINE
                          ID no. ME04315 at SEQ ID NO. 20
source                  1..307
                        mol_type = protein
                        organism = Raphanus sativus
SEQUENCE: 52
MASRLCDSCR  SAAATLYCRA  DAAFLCGECD  GKIHTANKLA  SRHERVLLCQ  ICEQAPAHVT    60
CEADAAALCV  TCDRDIHSAN  PLSRRHERVS  VTPFYDAPAQ  GGSPATTKSA  ASSNLFGEDA   120
DVSMEAVSWL  LPNPSVKEGV  VVEIPNLFAD  LDYSAVDPKM  EASENSSGND  GVVPVQTKAL   180
FLNEDYFNFD  VSASKTTFPH  GYSCINQTVS  STSLEVPLVP  EGGAVTTTNA  TPAVQLSPAE   240
REARVLRYRE  KRKNRKFEKT  IRYASRKAYA  EVRPRIKGRF  AKRTDSRVND  GGGDVGVYGG   300
FGVVPSF                                                                 307

SEQ ID NO: 53           moltype = AA  length = 329
FEATURE                 Location/Qualifiers
REGION                  1..329
                        note = misc_feature - Public GI ID no.4091806
REGION                  1..329
                        note = misc_feature - Bit score of 506.4 for hmm based on
                          sequences of FIGURE 2.
REGION                  1..48
                        note = misc_feature - Pfam Name: zf-B_box Pfam Description:
                          B-box zinc finger
REGION                  268..312
                        note = misc_feature - Pfam Name: CCT Pfam Description: CCT
                          motif
REGION                  1..329
                        note = misc_feature - Functional Homolog Of Ceres SEEDLINE
                          ID no. ME04315 at SEQ ID NO. 20
source                  1..329
                        mol_type = protein
                        organism = Malus x domestica
SEQUENCE: 53
MASKLCDSCQ  SATATLFCRA  DSAFLCVNCD  SKIHAANKLA  SRHPRVWLCE  VCEQAPAHVT    60
CKADDAALCV  TCDRDIHSAN  PLSSRHDRVP  VTPFYDSVNS  AANSVPVVKS  VVNFLDDRYL   120
SDVDGETEVS  REEEAASWL   LPNPKAMENP  DLNSGQYLFQ  EMDPYLDLDY  GHVDPKLEEA   180
QEQNSCGADG  VVPVQSKNMQ  PLLVNDQSFE  LDFSAGSKPF  VYGYHHARCL  SQSVSSSSMD   240
ISVVPDGNAV  TAAVETSQPA  VQLSSVDRVA  RVLRYREKRK  NRKFEKTIRY  ASRKAYAETR   300
PRIKGRFAKR  TEVEIEAERM  CRYGVVPSF                                       329

SEQ ID NO: 54           moltype = AA  length = 312
FEATURE                 Location/Qualifiers
REGION                  1..312
                        note = misc_feature - Public GI ID no.60459257
REGION                  1..312
                        note = misc_feature - Bit score of 400.3 for hmm based on
                          sequences of FIGURE 2.
REGION                  1..48
                        note = misc_feature - Pfam Name: zf-B_box Pfam Description:
                          B-box zinc finger
REGION                  245..289
                        note = misc_feature - Pfam Name: CCT Pfam Description: CCT
                          motif
REGION                  1..312
                        note = misc_feature - Functional Homolog Of Ceres SEEDLINE
                          ID no. ME04315 at SEQ ID NO. 20
source                  1..312
                        mol_type = protein
                        organism = Pisum sativum
SEQUENCE: 54
MATKLCDSCK  STKATLFCRS  DSAFLCITCD  SNIQAANKLA  SRHHRVTLCE  VCEQAPAHVT    60
CKADAAALCV  SCDHDIHSAN  PPASRHERIP  LNTFHHNSKQ  QFFSESDPDA  DVSTEEAEAA   120
SWLLQTPANP  KGPDLNSSHY  SFTEIDATDL  NFVCVDAKTD  SPEQHSPGTA  DGVVPVQSHS   180
KTVTEHYSDI  NNDFSTSKPF  TYNYNHSVSS  SSLEVGVVPD  GNVMSEMSYC  GYGRTEAVQI   240
TAADREARVM  RYREKRKNRR  FEKTIRYASR  KAYAETRPRI  KGRFAKRTDL  NMNVNLIGED   300
ESYDGYGVVP  SC                                                          312
```

```
SEQ ID NO: 55          moltype = DNA  length = 1283
FEATURE                Location/Qualifiers
misc_feature           1..1283
                       note = Ceres CLONE ID no.1756710
misc_feature           1..1283
                       note = Encodes the peptide sequence at SEQ ID NO 56
source                 1..1283
                       mol_type = other DNA
                       organism = Panicum virgatum
SEQUENCE: 55
agcagccact acaagctgcc gtgccgagtg agctagtgag cgagcgagct cccggcgcgc    60
gatggagggt gacaagaagt cggcgggcgg ggccccggcc tactgggccc tgggcgcgcg   120
gccctgcgac gagtgcggcg ccgaggcgga gcggctctac tgccgcgcgg acgcggcgtt   180
cctctgcgcc gggtgcgacg cgcgcgcgca cggcgcgtcg tcgccacg cccgcgtctg     240
gctgtgcgag gtctgcgagc acgcgccggc cgccgtcacg tgccgcgcgg acgccgccgc   300
gctctgcgcc tcctgcgacg ccgacatcca ctccgccaac ccgctcgcgc gccgccacga   360
gcgccagacc gtggcgccct tctacggcgc gctcgccgac gcgcccaagc ccttcgcctc   420
gtcggtggcc gtgcccaaag cggccgacga cgacggaagc aacgaggccg aggcggcgtc   480
gtggctcctc cccgagcccg accacggcca caaggaaggc gccacgacgg aggtgttctt   540
cgcggactcc gacccgtacc tcgacctcga ctttgcgcgc accatggacg acatcaaggc   600
catcggcgcc cagaacggcc ccgccggcgc cgagctcgac ctcaccggcg ccaagctctt   660
ctactccgac cactccatga actacagcgt gtcgtcgtcg gaggcagcgg tggtgcccga   720
cgccgccgcg ggcgcggcgc ccgtcgtgcc tgtggtgagc aggggcctgg agcgggaggc   780
ccggctgatg cggtaccggg agaagcgcaa gagccggcgg ttcgagaaga cgatccggta   840
ccgcgtcccg aaggcgtacg cggagacgcg ccgcgcatc aagggccggt tcgccaagcg    900
cacccccggg cccggcgcgg acggggagga cccgctggag gacgcaggag aggagatgta   960
ctcctccgcc gcggccgccg tggccgcgct catggccccc ggcggcgccg acgccgacta  1020
cggcgtcgtg cccacgtatt gatcggcgcg ggcctgctgt acactagcta gcctcgacct  1080
ctcggggctg taatttttgc tgcatgcctt gcatgcaaaa agctgccgtg tagcattgat  1140
tacctgtaat atgattccac ggaagccatg aggcggact tccaagctct tcttcctccc   1200
taatgattcc gtcatgtacg gatgtatatt attattattt atcacgaact gctgctaatc  1260
tgcaactgta atttctaatt agc                                          1283

SEQ ID NO: 56          moltype = AA  length = 326
FEATURE                Location/Qualifiers
REGION                 1..326
                       note = misc_feature - Ceres CLONE ID no.1756710
REGION                 1..326
                       note = misc_feature - Bit score of 628.3 for hmm based on
                        sequences of FIGURE 2.
REGION                 238..282
                       note = misc_feature - Pfam Name: CCT Pfam Description: CCT
                        motif
REGION                 62..104
                       note = misc_feature - Pfam Name: zf-B_box Pfam Description:
                        B-box zinc finger
REGION                 1..326
                       note = misc_feature - Functional Homolog Of Ceres SEEDLINE
                        ID no. ME04315 at SEQ ID NO. 20
source                 1..326
                       mol_type = protein
                       organism = Panicum virgatum
SEQUENCE: 56
MEGDKKSAGG APAYWGLGAR PCDECGAEAA RLYCRADAAF LCAGCDARAH GAGSRHARVW    60
LCEVCEHAPA AVTCRADAAA LCASCDADIH SANPLARRHE RQTVAPFYGA LADAPKPFAS   120
SVAVPKAADD DGSNEAEAAS WLLPEPDHGH KEGATTEVFF ADSDPYLDLD FARTMDDIKA   180
IGAQNGPAGA ELDLTGAKLF YSDHSMNYSV SSEEAAVVPD AAAGAAPVVP VVSRGLEREA   240
RLMRYREKRK SRRFEKTIRY ASRKAYAETR PRIKGRFAKR TPGPGADGED PLEEHEEEMY   300
SSAAAAVAAL MAPGGADADY GVVPTY                                       326

SEQ ID NO: 57          moltype = DNA  length = 1398
FEATURE                Location/Qualifiers
misc_feature           1..1398
                       note = Ceres CLONE ID no.907473
misc_feature           1..1398
                       note = Encodes the peptide sequence at SEQ ID NO 58
source                 1..1398
                       mol_type = other DNA
                       organism = Triticum aestivum
SEQUENCE: 57
gtttttaact cgacttagcc aagtttggca acgaacagg ccccgtggcc ccgccccgc      60
gcgacagcga ccgggcgccc gaagtgtctc gcgctcgccc acggcacccg agcggagccc   120
ccgcccctac catgtgctct ccctgccgc agacccctca aaccaccc gcgccgcac       180
ccaggcaccg agcaccagc agaaagaaac gcaccaaatc tttatccct gccctcagca    240
gtgccgacct gagcgccgga gatctgcggc gagcgagatg aaagtggagg agcagacggt   300
ggtgggagga ggaggagggg ggctctgggg gctggccggg cggccgtgcg acacgacgcg   360
cgtggacgcg gcgcggctct actgccggtc ggacggcgcc tacctctgcg ccgggtgcga   420
cgcgcgcgct cacggggccg gctccgccga ccgcgccgtc tggctctgcg aggtctgcga   480
gcacgcgccc gccgcggtca cctgccgcgc cgacgccgcc gcgctctgcg ccacgtgcga   540
```

-continued

```
cgccgacatc cactccgcca acccgctcgc cagccggcac gagcgcctcc ccgtcacgcc    600
tttcttcggc gcgctcgccg acccgcccca gcccgccccc tccccgtcct ccgccgccgc    660
gacgcaggag gacgcggacg acgacgggag caacgaggcc gaggcggcct cctggcttct    720
tcccgagcct ggcgatagcc ccgaggacag caccgctacc ttcttccctg actcggacgc    780
gtacctcgat ctggacttcg tccggtctat ggacgggatc aaggccatcg gggtgcccgt    840
cgccccttcc gagctcgacg tcgccggcgg cgctctcttc taccccgaac actccatgaa    900
ccacagcatg tcaacgtccg aggtcgcggt ggtgccggac gcgctgtcag ccggcggggc    960
cccggcgccg gcgccgtcgg tggcggtggt ggctagcaag gggaaggagc gggaggcccg   1020
gctgatgcgg taccgggaga agcgcaagaa ccggaggttc cagaagacca tccgctacgc   1080
gtcccgcaag gcgtacgccg agacgcgccc gcgcatcaag ggccggttcg ccaagcgcac   1140
cgccgaggac gacgcgctgg agcgggacgg gccgttctcg cccgcgtcgt cggcgcacct   1200
ggcgtcggac ggtgactacg gcgtcgtgcc gtccttctga ggagaccggc gacggcgacg   1260
gcgactctgc tgtagttttg gcgcgcgcat ccatccgagt gcgctcgcgt gcggtggctg   1320
cgacgcgcgc tccgtgtaac attgaataat ctgtacagtt ttgttccatg ggattagtgc   1380
cgtgaccgtg ccgacctg                                                 1398
```

```
SEQ ID NO: 58          moltype = AA   length = 320
FEATURE                Location/Qualifiers
REGION                 1..320
                       note = misc_feature - Ceres CLONE ID no.907473
REGION                 1..320
                       note = misc_feature - Bit score of 719.5 for hmm based on
                         sequences of FIGURE 2.
REGION                 245..289
                       note = misc_feature - Pfam Name: CCT Pfam Description: CCT
                         motif
REGION                 64..106
                       note = misc_feature - Pfam Name: zf-B_box Pfam Description:
                         B-box zinc finger
REGION                 1..320
                       note = misc_feature - Functional Homolog Of Ceres SEEDLINE
                         ID no. ME04315 at SEQ ID NO. 20
source                 1..320
                       mol_type = protein
                       organism = Triticum aestivum
SEQUENCE: 58
MKVEEQTVVG GGGGGLWGLA GRPCDTCAVD AARLYCRSDG AYLCAGCDAR AHGAGSRHAR    60
VWLCEVCEHA PAAVTCRADA AALCATCDAD IHSANPLASR HERLPVTPFF GALADPPQPA   120
PSPSSAAATQ EDADDDGSNE AEAASWLLPE PGDSPEDSTA TFFPDSDAYL DLDFVRSMDG   180
IKAIGVPVAP SELDVAGGAL FYPEHSMNHS MSTSEVAVVP DALSAGGAPA PAPSVAVVAS   240
KGKEREARLM RYREKRKNRR FQKTIRYASR KAYAETRPRI KGRFAKRTAE DDALERDGPF   300
SPASSAHLAS DGDYGVVPSF                                               320
```

```
SEQ ID NO: 59          moltype = AA   length = 340
FEATURE                Location/Qualifiers
REGION                 1..340
                       note = misc_feature - Public GI ID no.4091804
REGION                 1..340
                       note = misc_feature - Bit score of 486.8 for hmm based on
                         sequences of FIGURE 2.
REGION                 1..48
                       note = misc_feature - Pfam Name: zf-B_box Pfam Description:
                         B-box zinc finger
REGION                 279..323
                       note = misc_feature - Pfam Name: CCT Pfam Description: CCT
                         motif
REGION                 1..340
                       note = misc_feature - Functional Homolog Of Ceres SEEDLINE
                         ID no. ME04315 at SEQ ID NO. 20
source                 1..340
                       mol_type = protein
                       organism = Malus x domestica
SEQUENCE: 59
MALKLCDSCK SATGTLFCRA DSAFLCVNCD SKIHAANKLA SRHARVWLCE VCEQAPAHVT    60
CKADDAALCV TCDRDIHSAN PLSHADERVP VTPFYDSVNS ATDSVPAVKS AVNFLNDRYF   120
SDVDGEIEAR REEAEAASWL LPNPKAMENP DLNSGQYLFP EMDPYMDLDY GHVDPKLEDA   180
QEQNSCITDG VVPEQSKNMQ PQLVNDHSFE IDFSAASKPF VYGYHHAQCL RQSVSSSSMD   240
VSIVPDDNAM TDDSNPYNKS MTSAVESSHP AVQLSSADRE ARVLRYREKR KNRKFEKTIR   300
YASRKAYAET RPRIKGRFAK RTEVEIEAEP MCRYGIVPSF                         340
```

```
SEQ ID NO: 60          moltype = AA   length = 323
FEATURE                Location/Qualifiers
REGION                 1..323
                       note = misc_feature - Public GI ID no.21667487
REGION                 1..323
                       note = misc_feature - Bit score of 599.5 for hmm based on
                         sequences of FIGURE 2.
REGION                 236..280
                       note = misc_feature - Pfam Name: CCT Pfam Description: CCT
```

-continued

```
                                  motif
REGION                  61..103
                                  note = misc_feature - Pfam Name: zf-B_box Pfam Description:
                                     B-box zinc finger
REGION                  1..323
                                  note = misc_feature - Functional Homolog Of Ceres SEEDLINE
                                     ID no. ME04315 at SEQ ID NO. 20
source                  1..323
                                  mol_type = protein
                                  note = subspecies = vulgare
                                  organism = Hordeum vulgare
SEQUENCE: 60
MEGEEKPVVG GAYWGVGARA CDSCATEAAR LFCRADAAFL CAGCDARAHG SGSRHARVWL     60
CEVCEHAPAA VTCKADAAVL CASCDADIHA ANPLARRHER VPVAPFFGAA ADAHKPFPSS    120
GAQAGAAASA EDDGSNDAEA ASWLLPEPDH KDGANGATAD VFFADSDHYL DLDFARSMDD    180
IKAISVQLNG QPEIDLNGGN KGFYSDHSMN HSLSSSEAAV VPDAAAAPVV SRGREREARL    240
MRYREKRKSR RFEKTIRYAS RKAYAETRPR VKGRFAKRTG TADADALEEH EEMYSSAAAA    300
VAALMAPGPD HDYGVDGVVP TLV                                            323

SEQ ID NO: 61           moltype = AA   length = 325
FEATURE                 Location/Qualifiers
REGION                  1..325
                                  note = misc_feature - Public GI ID no.21655154
REGION                  1..325
                                  note = misc_feature - Bit score of 678.1 for hmm based on
                                     sequences of FIGURE 2.
REGION                  250..294
                                  note = misc_feature - Pfam Name: CCT Pfam Description: CCT
                                     motif
REGION                  70..112
                                  note = misc_feature - Pfam Name: zf-B_box Pfam Description:
                                     B-box zinc finger
REGION                  1..325
                                  note = misc_feature - Functional Homolog Of Ceres SEEDLINE
                                     ID no. ME04315 at SEQ ID NO. 20
source                  1..325
                                  mol_type = protein
                                  note = subspecies = vulgare
                                  organism = Hordeum vulgare
SEQUENCE: 61
MKVEEQTVVG GGGGAGQGGA GFWGLAGRPC DTCAVDAARL YCRLDGAYLC AGCDARAHGA     60
GSRHARVWLC EVCEHAPAAV TCRADAAALC ATCDADIHSA NPLASRHLLL PTPFFGALAD    120
PPQPVPSPSS AAATQEDAED DGSNEAEAAS WLLPEPGDSP EDSAATFFAD SDAYLDLDFV    180
RSMDGIKAIG VPVAPSELDL AGGTLFYPEH SMNHSMSTSE VAVVPDALSA GGAPAPAPSV    240
AVVASKGKER EARLMRYREK RKNRRFQKTI RYASRKAYAE TRPRIKGRFA KRTAEDDALE    300
QDGPFSPASS AHLASDGDYG VVPSF                                          325

SEQ ID NO: 62           moltype = AA   length = 391
FEATURE                 Location/Qualifiers
REGION                  1..391
                                  note = misc_feature - Public GI ID no.45544883
REGION                  1..391
                                  note = misc_feature - Bit score of 432.4 for hmm based on
                                     sequences of FIGURE 2.
REGION                  322..366
                                  note = misc_feature - Pfam Name: CCT Pfam Description: CCT
                                     motif
REGION                  52..99
                                  note = misc_feature - Pfam Name: zf-B_box Pfam Description:
                                     B-box zinc finger
REGION                  1..391
                                  note = misc_feature - Functional Homolog Of Ceres SEEDLINE
                                     ID no. ME04315 at SEQ ID NO. 20
source                  1..391
                                  mol_type = protein
                                  organism = Solanum lycopersicum
SEQUENCE: 62
MLKKENSNNW ARVCDSCHSA TCTVYCRADS AYLCAGCDAR IHTASLMASR HERVWVCEAC     60
ERAPAAFLCK ADAASLCASC DADIHSANPL ARRHHRVPIM PIPGTIYGPP AVHTITGGSM    120
MIGGTTGEGT EDDGFLSLNQ DADDTTIDEE DEDEAASWLL LNPPVKNNNK NNNYGMLFGG    180
EVVDDYLDLA EYGGDSQFND QYSVNQQQQH YSVPQKSYVE DSVVPVQNGQ RKSLILYQTP    240
QQQQSHHLNF QLGMEYDNSN TGYGYPASLS HSVSISSMDV SVVPESAQSE TSNSHPRPPK    300
GTIDLFSGPP IQIPPQLTPM DREARVLRYR EKKNRKFEK TIRYASRKAY AETRPRIKGR    360
FAKRTDVEAE VDQMFSTQLM TDSNYGIVPS F                                   391

SEQ ID NO: 63           moltype = AA   length = 376
FEATURE                 Location/Qualifiers
REGION                  1..376
                                  note = misc_feature - Public GI ID no.21655166
```

```
REGION                   1..376
                         note = misc_feature - Bit score of 528.8 for hmm based on
                           sequences of FIGURE 2.
REGION                   297..341
                         note = misc_feature - Pfam Name: CCT Pfam Description: CCT
                           motif
REGION                   51..98
                         note = misc_feature - Pfam Name: zf-B_box Pfam Description:
                           B-box zinc finger
REGION                   1..376
                         note = misc_feature - Functional Homolog Of Ceres SEEDLINE
                           ID no. ME04315 at SEQ ID NO. 20
source                   1..376
                         mol_type = protein
                         note = subspecies = vulgare
                         organism = Hordeum vulgare
SEQUENCE: 63
MMELRKYWGV GGRRCGGCEG AAPAAVHCRD CAGYLCTGCD ARPAHARAGH ERVWVCEVCE  60
VSPAAVTCKA DAAVLCAACD ADIHHANPLA ERHVRVPIAP IGSPEAAAVA AEAMMLCGAG 120
DGDARADPDE VHDQLHHHGH GGMLNLNVEA GKEGGKMDYL FSDLVDPYLA VDFTRFAHAD 180
SVVPNGVATA AVPAVVDLDF ACGIGAKPPP SYSSSYTANG SGAHSGSSSE VGVVPEAIHG 240
GAGSFELDFT RPKPQAYMPA YTPAPPSHGV GMQQASAVDM GYLTVPERPV AVTGEGRVAR 300
LMRYREKRKN RRFEKTIRYA SRKAYAESRP RVKGRFAKRA DQDADGDGDD LDAEAHAVPS 360
STSYLLDFGY GVVPSF                                                376

SEQ ID NO: 64            moltype = AA  length = 417
FEATURE                  Location/Qualifiers
REGION                   1..417
                         note = misc_feature - Public GI ID no.10946337
REGION                   1..417
                         note = misc_feature - Bit score of 351.2 for hmm based on
                           sequences of FIGURE 2.
REGION                   348..392
                         note = misc_feature - Pfam Name: CCT Pfam Description: CCT
                           motif
REGION                   77..119
                         note = misc_feature - Pfam Name: zf-B_box Pfam Description:
                           B-box zinc finger
REGION                   1..417
                         note = misc_feature - Functional Homolog Of Ceres SEEDLINE
                           ID no. ME04315 at SEQ ID NO. 20
source                   1..417
                         mol_type = protein
                         organism = Ipomoea nil
SEQUENCE: 64
MLKEESCEVL DLDVTIGSSS GSRSGNKQNW ARVCDICRSA ACSVYCRADL AYLCGGCDAR  60
VHGANTVAGR HERVLVCEAC ESAPATVICK ADAASLCAAC DSDIHSANPL ARRHHRVPIL 120
PISGTLYGPP TSNPCRESSM MVGLTGDAAE EDNGFLTQDA EETTMDEDED EAASWLLLNP 180
NPNPNPNPVK SNNSTNMCKG GNNNNNEMSC AVEAVDAYLD LAEFSSCHNN LFEDKYSINQ 240
QQNYSVPQRN MSYRGDSIVP NHGKNQFHYT QGLQQHNHHA IFNCKEWNMR ILTRDMVSIS 300
SMDVGVVPES TLSDTSISHS RASKGTIDLF SGPPIQMPPQ LQLSQMDREA RVLRYREKKK 360
TRKFEKTIRY ASRKAYAETR PRIKGRFAKR TDVDTEVDQI FYAPLMAESG YGIVPSF    417

SEQ ID NO: 65            moltype = AA  length = 381
FEATURE                  Location/Qualifiers
REGION                   1..381
                         note = misc_feature - Public GI ID no.90657642
REGION                   1..381
                         note = misc_feature - Bit score of 456.0 for hmm based on
                           sequences of FIGURE 2.
REGION                   312..356
                         note = misc_feature - Pfam Name: CCT Pfam Description: CCT
                           motif
REGION                   59..106
                         note = misc_feature - Pfam Name: zf-B_box Pfam Description:
                           B-box zinc finger
REGION                   1..381
                         note = misc_feature - Functional Homolog Of Ceres SEEDLINE
                           ID no. ME04315 at SEQ ID NO. 20
source                   1..381
                         mol_type = protein
                         organism = Cleome spinosa
SEQUENCE: 65
MLKEERTSGG ETGENNWARI CDTCRSAACT VYCRADSAYL CTSCDARVHA ANHVASRHER  60
VWVCESCERA PAAFLCKADA ASLCAACDAE IHSANPLARR HHRVPILPIS GSMSGPMANH 120
HPSETAMTDT ENDMVVGREE AEDEDEDDEE AASWLLLNPG KNSGNNNNQN NGFFFDGEAD 180
EYLDLVEYNS SMENQFSDQY SQYHQDCGVP QKSFGGDGVV PLQVEESRGQ LHHEQQSFQL 240
AITYGSPGAL YGSYNGSMNH SVSMSSMDIV VVPESTASDM AVVSQLRAPK GTTDLLIGPP 300
IQMMPQLSPM DREARVLRYR EKKKTRKFEK TIRYASRKAY AETRPRIKGR FAKRTDIEAE 360
```

```
VDQAFSTTLM QESGYGIVPS F                                              381

SEQ ID NO: 66           moltype = DNA   length = 155
FEATURE                 Location/Qualifiers
misc_feature            1..155
                        note = 000HORDEUM
misc_feature            1..155
                        note = Homolog Of Ceres SEEDLINE ID no. ME00572 at SEQ ID
                          NO. 111
source                  1..155
                        mol_type = other DNA
                        organism = Hordeum vulgare
                        sub_species = vulgare
SEQUENCE: 66
tcctcgtgtc agaattaacg ttcttgacct tgtaaggcct tttcttgacc ttgtaaggcc    60
ctccccta ac gtttctcctg gtgtctccaa cctcacactt tctttcccct ttctatccct   120
cctgagctat tccctatttt gtacgtctac aatct                               155

SEQ ID NO: 67           moltype = DNA   length = 161
FEATURE                 Location/Qualifiers
misc_feature            1..161
                        note = 000PICEA
misc_feature            1..161
                        note = Homolog Of Ceres SEEDLINE ID no. ME00572 at SEQ ID
                          NO. 111
source                  1..161
                        mol_type = other DNA
                        organism = Picea sp.
SEQUENCE: 67
atcaccccaa actgagcctt tcttgacctt gtaagacctt tcttgacct tgtaagacca     60
gccatagaat cccgagaaca aggtcgctca actctcaaac aatcttcttc taattagtct    120
atccctcctg agctatttac agttgagttt caagttcttc c                        161

SEQ ID NO: 68           moltype = AA   length = 409
FEATURE                 Location/Qualifiers
REGION                  1..409
                        note = misc_feature - Public GI ID no.45544887
REGION                  1..409
                        note = misc_feature - Bit score of 383.3 for hmm based on
                          sequences of FIGURE 2.
REGION                  340..384
                        note = misc_feature - Pfam Name: CCT Pfam Description: CCT
                          motif
REGION                  59..106
                        note = misc_feature - Pfam Name: zf-B_box Pfam Description:
                          B-box zinc finger
REGION                  1..409
                        note = misc_feature - Functional Homolog Of Ceres SEEDLINE
                          ID no. ME04315 at SEQ ID NO. 20
source                  1..409
                        mol_type = protein
                        organism = Solanum lycopersicum
SEQUENCE: 68
MLKKENSGGL DGSSNYWARV CDSCRSVTCT IYCQADSAYL CADCDARIHA ASLVTSRHKR    60
VWVCEACERA PAAFLCKADA ASLCASCDAD IHSANPLAHR HHRIPIITIP GTLYGPPAVE   120
TVGGDSMMIS GSTGEGTEDD GFLSLTQDAD DTIIDEEDED EDEAASWLLL NHPVKNNNKN   180
NVNNNNNQTN NYDMLFGGEV VDDYLDLAEY GGDSQFNDQY NVNQQQQQYF VPQMSYGGDS   240
VVPVQDGQGK PLIFYQQQQQ QQQSHHQNFQ LGMEYDNSNT RLGLPASMSH SVSVVSMDVS   300
VVPESALCET SNSQPRPQKG TIELFSGHPI QIPLLTPMDR EARVLRYREK KKNRKFEKTI   360
RYASRKAYAE TRPRIKGRFA KRTDVEAEVD QMFSTQLMTD SSYRIVPSF              409

SEQ ID NO: 69           moltype = AA   length = 376
FEATURE                 Location/Qualifiers
REGION                  1..376
                        note = misc_feature - Public GI ID no.47606678
REGION                  1..376
                        note = misc_feature - Bit score of 188.5 for hmm based on
                          sequences of FIGURE 2.
REGION                  307..351
                        note = misc_feature - Pfam Name: CCT Pfam Description: CCT
                          motif
REGION                  34..66
                        note = misc_feature - Pfam Name: zf-B_box Pfam Description:
                          B-box zinc finger
REGION                  1..376
                        note = misc_feature - Functional Homolog Of Ceres SEEDLINE
                          ID no. ME04315 at SEQ ID NO. 20
source                  1..376
                        mol_type = protein
```

```
                        organism = Lolium temulentum
SEQUENCE: 69
MNSNSSSTIY EEAVGQEGSW SRLCDGCCMV PSVVYCHADS AYLCASCDVR IHSANRVASR    60
HERVCLSKAH EHAPALLQCR TDAVASCAAY EAQAHYANLL AGMHQCVPVV SHPATAIPAA   120
SLLAEAAVTT TILSCKEEEA FWLLLSKNSA NQNCSGDNRS SSTYFGEVDE YFDLVGYNSY   180
YDSRMNNNQA QYGMQEQQHL QPMQKEYAEK EGSECVVPSQ FATVSKPQQS GYALVGSEQA   240
ASMTAGVSVY TDSVNNSISF SSMEGGIVPD NTVVDLPYSI IPTPAGASSL HSGPPLQMPL   300
HFSSMDREAK VLRYKEKKKT RTFEKTTRYA TKKAYAEARP RIKGRFAKIS EAEMEVDQLF   360
SAAALSDSSY STVPWF                                                  376

SEQ ID NO: 70           moltype = DNA  length = 1350
FEATURE                 Location/Qualifiers
misc_feature            1..1350
                        note = Ceres CLONE ID no.1755065
misc_feature            1..1350
                        note = Encodes the peptide sequence at SEQ ID NO 71
source                  1..1350
                        mol_type = other DNA
                        organism = Panicum virgatum
SEQUENCE: 70
aaccatttcc gacgcagaac ccccgggggc cggaatccgt gacacccacc cggaggagag    60
cagagcagag gcatcaggca tggccgccgc ggtggagctg gacagaaagc cggcggtggg   120
gtactggggc gtggccggcg cgcggccctg cgacgcgtgc gccgcggagc cggcgcggct   180
gcactggccg cgcgacggcg cgttcctgtg ccccggggtgc gacgcccgcg cgcacggcgc   240
cgggtcgcgc cacgcgcgcg tctggctctg cgaggtctgt gagcacgctc cgccgccgt   300
cacgtgccgc gccgacgccg ccgcgctctg gcggcctgc gacgccgaca tccactcgg   360
caacccgctc gcgcgccgcc acgagcggct cccccgtcgcg cccttcttcg gcgcgctcgc   420
cgacgcgccg cagccgttcc cgtccgcggc cttcgccacc gcggggggcc agtcccaggg   480
ggacgcggcg gcgcggcgg cggcggacga cgacgggagc aacgaggccg aggccgcctc   540
atggctcctc cccgagcccg acaccagcca cgaggacgag ccgacgcgtt   600
cttcgcggac tccgacaagt acctcggcgt cgacctcgac ttcgcccggt ccatggacgg   660
catcaaggcc atcggcgtcc cggtcgcgcc gccggagctg gacatcgccg ctggcgcttt   720
ctactaccccc gaacactcca tgaaccatag cgtgtcgtca tcagaggtgg cggtcgtgcc   780
ggacgtgctg gcgggcgg cg tcccggccggt gccggtggcg agccggggga aggagcggga   840
agcgcggctg atgcggtacc gcgagaagcg caagaaccgg cggttcgaca agaccatccg   900
gtacgcgtcc cgcaaggcgt acgccgagac gcggccgcgc atcaagggcc gcttcgccaa   960
gcgctgctcc gccgaggccg aggacgagga cgaggcgctg ctggagcacg aggaagggcc   1020
gtgcttctcg ccgcggtgt cggccccgc ggcctcggac ggcgtcgtcc cgtccttctg   1080
ctaaggggga cgacgggtgg cggccgcgcc tcctcctcct ccccggctcc caggcggcaa   1140
cccccttaatt ttgccgactc tgaatcgacc cccaacgcat gccaacatgc gaatgcgatg   1200
cgcgcgctcc gtgtagcata ataattgtac agcagctcgt ccgacgcaac gagctcaatc   1260
gcggtcgcac ggaacgcctg taatcctcct caccatccgt gtaatccagc cttgtacatt   1320
accatctaga ggtgtttgtg cttctcttgc                                    1350

SEQ ID NO: 71           moltype = AA  length = 334
FEATURE                 Location/Qualifiers
REGION                  1..334
                        note = misc_feature - Ceres CLONE ID no.1755065
REGION                  1..334
                        note = misc_feature - Bit score of 736.3 for hmm based on
                          sequences of FIGURE 2.
REGION                  253..297
                        note = misc_feature - Pfam Name: CCT Pfam Description: CCT
                          motif
REGION                  64..106
                        note = misc_feature - Pfam Name: zf-B_box Pfam Description:
                          B-box zinc finger
REGION                  1..334
                        note = misc_feature - Functional Homolog Of Ceres SEEDLINE
                          ID no. ME04315 at SEQ ID NO. 20
source                  1..334
                        mol_type = protein
                        organism = Panicum virgatum
SEQUENCE: 71
MAAAVELEQK PAVGYWGVAG ARPCDACAAE PARLHCRADG AFLCPGCDAR AHGAGSRHAR    60
VWLCEVCEHA PAAVTCRADA AALCAACDAD IHSANPLARR HERLPVAPFF GALADAPQPF   120
PSAAFATAGG QSQGDAAAAA ADDDGSNEA EAASWLLPEP DTSHEDSAAA TDAFFADSDK   180
YLGVDLDFAR SMDGIKAIGV PVAPPELDIA AGAFYYPEHS MNHSVSSSEV AVVPDVLAGG   240
VPAVPVASRG KEREARLMRY REKRKNRRFD KTIRYASRKA YAETRPRIKG RFAKRCSAEA   300
EDEDEALLEH EEGACFSPAV SAPAASDGVV PSFC                              334

SEQ ID NO: 72           moltype = DNA  length = 166
FEATURE                 Location/Qualifiers
misc_feature            1..166
                        note = 000SORGHUM
misc_feature            1..166
                        note = Homolog Of Ceres SEEDLINE ID no. ME00572 at SEQ ID
                          NO. 111
source                  1..166
```

```
                            mol_type = other DNA
                            organism = Sorghum bicolor
SEQUENCE: 72
tggtttcgca aggtgaggtc ttcttgacct tgcaagacct tttcttgacc ttgtaagacc    60
caactctgcg acatctcttt cctgtcttac accttcctct tcattcttac ttcttttcta   120
tgtctatccc ttatgagctg tgttgagcta tgttaggtcc tagtta                  166

SEQ ID NO: 73              moltype = DNA   length = 154
FEATURE                    Location/Qualifiers
misc_feature               1..154
                           note = 000TRITICUM
misc_feature               1..154
                           note = Homolog Of Ceres SEEDLINE ID no. ME00572 at SEQ ID
                             NO. 111
source                     1..154
                           mol_type = other DNA
                           organism = Triticum aestivum
SEQUENCE: 73
tcctcatgcc agaattaatg ttcttgacct tgtaaggcct tttcttgacc ttgtaaggcc    60
ctccccttac gtttctccgg gtgtctccaa cctcacactt tctccccct tctatccctc    120
ctgagctatc tccatgcata ttttgtctag caat                               154

SEQ ID NO: 74              moltype = AA   length = 314
FEATURE                    Location/Qualifiers
REGION                     1..314
                           note = misc_feature - Ceres CLONE ID no.1844076
REGION                     1..314
                           note = misc_feature - Bit score of 824.2 for hmm based on
                             sequences of FIGURE 3.
REGION                     38..173
                           note = misc_feature - Pfam Name: adh_short Pfam
                             Description: short chain dehydrogenase
source                     1..314
                           mol_type = protein
                           organism = Arabidopsis thaliana
SEQUENCE: 74
MSGKKERNKE RREKRLQEIS LLRTIPYSDH QRWWSQETVA VVTGANRGIG FEIARQLAGH    60
GLTVILTSRN ISVGIEATKA LQEGGFSYDV HQLDILDGES ISAFVEWIKQ KYGGIDILVN   120
NAGVNYNLGF DNSVEFARQV VDTNYYGTKN MIKAMIPVMK PSTAGARIVN VSSRLGRLNG   180
RRNRIQDATL REKLTNLETL SEELIDRTVS SFLQQVEDET WQSGGWPQTF TDYSVSKLAV   240
NAYTRLVAKE LCDRPQGEKI YINCYCPGWV KTAMTGWAGN ISPEVAADTG VWLSLLSDQA   300
ITGKFFAERR EINF                                                     314

SEQ ID NO: 75              moltype = DNA   length = 1167
FEATURE                    Location/Qualifiers
misc_feature               1..1167
                           note = Ceres CLONE ID no.35974
misc_feature               1..1167
                           note = Encodes the peptide sequence at SEQ ID NO 76
source                     1..1167
                           mol_type = other DNA
                           organism = Arabidopsis thaliana
SEQUENCE: 75
acacccaaac acgcgacgcg agcgaaagaa gacgatgacg aacaaggaga aagctcgaga    60
gagaagggag aaaaaaatgc aggagatctc tctccttcga actattcctt actctgacca   120
ccataggtgg tggtcttgtg aaaatgtagc agtagtgact ggttcaaacc gcgggattgg   180
attcgagatt gcaagacagc ttgcggttca cggattgacg gttgttctta cagctagaaa   240
cgtgaatgct ggtcttgaag cagttaaatc tttgaggcac caagaagaag gtctcaaggt   300
ttatttcat caacttgatg tcacagactc ttcctcgatt agagagtttg gttgctggct   360
taagcaaaca tttggaggtt tagatattct cgtgaataat gcaggtgtta actacaatct   420
cggctcagat aatacggttg aatttgctga aacagttata tctactaact accaaggaac   480
caaaaacatg acaaaagcta tgatacccgt tgatgagacca tctcctcatg gcgctcgtgt   540
agtcaatgtt agttctcggc taggtagagt aaatggaaga cgtaatagac tggcaaatgt   600
agagttgaga gatcagctaa gcagtccaga tttgctgaac gggaactta tagacagaac   660
tgtctctaaa ttcatcaacc aagtaaaaga cggaacttgg gaatcaggcg ggtggcctca   720
gacattcact gactactcca tgtctaagct tgcagtcaat gcttacacga gactaatggc   780
aaaagaactt gagagacgag gagaggaaga gaagatttat gttaacagct ttgcccctgg   840
ttgggtgaag actgcgatga ctggctacgc cggaaatatg ccacctgaag atgcagctga   900
tactggagtt tggcttagcc tggtccttc cgaagagtca gtaaccggaa aattcttcgc   960
agagagacgt gagatcaact tctgagggtt gttgaatgtt tgtaaacgtt ggaatagatt  1020
gtgtcgtctt cgtttagtgc catagtttta gtcaaaggtt tacaaaatca attgtaattg  1080
gtaagtgaat ggttgtagtc atgatacgcg tcagatttgc cacaaaacta ggagtttata  1140
atttaaatat aattaatttt taattgc                                      1167

SEQ ID NO: 76              moltype = AA   length = 316
FEATURE                    Location/Qualifiers
REGION                     1..316
                           note = misc_feature - Ceres CLONE ID no.35974
REGION                     1..316
```

```
                        note = misc_feature - Bit score of 817.6 for hmm based on
                            sequences of FIGURE 3.
REGION                  37..174
                        note = misc_feature - Pfam Name: adh_short Pfam
                            Description: short chain dehydrogenase
REGION                  1..316
                        note = misc_feature - Functional Homolog Of Full Length
                            Ceres SEEDLINE ID no.ME17294 at SEQ ID NO. 74
source                  1..316
                        mol_type = protein
                        organism = Arabidopsis thaliana
SEQUENCE: 76
MTNKEKARER REKKMQEISL LRTIPYSDHH RWWSCENVAV VTGSNRGIGF EIARQLAVHG    60
LTVVLTARNV NAGLEAVKSL RHQEEGLKVY FHQLDVTDSS SIREFGCWLK QTFGGLDILV   120
NNAGVNYNLG SDNTVEFAET VISTNYQGTK NMTKAMIPLM RPSPHGARVV NVSSRLGRVN   180
GRRNRLANVE LRDQLSSPDL LTEELIDRTV SKFINQVKDG TWESGGWPQT FTDYSMSKLA   240
VNAYTRLMAK ELERRGEEEK IYVNSFCPGW VKTAMTGYAG NMPPEDAADT GVWLSLVLSE   300
ESVTGKFFAE RREINF                                                   316

SEQ ID NO: 77           moltype = AA  length = 304
FEATURE                 Location/Qualifiers
REGION                  1..304
                        note = misc_feature - Public GI ID no.10176876
REGION                  1..304
                        note = misc_feature - Bit score of 730.9 for hmm based on
                            sequences of FIGURE 3.
REGION                  23..160
                        note = misc_feature - Pfam Name: adh_short Pfam
                            Description: short chain dehydrogenase
REGION                  1..304
                        note = misc_feature - Functional Homolog Of Full Length
                            Ceres SEEDLINE ID no.ME17294 at SEQ ID NO. 74
source                  1..304
                        mol_type = protein
                        organism = Arabidopsis thaliana
SEQUENCE: 77
MQEISLLRTI PYSDHHRWWS CENVAVVTGS NRGIGFEIAR QLAVHGLTVV LTARNVNAGL    60
EAVKSLRHQE EGLKVYFHQL DVTDSSSIRE FGCWLKQTFG GLDILVNNAG VNYNLGSDNT   120
VEFAETVIST NYQGTKNMTK AMIPLMRPSP HGARVVNVSS RLENLVEIHE LQRLANVELR   180
DQLSSPDLLT EELIDRTVSK FINQVKDGTW ESGGWPQTFT DYSMSKLAVN AYTRLMAKEL   240
ERRGEEEKIY VNSFCPGWVK TAMTGYAGNM PPEDAADTGV WLSLVLSEEA VTGKFFAERR   300
EINF                                                                304

SEQ ID NO: 78           moltype = DNA  length = 1164
FEATURE                 Location/Qualifiers
misc_feature            1..1164
                        note = Ceres CLONE ID no.473040
misc_feature            1..1164
                        note = Encodes the peptide sequence at SEQ ID NO 79
source                  1..1164
                        mol_type = other DNA
                        organism = Glycine max
SEQUENCE: 78
acttcttaaa actggtatct gatttacaaa aggttacaaa cttctcttgc ataaagaatg    60
gcatcagcaa caataaggaa tgcagttgtc acgggagcaa acaaagggat aggatttgga   120
atatgcaagc aattggtttc taatggcatc acagtggtgc taacagcaag ggatgagaaa   180
aggggtcttg aagctgttga aaagctgaaa gagtttggtg tgtctgatca agtggtgttt   240
catcagcttg atgtgactga ccctaaaagc attgaatccc ttgcaaattt catcaaaacc   300
cagtttggaa aacttgatat cttggtgaat aatgcaggaa ttcatggagc tgatgttgac   360
cgtgatgctt tagctgctgc tggggaaaaa gttgccaatg ttgattggaa aaaaatctca   420
actgaaaatt ttgaagctgc cgaagcaggc attagaacaa attactatgg agtcaaatta   480
atgtgtgaag cacttattcc ccttctagaa ttgtcaggca caccaaggat tgtcaatgtt   540
tcctcctcca tggggaagtt ggagaaaata ccaaatgcat gggctagagg agccctaagt   600
gatgctgaga gcctaacaga agaaaaggtg gatgaggttt gaatcagtt tctaaagat    660
tttaaagagg gttcattaga aaccaaaggg tggccacatg cttttctgc atatatagtc   720
tcaaaagctg ctttgactgc ctacacaagg attcttgcta gaagtaccc atctttctgc   780
atcaatgctg tttgccctgg ctttgtgaaa acagatctca actacaatac tggctatctt   840
agtgttgatg aaggtgctga aagtgttgta aggttggctc tgctacctaa tggaggtcct   900
tctggtctat tcttttctcg aagtgaagtg gcaccattct gatccaaaga ctgttcgtta   960
cttgaagagg ataaataata agcatggttt catgataaga catgtatcaa atttgtacct  1020
agcacaacaa gaaaataagc cacatgtctg atcactgatg gctgcccatc attgatgaga  1080
acaacccctat agtgaattct agatattaca atgcacattac taattgaga aatctaattt  1140
tggatataaa gatatctgtt tgtc                                         1164

SEQ ID NO: 79           moltype = AA  length = 294
FEATURE                 Location/Qualifiers
REGION                  1..294
                        note = misc_feature - Ceres CLONE ID no.473040
REGION                  1..294
```

```
                        note = misc_feature - Bit score of 656.1 for hmm based on
                            sequences of FIGURE 3.
REGION                  7..168
                        note = misc_feature - Pfam Name: adh_short Pfam
                            Description: short chain dehydrogenase
REGION                  1..294
                        note = misc_feature - Functional Homolog Of Full Length
                            Ceres SEEDLINE ID no.ME17294 at SEQ ID NO. 74
source                  1..294
                        mol_type = protein
                        organism = Glycine max
SEQUENCE: 79
MASATIRNAV VTGANKGIGF GICKQLVSNG ITVVLTARDE KRGLEAVEKL KEFGVSDQVV    60
FHQLDVTDPK SIESLANFIK TQFGKLDILV NNAGIHGAYV DRDALAAAGE KVANVDWRKI   120
STENFEAAEA GIRTNYYGVK LMCEALIPLL ELSGTPRIVN VSSSMGKLEK IPNAWARGAL   180
SDAESLTEEK VDEVLNQFLK DFKEGSLETK GWPHAFSAYI VSKAALTAYT RILAKKYPSF   240
CINAVCPGFV KTDLNYNTGY LSVDEGAESV VRLALLPNGG PSGLFFSRSE VAPF         294

SEQ ID NO: 80           moltype = DNA   length = 2073
FEATURE                 Location/Qualifiers
misc_feature            1..2073
                        note = Ceres CLONE ID no.922223
misc_feature            1..2073
                        note = Encodes the peptide sequence at SEQ ID NO 81
source                  1..2073
                        mol_type = other DNA
                        organism = Triticum aestivum
SEQUENCE: 80
gtaaacaagc ccatggactc ttattttctc tttatgttgg gcttaatgtt cttggggcta    60
tggttccgag ttctcaaaaa aaaaagttcg attccggcga acacagtaca gcagagggag   120
cgagagatgg ggaagaaggg caaggcggcg gcaagggagc gccgggagga gcggcggcgg   180
gaagtcacgc tcctccgcgc cgtaccctac gagccccacc agcggtggtg ggacggcctc   240
gcgccggcgc gcgccgtggc ggtggtgacg ggggccagcc gcggcatcgg ctacgagatc   300
tcccgccagc tcgcgcgcca cggcctccac gtcgtcctcg cctcgcgcga cgccgcgcgg   360
ggcagggacg ccgcggaggg gatcctccgc gaggagggca cgagcgcgga gtggcggcag   420
ctcgacgtgg cggacgccgc gtcggtcgag gcctcgccg cctggacggc gcggaccac    480
ggcggcatcc atgtccttat taacaatgca ggtgtaaact tcaacagagg agcagataac   540
tctgttgaat ttgcagagca agtaattgag acaaattatt ttggtacaag gcggatgatt   600
gaagccatgc taccattact gaaaccttct ccgtatggtg gccggatagt gaatgtgagc   660
tcaaggcttg gcagggccaa tggcagacgc aataaaatcg gcgatgcgat cctaagagag   720
caactattaa ctgatgattg cttatctgag gaattgattg atgggatggt cactaaattc   780
cttgaacaag tgaagcaaaa tagttggtcc tccattgagt ggcctcagat gtacacggac   840
tattcggtct caaagtttgc tgttaatgtg tatacaagac tcatggcaag gaggttatct   900
gacaggtctg aaggccaaaa gatttacatt aactgttttct gtcctggctg ggtaaagact   960
gccatgactg attgggaagg aacatttcca gccgaagaag tgctgatact ggagtgtgg   1020
cttgctctgt taccccagga acaagcaaca attggaaagt tctatgctga gagacgcgag   1080
ataagcttct gaggtgatcg gaatggtgga tatgcggatg ggagtggtac atttaaccat   1140
atgtatttaa ttaaagtttt aaactatgta ggtgatcgga atggtggata tgcgagtggg   1200
agtggcatgt tcatgaagag caatccacat gattggcaga ctccagcatg gttttcgagt   1260
cgcgactcat gcgagttgct ctggggcagc gactcggaag aagtcgagcc tgcgttgtga   1320
ctagtcatga ctcagagtcg cgagtcgata ctaagctgaa ttgaccatat ttttgcgact   1380
catagactag tcgtcgacta gtcgcaacta gtcgagcgac tcgaaatcca tggactccag   1440
tcggtcaaag agcattgagt cttcacactg atggaaggcc atgctctcta attttgtcaa   1500
taaatgatgc agtaccagat gctttcagac gatactcaga cgacgttgcc catcagaccg   1560
tttgttaatt agattcacgt caatctcatg gtgtagagtc tgcgtcggct gcacatccgt   1620
cataccatgt cgtgtgtaca tcaatttcgt gaagttgctg gaaacaggga aatgttcacc   1680
aggcccacca ccactagtcc acaacggcag taagcaggca tggcatgctg gactgctgca   1740
ccgaatatat gattaggctg gatctcaagc aactccactg tcagattctc tcattatctt   1800
ccaagtagag gtggaatcct tatgacccaa tggatgagag cgatgcaacg ctgcctcacc   1860
cacgcatgca gaagatcgat atgtttggga acgaaccggt cggcctacct tgggaattct   1920
ggagctatag tcatggctag gccgccattc atggaccgga gactacatgt cttgcagtat   1980
attgttctga ttttgccgcc acctgcatat gtgtggtaca tactttgtta tgttcgtgtt   2040
tgtatgcaat ggttggatcg tgtgatttgc tgg                                2073

SEQ ID NO: 81           moltype = AA   length = 321
FEATURE                 Location/Qualifiers
REGION                  1..321
                        note = misc_feature - Ceres CLONE ID no.922223
REGION                  1..321
                        note = misc_feature - Bit score of 823.6 for hmm based on
                            sequences of FIGURE 3.
REGION                  43..179
                        note = misc_feature - Pfam Name: adh_short Pfam
                            Description: short chain dehydrogenase
REGION                  1..321
                        note = misc_feature - Functional Homolog Of Full Length
                            Ceres SEEDLINE ID no.ME17294 at SEQ ID NO. 74
source                  1..321
                        mol_type = protein
```

```
                        organism = Triticum aestivum
SEQUENCE: 81
MGKKGKAAAR ERREERRREV TLLRAVPYEP HQRWWDGLAP ARAVAVVTGA SRGIGYEISR   60
QLARHGLHVV LASRDAARGR DAAEGILREE GTSAEWRQLD VADAASVEAF AAWTARTHGG  120
IHVLINNAGV NFNRGADNSV EFAEQVIETN YFGTRRMIEA MLPLLKPSPY GGRIVNVSSR  180
LGRANGRRNK IGDAILREQL LTDDCLSEEL IDGMVTKFLE QVKQNSWSSI EWPQMYTDYS  240
VSKFAVNVYT RLMARRLSDR SEGQKIYINC FCPGWVKTAM TDWEGNISAE EGADTGVWLA  300
LLPQEQATIG KFYAERREIS F                                           321

SEQ ID NO: 82           moltype = AA  length = 331
FEATURE                 Location/Qualifiers
REGION                  1..331
                        note = misc_feature - Public GI ID no.125528967
REGION                  1..331
                        note = misc_feature - Bit score of 831.3 for hmm based on
                          sequences of FIGURE 3.
REGION                  49..188
                        note = misc_feature - Pfam Name: adh_short Pfam
                          Description: short chain dehydrogenase
REGION                  1..331
                        note = misc_feature - Functional Homolog Of Full Length
                          Ceres SEEDLINE ID no.ME17294 at SEQ ID NO. 74
source                  1..331
                        mol_type = protein
                        note = subspecies = indica
                        organism = Oryza sativa
SEQUENCE: 82
MGKKGKEAAR ERREQRRREV TLLRAVPYEP HQRWWDGLAP PPPPPPGRAV AVVTGANRGI   60
GYEAARQLAT HGLHVVLTSR DAARGRDAAE QIRAAAGKPG VSVEWRQLDV TDAASVEGFA  120
TWVERTHGGV HVLVNNAGVN FNRGADNSVE FAEQVTETNY FGTKRMIEAM MPLMITSPHG  180
GRIVNVSSRL GRVNGRRNRI GDPSLRERLL NDDHLSEELI NEMVKFLEQ TKQDNWSSSN  240
EWPQMYTDYS ISKLAVNAYT RLLARRLLDR PEGQKIYINC FCPGWVKTAM TGWEGNISAE  300
EGADTGVWLA LVPQEQATIG KFFAERREIS F                                331

SEQ ID NO: 83           moltype = AA  length = 330
FEATURE                 Location/Qualifiers
REGION                  1..330
                        note = misc_feature - Public GI ID no.125573200
REGION                  1..330
                        note = misc_feature - Bit score of 834.6 for hmm based on
                          sequences of FIGURE 3.
REGION                  48..187
                        note = misc_feature - Pfam Name: adh_short Pfam
                          Description: short chain dehydrogenase
REGION                  1..330
                        note = misc_feature - Functional Homolog Of Full Length
                          Ceres SEEDLINE ID no.ME17294 at SEQ ID NO. 74
source                  1..330
                        mol_type = protein
                        note = subspecies = japonica
                        organism = Oryza sativa
SEQUENCE: 83
MGKKGKEAAR ERREQRRREV TLLRAVPYEP HQRWWDGLAP PPPPPGRAVA VVTGANRGIG   60
YEAARQLATH GLHVVLTSRD AARGRDATEQ IRAAAGKPGV SVEWRQLDVT DAASVEGFAT  120
WVERTHGGVH VLVNNAGVNF NRGADNSVEF AEQVIETNYG GTKRMIEAMM PLMITSPHGG  180
RIVNVSSRLG RVNGRRNRIG DPSLRERLLN DDHLSEELIN EMVKFLEQT KQDNWSSGNE  240
WPQMYTDYSI SKLAVNAYTR LLARRLLDRP EGQKIYINCF CPGWVKTAMT GWEGNISAEE  300
GADTGVWLAL VPQEQATIGK FFAERREISF                                  330

SEQ ID NO: 84           moltype = DNA  length = 942
FEATURE                 Location/Qualifiers
misc_feature            1..942
                        note = Ceres ANNOT ID no.1527409
misc_feature            1..942
                        note = Encodes the peptide sequence at SEQ ID NO 85
source                  1..942
                        mol_type = other DNA
                        organism = Populus balsamifera
                        sub_species = trichocarpa
SEQUENCE: 84
atggggaagta aagagccagc aaaggaaaag agagaaaaaa gactccaaga aatttctctt   60
ctccgtacca ttccttactc tgatcatcaa aggtggtggt catcagaaac tgttgctgtg  120
gtgaccggtg aaatagagg aataggattt gagattgcga ggcaacttgc agaccatgga  180
ttgtctgtta tcctgacatc acgagaaagt agcgcaggc ttgaagctgc caatgtcttg  240
cgagagttgg gtttgagtgt ggacttccat caacttgatg tcttagattc tttatccatc  300
aaaacgtttg ctgagtggat acaacaaact tacggcggat tagatgtttt ggtgaataat  360
gctggtgtta attacaatat ggggtctgac aattctgttg aaaatgccaa gaatgttgtt  420
gatacaaaact attatggtat caaaaatgtc actgaagctc tgattccttt gatgagacct  480
tcttctgtag gtgctcgtat tgttaatgta agttcacggc ttgaagact aaatggcaaa  540
```

```
cgaaacagac ttgaagacaa agatttgaga gagcaactgg ctaacctgga aacactttca    600
gaggaactca ttgataggac ggtgtctact ttcctacaac aagtagaaga ccgcacatat    660
acatcaggtg gatggcctca ggtgaacact gattactcgg tgtcaaaact tgcagttaat    720
gcttatacta ggctaatggc aaagaaactg tccgatcggc taatggtca gaagatctat     780
ataaactgct actgcccagg gtgggtgaag acagcctggc tggtaatgta               840
tcagctgagg atggagctga cacaggagta tggctggccc tgcttccaga ccaagcaatc    900
acagggaaat tttttgctga gagacgtgag gtaaacttct ga                       942
```

| | |
|---|---|
| SEQ ID NO: 85 | moltype = AA  length = 313 |
| FEATURE | Location/Qualifiers |
| REGION | 1..313 |
| | note = misc_feature - Ceres ANNOT ID no.1527409 |
| REGION | 1..313 |
| | note = misc_feature - Bit score of 836.2 for hmm based on sequences of FIGURE 3. |
| REGION | 37..172 |
| | note = misc_feature - Pfam Name: adh_short Pfam Description: short chain dehydrogenase |
| REGION | 1..313 |
| | note = misc_feature - Functional Homolog Of Full Length Ceres SEEDLINE ID no.ME17294 at SEQ ID NO. 74 |
| source | 1..313 |
| | mol_type = protein |
| | note = subspecies = trichocarpa |
| | organism = Populus balsamifera |

```
SEQUENCE: 85
MGSKEPAKEK REKRLQEISL LRTIPYSDHQ RWWSSETVAV VTGGNRGIGF EIARQLADHG    60
LSVILTSRES SAGLEAANVL RELGLSVDFH QLDVLDSLSI KTFAEWIQQT YGGLDVLVNN   120
AGVNYNMGSD NSVENAKNVV DTNYYGIKNV TEALIPLMRP SSVGARIVNV SSRLGRLNGK   180
RNRLEDKDLR EQLANLETLS EELIDRTVST FLQQVEDRTY TSGGWPQVNT DYSVSKLAVN   240
AYTRLMAKKL SDRPNGQKIY INCYCPGWVK TAMTGWAGNV SAEDGADTGV WLALLPDQAI   300
TGKFFAERRE VNF                                                     313
```

| | |
|---|---|
| SEQ ID NO: 86 | moltype = AA  length = 311 |
| FEATURE | Location/Qualifiers |
| REGION | 1..311 |
| | note = misc_feature - Public GI ID no.92871098 |
| REGION | 1..311 |
| | note = misc_feature - Bit score of 828.1 for hmm based on sequences of FIGURE 3. |
| REGION | 35..170 |
| | note = misc_feature - Pfam Name: adh_short Pfam Description: short chain dehydrogenase |
| REGION | 1..311 |
| | note = misc_feature - Functional Homolog Of Full Length Ceres SEEDLINE ID no.ME17294 at SEQ ID NO. 74 |
| source | 1..311 |
| | mol_type = protein |
| | organism = Medicago truncatula |

```
SEQUENCE: 86
MGHKEKSRKD KRLQEISLLR TIPYSDHQRW WSKETIAVVT GGNRGIGFEI SRQLADHGVT    60
VVLTSRDASV GVESIKVLQE GGLDVHCHQL DILDSSSVNE FAEWLKEEYG GLDILVNNAG   120
VNSNMGSDNS VENARKCIET NYYGTKRMIE AMIPLMKPSA AGGRIVNVSS RLGRLNGKRN   180
RIENEELREK LSDVESLSEE LIDETINNFL QQIEDGSWKT GGWPQTFTDY SVSKLAVNTY   240
TRYMAKKLSD RPEGEKIYIN CYCPGWVKTA LTGYAGSVTV EQGADTGVWI ALVPDQEITG   300
KFFAERREIN F                                                       311
```

| | |
|---|---|
| SEQ ID NO: 87 | moltype = DNA  length = 1171 |
| FEATURE | Location/Qualifiers |
| misc_feature | 1..1171 |
| | note = Ceres CLONE ID no.1831117 |
| misc_feature | 1..1171 |
| | note = Encodes the peptide sequence at SEQ ID NO 88 |
| source | 1..1171 |
| | mol_type = other DNA |
| | organism = Panicum virgatum |

```
SEQUENCE: 87
ctcccacccg cgctcccagc acgcccaccg tcgcctaccc cgtctccagc tcgatggact     60
actcgagcac caaggagtta cctccggccg gggcctggtg gtcgagggag acggtggccg   120
tggtgacggg cgccgaaccgg ggcatcgggc acgccctcgc cgcgcgcctg gcggagcacg   180
ggctcaccgt ggtgctcacc gcgcgggacg gcgcgcgcgg ggaggccgcc gcggccccgc   240
tccgcgcgcg cgggctcgcc gtcgccttcc gcaggctcga cgtctccgac gccgcctccg   300
tcgccgagtt cgccgcctgg ctccgcgacg ccgtcgcgcg cctcgacatc ctggtgaaca   360
acgccggcgt gtccttcaac gagatcgaca ccaactgggt ggagcacgcc gagacggtcc   420
tccggaccaa cttctacggc gccaagatgc tcacggaagc gctcctgccg ctgttccggc   480
agtcccggc caccagcagg atcctcaaca tcagctcgca gctcggcctt ctcaacaagg   540
tgagcgaccc gtccctgaag gcgttgctgc tggacgagga gacctgacg gagcggcga    600
tcgacggcat ggtgtcgcgg ttcctggcgc aggtgaagga cgggacgtgg ggcgcgcagg   660
gttggccaa ggtgtggacg gactactcgg tctccaagct ggccctgaac gcctactccc    720
```

-continued

```
ggctgctggc gcggcggctg caggcgcgcg gcgcccgcgt gagcgtcaac tgcttctgcc    780
ccggggttcac gcgcaccgac atgaccaggg gctgggggaa gcgcaccgcc gaggaggcgg   840
ccgacgtcgg gcgcggctc gcgctgctgc gcccggcga gctccccacg ggggccttct    900
tcaagtggtg cacgccgcag ccctactcca agctgtgacc tgccgagcca cgccgccggc   960
ccgcgcgccc cggccatggc ggccgcagga gtatgtgagc ttggtttagc tgcttcctagt 1020
tactttcaat gcagacaaga agccgatcga gtagtgtctc ttagcagtct ggctttctgt  1080
caaggtgctt tggttgagca atgcaaccaa accatgtcag cgatcaatgt actatgcgtg  1140
cttagccgtg caagatttag gtcaacttcc g                                 1171
```

| SEQ ID NO: 88 | moltype = AA length = 294 |
|---|---|
| FEATURE | Location/Qualifiers |
| REGION | 1..294 |
| | note = misc_feature - Ceres CLONE ID no.1831117 |
| REGION | 1..294 |
| | note = misc_feature - Bit score of 671.6 for hmm based on sequences of FIGURE 3. |
| REGION | 20..160 |
| | note = misc_feature - Pfam Name: adh_short Pfam Description: short chain dehydrogenase |
| REGION | 1..294 |
| | note = misc_feature - Functional Homolog Of Full Length Ceres SEEDLINE ID no.ME17294 at SEQ ID NO. 74 |
| source | 1..294 |
| | mol_type = protein |
| | organism = Panicum virgatum |

SEQUENCE: 88

```
MDYSSTKELP PAGAWWSRET VAVVTGANRG IGHALAARLA EHGLTVVLTA RDGARGEAAA    60
APLRARGLAV AFRRLDVSDA ASVAEFAAWL RDAVGGLDIL VNNAAVSFNE IDTNSVEHAE  120
TVLRTNFYGA KMLTEALLPL FRQSPATSRI LNISSQLGLL NKVSDPSLKA LLLDEETLTE  180
AAIDAMVSRF LAQVKDGTWG AQGWPKVWTD YSVSKLALNA YSRLLARRLQ ARGARVSVNC  240
FCPGFTRTDM TRGWGKRTAE EAADVGARLA LLPPGELPTG AFFKWCTPQP YSKL        294
```

| SEQ ID NO: 89 | moltype = DNA length = 951 |
|---|---|
| FEATURE | Location/Qualifiers |
| misc_feature | 1..951 |
| | note = Ceres ANNOT ID no.857222 |
| misc_feature | 1..951 |
| | note = Encodes the peptide sequence at SEQ ID NO 90 |
| source | 1..951 |
| | mol_type = other DNA |
| | organism = Arabidopsis thaliana |

SEQUENCE: 89

```
atgacgaaca aggagaaagc tcgagagaga agggagaaaa gaatgcagga gatctctctc    60
cttcgaacta ttccttactc tgaccaccat aggtggtggt cttgtgaaaa tgtagcagta  120
gtgactggtt caaaccgcgg gattggattc gagattgcaa gacagcttgc ggttcacgga  180
ttgacggttg ttcttacagc tagaaacgtg aatgctggtc ttgaagcagt taatctttg   240
aggcaccaag aagaaggtct caaggtttat tttcatcaag ttgatgtcac agactcttcg  300
tcgattagag agtttggttg ctggcttaag caaacatttg gaggtttaga tattctcgtg  360
aataatgcag gtgttaacta caatctcggc tcagataata cggttgaatt tgctgaaaca  420
gttatatcta ctaactacca aggaaccaaa aacatgacaa agctatgat acccttgatg   480
agaccatctc ctcatgggcg tcgtgtagtc aatgttagtt ctcggctagg tagagtaaat  540
ggaagacgta atagactggc aaatgtagag ttgagagatc agctaagcag tccagatttg  600
ctgaccgagg aacttataga cagaactgtc tctaaattca tcaaccaagt aaaagacgga  660
acttgggaat caggcgggtg gcctcagaca ttcactgact actccatgtc taagcttgca  720
gtcaatgctt acacgagact aatggcaaaa gaacttgaga gacgaggaga ggaagagaag  780
atttatgtta acagctttg ccctggttgg gtgaagactg cgatgactgg ctacgccgga  840
aatatgccac ctgaagatgc agctgatact ggagttggc ttagcctggt cctttccgaa   900
gaggcagtaa ccggaaaatt cttcgcagag agacgtgaga tcaacttctg a            951
```

| SEQ ID NO: 90 | moltype = AA length = 316 |
|---|---|
| FEATURE | Location/Qualifiers |
| REGION | 1..316 |
| | note = misc_feature - Ceres ANNOT ID no.857222 |
| REGION | 1..316 |
| | note = misc_feature - Bit score of 823.3 for hmm based on sequences of FIGURE 3. |
| REGION | 37..174 |
| | note = misc_feature - Pfam Name: adh_short Pfam Description: short chain dehydrogenase |
| REGION | 1..316 |
| | note = misc_feature - Functional Homolog Of Full Length Ceres SEEDLINE ID no.ME17294 at SEQ ID NO. 74 |
| source | 1..316 |
| | mol_type = protein |
| | organism = Arabidopsis thaliana |

SEQUENCE: 90

```
MTNKEKARER REKRMQEISL LRTIPYSDHH RWWSCENVAV VTGSNRGIGF EIARQLAVHG    60
LTVVLTARNV NAGLEAVKSL RHQEEGLKVY FHQLDVTDSS SIREFGCWLK QTFGGLDILV  120
NNAGVNYNLG SDNTVEFAET VISTNYQGTK NMTKAMIPLM RPSPHGARVV NVSSRLGRVN  180
```

```
GRRNRLANVE LRDQLSSPDL LTEELIDRTV SKFINQVKDG TWESGGWPQT FTDYSMSKLA    240
VNAYTRLMAK ELERRGEEEK IYVNSFCPGW VKTAMTGYAG NMPPEDAADT GVWLSLVLSE    300
EAVTGKFFAE RREINF                                                   316

SEQ ID NO: 91              moltype = DNA  length = 1213
FEATURE                    Location/Qualifiers
misc_feature               1..1213
                           note = Expected Sequence
misc_feature               1..1213
                           note = Encodes the peptide sequence at SEQ ID NO. 93
source                     1..1213
                           mol_type = other DNA
                           organism = Triticum aestivum
SEQUENCE: 91
acacggctgt ggtttcaatt ttatttcatc tctatccaat tgagtgatgg aacggctgag     60
agtagtggtg cctaattgcc tgagctgtat tgagttctga atattcatgt tcaaaaaatt    120
cctactacca tgcatagaag tctgaatatt tagcagaaaa tagcttggac atgggcagtc    180
taaaaatgat attcagtttc atacatgtga gactatgata cataggttct gcacaaagca    240
aggaggaaac cgatatgcaa tgagtggtta ggtgctgata ctggcagatt tttgtctgaa    300
tatctctggt aacccagcta cagattaaca atgcaggtgt aaacttcaac agaggagcag    360
ataactctgt tgaatttgca gagcaagtaa ttgagacaaa ttattttggt acaaagcgga    420
tgattgaagc catgctacca ttactgaaac cttctccgta tggtggccgg atagtgaatg    480
taagctcaag gcttggtagg gccaatggca ggcgcaataa aatcggcgat gcgatcctaa    540
gagagcaact attaactgat gattgcttat ctgaagaatt gatttgatgg gattgtcact    600
aaattccttg aacaagtgaa gcaaaatagt tggtcctcca ttgagtggcc tcagatgtac    660
acggactatt ctatytcaaa gcttgctgtt aatgtgtata caagactcat gctaagaggg    720
cttgctgaca ggtytgaagg ccaaaagatt tacattaact gtttctgtcc tggctgggta    780
aagactgcca tgactgattg ggaagggaac atttmagycg aagaaggtgc tgatactgga    840
gtgtggcttg mtctgttacc ccaggcacaa gcaacaattg gaaagttcta tgctgagaga    900
cgcgagataa gcttctgagg tgactagtct tgtccatact tttgctccag ctagacagta    960
acaagttgaa attttccata gttttgcccc cagctataag tagagaaaag ccatgaccca   1020
aggttcgtat gttcaaattg ctttgtgtta cttgcaccta ttggcataga agtgatacat   1080
gcttactttt atctatgtcc tcttaaaggg cttgtggttt gcttttttatt ttgcacgtta   1140
gctgaagagc agtagaactg agatgtgttc ccatttcctc tgatatttaa tgcagtaacg   1200
gatccatctt tct                                                      1213

SEQ ID NO: 92              moltype = DNA  length = 1212
FEATURE                    Location/Qualifiers
misc_feature               1..1212
                           note = Inplanta Sequence
misc_feature               1..1212
                           note = Encodes the peptide sequence at SEQ ID NO. 93
source                     1..1212
                           mol_type = other DNA
                           organism = Triticum aestivum
SEQUENCE: 92
acacggctgt ggtttcaatt ttatttcatc tctatccaat tgagtgatgg aacggctgag     60
agtagtggtg cctaattgcc tgagctgtat tgagttctga atattcatgt tcaaaaaatt    120
cctactacca tgcatagaag tctgaatatt tagcagaaaa tagcttggac atgggcagtc    180
taaaaatgat attcagtttc atacatgtga gactatgata cataggttct gcacaaagca    240
aggaggaaac cgatatgcaa tgagtggtta ggtgctgata ctggcagatt tttgtctgaa    300
tatctctggt aacccagcta cagattaaca atgcaggtgt aaacttcaac agaggagcag    360
ataactctgt tgaatttgca gagcaagtaa ttgagacaaa ttattttggt acaaagcgga    420
tgattgaagc catgctacca ttactgaaac cttctccgta tggtggccgg atagtgaatg    480
taagctcaag gcttggtagg gccaatggca ggcgcaataa aatcggcgat gcgatcctaa    540
gagagcaact attaactgat gattgcttat ctgaggaatt gattggtggg attgtcacta    600
aattccttga acaagtgaag caaaatagtt ggtcctccat tgagtggcct cagatgtaca    660
cggactatta tatctcaaag cttgctgtta atgtgtatac aagactcatg ctaagaggct    720
ttgctgacag gtctgaaggc caaaagattt acattaactg tttctgtcct ggctgggtaa    780
agactgccat gactgattgg gaagggaaca tttcagccga agaaggtgct gatactggag    840
tgtggcttgc tctgttaccc caggcacaag caacaattgg aaagttctat gctgagagac    900
gcgagataag cttctgaggt gactagtctt gtccatactt ttactccagc tagacagcta    960
caagttgaaa ttttccatag ttttgccccc agctataagt agagaaaagc catgacccaa   1020
ggttcgtatg ttcaaattgc tttgtgttac ttgcaccatt ggcatagaa gtgatacatg   1080
cttactttta tctatgtcct cttaaagggc ttgtggtttg cttttttatt tgcacgttag   1140
ctgaagagca gtagaactga gatgtgttcc catttcctct gatatttaat gcagtaacgg   1200
atccatcttt ct                                                       1212

SEQ ID NO: 93              moltype = AA  length = 165
FEATURE                    Location/Qualifiers
REGION                     1..165
                           note = misc_feature - Functional Homolog Of Ceres SEEDLINE
                             ID no.ME17294 at SEQ ID NO. 93
REGION                     1..165
                           note = misc_feature - Bit score of 449.7 for hmm based on
                             sequences of FIGURE 4.
source                     1..165
                           mol_type = protein
                           organism = Triticum aestivum
```

```
SEQUENCE: 93
MIEAMLPLLK PSPYGGRIVN VSSRLGRANG RRNKIGDAIL REQLLTDDCL SEELIGGIVT    60
KPLEQVKQNS WSSIEWPQMY TDYSISKLAV NVYTRLMAKR LADRSEGQKI YINCFCPGWV   120
KTAMTDWEGN ISAEEGADTG VWLALLPQAQ ATIGKFYAER REISF                  165

SEQ ID NO: 94           moltype = DNA  length = 1171
FEATURE                 Location/Qualifiers
misc_feature            1..1171
                        note = Ceres CLONE ID no.1831117
misc_feature            1..1171
                        note = Encodes the peptide sequence at SEQ ID NO 95
source                  1..1171
                        mol_type = other DNA
                        organism = Panicum virgatum
SEQUENCE: 94
ctcccacccg cgctcccagc acgcccaccg tcgcctaccc cgtctccagc tcgatggact     60
actcgagcac caaggagtta cctccggccg gggcctggtg gtcgagggag acgtggccg    120
tggtgacggg cgcgaaccgg ggcatcgggc acgccctcgc cgcggcgctg gcggagcag    180
ggctcaccgt ggtgctcacc gcgcgggacg cgcgcgcgcg ggaggccgcc gcggccccgc   240
tccgcgcgcg cgggctcgcc gtcgccttcc gcaggctcga cgtctccgac gccgcctccg   300
tcgccgagtt cgccgcctgg ctccgcgacg ccgtcggcgg cctcgacatc ctggtgaaca   360
acgccgccgt gtccttcaac gagatcgaca ccaactcgtt ggagcacgcc gagacggtcc   420
tccggaccaa cttctacggc gccaagatgc tcacggaagc gctcctgccg ctgttccggc   480
agtcccccggc caccagcagg atcctcaaca tcagctcgca gctcggcctt ctcaacaagg   540
tgagcgaccc gtccctgaag gcgttgctgc tggacgagga gaccctgacg gaggcggcga   600
tcgacgccat ggtgtcgcgg ttcctggcgc aggtgaagga cgggacgtgg ggcgcgcagg   660
gttggcccaa ggtgtggacg gactactcgg tctccaagct ggccctgaac gcctactccc   720
ggctgctggc gcggcggctg caggcgcgcg cgcccgcgt gagcgtcaac tgcttctgcc    780
ccgggttcac gcgcaccgac atgaccaggg gctgggggaa gcgcaccgcc gaggaggcgg   840
ccgacgtcgg cgcgcggctc gcgctgctgc cgccccgacg gctccccacg ggggccttct   900
tcaagtggtg cacgccgcag ccctactcca agctgtgacc tgccgagcca cgccgccggc   960
ccgcgcgccc cggccatggc ggccgcagga gtatgtagcg ttggtttagc tgcttctagt  1020
tactttcaat gcagacaaga agccgatcga gtagtgtctc ttagcagtct ggctttctgc  1080
caaggtgctt tggttgagca atgcaaccaa accatgtcag cgatcaatgt actatgcgtg  1140
cttagccgtg caagatttag gtcaacttcc g                                 1171

SEQ ID NO: 95           moltype = AA  length = 163
FEATURE                 Location/Qualifiers
REGION                  1..163
                        note = misc_feature - Ceres CLONE ID no.1831117
REGION                  1..163
                        note = misc_feature - Bit score of 411.8 for hmm based on
                         sequences of FIGURE 4.
REGION                  1..163
                        note = misc_feature - Functional Homolog Of Ceres SEEDLINE
                         ID no.ME17294 at SEQ ID NO. 93
source                  1..163
                        mol_type = protein
                        organism = Panicum virgatum
SEQUENCE: 95
MLTEALLPLF RQSPATSRIL NISSQLGLLN KVSDPSLKAL LLDEETLTEA AIDAMVSRFL    60
AQVKDGTWGA QGWPKVWTDY SVSKLALNAY SRLLARRLQA RGARVSVNCF CPGFTRTDMT   120
RGWGKRTAEE AADVGARLAL LPPGELPTGA FFKWCTPQPY SKL                    163

SEQ ID NO: 96           moltype = AA  length = 164
FEATURE                 Location/Qualifiers
REGION                  1..164
                        note = misc_feature - Public GI ID no.92871098
REGION                  1..164
                        note = misc_feature - Truncated
REGION                  1..164
                        note = misc_feature - Bit score of 389.1 for hmm based on
                         sequences of FIGURE 4.
REGION                  1..164
                        note = misc_feature - Functional Homolog Of Ceres SEEDLINE
                         ID no.ME17294 at SEQ ID NO. 93
source                  1..164
                        mol_type = protein
                        organism = Medicago truncatula
SEQUENCE: 96
MIEAMIPLMK PSAAGGRIVN VSSRLGRLNG KRNRIENEEL REKLSDVESL SEELIDETIN    60
NFLQQIEDGS WKTGGWPQTF TDYSVSKLAV NTYTRYMAKK LSDRPEGEKI YINCYCPGWV   120
KTALTGYAGS VTVEQGADTG VWIALVPDQE ITGKFFAERR EINF                   164

SEQ ID NO: 97           moltype = DNA  length = 1243
FEATURE                 Location/Qualifiers
misc_feature            1..1243
                        note = Ceres CLONE ID no.1844076
misc_feature            1..1243
```

```
                        note = Truncated
misc_feature            1..1243
                        note = Encodes the peptide sequence at SEQ ID NO 98
source                  1..1243
                        mol_type = other DNA
                        organism = Gossypium hirsutum
SEQUENCE: 97
atttcagtcc aataactttc ctagaccttα tttgcgtttc agctccgtgc atccatttac   60
tttctccttc tccattttga ctcgtcacct caaaattgcc ccacacctga aagacggagc  120
aaacactagg atatgtcagg gaaaaaggaa agaaacaagg agagaagaga aaagagactc  180
caagagattt cacttctcag gaccattcct tattctgatc atcaaaggtg gtggtcacaa  240
gaaactgttg cagttgtaac tggtgctaat agaggaatcg ggtttgagat tgcaagacaa  300
cttgccgggc atggattgac agtaatacta acatcaagga acattagtgt cggcattgat  360
gcaaccaagg ccttacaaga aggggtttc agttatgatg ttcatcagct tgatatcttg  420
gatggtgaat caatttcagc gtttgttgaa tggataaaac aaaaatacgg tggcattgat  480
atcctggtga ataatgcagg tgttaactac aacctcgggt tcgataattc tgtggaattc  540
gcacgacagg tagttgacac caattattat ggcactaaaa atatgattaa agcaatgata  600
ccagtaatga aaccttccac tgctggtgct cgtatcgtta atgtaagctc acggctaggc  660
agactaaacg gccgccgcaa tagaattcaa gatgcaactt tgagagaaaa actaactaat  720
ttggaaactc tctcagagga attgattgat agaacagtgt ctagtttctt acaacaagtt  780
gaagatgaaa cttggcaatc aggcggatgg cctcaaacat tcactgatta ctctgtatct  840
aaacttgctg tcaatgctta caccagactg gtggccaaga aactctgcga tcgaccacaa  900
ggcgaaaaga tatatatcaa ctgttattgt ccaggatggg tgaagactgc aatgacaggt  960
tgggcaggca atatttctcc tgaggttgca gctgacactg gagtcggct ttccttgctt  1020
tctgaccaag caataactgg aaagtttttt gcagagagac gagaaatcaa cttttgagta  1080
aattaagttc tgcattgtag agtcaaaaat ttgttctatt cttgaagatt cgatgaaaca  1140
gttgaaagta acttgtttta gaagcaattt ggcccatacg tagcaccaaa ctaaaaccga  1200
acatatgaat caatgctgct ttctgtctaa ccttaaaaga ccc                   1243

SEQ ID NO: 98           moltype = AA  length = 164
FEATURE                 Location/Qualifiers
REGION                  1..164
                        note = misc_feature - Ceres CLONE ID no.1844076
REGION                  1..164
                        note = misc_feature - Bit score of 438.0 for hmm based on
                          sequences of FIGURE 4.
REGION                  1..164
                        note = misc_feature - Truncated
REGION                  1..164
                        note = misc_feature - Functional Homolog Of Ceres SEEDLINE
                          ID no.ME17294 at SEQ ID NO. 93
source                  1..164
                        mol_type = protein
                        organism = Gossypium hirsutum
SEQUENCE: 98
MIKAMIPVMK PSTAGARIVN VSSRLGRLNG RRNRIQDATL REKLTNLETL SEELIDRTVS   60
SFLQQVEDET WQSGGWPQTF TDYSVSKLAV NAYTRLVAKE LCDRPQGEKI YINCYCPGWV  120
KTAMTGWAGN ISPEVAADTG VWLSLLSDQA ITGKFFAERR EINF                  164

SEQ ID NO: 99           moltype = DNA  length = 1167
FEATURE                 Location/Qualifiers
misc_feature            1..1167
                        note = Ceres CLONE ID no.35974
misc_feature            1..1167
                        note = Encodes the peptide sequence at SEQ ID NO 100
source                  1..1167
                        mol_type = other DNA
                        organism = Arabidopsis thaliana
SEQUENCE: 99
acacccaaac acgcgacgcg agcgaaagaa gacgatgacg aacaaggaga aagctcgaga   60
gagaagggag aaaaaaatgc aggagatctc tctccttcga actattcctt actctgacca  120
ccataggtgg tggtcttgtg aaaatgtagc agtagtgact ggttcaaacc gcgggattgg  180
attcgagatt gcaagacagc ttgcggttca cggattgacg gttgttctta cagctagaaa  240
cgtgaatgct ggtcttgaag cagttaaatc tttgaggcag caagaagaag gtctcaaggt  300
ttattttcat caacttgatg tcacagactc ttcctcgatt agagagtttg gttgctggct  360
taagcaaaca tttggaggtt tagatattct cgtgaataat gcaggtgtta actacaatct  420
cggctcagat aatacggttg aatttgctga acagttatat tctactaact accaaggaac  480
caaaaacatg acaaaaagcta tgatacccct gatgagacca tctccctcatg cgcctcgtgt  540
agtcaatgtt agttctcggc taggtagagt aaatgaagga cgtaatagac ttggcaaatgt  600
agagttgaga gatcagctaa gcagtccaga tttgctgacc gaggaactta tagacagaac  660
tgtctctaaa ttcatcaacc aagtaaaaga cggaacttgg aatcaggcg gtggcctca  720
gacattcact gactactcca tgtctaagct tgcagtcaat gcttacacga gactaatggc  780
aaaagaactt gagagacgag gagaggaaga gaagatttat gttaacagct tttgccctgg  840
ttgggtgaag gtcgcagtga ctggctacgc cggaaattga ccacctgaag atgcagctgg  900
tactggagtt tggcttagcc tggtcctttc cgaagagtca gtaaccgaa aattcttcgc  960
agagagacgt gagatcaact tctgagggtt gttgaatgtt tgtaaacgtt ggaatagatt  1020
gtgtcgtctt cgtttagtgc catagtttta gtcaaaggtt tacaaaatca attgtaattg  1080
gtaagtgaat ggttgtagtc atgatacgcg tcagatttgc cacaaaacta ggagtttata  1140
atttaaatat aattaatttt taattgc                                     1167
```

```
SEQ ID NO: 100          moltype = AA  length = 165
FEATURE                 Location/Qualifiers
REGION                  1..165
                        note = misc_feature - Ceres CLONE ID no.35974
REGION                  1..165
                        note = misc_feature - Bit score of 357.4 for hmm based on
                         sequences of FIGURE 4.
REGION                  1..165
                        note = misc_feature - Truncated
REGION                  1..165
                        note = misc_feature - Functional Homolog Of Ceres SEEDLINE
                         ID no.ME17294 at SEQ ID NO. 93
source                  1..165
                        mol_type = protein
                        organism = Arabidopsis thaliana
SEQUENCE: 100
MTKAMIPLMR PSPHGARVVN VSSRLGRVNG RRNRLANVEL RDQLSSPDLL TEELIDRTVS    60
KFINQVKDGT WESGGWPQTF TDYSMSKLAV NAYTRLMAKE LERRGEEEKI YVNSFCPGWV   120
KTAMTGYAGN MPPEDAADTG VWLSLVLSEE SVTGKFFAER REINF                  165

SEQ ID NO: 101          moltype = AA  length = 165
FEATURE                 Location/Qualifiers
REGION                  1..165
                        note = misc_feature - Public GI ID no.110737329
REGION                  1..165
                        note = misc_feature - Bit score of 355.4 for hmm based on
                         sequences of FIGURE 4.
REGION                  1..165
                        note = misc_feature - Functional Homolog Of Ceres SEEDLINE
                         ID no.ME17294 at SEQ ID NO. 93
source                  1..165
                        mol_type = protein
                        organism = Arabidopsis thaliana
SEQUENCE: 101
MTKAMIPLMR PSPHGARVVN VSSRLGRVNG RRNRLANVEL RDQLSSPDLL TEELIDRTVS    60
KFINQVKDGT WESGGWPQTF TDYPMSKLAV NAYTRLMAKE LERRGEEEKI YVNSFCPGWV   120
KTAMTGYAGN MPPEDAADTG VWLSLVLSEE AVTGKFFAER REINF                  165

SEQ ID NO: 102          moltype = AA  length = 167
FEATURE                 Location/Qualifiers
REGION                  1..167
                        note = misc_feature - Public GI ID no.10176876
REGION                  1..167
                        note = misc_feature - Bit score of 316.9 for hmm based on
                         sequences of FIGURE 4.
REGION                  1..167
                        note = misc_feature - Truncated
REGION                  1..167
                        note = misc_feature - Functional Homolog Of Ceres SEEDLINE
                         ID no.ME17294 at SEQ ID NO. 93
source                  1..167
                        mol_type = protein
                        organism = Arabidopsis thaliana
SEQUENCE: 102
MTKAMIPLMR PSPHGARVVN VSSRLENLVE IHELQRLANV ELRDQLSSPD LLTEELIDRT    60
VSKFINQVKD GTWESGGWPQ TFTDYSMSKL AVNAYTRLMA KELERRGEEE KIYVNSFCPG   120
WVKTAMTGYA GNMPPEDAAD TGVWLSLVLS EEAVTGKFFA ERREINF                167

SEQ ID NO: 103          moltype = DNA  length = 1164
FEATURE                 Location/Qualifiers
misc_feature            1..1164
                        note = Ceres CLONE ID no.473040
misc_feature            1..1164
                        note = Encodes the peptide sequence at SEQ ID NO 104
source                  1..1164
                        mol_type = other DNA
                        organism = Glycine max
SEQUENCE: 103
acttcttaaa actggtatct gatttacaaa aggttacaaa cttctcttgc ataaagaatg    60
gcatcagcaa caataaggaa tgcagttgtc acgggagcaa acaagggat aggatttgga   120
atatgcaagc aattggtttc taatggcatc acagtggtgc taacagcaag ggatgagaaa   180
aggggtcttg aagctgttga aaagctgaaa gagtttggtg tgtctgatca agtggtgttt   240
catcagcttg atgtgactga ccctaaaagc attgaatgct ttgcaaattt catcaaaacc   300
cagtttggaa aacttgatat cttggtgaat aatgcaggaa ttcatggagc atatgttgac   360
cgtgatgctt tagctgctgc tggggaaaaa gttgccaatg ttgattggag aaaaatctca   420
actgaaaatt ttgaagctgc cgaagcaggc attagaacaa attactatgg agtcaaatta   480
atgtgtgaag cacttattcc ccttctagaa ttgtcaggca caccaaggat tgtcaatgtt   540
tcctcctcca tggggaagtt ggagaaaata ccaaatgcat gggctagagg agccctaagt   600
```

```
gatgctgaga gcctaacaga agaaaaggtg gatgaggttt tgaatcagtt tctaaaagat    660
tttaaagagg gttcattaga aaccaaaggg tggccacatg ctttttctgc atatatagtc    720
tcaaaagctg ctttgactgc ctacacaagg attcttgcta agaagtaccc atctttctgc    780
atcaatgctg tttgccctgg ctttgtgaaa acagatctca actacaatac tggctatctt    840
agtgttgatg aaggtgctga aagtgttgta aggttggctc tgctacctaa tggaggtcct    900
tctggtctat tcttttctcg aagtgaagtg gcaccattct gatccaaaga ctgttgtgta    960
cttgaagagg ataaataata agcatggttt catgataaga catgtatcaa atttgtacct   1020
agcacaacaa gaaaataagc cacatgtctg atcactgatg gctgcccatc attgatgaga   1080
acaaccctat agtgaattct agatattaca atgacattac taatttgaga aatctaattt   1140
tggatataaa gatatctgtt tgtc                                          1164

SEQ ID NO: 104          moltype = AA  length = 153
FEATURE                 Location/Qualifiers
REGION                  1..153
                        note = misc_feature - Ceres CLONE ID no.473040
REGION                  1..153
                        note = misc_feature - Bit score of 360.8 for hmm based on
                          sequences of FIGURE 4.
REGION                  1..153
                        note = misc_feature - Truncated
REGION                  1..153
                        note = misc_feature - Functional Homolog Of Ceres SEEDLINE
                          ID no.ME17294 at SEQ ID NO. 93
source                  1..153
                        mol_type = protein
                        organism = Glycine max
SEQUENCE: 104
MCEALIPLLE LSGTPRIVNV SSSMGKLEKI PNAWARGALS DAESLTEEKV DEVLNQFLKD    60
FKEGSLETKG WPHAFSAYIV SKAALTAYTR ILAKKYPSFC INAVCPGFVK TDLNYNTGYL   120
SVDEGAESVV RLALLPNGGP SGLFFSRSEV APF                                153

SEQ ID NO: 105          moltype = DNA  length = 2073
FEATURE                 Location/Qualifiers
misc_feature            1..2073
                        note = Ceres CLONE ID no.922223
misc_feature            1..2073
                        note = Encodes the peptide sequence at SEQ ID NO 106
source                  1..2073
                        mol_type = other DNA
                        organism = Triticum aestivum
SEQUENCE: 105
gtaaacaagc ccatggactc ttattttctc tttatgttgg gcttaatgtt cttggggcta     60
tggttccgag ttctcaaaaa aaaaagttcg attccggcga acacagtaca gcagagggag    120
cgagagatgg ggaagaaggg caaggcggcg gcaaggagc gccggggagga gcggcggcgg    180
gaagtcacgc tcctccgcgc cgtaccctac gagcccacc agcggtggtg ggacggcctc    240
gcgccggcgc gcgccgtggc ggtggtgacg ggggccagcc gcggcatcgg ctacgagatc    300
tcccgccagc tcgcgcgcca cggcctccac gtcgtcctcg cctcgcgcga gcccgccggg    360
ggcagggacg ccgcggaggg gatcctccgc gaggagggca cgagcgcgga gtggcggcag    420
ctcgacgtgg cggacgccgc gtcggtcgag gccttcgccg cctggacggc gcggacccac    480
ggcggcatcc atgtccttat taacaatgca ggtgtaaact tcaacagagg agcagataac    540
tctgttgaat ttgcagagca agtaattgag acaaattatt ttggtacaag gcggatgatt    600
gaagccatgc taccattact gaaaccttct ccgtatggtg gccggatagt gaatgtgagc    660
tcaaggcttg gcagggccaa tggcagacgc aataaaatcg gcgatgcgat cctaagagag    720
caactattaa ctgatgattg cttatctgag gaattgattg atgggatggt cactaaattc    780
cttgaacaag tgaagcaaaa tagttggtcc tccattgagt ggcctcagat gtacacggac    840
tattcggtct caaagtttgc tgttaatgtg tatacaagac tcatggcaag gaggttatct    900
gacaggtctg aaggccaaaa gatttacatt aactgtttct gtcctggctg ggtaaagact    960
gccatgactg attgggaagg gaacatttca gccgaagaag tgctgatac tggagtgtgg   1020
cttgctctgt taccccagga acaagcaaca attggaaagt tctatgctga gagacgcgag   1080
ataagcttct gaggtgatcg gaatggtgga tatgcgagtg ggagtggtac atttaaccat   1140
atgtatttaa ttaaagtttt aaactatgta ggtgatcgga atggtggata tgcgagtggg   1200
agtggcatgt tcatgaagag caatccacat gattggcaga ctccagcatg ttttcgagt   1260
cgcgactcat gcgagttgct ctggggcagc gactcggaag aagtcgagcc tgcgttgtga   1320
ctagtcatga ctcagagtcg cgagtcgata taagctgag ttgaccatat ttttgcgact   1380
catagactag tcgtcgacta gtcgcaacta gtcgagcgac tcgaaatcca tggactccag   1440
tcggtcaaag agcattgagt cttcacactg atggaaggcc atgctctcta attttgtcaa   1500
taaatgatgc agtaccagat gctttcgac gatactcaga cgacgttgcc catcagaccg   1560
tttgttaatt agattcacgt caatctcatg gtgtagagtc tgcgtcggct gcacatcggc   1620
cataccatgt cgtgtgtaca tcaatttcgt gaagttgctg gaaacaggga aatgttcacc   1680
aggcccacca ccactagtcc acaacgcag taagcaggca tggcatgctg gactgctgca   1740
ccgaatatat gattaggctg gatccaagc aactccactg tcagattctc tcattatctt   1800
ccaagtagag gtgaatcct tatgacccaa tggatgagag cgatgcaacg ctgcctcacc   1860
cacgcatgca gaagatcgat atgtttggga acgaaccggg cggcctacct tgggaattct   1920
ggagctataa tcatggctag gccgccattc atggaccgga gactacatgt cttgcagtat   1980
attgttctga ttttgccgcc acctgcatat gtgctggtaca tactttgtta tgttcgtgtt   2040
tgtatgcaat ggttggatcg tgtgatttgc tgg                                2073

SEQ ID NO: 106          moltype = AA  length = 165
FEATURE                 Location/Qualifiers
```

| | |
|---|---|
| REGION | 1..165 |
| | note = misc_feature - Ceres CLONE ID no.922223 |
| REGION | 1..165 |
| | note = misc_feature - Bit score of 455.9 for hmm based on sequences of FIGURE 4. |
| REGION | 1..165 |
| | note = misc_feature - Truncated |
| REGION | 1..165 |
| | note = misc_feature - Functional Homolog Of Ceres SEEDLINE ID no.ME17294 at SEQ ID NO. 93 |
| source | 1..165 |
| | mol_type = protein |
| | organism = Triticum aestivum |
| SEQUENCE: 106 | |

```
MIEAMLPLLK PSPYGGRIVN VSSRLGRANG RRNKIGDAIL REQLLTDDCL SEELIDGMVT   60
KFLEQVKQNS WSSIEWPQMY TDYSVSKFAV NVYTRLMARR LSDRSEGQKI YINCFCPGWV  120
KTAMTDWEGN ISAEEGADTG VWLALLPQEQ ATIGKFYAER REISF                 165
```

| | |
|---|---|
| SEQ ID NO: 107 | moltype = AA   length = 166 |
| FEATURE | Location/Qualifiers |
| REGION | 1..166 |
| | note = misc_feature - Public GI ID no.125528967 |
| REGION | 1..166 |
| | note = misc_feature - Bit score of 452.6 for hmm based on sequences of FIGURE 4. |
| REGION | 1..166 |
| | note = misc_feature - Truncated |
| REGION | 1..166 |
| | note = misc_feature - Functional Homolog Of Ceres SEEDLINE ID no.ME17294 at SEQ ID NO. 93 |
| source | 1..166 |
| | mol_type = protein |
| | note = subspecies = indica |
| | organism = Oryza sativa |
| SEQUENCE: 107 | |

```
MIEAMMPLMI TSPHGGRIVN VSSRLGRVNG RRNRIGDPSL RERLLNDDHL SEELINEMVM   60
KFLEQTKQDN WSSSNEWPQM YTDYSISKLA VNAYTRLLAR RLLDRPEGQK IYINCFCPGW  120
VKTAMTGWEG NISAEEGADT GVWLALVPQE QATIGKFFAE RREISF                166
```

| | |
|---|---|
| SEQ ID NO: 108 | moltype = AA   length = 158 |
| FEATURE | Location/Qualifiers |
| REGION | 1..158 |
| | note = misc_feature - Public GI ID no.115442007 |
| REGION | 1..158 |
| | note = misc_feature - Truncated |
| REGION | 1..158 |
| | note = misc_feature - Bit score of 417.1 for hmm based on sequences of FIGURE 4. |
| REGION | 1..158 |
| | note = misc_feature - Functional Homolog Of Ceres SEEDLINE ID no.ME17294 at SEQ ID NO. 93 |
| source | 1..158 |
| | mol_type = protein |
| | note = subspecies = japonica |
| | organism = Oryza sativa |
| SEQUENCE: 108 | |

```
MITSPHGGRI VNVSSRLGRV NGRRNRIGDP SLRERLLNDD HLSEELINEM VMKFLEQTKQ   60
DNWSSGNEWP QMYTDYSISK LAVNAYTRLL ARRLLDRPEG QKIYINCFCP GWVKTAMTGW  120
EGNISAEEGA DTGVWLALVP QEQATIGKFF AERREISF                         158
```

| | |
|---|---|
| SEQ ID NO: 109 | moltype = DNA   length = 951 |
| FEATURE | Location/Qualifiers |
| misc_feature | 1..951 |
| | note = Ceres ANNOT ID no.857222 |
| misc_feature | 1..951 |
| | note = Encodes the peptide sequence at SEQ ID NO 110 |
| source | 1..951 |
| | mol_type = other DNA |
| | organism = Arabidopsis thaliana |
| SEQUENCE: 109 | |

```
atgacgaaca aggagaaagc tcgagagaga agggagaaaa gaatgcagga gatctctctc   60
cttcgaacta ttccttactc tgaccaccat aggtggtggt cttgtgaaaa tgtagcagta  120
gtgactggtt caaaccgcgg gattggattc gagattgcaa acagcttgc ggttcacgga   180
ttgacggttg ttcttacagc tagaaacgtg aatgctggtc ttgaagcagt taaatctttg  240
aggcaccaag aagaaggtct caaggtttat tttcatcaac ttgatgtcac agactcttcg  300
tcgattagag agtttggttg ctggcttaag caaacatttg gaggtttaga tattctcgtg  360
aataatgcag gtgttaacta caatctcggc tcagataata cggttgaatt tgctgaaaca  420
gttatatcta ctaactacca aggaaccaaa aacatgacaa agctatgat  acccttgatg   480
agaccatctc ctcatggcgc tcgtgtagtc aatgttagtt ctcggctagg tagagtaaat  540
```

-continued

```
ggaagacgta ataqactggc aaatgtagag ttgagagatc agctaagcag tccagatttg  600
ctgaccgagg aacttataga cagaactgtc tctaaattca tcaaccaagt aaaagacgga  660
acttgggaat caggcgggtg gcctcagaca ttcactgact actccatgtc taagcttgca  720
gtcaatgctt acacgagact aatggcaaaa gaacttgaga gacgaggaga ggaagagaag  780
atttatgtta acagcttttg ccctggttgg gtgaagacta cgatgactgg ctacgccgga  840
aatatgccac ctgaagatgc agctgatact ggagtttggc ttagcctggt ccttccgaa   900
gaggcagtaa ccggaaaatt cttcgcagag acgtgaga  tcaacttctg a            951
```

SEQ ID NO: 110            moltype = AA   length = 165
FEATURE                   Location/Qualifiers
REGION                    1..165
                          note = misc_feature - Ceres ANNOT ID no.857222
REGION                    1..165
                          note = misc_feature - Truncated
REGION                    1..165
                          note = misc_feature - Bit score of 401.6 for hmm based on
                            sequences of FIGURE 4.
REGION                    1..165
                          note = misc_feature - Functional Homolog Of Ceres SEEDLINE
                            ID no.ME17294 at SEQ ID NO. 93
source                    1..165
                          mol_type = protein
                          organism = Arabidopsis thaliana
SEQUENCE: 110
MTKAMIPLMR PSPHGARVVN VSSRLGRVNG RRNRLANVEL RDQLSSPDLL TEELIDRTVS   60
KPINQVKDGT WESGGWPQTF TDYSMSKLAV NAYTRLMAKE LERRGEEEKI YVNSFCPGWV  120
KTAMTGYAGN MPPEDAADTG VWLSLVLSEE AVTGKFFAER REINF                  165

SEQ ID NO: 111            moltype = DNA   length = 557
FEATURE                   Location/Qualifiers
misc_feature              1..557
                          note = Ceres SEEDLINE ID no. ME00572
misc_feature              1..557
                          note = Inplanta Sequence
source                    1..557
                          mol_type = other DNA
                          organism = Arabidopsis thaliana
SEQUENCE: 111
atcccaccgt ttcttaagac tctctctctc tttctgtttt ctatttctct ctctctcaaa   60
tgaaagagag agaagagctc ccatggatga aaatagcgag accgaagttt ctccaaggca  120
ttaaggaaaa cataacctcc gtgatgcata gagattattg gatccgctgt gctgagacat  180
tgagtttttc ttcggcattc cagtttcaat gataaagggg tgttatccta tctgagcttt  240
tagtcggatt ttttcttttc aattattgtg ttttatctag atgatgcatt tcattattct  300
cttttttcttg accttgtaag gccttttctt gaccttgtaa gaccccatct ctttctaaac  360
gttttattat tttctcgttt tacagattct attctatctc ttctcaatat agaatagata  420
tctatctcta cctctaattc gttcgagtca ttttctccta ccttgtctat ccctcctgag  480
ctaatctcca catatatctt ttgtttgtta ttgatgtatg gttgacataa attcaataaa  540
gaagttgacg ttttttcc                                                557

SEQ ID NO: 112            moltype = AA   length = 859
FEATURE                   Location/Qualifiers
REGION                    1..859
                          note = misc_feature - Ceres LOCUS ID no. AT5G62000
REGION                    1..859
                          note = misc_feature - Is Acted Upon By Ceres SEEDLINE ID
                            no. ME00572 at SEQ ID NO. 111
REGION                    1..859
                          note = misc_feature - Bit score of 2157.8 for hmm based on
                            sequences of FIGURE 5.
REGION                    163..268
                          note = misc_feature - Pfam Name: B3 Pfam Description: B3
                            DNA binding domain
REGION                    290..372
                          note = misc_feature - Pfam Name: Auxin_resp Pfam
                            Description: Auxin response factor
source                    1..859
                          mol_type = protein
                          organism = Arabidopsis thaliana
SEQUENCE: 112
MASSEVSMKG NRGGDNFSSS GFSDPKETRN VSVAGEGQKS NSTRSAAAER ALDPEAALYR   60
ELWHACAGPL VTVPRQDDRV FYFPQGHIEQ VEASTNQAAE QQMPLYDLPS KLLCRVINVD  120
LKAEADTDEV YAQITLLPEA NQDENAIEKE APLPPPPRFQ VHSFCKTLTA SDTSTHGGFS  180
VLRRHADECL PPLDMSRQPP TQELVAKDLH ANEWRFRHIF RGQPRRHLLQ SGWSVFVSSK  240
RLVAGDAFIF LRGENGELRV GVRRAMRQQG NVPSSVISSH SMHLGVLATA WHAISTGTMF  300
TVYYKPRTSP SEFIVPFDQY MESVKNNYSI GMRFKMRFEG EEAPEQRFTG TIVGIEESDP  360
TRWPKSKWRS LKVRWDETSS IPRPDRVSPW KVEPALAPPA LSPVPMPRPK RPRSNIAPSS  420
PDSSMLTREG TTKANMDPLP ASGLSRVLQG QEYSTLRTKH TESVECDAPE NSVVWQSSAD  480
DDKVDVVSGS RRYGSENWMS SARHEPTYTD LLSGFGTNID PSHGQRIPFY DHSSSPSMPA  540
KRILSDSEGK FDYLANQWQM IHSGLSLKLH ESPKVPAATD ASLQGRCNVK YSEYPVLNGL  600
```

```
STENAGGNWP IRPRALNYYE EVVNAQAQAQ AREQVTKQPF TIQEETAKSR EGNCRLFGIP   660
LTNNMNGTDS TMSQRNNLND AAGLTQIASP KVQDLSDQSK GSKSTNDHRE QGRPFQTNNP   720
HPKDAQTKTN SSRSCTKVHK QGIALGRSVD LSKFQNYEEL VAELDRLFEF NGELMAPKKD   780
WLIVYTDEEN DMMLVGDDPW QEFCCMVRKI FIYTKEEVRK MNPGTLSCRS EEEAVVGEGS   840
DAKDAKSASN PSLSSAGNS                                                859

SEQ ID NO: 113           moltype = DNA   length = 2538
FEATURE                  Location/Qualifiers
misc_feature             1..2538
                         note = Ceres ANNOT ID no.1527370
misc_feature             1..2538
                         note = Encodes the peptide sequence at SEQ ID NO. 114
source                   1..2538
                         mol_type = other DNA
                         organism = Populus balsamifera
                         sub_species = trichocarpa
SEQUENCE: 113
atggcttctt cagagatttc agcgaaagct aacagtggaa acattagagg aggaggagag    60
agcttcactt ctggttacag tgaagccatg gaagggcaga aaaatcattc tactcatcca   120
agttcagcta gagttgtaga tgctgaaacg gcgctgtata atgagctatg gcatgcttgt   180
gctggtcctt tagtgactgt acctcgtgaa ggagatcgtg tgttttattt ccctcaagga   240
catatagagc aggtggaggc atcaacgaat caggtagcac accagcagat gccgctgtat   300
aatcttctac cgaagatctt atgtcgtgtg gttaatgttc agttgaaggc tgaaccagat   360
actgatgagg tgtttgcgca agtgactctg cttcctgagc acaaccaaga tgagagtgtg   420
ttggagaagg agcctcctcc acctccacca ccgcgatttc atgtacattc attttgtaaa   480
accctgactg cttcggatac cagtactcat ggtggatttt cggttcttag aagacatgca   540
gatgaatgtc ttccacctt ggatatgtca aggcagcctc caacacagga attggttgcc   600
aaggatttgc atggaaatga atggcgtttc cgacacattt tcggggcca accacgagg    660
cacttgcttc agagtggatg gagcgtgttt gttagctcca aaaggcttgt tgcgggtgat   720
gcgtttatat ttctaagagg tgagaatgga gaacttcgag tgtgttag acgtgcaatg    780
agacagcagg gtaatgttcc atcatctgtc atatccagcc acagcatgca tcttggggtg   840
cttgctacag catggcatgc tgtttcaacg gggaccctgt tcactgttta ttacaagcca   900
aggacaagtc ctgcagagtt cattgtcccc tttgatcaat acatggagtc tgtcaagaat   960
aattattcca tagggatgag gttaaaatg agatttgaag gagaagaagc tcctgagcag  1020
agatttactg gcactattgt tggaattgaa gatgccgatc ccgggaggtg gaagaattct  1080
aaatggaggt gccttaaggt gagatgggat gaaacttcta ccatgcctcg gccagagaga  1140
gtttcaccat ggaaaattga gcctgctcta gcacctcctg cactaaatcc tcttccattg  1200
cccaggccta aaaggcctcg agcaaacatg gtgccctcat cccctgactg ctcagttctt  1260
actagaagtg accctccatc agcaggtgga ttttcaaggg tcttgcaagg tcaagaattc  1320
tcgaccttga gaggcacttt tgcagagagc aatgagtcca atgctgctga aaagtctgtt  1380
atgtggccat cctcagcaga tgatgagaag atcgatgtgt tatctacttc aagaagattt  1440
ggatcagaga ggtggatgtc ctctgcgagg catgaaccaa cctgcacaga tttgctatct  1500
ggctttggga caaattctga ttcattccat gggtttggtt ccccgtttgt tgaccaaact  1560
gccgtggctg ctaatccaac gaagaaacac ttgtcagatc aagggcagtt taacttgctt  1620
gccagcccgt ggtccataat gtcctcgggt ctcttgctaa agttgtcaga gtcaaataca  1680
aaggttccga tacaaggcag cgatgtaaca tatcaagcac gggcaaatgt gtttagtgag  1740
tatcctgtgc ttcaaggtca tagagttgag cagtcgcata aaaactggat gatgcatccc  1800
ccgccatctc atttttgataa tcatgctaat tcgagagagt taatgcccaa acctgttttg  1860
atgcaagaac atgattctgg aaaatccctg aaggaaact gcaagctctt tgggattcct   1920
ttgaaaatta gtaaacctgt tgcaccagag gcagcaggga ccacaatcac gatgaacgaa  1980
ccactgagtc atatccaacc tgtgagtcac caacttacat tgaatctga tcagaagtca   2040
gaacaatcca aaggtcgaa gatgactgat gaaaatgaaa acgagaaacc attccaagct   2100
ggtcatttgc gaacaaagga caaccatgga aaagcacaaa atggctcaac caggagttgt  2160
acgaaggttc acaagcaggg gattgcactt ggtaggtctg ttgatcttgc caagttcaat   2220
aactatgatg agttgattgc tgaattggac aggctgtttg aatttaatgg tgaattaatg   2280
gctccccaaa agaattggct gattgtgtac acagacgatg aggatgatat gatgcttgtt   2340
ggagatgatc cctggcagga atttgttggc atggttagga atagttat ttacaccaaa    2400
gaggaggcac agaagattaa accaggcgcc ttgaattcaa agggcgttga aatccaatg   2460
gatatggagg gtgaggatga tgccaaggaa gccaaacatc tgccacttcc ttcagcatgt   2520
agccctatga attgttag                                                2538

SEQ ID NO: 114           moltype = AA    length = 845
FEATURE                  Location/Qualifiers
REGION                   1..845
                         note = misc_feature - Ceres ANNOT ID no.1527370
REGION                   1..845
                         note = misc_feature - Bit score of 2089.3 for hmm based on
                         sequences of FIGURE 5.
REGION                   157..262
                         note = misc_feature - Pfam Name: B3 Pfam Description: B3
                         DNA binding domain
REGION                   284..366
                         note = misc_feature - Pfam Name: Auxin_resp Pfam
                         Description: Auxin response factor
REGION                   1..845
                         note = misc_feature - Is Acted Upon By Ceres SEEDLINE ID
                         no. ME00572 at SEQ ID NO. 111
source                   1..845
                         mol_type = protein
```

```
                        note = subspecies = trichocarpa
                        organism = Populus balsamifera
SEQUENCE: 114
MASSEISAKA NSGNIRGGGE SFTSGYSEAM EGQKNHSTHP SSARVVDAET ALYNELWHAC  60
AGPLVTVPRE GDRVFYFPQG HIEQVEASTN QVADQQMPLY NLLPKILCRV VNVQLKAEPD 120
TDEVFAQVTL LPEHNQDESV LEKEPPPPPP PRFHVHSFCK TLTASDTSTH GGFSVLRRHA 180
DECLPPLDMS RQPPTQELVA KDLHGNEWRF RHIFRGQPRR HLLQSGWSVF VSSKRLVAGD 240
AFIFLRGENG ELRVGVRRAM RQQGNVPSSV ISSHSMHLGV LATAWHAVST GTLFTVYYKP 300
RTSPAEFIVP FDQYMESVKN NYSIGMRFKM RFEGEEAPEQ RFTGTIVGIE DADPGRWKNS 360
KWRCLKVRWD ETSTMPRPER VSPWKIEPAL APPALNPLPL PRPKRPRANM VPSSPDSSVL 420
TRDDPPSASG FSRVLQGQEF STLRGTFAES NESNAAEKSV MWPSSADDEK IDVLSTSRRF 480
GSERWMSSAR HEPTCTDLLS GFGTNSDSFH GFGAPFVDQT AVAANPTKKH LSDQGQFNLL 540
ASPWSIMSSG LLLKLSESNT KVPVQGSDVT YQARANVFSE YPVLQGHRVE QSHKNWMMHP 600
PPSHFDNHAN SRELMPKPVL MQEHDSGKSL EGNCKLFGIP LKISKPVAPE AAGTTITMNE 660
PLSHIQPVSH QLTFESDQKS EQSKGSKMTD ENENEKPFQA GHLRTKDNHG KAQNGSTRSC 720
TKVHKQGIAL GRSVDLAKFN NYDELIAELD RLFEFNGELM APQKNWLIVY TDDEDDMMLV 780
GDDPWQEFVG MVRKIVIYTK EEAQKIKPGA LNSKGVENPM DMEGEDDAKE AKHLPLPSAC 840
SPMNC                                                            845

SEQ ID NO: 115          moltype = DNA  length = 2637
FEATURE                 Location/Qualifiers
misc_feature            1..2637
                        note = Ceres ANNOT ID no.1473961
misc_feature            1..2637
                        note = Encodes the peptide sequence at SEQ ID NO. 116
source                  1..2637
                        mol_type = other DNA
                        organism = Populus balsamifera
                        sub_species = trichocarpa
SEQUENCE: 115
atggcttctt cagagatttc agcgaaagct aacagtggaa acattagagg aggaggagag   60
agcttcactt ctggttacag tgaagccatg gaagggcaga aaaatcattc tactcatcca  120
agttcagcta gagttgtaga tgctgaaacg gcgctgtata tgagctatg gcatgcttgt  180
gctgtccttt tagtgactgt acctcgtgaa ggagatcgtg tgttttattt ccctcaagga  240
catatagagc aggtggaggc atcaacgaat caggtagcag accagcagat gccgctgta   300
aatcttctac gaagatcttt atgtcgtgtg ttaatgttc agttgaaggc tgaaccagat  360
actgatgagg tgtttgcgca agtgactctg cttcctgagc acaaccaaga tgagagtgtg  420
ttggagaagg agcctcctcc acctccacca ccgcgatttc atgtacattc attttgtaaa  480
accctgactc cttcggatac cagtactcat ggtgatttct cggttcttag aagacatgca  540
gatgaatgtc ttccaccttt ggatatgtca aggcagcctc caacacagga attggttgcc  600
aaggatttgc atggaaatga atggcgtttc gacacatttt tcgggggtaa tcatctcata  660
ctcgaacaat caacttgcat tcaagatgcc agttgcttaa tatgcacaat gatttcaatg  720
ccaggccaac cacggaggca cttgcttcag agtggatgga gcgtgtttgt tagctccaaa  780
aggcttgttg cgggtgatgc gtttatattt ctaagaggtg agaatggaga acttcgagtt  840
ggtgttagac gtgcaatgag acagcagggt aatgttccat catctgtcat atccagccac  900
agcatgcatc ttggggtgct tgctacagca tggcatgctg tttcaacggg gaccctgttc  960
actgtttatt acaagccaag gacaagtcct gcagagttca ttgtccccct tgatcaatac 1020
atggagtctg tcaagaataa ttattccata gggatgaggt ttaaaatgag atttgaagga 1080
gaagaagctc ctgagcaaag atttactggc actattgttg gaattgaaga tgccgatccc 1140
gggaggtgga agaattctaa atggaggtgc cttaaggtga gatgggatga acttctacc  1200
atgcctcgac cagagagagt ttcaccatgg aaaattgagc ctgctctagc acctcctgca 1260
ctaaatcctc ttccattgcc caggcctaaa aggcctcgag caaacatggt gccctcatcc 1320
cctgactcct cagttcttac tagagatggt tcattcaaag taactgcaga ccctccatca 1380
gcaagtggat tttcaagggt cttgcaaggt caagaattct cgaccttgag aggcactttt 1440
gcagagagca atgagtccaa tgctgctgaa aagtctgtta tgtggccatc ctcagcagat 1500
gatgagaaga tcgatgtgtt atctacttca agaagatttg gatcagagag gtggatgtcc 1560
tctgcgaggc atgaaccaac ctgcacagat ttgctatctg gctttgggac aaattctgat 1620
tcattccatg ggtttggtgc cccgtttgtt gaccaaactg ccgtggctgc taatccaacg 1680
aagaaacact tgtcagatca agggcagttt aacttgcttg ccagcccgtg gtccataatg 1740
tcctcgggtc tcttgctaaa gttgtcagag tcaaatacaa aggttccagt acaaggcagc 1800
gatgtaacat atcaagcacg ggcaaatgtg tttagtgagt atcctgtgct tcaaggtcat 1860
agagttgagc agtcgcataa aaactggatg atgcatcccc cgccatctca ttttgataat 1920
catgctaatt cgagagagtt aatgcccaaa cctgttttga tgcaagaaca tgattctgga 1980
aaatccctgg aaggaaactg caagctctt gggattcctt tgaaaattag taaacctgtt 2040
gcaccagagg cagcagggac cacaatcacg atgaacgaac cactgagtca tatccaacct 2100
gtgagtcacc aacttacatt tgaatctgat cagaagtcag aacaatccaa aggttcgaag 2160
atgactgatg aaaatgaaaa cgagaaacca ttccaagctg tcatttgcg aacaaaggac 2220
aaccatggaa aagcacaaaa tggctcaacc aggagttgta cgaaggttca caagcagggg 2280
attgcacttg gtaggtctgt tgatcttgcc aagttcaata actatgatga gttgattgct 2340
gaattggaca ggctgtttga atttaatggt gaattaatgg ctccccaaaa gaattggctg 2400
attgtgtaca cagacgatga ggatgatatg atgcttgttg gagatgatcc ctggcaggaa 2460
tttgttggca tggttaggaa gatagttatt tacaccaaag aggaggcaca gaagattaaa 2520
ccaggcgcct tgaattcaaa gggcgttgag aatccaatgg atatggaggg tgaggatgat 2580
gccaaggaag ccaaacatct gccacttcct tcagcatgta gccctatgaa ttgttag    2637

SEQ ID NO: 116          moltype = AA  length = 852
FEATURE                 Location/Qualifiers
REGION                  1..852
                        note = misc_feature - Ceres ANNOT ID no.1473961
```

```
REGION              1..852
                    note = misc_feature - Bit score of 2110.3 for hmm based on
                      sequences of FIGURE 5.
REGION              157..262
                    note = misc_feature - Pfam Name: B3 Pfam Description: B3
                      DNA binding domain
REGION              284..366
                    note = misc_feature - Pfam Name: Auxin_resp Pfam
                      Description: Auxin response factor
REGION              1..852
                    note = misc_feature - Is Acted Upon By Ceres SEEDLINE ID
                      no. ME00572 at SEQ ID NO. 111
source              1..852
                    mol_type = protein
                    note = subspecies = trichocarpa
                    organism = Populus balsamifera
SEQUENCE: 116
MASSEISAKA NSGNIRGGGE SFTSGYSEAM EGQKNHSTHP SSARVVDAET ALYNELWHAC   60
AGPLVTVPRE GDRVFYFPQG HIEQVEASTN QVADQQMPLY NLLPKILCRV VNVQLKAEPD  120
TDEVFAQVTL LPEHNQDESV LEKEPPPPPP PRFHVHSFCK TLTASDTSTH GGFSVLRRHA  180
DECLPPLDMS RQPPTQELVA KDLHGNEWRF RHIFRGQPRR HLLQSGWSVF VSSKRLVAGD  240
AFIFLRGENG ELRVGVRRAM RQQGNVPSSV ISSHSMHLGV LATAWHAVST GTLFTVYYKP  300
RTSPAEFIVP FDQYMESVKN NYSIGMRFKM RFEGEEAPEQ RFTGTIVGIE DADPGRWKNS  360
KWRCLKVRWD ETSTMPRPER VSPWKIEPAL APPALNPLPL PRPKRPRANM VPSSPDSSVL  420
TRDGSFKVTA DPPSASGFSR VLQGQEFSTL RGTFAESNES NAAEKSVMWP SSADDEKIDV  480
LSTSRRFGSE RWMSSARHEP TCTDLLSGFG TNSDSFHGFG APFVDQTAVA ANPTKKHLSD  540
QGQFNLLASP WSIMSSGLLL KLSESNTKVP VQGSDVTYQA RANVFSEYPV LQGHRVEQSH  600
KNWMMHPPPS HFDNHANSRE LMPKPVLMQE HDSGKSLEGN CKLFGIPLKI SKPVAPEAAG  660
TTITMNEPLS HIQPVSHQLT FESDQKSEQS KGSKMTDENE NEKPFQAGHL RTKDNHGKAQ  720
NGSTRSCTKV HKQGIALGRS VDLAKFNNYD ELIAELDRLF EFNGELMAPQ KNWLIVYTDD  780
EDDMMLVGDD PWQEFVGMVR KIVIYTKEEA QKIKPGALNS KGVENPMDME GEDDAKEAKH  840
LPLPSACSPM NC                                                     852

SEQ ID NO: 117      moltype = AA  length = 859
FEATURE             Location/Qualifiers
REGION              1..859
                    note = misc_feature - Public GI ID no.62319853
REGION              1..859
                    note = misc_feature - Bit score of 2155.3 for hmm based on
                      sequences of FIGURE 5.
REGION              163..268
                    note = misc_feature - Pfam Name: B3 Pfam Description: B3
                      DNA binding domain
REGION              290..372
                    note = misc_feature - Pfam Name: Auxin_resp Pfam
                      Description: Auxin response factor
REGION              1..859
                    note = misc_feature - Is Acted Upon By Ceres SEEDLINE ID
                      no. ME00572 at SEQ ID NO. 111
source              1..859
                    mol_type = protein
                    organism = Arabidopsis thaliana
SEQUENCE: 117
MASSEVSMKG NRGGDNFSSS GFSDPKETRN VSVAGEGQKS NSTRSAAAER ALDPEAALYR   60
ELWHACAGPL VTVPRQDDRV FYFPQGHIEQ VEASTNQAAE QQMPLYDLPS KLLCRVINVD  120
LKAEADTDEV YAQITLLPEA NQDENAIEKE APLPPPPRFQ VHSFCKTLTA SDTSTHGGFS  180
VLRRHADECL PPLDMSRQPP TQELVAKDLH ANEWRFRHIF RGQPRRHLLQ SGWSVFVSSK  240
RLVAGDAFIF LRGENGELRV GVRRAMRQQG NVPSSVISSH SMHLGVLATA WHAISTGTMF  300
TVYYKPRTSP SEFIVPFDQY MESVKNNYSI GMRFKMRFEG EEAPEQRFTG TIVGIEESDP  360
TRWPKSKWRS LKVRWDETSS IPRPDRVSPW KVEPALAPPA LSPVPMPRPK RPRSNIAPSS  420
PDSSMLTREG TTKANMDPLP ASGLSRVLQG QEYSTLRTKH TESVECDAPE NSVVWQSSAD  480
DDKVDVVSGS RRYGSENWMS SARHEPTYTD LLSGFGTNID PSHGQRIPFY DHSSSPSMPA  540
KRILSDSEGK FDYLANQWQM IHSGLSLKLH ESPKVPAATD ASLQGRCNVK YSEYPVLNGL  600
STENAGGNWP IRPRALNYYE EVVNAQAQAQ AREQVTKQPF TIQEETAKSR EGNCRLFGIP  660
LTNNMNGTDS TMSQRNNLND AAGLTQIASP KVQDLSDQSK GSKSTNDHRE QGRPFQTNNP  720
HPKDAQTKTN SSRSCTKVHK QGIALGRSVD LSKFQNYEEL VAELDRLFEF NGELMAPKKD  780
WLIVYTDEEN DMMLVGDDPW QEFCCMVRKI FIYTKEEVRK MNPGTVSCRS EEEAVVGEGS  840
DAKDAKSASN PSLSSAGNS                                              859

SEQ ID NO: 118      moltype = AA  length = 859
FEATURE             Location/Qualifiers
REGION              1..859
                    note = misc_feature - Public GI ID no.62319903
REGION              1..859
                    note = misc_feature - Bit score of 2157 for hmm based on
                      sequences of FIGURE 5.
REGION              163..268
                    note = misc_feature - Pfam Name: B3 Pfam Description: B3
                      DNA binding domain
```

```
REGION                  290..372
                        note = misc_feature - Pfam Name: Auxin_resp Pfam
                          Description: Auxin response factor
REGION                  1..859
                        note = misc_feature - Is Acted Upon By Ceres SEEDLINE ID
                          no. ME00572 at SEQ ID NO. 111
source                  1..859
                        mol_type = protein
                        organism = Arabidopsis thaliana
SEQUENCE: 118
MASSEVSMKG  NRGGDNFSSS  GFSDPKETRN  VSVAGEGQKS  NSTRSAAAER  ALDPEAALYR   60
ELWHACAGPL  VTVPRQDDRV  FYFPQGHIEQ  VEASTNQAAE  QQMPLYDLPS  KLLCRVINVD  120
LKAEADTDEV  YAQITLLPEA  NQDENAIEKE  APLPPPPRFQ  VHSFCKTLTA  SDTSTHGGFS  180
VLRRHADECL  PPLDMSRQPP  TQELVAKDLH  ANEWRFRHIF  RGQPRRHLLQ  SGWSVFVSSK  240
RLVAGDAFIF  LRGENGELRV  GVRRAMRQQG  NVPSSVISSH  SMHLGVLATA  WHAISTGTMF  300
TVYYKPRTSP  SEFIVPFDQY  MESVKNNYSI  GMRFKMRFEG  EEAPEQRFTG  TIVGIEESDP  360
TRWPKSKWRS  LKVRWDETSS  IPRPDRVSPW  KVEPALAPPA  LSPVPMPRPK  RPRSNIAPSS  420
PDSSMLTREG  TTKANMDPLP  ASGLSRVLQG  QEYSTLRTKH  TESVECDAPE  NSVVWQSSAD  480
DDKVDVVSGS  RRYGSENWMS  SARHEPTYTD  LLSGFGTNID  PSHGQRIPFY  DHSSSPSMPA  540
KRILSDSEGK  FDYLANQWQM  IHSGLSLKLH  ESPKVPAATD  ASLQGRCNVK  YSEYPALNGL  600
STENAGGNWP  IRPRALNYYE  EVVNAQAQAQ  AREQVTKQPF  TIQEETAKSR  EGNCRLFGIP  660
LTNNMMNGTDS  TMSQRNNLND  AAGLTQIASP  KVQDLSGHQS  GSKSTNDHRE  QGRPFQTNNP  720
HPKDAQTKTN  SSRSCTKVHK  QGIALGRSVD  LSKFQNYEEL  VAELDRLFEF  NGELMAPKKD  780
WLIVYTDEEN  DMMLVGDDPW  QEFCCMVRKI  FIYTKEEVRK  MNPGTLSCRS  EEEAVVGEGS  840
DAKDAKSASN  PSLSSAGNS                                                  859

SEQ ID NO: 119          moltype = AA  length = 848
FEATURE                 Location/Qualifiers
REGION                  1..848
                        note = misc_feature - Public GI ID no.47716275
REGION                  1..848
                        note = misc_feature - Bit score of 2099.9 for hmm based on
                          sequences of FIGURE 5.
REGION                  158..263
                        note = misc_feature - Pfam Name: B3 Pfam Description: B3
                          DNA binding domain
REGION                  285..367
                        note = misc_feature - Pfam Name: Auxin_resp Pfam
                          Description: Auxin response factor
REGION                  1..848
                        note = misc_feature - Is Acted Upon By Ceres SEEDLINE ID
                          no. ME00572 at SEQ ID NO. 111
source                  1..848
                        mol_type = protein
                        organism = Brassica napus
SEQUENCE: 119
MASSEVSMKG  NRGRGENFSS  AGYSDPTVAG  EAQKTQSNRS  VAAERVVDPE  AALYRELWHA   60
CAGPLVTVPR  QDDRVFYFPQ  GHIEQVEAST  NQAAEQQMPL  YDLPSKILCR  VINVDLKAEA  120
DTDEVYAQIT  LLPEPVQDEN  SIEKEAPPPP  PPRFQVHSFC  KTLTASDTST  HGGFSVLRRH  180
ADECLPPLDM  SRQPPTQELV  AKDLHASEWR  FRHIFRGQPR  RHLLQSGWSV  FVSSKRLVAG  240
DAFIFLRGEN  GELRVGVRRA  MRQQGNVPSS  VISSHSMHLG  VLATAWHAIS  TGTMFTVYYK  300
PRTSPSEFIV  PFDQYTESVK  INYSIGMRFK  MRFEGEEAPE  QRFTGTIVGI  EDSDPTRWAK  360
SKWRSLKVRW  DETTSIPRPD  RVSPWKIEPA  LSPPALSPVP  MPRPKRPRSN  LASSTPDSSM  420
RIREGSSKAN  MDPLPASGLS  RVLQGQEYPT  LRTKHVESVE  CDAPENSVVW  QSSTDDDKVD  480
VISASRRYEN  WISSGRHGPT  CTDLLSGFGT  NIEPPHGHQI  PFYDRLSSPP  SVAARKILSD  540
QDGKFEYLAN  QWMMHSGLSL  KLHESPKVPA  ASDASFQGIG  NPNYGEYALP  RAVTTENAAG  600
NWPIRPRALN  YFEEAVHAQA  REHVTKRPAV  VQEEAAKPRD  GNCRLFGIPL  VNNVNGTDTT  660
LSQRNNLNDP  AGPTQMASPK  VQDLSDQSKG  SKSTNDHREQ  GRPFPVSKPH  PKDVQTKTNS  720
CRSCTKVQKQ  GIALGRSVDL  SKFQNYEELV  TELDRLFEFN  GELMAPKKDW  LIVYTDDEND  780
MMLVGDDPWQ  EFCCMVRKIF  IYTKEEVRKM  NPGTLCCRNE  EEPVVGEGSD  AKDAKSASNP  840
SLSSAGNS                                                               848

SEQ ID NO: 120          moltype = AA  length = 853
FEATURE                 Location/Qualifiers
REGION                  1..853
                        note = misc_feature - Public GI ID no.125534572
REGION                  1..853
                        note = misc_feature - Bit score of 2096 for hmm based on
                          sequences of FIGURE 5.
REGION                  148..253
                        note = misc_feature - Pfam Name: B3 Pfam Description: B3
                          DNA binding domain
REGION                  275..357
                        note = misc_feature - Pfam Name: Auxin_resp Pfam
                          Description: Auxin response factor
REGION                  1..853
                        note = misc_feature - Is Acted Upon By Ceres SEEDLINE ID
                          no. ME00572 at SEQ ID NO. 111
source                  1..853
```

```
                        mol_type = protein
                        note = subspecies = indica
                        organism = Oryza sativa
SEQUENCE: 120
MATAEVGGGG GEGDAAAAAV ARAGGGGGGG GGGGEDALFT ELWSACAGPL VTVPRVGEKV    60
FYFPQGHIEQ VEASTNQVGE QRMQLYNLPW KILCEVMNVE LKAEPDTDEV YAQLTLLPEL   120
KQQEDNGSTE EEVPSAPAAG HVRPRVHSFC KTLTASDTST HGGFSVLRRH ADECLPPLDM   180
SRQPPTQELV AKDLHGVEWR FRHIFRGQPR RHLLQSGWSV FVSAKRLVAG DAFIFLRGEN   240
GELRVGVRRA MRQQTNVPSS VISSHSMHLG VLATAWHAVN TGTMFTVYYK PRTSPAEFVV   300
PYDRYMESLK RNYSIGMRFK MRFEGEEAPE QRFTGTIVGM GDSDPAGWPE SKWRSLKVRW   360
DEASSIPRPE RVSPWQIEPA VSPPPVNPLP VPRTKRLRPN ATALPADSSA IAKEAATKVV   420
VESEPNGTQR TFQTQENATP KSGFGNSSEL ESAQKSIMRP SGFDREKNNT PIQWKLGSDG   480
WMQMSKPESY SEMLSGFQPP KDVQTPQGFC SLPEQITAGH SNFWHTVNAQ YQDQQSNHNM   540
FPSSWSFMPP NTRLGLNKQN YSMIQEAGVL SQRPGNTKFG NGVYAALPGR GTEQYSGGWF   600
GHMMPNSHMD DTQPRLIKPK PLVVAHGDVQ KAKGASCKLF GIHLDSPAKS EPLKSPSSVV   660
YDGTPQTPGA TEWRRPDVTE VEKCSDPSKA MKPLDTPQPD SVPEKPSSQQ ASRNMSCKSQ   720
GVSTRSCKKV HKQGIALGRS VDLTKFNGYE ELIAELDDMF DFNGELKGPK KEWMVVYTDN   780
EGDMMLVGDD PWIEFCDMVH KIFIYTREEV QRMNPGTLNS RSEDSHANSM ERGSVGREMR   840
GCLSTSSLNS ENC                                                     853

SEQ ID NO: 121          moltype = AA  length = 857
FEATURE                 Location/Qualifiers
REGION                  1..857
                        note = misc_feature - Public GI ID no.26251300
REGION                  1..857
                        note = misc_feature - Bit score of 2070.6 for hmm based on
                          sequences of FIGURE 5.
REGION                  147..252
                        note = misc_feature - Pfam Name: B3 Pfam Description: B3
                          DNA binding domain
REGION                  274..356
                        note = misc_feature - Pfam Name: Auxin_resp Pfam
                          Description: Auxin response factor
REGION                  1..857
                        note = misc_feature - Is Acted Upon By Ceres SEEDLINE ID
                          no. ME00572 at SEQ ID NO. 111
source                  1..857
                        mol_type = protein
                        note = subspecies = indica
                        organism = Oryza sativa
SEQUENCE: 121
MATAEVGGGG GEGDAAAAAV ARAGGGGGGG GGGGEDALFTE LWSACAGPLV TVPRVGEKEF    60
YFPQGHIEQV EASTNQVGEQ RMQLYNLPWK ILCEVMNVEL KAEPDTDEVY AQLTLLPELK   120
RQEDNGSTEE EVPSAPAAGH VRPRVHSFCK TLTASDTSTH GGFSVLRRHA DECLPPLDMS   180
RQPPTQELVA KDLHGVEWRF RHIFRGQPRR HLLQSGWSVF VSAKRLVAGD AFIFLRGENG   240
ELRVGVRRAM RQQTNVPSSV ISSHSMHLGV LATAWHAVNT GTMFTVYYKP RTSPAEFVVP   300
YDRYMESLKR NYSIGMRFKM RFESEEAPEQ RFTGTIVGMD DSDPAGWPES KWRSLKVRWD   360
EASSIPRPER VSPWQIEPAV SPPPVNPLPV PRTKRLRPNA TALPADSSAI AKEAATKVVV   420
ESEPNGTQRT FQTQENATPK SGFGNSSELE SAQKSIMRPS GFDREKNNTP IQWKLGSDGR   480
MQMSKPESYS EMLSGFQPPK DVQTPQGFCS LPEQITAGHS NFWHTVNAQY QDQQSNHNMF   540
PSSWSFMPPN TRLGLNKQNY SMIQEAGVLS QRPGNTKFGN GVYAALPGRG TEQYSGGWFG   600
LMMPNSHMDD TQPRLIKPKP LVVAHGDVQK AKGASCKLFG IHLDSPAKSE PSKSPSSVVY   660
DGTPQTPGAT EWRRPDVTEV EKCSDPSKAM KPLDTPQPDS VPEKPSSQQA SSQQASRNMS   720
CKSQGVSTRS CKKVHKQGIA LGRSVDLTKF NGYEELIAEL DDMFDFNGEL KGPKKEWMVV   780
YTDNEGDMML VGDDPWIEFC DMVHKIFIYT REEVQRMNPG TLNLRSEDSH ANSMERGSVG   840
REMRGCLSTS SLNSENC                                                 857

SEQ ID NO: 122          moltype = AA  length = 853
FEATURE                 Location/Qualifiers
REGION                  1..853
                        note = misc_feature - Public GI ID no.125528952
REGION                  1..853
                        note = misc_feature - Bit score of 1880.3 for hmm based on
                          sequences of FIGURE 5.
REGION                  123..228
                        note = misc_feature - Pfam Name: B3 Pfam Description: B3
                          DNA binding domain
REGION                  250..331
                        note = misc_feature - Pfam Name: Auxin_resp Pfam
                          Description: Auxin response factor
REGION                  1..853
                        note = misc_feature - Is Acted Upon By Ceres SEEDLINE ID
                          no. ME00572 at SEQ ID NO. 111
source                  1..853
                        mol_type = protein
                        note = subspecies = indica
                        organism = Oryza sativa
SEQUENCE: 122
MAPPPPPQGS STGDPLYDEL WHACAGPLVT VPRVGDLVFY FPQGHIEQVE ASMNQVADSQ    60
```

```
MRLYDLPSKL LCRVLNVELK AEQDTDEVYA QVMLMPEPEQ NEMAVEKTTP TSGPVQARPP    120
VRSFCKTLTA SDTSTHGGFS VLRRHADECL PPLDMTQSPP TQELVAKDLH SMDWRFRHIF    180
RGQPRRHLLQ SGWSVFVSSK RLVAGDAFIF LRGENGELRV GVRRAMRQLS NVPSSVISSQ    240
SMHLGVLATA WHAINTKSMF TVYYKPRTSP SEFIIPYDQY MESVKNNYSV GMRFRMRFEG    300
EEAPEQRFTG TIIGSENLDP VWPESSWRSL KVRWDEPSTI PRPDRVSPWK IEPASSPPVN    360
PLPLSRVKRP RPNAPPASPE SPILTKEAAT KVDTDPAQAQ RSQNSTVLQG QEQMTLRSNL    420
TESNDSDVTA HKPMMWSPSP NAAKAHPLTF QQRPPMDNWM QLGRRETDFK DVRSGSQSFG    480
DSPGFFMQNF DEAPNRLTSF KNQFQDQGSA RHFSDPYYYV SPQPSLTVES STQMHTDSKE    540
LHFWNGQSTV YGNSRDRPQN FRFEQNSSSW LNQSFARPEQ PRVIRPHASI APVELEKTEG    600
SGFKIFGFKV DTTNAPNNHL SSPMAATHEP MLQTPSSLNQ LQPVQTDCIP EVSVSTAGTA    660
TENEKSGQQA QQSSKDVQSK TQVASTRSCT KHMKFFLLVV DMLKFSFCKF LAKSQFYPLC    720
GMVHKQGVAL GRSVDLSKFS NYDELKAELD KMFEFDGELV SSNKNWQIVY TDNEGDMMLV    780
GDDPWEEFCS IVRKIYIYTK EEVQKMNSKS NAPRKDDSSE NEKGSVKRDD TRDGGVLQKA    840
ASASVLSILR YSS                                                      853

SEQ ID NO: 123          moltype = AA  length = 808
FEATURE                 Location/Qualifiers
REGION                  1..808
                        note = misc_feature - Public GI ID no.115441981
REGION                  1..808
                        note = misc_feature - Bit score of 1951.3 for hmm based on
                          sequences of FIGURE 5.
REGION                  128..233
                        note = misc_feature - Pfam Name: B3 Pfam Description: B3
                          DNA binding domain
REGION                  255..336
                        note = misc_feature - Pfam Name: Auxin_resp Pfam
                          Description: Auxin response factor
REGION                  1..808
                        note = misc_feature - Is Acted Upon By Ceres SEEDLINE ID
                          no. ME00572 at SEQ ID NO. 111
source                  1..808
                        mol_type = protein
                        note = subspecies = japonica
                        organism = Oryza sativa
SEQUENCE: 123
MPPAAMAPPP PPQGSSTGDP LYDELWHACA GPLVTVPRVG DLVFYFPQGH IEQVEASMNQ    60
VADSQMRLYD LPSKLLCRVL NVELKAEQDT DEVYAQVMLM PEPEQNEMAV EKTTPTSGPV    120
QARPPVRSFC KTLTASDTST HGGFSVLRRH ADECLPPLDM TQSPPTQELV AKDLHSMDWR    180
FRHIFRGQPR RHLLQSGWSV FVSSKRLVAG DAFIFLRGEN GELRVGVRRA MRQLSNVPSS    240
VISSQSMHLG VLATAWHAIN TKSMFTVYYK PRTSPSEFII PYDQYMESVK NNYSVGMRFR    300
MRFEGEEAPE QRFTGTIIGS ENLDPVWPES SWRSLKVRWD EPSTIPRPDR VSPWKIEPAS    360
SPPVNPLPLS RVKRPRPNAP PASPESPILT KEAATKVDTD PAQAQRSQNS TVLQGQEQMT    420
LRSNLTESND SDVTAHKPMM WSPSPNAAKA HPLTFQQRPP MDNWMQLGRR ETDFKDVRSG    480
SQSFGDSPGF FMQNFDEAPN RLTSFKNQFQ DQGSARHFSD PYYYVSPQPS LTVESSTQMH    540
TDSKELHFWN GQSTVYGNSR DRPQNFRFEQ NSSSWLNQSF ARPEQPRVIR PHASIAPVEL    600
EKTEGSSGFKI FGFKVDTTNA PNNHLSSPMA ATHEPMLQTP SSLNQLQPVQ TDCIPEVSVS    660
TAGTATENEK SGQQAQQSSK DVQSKTQVAS TRSCTKVHKQ GVALGRSVDL SKFSNYDELK    720
AELDKMFEFD GELVSSNKNW QIVYTDNEGD MMLVGDDPWE EFCSIVRKIY IYTKEEVQKM    780
NSKSNAPRKD DSSENEKGHL PMPNKSDN                                      808

SEQ ID NO: 124          moltype = AA  length = 836
FEATURE                 Location/Qualifiers
REGION                  1..836
                        note = misc_feature - Public GI ID no.23893346
REGION                  1..836
                        note = misc_feature - Bit score of 2065.7 for hmm based on
                          sequences of FIGURE 5.
REGION                  131..236
                        note = misc_feature - Pfam Name: B3 Pfam Description: B3
                          DNA binding domain
REGION                  258..340
                        note = misc_feature - Pfam Name: Auxin_resp Pfam
                          Description: Auxin response factor
REGION                  1..836
                        note = misc_feature - Is Acted Upon By Ceres SEEDLINE ID
                          no. ME00572 at SEQ ID NO. 111
source                  1..836
                        mol_type = protein
                        note = subspecies = japonica
                        organism = Oryza sativa
SEQUENCE: 124
MATAEVGGGG GGGGGGGEDA LFTELWSACA GPLVTVPRVG EKVFYFPQGH IEQVEASTNQ    60
VGEQRMQLYN LPWKILCEVM NVELKAEPDT DEVYAQLTLL PESKQQEDNG STEEEVPSAP    120
AAGHVRPRVH SFCKTLTASD TSTHGGFSVL RRHADECLPP LDMSRQPPTQ ELVAKDLHGV    180
EWRFRHIFRG QPRRHLLQSG WSVFVSAKRL VAGDAFIFLR GENGELRVGV RRAMRQQTNV    240
PSSVISSHSM HLGVLATAWH AVNTGTMFTV YYKPRTSPAE FVVPYDRYME SLKQNYSIGM    300
RFKMRFEGEE APEQRFTGTI VGMGDSDPAG WPESKWRSLK VRWDEASSIP RPERVSPWQI    360
EPAVSPPPVN PLPVPRTKRL RPNATALPAD SSAIAKEAAT KVVVESEPNG TQRTFQTQEN    420
```

```
ATPKSGFGNS SELESAQKSI MRPSGFDREK NNTPIQWKLG SDGRMQMSKP ESYSEMLSGF    480
QPPKDVQIPQ GFWSLPEQIT AGHSNFWHTV NAQYQDQQSN HNMFPSSWSF MPPNTRLGLN    540
KQNYSMIQEA GVLSQRPGNT KFGNGVYAAL PGRGTEQYSG GWFGHMMPNS HMDDTQPRLI    600
KPKPLVVAHG DVQKAKGASC KLFGIHLDSP AKSEPLKSPS SVVYDGTPQT PGATEWRRPD    660
VTEVEKCSDP SKAMKPLDTP QPDSVPEKPS SQQASRNMSC KSQGVSTRSC KKVHKQGIAL    720
GRSVDLTKFN GYEELIAELD DMFDFNGELK GPKKEWMVVY TDNEGDMMLV GDDPWIEFCD    780
MVHKIFIYTR EEVQRMNPGT LNSRSEDSHA NSMERGSVGR EMRGCLSTSS LNSENC        836

SEQ ID NO: 125          moltype = AA  length = 852
FEATURE                 Location/Qualifiers
REGION                  1..852
                        note = misc_feature - Public GI ID no.115485689
REGION                  1..852
                        note = misc_feature - Bit score of 2092.5 for hmm based on
                         sequences of FIGURE 5.
REGION                  147..252
                        note = misc_feature - Pfam Name: B3 Pfam Description: B3
                         DNA binding domain
REGION                  274..356
                        note = misc_feature - Pfam Name: Auxin_resp Pfam
                         Description: Auxin response factor
REGION                  1..852
                        note = misc_feature - Is Acted Upon By Ceres SEEDLINE ID
                         no. ME00572 at SEQ ID NO. 111
source                  1..852
                        mol_type = protein
                        note = subspecies = japonica
                        organism = Oryza sativa
SEQUENCE: 125
MATAEVGGGG GEGDAAAAAV ARGGGGGGGG GGGEDALFTE LWSACAGPLV TVPRVGEKVF     60
YFPQGHIEQV EASTNQVGEQ RMQLYNLPWK ILCEVMNVEL KAEPDTDEVY AQLTLLPESK    120
QQEDNGSTEE EVPSAPAAGH VRPRVHSFCK TLTASDTSTH GGFSVLRRHA DECLPPLDMS    180
RQPPTQELVA KDLHGVEWRF RHIFRGQPRR HLLQSGWSVF VSAKRLVAGD AFIFLRGENG    240
ELRVGVRRAM RQQTNVPSSV ISSHSMHLGV LATAWHAVNT GTMFTVYYKP RTSPAEFVVP    300
YDRYMESLKQ NYSIGMRFKM RFEGEEAPEQ RFTGTIVGMG DSDPAGWPES KWRSLKVRWD    360
EASSIPRPER VSPWQIEPAV SPPPVNPLPV PRTKRLRPNA TALPADSSAI AKEAATKVVV    420
ESEPNGTQRT FQTQENATPK SGFGNSSELE SAQKSIMRPS GFDREKNNTP IQWKLGSDGR    480
MQMSKPESYS EMLSGFQPPK DVQIPQGFCS LPEQITAGHS NFWHTVNAQY QDQQSNHNMF    540
PSSWSFMPPN TRLGLNKQNY SMIQEAGVLS QRPGNTKFGN GVYAALPGRG TEQYSGGWFG    600
HMMPNSHMDD TQPRLIKPKP LVVAHGDVQK AKGASCKLFG IHLDSPAKSE PLKSPSSVVY    660
DGTPQTPGAT EWRRPDVTEV EKCSDPSKAM KPLDTPQPDS VPEKPSSQQA SRNMSCKSQG    720
VSTRSCKKVH KQGIALGRSV DLTKFNGYEE LIAELDDMFD FNGELKGPKK EWMVVYTDNE    780
GDMMLVGDDP WIEFCDMVHK IFIYTREEVQ RMNPGTLNSR SEDSHANSME RGSVGREMRG    840
CLSTSSLNSE NC                                                       852

SEQ ID NO: 126          moltype = AA  length = 853
FEATURE                 Location/Qualifiers
REGION                  1..853
                        note = misc_feature - Public GI ID no.108864435
REGION                  1..853
                        note = misc_feature - Bit score of 2094.3 for hmm based on
                         sequences of FIGURE 5.
REGION                  148..253
                        note = misc_feature - Pfam Name: B3 Pfam Description: B3
                         DNA binding domain
REGION                  275..357
                        note = misc_feature - Pfam Name: Auxin_resp Pfam
                         Description: Auxin response factor
REGION                  1..853
                        note = misc_feature - Is Acted Upon By Ceres SEEDLINE ID
                         no. ME00572 at SEQ ID NO. 111
source                  1..853
                        mol_type = protein
                        note = subspecies = japonica
                        organism = Oryza sativa
SEQUENCE: 126
MATAEVGGGG GEGDAAAAAV ARAGGGGGGG GGGGEDALFT ELWSACAGPL VTVPRVGEKV     60
FYFPQGHIEQ VEASTNQVGE QRMQLYNLPW KILCEVMNVE LKAEPDTDEV YAQLTLLPES    120
KQQEDNGSTE EEVPSAPAAG HVRPRVHSFC KTLTASDTST HGGFSVLRRH ADECLPPLDM    180
SRQPPTQELV AKDLHGVEWR FRHIFRGQPR RHLLQSGWSV FVSAKRLVAG DAFIFLRGEN    240
GELRVGVRRA MRQQTNVPSS VISSHSMHLG VLATAWHAVN TGTMFTVYYK PRTSPAEFVV    300
PYDRYMESLK QNYSIGMRFK MRFEGEEAPE QRFTGTIVGM GDSDPAGWPE SKWRSLKVRW    360
DEASSIPRPE RVSPWQIEPA VSPPPVNPLP VPRTKRLRPN ATALPADSSA IAKEAATKVV    420
VESEPNGTQR TFQTQENATP KSGFGNSSEL ESAQKSIMRP SGFDREKNNT PIQWKLGSDG    480
RMQMSKPESY SEMLSGFQPP KDVQIPQGFC SLPEQITAGH SNFWHTVNAQ YQDQQSNHNM    540
FPSSWSFMPP NTRLGLNKQN YSMIQEAGVL SQRPGNTKFG NGVYAALPGR GTEQYSGGWF    600
GHMMPNSHMD DTQPRLIKPK PLVVAHGDVQ KAKGASCKLF GIHLDSPAKS EPLKSPSSVV    660
YDGTPQTPGA TEWRRPDVTE VEKCSDPSKA MKPLDTPQPD SVPEKPSSQQ ASRNMSCKSQ    720
GVSTRSCKKV HKQGIALGRS VDLTKFNGYE ELIAELDDMF DFNGELKGPK KEWMVVYTDN    780
```

```
EGDMMLVGDD PWIEFCDMVH KIFIYTREEV QRMNPGTLNS RSEDSHANSM ERGSVGREMR   840
GCLSTSSLNS ENC                                                    853

SEQ ID NO: 127          moltype = AA  length = 719
FEATURE                 Location/Qualifiers
REGION                  1..719
                        note = misc_feature - Public GI ID no.50511471
REGION                  1..719
                        note = misc_feature - Bit score of 1618.2 for hmm based on
                          sequences of FIGURE 5.
REGION                  141..246
                        note = misc_feature - Pfam Name: B3 Pfam Description: B3
                          DNA binding domain
REGION                  268..349
                        note = misc_feature - Pfam Name: Auxin_resp Pfam
                          Description: Auxin response factor
REGION                  1..719
                        note = misc_feature - Is Acted Upon By Ceres SEEDLINE ID
                          no. ME00572 at SEQ ID NO. 111
source                  1..719
                        mol_type = protein
                        note = subspecies = japonica
                        organism = Oryza sativa
SEQUENCE: 127
MTGIDLNTVE EDEEEAAEEV AANGSSPAPA RAGAVCLELW HACAGPVAPL PRKGGVVVYL    60
PQGHLEHLGD APAAAAAAAA VPPHVFCRVV DVTLLADAAT DEVYAQLSLV PEKEEVARRA   120
DDGEGEDGDG MKQRFARMPH MFCKTLTASD TSTHGGFSVP RRAAEDCFPP LDYSQQRPSQ   180
ELVAKDLHST EWRFRHIYRG QPRRHLLTTG WSAFVNKKKL VSGDAVLFLR GDDGELRLGV   240
RRAAQLKNGS AFPALYNQCS NLGTLANVAH AVATESVFNI YYNPRLSQSE FIVPYWKFMK   300
SLSQPFSVGL RFKMRYESED ATERRYTGII TGSGDTDPMW HGSKWKCLLV RWDDDAEFRR   360
PNRVSPWEIE LTSSVSGSHL STPHSKRLKP CLPHVNPEYM VPRGGGCPDF AESAQFHKVL   420
QGQELLGFKS HGGTAAATSQ PCEARHLQYI DERSCSSDAS NSILGVPRLG DRAPLGNPGF   480
SYHCSGFGES HRLQKVLQGQ ELFRPYRGTL VDASMGSNGF HQQDSPRAPG VVNKWQAQLH   540
GRAAFHGPPA LALPSQSSSP PSVLMFQQAN SKMPRLEFGH GQLDKHENDR RVRFGPSEGI   600
ERREQRIPLQ PYPTSGEVID GQVTVEKSHS PGRHGKDGPD NKAVGTNSCK IFGISLTEKV   660
PAREELDDGD ANYSLQSLKQ VPKSLGNSCA TMVAEYQGDG GTDDSDIFIL DVGVGALIM   719

SEQ ID NO: 128          moltype = AA  length = 608
FEATURE                 Location/Qualifiers
REGION                  1..608
                        note = misc_feature - Ceres LOCUS ID no. At2g33860
REGION                  1..608
                        note = misc_feature - Bit score of 1320.6 for hmm based on
                          sequences of FIGURE 5.
REGION                  158..263
                        note = misc_feature - Pfam Name: B3 Pfam Description: B3
                          DNA binding domain
REGION                  285..367
                        note = misc_feature - Pfam Name: Auxin_resp Pfam
                          Description: Auxin response factor
REGION                  1..608
                        note = misc_feature - Is Acted Upon By Ceres SEEDLINE ID
                          no. ME00572 at SEQ ID NO. 111
source                  1..608
                        mol_type = protein
                        organism = Arabidopsis thaliana
SEQUENCE: 128
MGGLIDLNVM ETEEDETQTQ TPSSASGSVS PTSSSSASVS VVSSNSAGGG VCLELWHACA    60
GPLISLPKRG SLVLYFPQGH LEQAPDFSAA IYGLPPHVFC RILDVKLHAE TTTDEVYAQV   120
SLLPESEDIE RKVREGIIDV DGGEEDYEVL KRSNTPHMFC KTLTASDTST HGGFSVPRRA   180
AEDCFPPLDY SQPRPSQELL ARDLHGLEWR FRHIYRGQPR RHLLTTGWSA FVNKKKLVSG   240
DAVLFLRGDD GKLRLGVRRA SQIEGTAALS AQYNQNMNHN NFSEVAHAIS THSVFSISYN   300
PKASWSNFII PAPKFLKVVD YPFCIGMRFK ARVESEDASE RRSPGIISGI SDLDPIRWFG   360
SKWRCLLVRW DDIVANGHQQ RVSPWEIEPS GSISNSGSFV TTGPKRSRIG FSSGKPDIPV   420
SEGIRATDFE ESLRFQRVLQ GQEIFPGFIN TCSDGGAGAR RGRFKGTEFG DSYGFHKVLQ   480
GQETVPAYSI TDHRQQHGLS QRNIWCGPFQ NFSTRILPPS VSSSPSSVLL TNSNSPNGRL   540
EDHHGGSGRC RLFGFPLTDE TTAVASATAV PCVEGNSMKG ASAVQSNHHH SQGRDIYAMR   600
DMLLDIAL                                                           608

SEQ ID NO: 129          moltype = DNA  length = 1995
FEATURE                 Location/Qualifiers
misc_feature            1..1995
                        note = Ceres ANNOT ID no.1536494
misc_feature            1..1995
                        note = Encodes the peptide sequence at SEQ ID NO. 130
source                  1..1995
                        mol_type = other DNA
                        organism = Populus balsamifera
                        sub_species = trichocarpa
```

US 12,024,713 B2

143                                                                    144
-continued

```
SEQUENCE: 129
atggtgggta tgatagatct caacactatt gaagaagatg aaactacacc gtcttgtggg    60
tctttatctt ctccatcatc atcctctgct gcttctgctt tgagtgcttc tggctctggt   120
tctagtacct cttctgtttg tttggagctt tggcatgctt gtgctggccc actaatatct   180
ttgccaaaga gagggagtgt tgttgtgtat ttccctcaag gccacttgga acaactccct   240
gatttgcctc ttgcagttta tgatctcccc tctcatgtct tctgtcgagt tgttgatgtc   300
aagctccatg tctccctggt tcctgagagt gaggaaattg agcagaagtt gagggagggg   360
atatttgagg gggatggtga ggaggaggat ggtgaagcca ctgtgaagat gacaacaccc   420
catatgttct gtaagaccct aactgcttct gacactagca ctctggagg cttttcagtc    480
cctcgtcgag ctgctgagga ctgcttccct cctctggatt atactcaaca aaggccttca   540
caagagcttg tggcaaagga tcttcatggc tctgagtgga agtttcgaca tatctacagg   600
ggtcagccac ggaggcattt gctcactact ggatggagtg cgtttgtcaa taagaaaaaa   660
cttgtctctg gggatgccgt tctctttctc aggggtgagg atgggaatt gagactggga    720
gttcgaagag cagcacaagt taaatgtggc cctacatttc cagctcaatg gaatcatcag   780
ctgaatcaga tctctcctgg ggatgtagct aatgctattt ctactagaag ttttttccac   840
atttactaca atccaagggc cagctcatca gagttcataa tacctttta taaattcttg     900
aagagccttg atcaatcctt ctcttctgga atgagattca aatgcgtttt tgaaacagaa   960
gatgcagcag agagaagata cactggaata ataactggaa tcagtgagct agatcctgct  1020
agatggcctg gttcaaaatg gaaatgcctg ttggtaaggt gggatgatag ggaggctaac  1080
aggctcagca gggtttctcc ttgggaagtt gagccttctg gttctggttc tatttccagc  1140
tccataact ttatggcacc tggtttgaag aggagcaggc ctggattgcc ttcatcaaag    1200
gcagaatttc caattcctga tgggatagga gcaccaggtt tagggaatc ttcaaggtcc   1260
caggaggtct tgcaaggaag tggtatcaga gactcgattc ccacttcaaa taactcctac  1320
aagggcatag gctttaacga atcttataga ttccataagg tcttccaagg tcaagaaatt  1380
tttccaagct caccatatgg aagaatccca aatgctaatg aggctcgtga aaattgtagt  1440
cttggattct ctgatggtca ccaaaggtca agctcaagaa atggatggtc tacattgatg  1500
cagggctata atactcaaat tcgacctcct gcacaagtat catcaccatc ttcggtgtta  1560
atgtttcaac atgccagcaa tccagttcca aagcgatctt ccaattttaa tttcaatgat  1620
catgtgcagc agacagctac caccccgaagt tggttttgtg gtcctgaaat gcagggggg   1680
aatttcaagt tgtctgcaca ttctgagccc agtgtaaaaa gagacggcca atggagcaat  1740
agtccttttg gtctgtccca tgagcatctt caacatggcg tttcacaacc tattgtagct  1800
caatcagcct ttaggggtag tcaagatttg gtgtcgtgca aaagcagctg cagactcttt  1860
ggtttctcat tgactgagga taaatgcctt gttaataagg aggacaatat gaccttaata  1920
acatctccat tgaatcctgg atcctccttt ctgcctcgcg ccggagagca cttccatcaa  1980
agcctccagc aataa                                                  1995

SEQ ID NO: 130      moltype = AA  length = 664
FEATURE             Location/Qualifiers
REGION              1..664
                    note = misc_feature - Ceres ANNOT ID no.1536494
REGION              1..664
                    note = misc_feature - Bit score of 802.9 for hmm based on
                      sequences of FIGURE 5.
REGION              142..247
                    note = misc_feature - Pfam Name: B3 Pfam Description: B3
                      DNA binding domain
REGION              269..351
                    note = misc_feature - Pfam Name: Auxin_resp Pfam
                      Description: Auxin response factor
REGION              1..664
                    note = misc_feature - Is Acted Upon By Ceres SEEDLINE ID
                      no. ME00572 at SEQ ID NO. 111
source              1..664
                    mol_type = protein
                    note = subspecies = trichocarpa
                    organism = Populus balsamifera
SEQUENCE: 130
MVGMIDLNTI EEDETTPSCG SLSSPSSSSA ASALSASGSG SSTSSVCLEL WHACAGPLIS    60
LPKRGSVVVY FPQGHLEQLP DLPLAVYDLP SHVFCRVVDV KLHVSLVPES EEIEQKLREG   120
IFEGDEEED  GEATVKMTTP HMFCKTLTAS DTSTHGGFSV PRRAAEDCFP PLDYTQQRPS   180
QELVAKDLHG SEWKFRHIYR GQPRRHLLTT GWSAFVNKKK LVSGDAVLFL RGEDGELRLG   240
VRRAAQVKCG PTFPAQWNHQ LNQISPGDVA NAISTRSFFH IYYNPRASSS EFIIPFNKFL   300
KSLDQSFSSG MRFKMRFETE DAAERRYTGI ITGVSELDPA RWPGSKWKCL LVRWDDREAN   360
RLSRVSPWEV EPSGSGSISS SNNFMAPGLK RSRSGLPSSK AEFPIPDGIG APGFRESSRS   420
QEVLQGSGIR DSIATSNNSY KGIGFNESYR FHKVFQGQEI FPSSPYGRIP NANEARENCS   480
LGFSDGVQRS SSRNGWSTLM QGYNTQIRPP AQVSSPSSVL MFQHASNPVP KRSSNFNFND   540
HVQQTATTRS WFCGPEMQGG NFKLSAHSEP SVKRDGQWSN SPFGLSHEHL QHGVSQPIVA   600
QSAFRGSQDL VSCKSSCRLF GFSLTEDKCL VNKEDNMTLI TSPLNPGSSF LPRAGEHFHQ   660
SLQQ                                                                 664

SEQ ID NO: 131      moltype = AA  length = 608
FEATURE             Location/Qualifiers
REGION              1..608
                    note = misc_feature - Public GI ID no.2245390
REGION              1..608
                    note = misc_feature - Bit score of 1323.9 for hmm based on
                      sequences of FIGURE 5.
REGION              158..263
                    note = misc_feature - Pfam Name: B3 Pfam Description: B3
```

|  |  |
|---|---|
| REGION | DNA binding domain<br>285..367<br>note = misc_feature - Pfam Name: Auxin_resp Pfam Description: Auxin response factor |
| REGION | 1..608<br>note = misc_feature - Is Acted Upon By Ceres SEEDLINE ID no. ME00572 at SEQ ID NO. 111 |
| source | 1..608<br>mol_type = protein<br>organism = Arabidopsis thaliana |

SEQUENCE: 131

```
MGGLIDLNVM ETEEDETQTQ TPSSASGSVS PTSSSSASVS VVSSNSAGGG VCLELWHACA   60
GPLISLPKRG SLVLYFPQGH LEQAPDFSAA IYGLPPHVFC RILDVKLHAE TTTDEVYAQV  120
SLLPESEDIE RKVREGIIDV DGGEEDYEVL KRSNTPHMFC KTLTASDTST HGGFSVPRRA  180
AEDCFPPLDY SQPRPSQELL ARDLHGLEWR FRHIYRGQPR RHLLTTGWSA FVNKKKLVSG  240
DAVLFLRGDD GKLRLGVRRA SQIEGTAALS AQYNQNMNHN NFSEVAHAIS THSVFSISYN  300
PKASWSNFII PAPKFLKVVD YPFCIGMRFK ARVESEDASE RRSPGIISGI SDLDPIRWPG  360
SKWRCLLVRW DDIVANGHQQ RVSPWEIEPS GSISNSGSFV TTGPKRSRIG FSSGKPDIPV  420
SEGIRATDFE ESLRFQRVLQ GQEIFPGFIN TCSDGGAGAR RGRFKGTEFG DSYGFHKVLQ  480
GQETVPAYSI TDHRQQHGLS QRNIWCGPFQ NFSTRILPPS VSSSPSSVLF TNSNSPNGRL  540
EDHHGGSGRC RLFGFPLTDE TTAVASATAV PCVEGNSMKG ASAVQSNHHH SQGRDIYAMR  600
DMLLDIAL                                                          608
```

|  |  |
|---|---|
| SEQ ID NO: 132 | moltype = AA  length = 608 |
| FEATURE | Location/Qualifiers |
| REGION | 1..608<br>note = misc_feature - Public GI ID no.3228517 |
| REGION | 1..608<br>note = misc_feature - Bit score of 1320.4 for hmm based on sequences of FIGURE 5. |
| REGION | 158..263<br>note = misc_feature - Pfam Name: B3 Pfam Description: B3 DNA binding domain |
| REGION | 285..367<br>note = misc_feature - Pfam Name: Auxin_resp Pfam Description: Auxin response factor |
| REGION | 1..608<br>note = misc_feature - Is Acted Upon By Ceres SEEDLINE ID no. ME00572 at SEQ ID NO. 111 |
| source | 1..608<br>mol_type = protein<br>organism = Arabidopsis thaliana |

SEQUENCE: 132

```
MGGLIDLNVM ETEEDETQTQ TPSSASGSVS PTSSSSASVS VVSSNSAGGG VCLELWHACA   60
GPLISLPKRG SLVLYFPQGH LEQAPDFSAA IYGLPPHVFC RILDVKLHAE TTTDEVYAQV  120
SLLPESEDIE RKVREGIIDV DGGEEDYEVL KRSNTPHMFC KTLTASDTST HGGFSVPRRA  180
AEDCFPPLDY SQPRPSQELL ARDLHGLEWR FRHIYRGQPR RHLLTTGWSA FVNKKKLVSG  240
DAVLFLRGDD GKLRLGVRRA SQIEGTAALS AQYNQNMNHN NFSEVAHAIS THSVFSISYN  300
PKASWSNFII PAPKFLKVVD YPFCIGMRFK ARVESEDASE RRSPGIISGI SDLDPIRWPG  360
SKWRCLLVRW DDIVANGHQQ RVSPWEIEPS GSISNSGSFV TTGPKRSRIG ISSGKPDIPV  420
SEGIRATDFE ESLRFQRVLQ GQEIFPGFIN TCSDGGAGAR RGRFKGTEFG DSYGFHKVLQ  480
GQETVPAYSI TDHRQQHGLS QRNIWCGPFQ NFSTRILPPS VSSSPSSVLL TNSNSPNGRL  540
EDHHGGSGRC RLFGFPLTDE TTAVASATAV PCVEGNSMKG ASAVQSNHHH SQGRDIYAMR  600
DMLLDIAL                                                          608
```

|  |  |
|---|---|
| SEQ ID NO: 133 | moltype = DNA  length = 2420 |
| FEATURE | Location/Qualifiers |
| misc_feature | 1..2420<br>note = Ceres CLONE ID no.827306 |
| misc_feature | 1..2420<br>note = Encodes the peptide sequence at SEQ ID NO. 134 |
| source | 1..2420<br>mol_type = other DNA<br>organism = Triticum aestivum |

SEQUENCE: 133

```
acgcctcacg cctcacgccc gcgtcataaa atcgtgggcg actcgtgtcc cagtcccagc   60
aggctcagcc acagcccaca gcgacgcggc agcggcagca ggaacagcaa cagcgacctt  120
gcttcccgcg cgcggcagcc gagggagggg aggaggagat cgaggggggc aagcggggca  180
gggcggcatg gggacggggg gctagaacaa ggagatggct gcagagcgac gccctcgggg  240
gcattaatgg ggcccctccct ctgctccaca tcctgctgct cccacatcct ccccgcggcc  300
gcggttgatt cctcgcccgc ctacttttaa ccgcgccccc ccttttccgg acgggacggc  360
tgggctgtgg gcgggcgcca tgggcatcga tctcaacgcg gcggacgagc ctggcaaggc  420
ggcggcggtg tcggtgtgcc gggacctgtg gcacgcctgc gcggggccgg tcgtggcgct  480
gccgccgaag ggcagccgg tcgtctacct gccggcgccg cacctgcgcc ggcggacctc  540
cgggggggac gtgccggtgg ccctgccgcc gcatgtgggcg tgccgcgtgg tggacgtcga  600
gctatgcgcg gatccggcga ccgacgaggt ctacgcgcgg ctggctatgg tggcggaggg  660
cgagatcttt gagaagaaca tgggaggtgg tcggtttgaa ggggaagatg acatggaaga  720
tggcgatgga gaaaggaagt cccggatgct gcacatgttc tgcaagacac taacagcctc  780
tgacacaagc acacacgggg gattctctgt tccccgcgcg gctgccgagg actgtttccc  840
```

```
cccactggac taccagcaga tcaggccttc ccaagagctt gttgcaaagg atttgcatgg    900
agcgaagtgg aggttccgcc atatctatag aggtcaacca cgtaggcatc ttttaacgac    960
tggatggagt tcatttgtca ataaaaagaa acttgtctct ggggatgcag tcttatttct   1020
ccgtggtgat gatggtgaac tacgacttgg tgtaaggaga gccattcagc ttaaaaatga   1080
ggcccttctg aaagctttca atagcaacag ctcaaagata cacacactgt ctgctgtgcc   1140
taattccttg aaacatagaa gtgtttttca catctgttac aatccaaggg ctgctgcatc   1200
cgaatttatt gttccgtact ggaagttcct gaagagcctg aatcgtccat tttgtattgg   1260
aatgaggttt aagattcagt atgggagtga agatgttaat gagaggcgat ctggaatgat   1320
tacaggtatt aatgaagtag accccattag gtggactggt tcaaaatgga aaagcctgca   1380
ggtaagatgg gaggatggca ccgactgtaa tagccaaaat agactatcgc catgggatat   1440
cgagatagtt ggtggctcgg tctctattgc ccagtctctg tcagcatcca gttctaaacg   1500
aactaaactg tgccctcagg gcaatgtgga cgtcccaact ctgtatggga atgttcgtcc   1560
ggactccgtg ggagctgata aactccccag ggtcttgcaa ggtcaagaat tgatgggttc   1620
tggaactcat cgttttacat gtcctcctca gccaggtggc gcacagaat tccgcgcttc   1680
tgatggtacg gggttcctta ctgatacacg aagctgcttg ctgagtggtc agcaagcag   1740
gcttccacct caaagctcct attttcgcct accaacctgta ggcttcggtg aatccgttgg   1800
gttcccggag gtcttgcaag gtcaagaagt ttgtcagacg gttcctctgt accaaggaat   1860
ggtgtctgat acatgttccg ctaaagcggg atacggtatg taacaattaca tgcgcacctc   1920
gtctgccatg aacggagggt tttcatctgc acctcagggt tatcctctct ccctgtctac   1980
tccgccccga gcagtggcgg cttcgccctc atccgcagcg gttccaccac agctttggct   2040
ggcaagcaag agcaatgaag aagctgcgaa tggcagccag cttaacccat ttggaattcg   2100
aaaggttcct ggtgatggtg ctgctaagct tggtgatggt cgtcgtaagc ttggatctga   2160
tggaaggaag gttgccagaa ccagttgcat gcttttcggg ttttccttga ccgagaagat   2220
gttgccaacg gaagaagact ctgccaagga agggaaccat gaagtcgact gtcagaatcc   2280
gcggatgcta gacttgtttg gatacaaccg cgccactccc ggcactcttc acgccctctg   2340
cgccgctccc ctgggaatat gatgccactc cagttccagt atgatccaag tactttgtag   2400
tgctcttcct aagaaacttt                                               2420

SEQ ID NO: 134          moltype = AA  length = 660
FEATURE                 Location/Qualifiers
REGION                  1..660
                        note = misc_feature - Ceres CLONE ID no.827306
REGION                  1..660
                        note = misc_feature - Bit score of 1417.6 for hmm based on
                         sequences of FIGURE 5.
REGION                  126..231
                        note = misc_feature - Pfam Name: B3 Pfam Description: B3
                         DNA binding domain
REGION                  253..334
                        note = misc_feature - Pfam Name: Auxin_resp Pfam
                         Description: Auxin response factor
REGION                  1..660
                        note = misc_feature - Is Acted Upon By Ceres SEEDLINE ID
                         no. ME00572 at SEQ ID NO. 111
source                  1..660
                        mol_type = protein
                        organism = Triticum aestivum
SEQUENCE: 134
MGIDLNAADE PGKAAAVSVC RDLWHACAGP VVALPRRGSA VVYLPQAHLA AAGGGGDVPV    60
ALPPHVACRV VDVELCADPA TDEVYARLAM VAEGEIFEKN MGGGRFEGED DMEDGDGERK   120
SRMLHMFCKT LTASDTSTHG GFSVPRRAAE DCFPPLDYQQ IRPSQELVAK DLHGAKWRFR   180
HIYRGQPRRH LLTTGWSSFV NKKKLVSGDA VLFLRGDDGE LRLGVRRAIQ LKNEALLKAF   240
NSNSSKIHTL SAVANSLKHR SVFHICYNPR AAASEFIVPY WKFLKSLNRP FCIGMRFKIQ   300
YGSEDVNERR SGMITGINEV DPIRWTGSKW KSLQVRWEDG TDCNSQNRLS PWDIEIVGGS   360
VSIAQSLSAS SSKRTKLCPQ GNVDVPTLYG NVRPDSVGAT KLPRVLQGQE LMGSGTHRFT   420
CPPQPGGATE FRRSDGTGFL TDTRSCLLSG PASRLPPQSS YFAYQPVGFG ESVGFPEVLQ   480
GQEVCQTVPL YQGMVSDTCS AKAGYGMYNY MRTSSAMNGG FSSAPQGYPL SLSTPPRAVA   540
ASPSSAAVPP QLWLASKSNE EAANGSQLNP FGIRKVPGDG AAKLGDGAAK LGSDGRKVAR   600
TSCMLFGFSL TEKMLPTEED SAKEGNHEVD CQNPRMLDLF GYNRATPGTL HALCAAPLGI   660

SEQ ID NO: 135          moltype = DNA  length = 2339
FEATURE                 Location/Qualifiers
misc_feature            1..2339
                        note = Ceres CLONE ID no.1598488
misc_feature            1..2339
                        note = Encodes the peptide sequence at SEQ ID NO. 136
source                  1..2339
                        mol_type = other DNA
                        organism = Zea mays
SEQUENCE: 135
cctgtacgcc gtcccgcttc gcttcggaga ggtcgctgcc tgccatcaac gttccctcgc     60
tggtagagta gaggtagacc caccgacccc cagtactagt cggagagag atgggggattg    120
atctcaacgc cgtgggggag gacgaccgg cgggcgcggt gtgcgcggag ctgtggcacg    180
cgtgcgcggg ggctggagtg gcgctgccgg cgcggggcag cgcggtgtgg tacctgcctc    240
aggcgcacct cgcggcgggc ggctgcgacg gtgtcgggat gtcggcgccg gcccgcgcgc    300
gcgtgccgcc gcacgtggtg tgtcgcgtcg tcgacgtcga gctacgcgcg gatgcggcca    360
cggacgaggt gtacgcgcgg cttcgcgctgg tggcgatgga tacgatgttt ggccgaaaca    420
tcaatgatgg tgaaactgaa gagaagaatg gcgaggaaga ggatgcgac ggagaaaaga    480
agcacgcatc acacatgttc tgcaagacac tcacagcttc tgataccagc acacatgggg    540
```

```
gattctctgt tccacggcga gctgcagagg actgctttcc acccttggac tatgagcagc    600
ttaggccttc ccaagagctt attgccaagg atttgcatgg catgaaatgg aggttccgtc    660
atatctatag aggtcaacct cgaaggcatc ttctgacaac tggatggagt tcatttatca    720
ataagaagaa actagtctca ggggatgcag tcttgtttct tagaggtaat gatggtgagc    780
taagattggg tgtgaggaga gcagttcaac tgaaaaatga agctctactt gaagctgtca    840
actgtactga ttcgaagcta cttatgctgt ctgctgtcgc caattctttg gacaacagaa    900
gtatatttca catctgtttc aacccaaggt tggtgcatc agaatttatt gtgccgtatt    960
gcaagttctt gaagagtttg aactatccct tttcagttgg aaccagattt aaagttggct   1020
gcgagaatga agatgctaac gagaggtcct ttggattgat cataggtatt agtgaagttg   1080
atcccataca ctggcctgga tcaaaatgga aatctctcct gataaagtgg gatggtgcta   1140
ctaagtacag ccaccagaat agagtatctc catgggacat cgaggagtt ggcagctcag   1200
tttcagttac tcaccgtctt tcctcttctg tttcgaagcg aacaaaactg tgcttccctc   1260
caagcgattt ggacacgcca attctagatg gaaatggtcg tccagactcc gtggaaactg   1320
aacgtttcca cagggtcttg caaggtcaag aattggtgca ctctagtatt cacggtgctg   1380
catgctctca ttcatcagat agccccagat gtcaaggctc ttatggcagg agattctctg   1440
ctgatgcatg gaactgcaag atgaatgatg taatgagtgg gcctcgacac ctaaatgcca   1500
ctgggtttgc ttaccagccc ctaggcttca gtgaatctgt caaattctca gaggtcttgc   1560
aaggtcaaga aatgctcag gcggttcctt ccttcatgag atctgctttc aactctgtca   1620
cgcagaatgg cagggttcga ccatttgatt atgtgcagag atcagatgca actcaaggat   1680
acgctctcca gcagtttaat ctgccagcaa cagaagtgca ttcgccctct tctgttctta   1740
tgtttaacca aaccatggta ccacatgctg agctagatg tgcgaccaac cgtgaagaag   1800
tacatggcag caggtacttg tcatccaatg caatagggag agaagctgaa ccatggccat   1860
ccatggagca gcaaagagcg agtgtaaatg gaagcgagcc tctcgacaca actgaagcct   1920
cagctcctgc aaggaacgct gaatctggat cggtcggcag gggcgtgggg cgaagcagct   1980
gtaagctttt tggtttctcc ctgactgaga agatccttgc aacggatggt ggtggtgtaa   2040
aagaaggaaa ctacgaagtg gaccgtcaaa ctccccgagt gctagacttg tttgggcacg   2100
gttctacgcc tggtgctctg catgctctct gtgctgctcc cttgggaata tgatgctgtt   2160
ctgcctagtt ttacagcagt tagatttatg taatccttca gccatttca tcgcgttgta   2220
cttgaccaat atgtccagcg tatgatttcc agttttaatt gtatgctgat gctacatatc   2280
ctctcttgag atccatgcat gagaattctg gcagaatgaa taaaggtaaa ttgatgtcc    2339

SEQ ID NO: 136          moltype = AA  length = 680
FEATURE                 Location/Qualifiers
REGION                  1..680
                        note = misc_feature - Ceres CLONE ID no.1598488
REGION                  1..680
                        note = misc_feature - Bit score of 1482.2 for hmm based on
                          sequences of FIGURE 5.
REGION                  129..234
                        note = misc_feature - Pfam Name: B3 Pfam Description: B3
                          DNA binding domain
REGION                  256..337
                        note = misc_feature - Pfam Name: Auxin_resp Pfam
                          Description: Auxin response factor
REGION                  1..680
                        note = misc_feature - Is Acted Upon By Ceres SEEDLINE ID
                          no. ME00572 at SEQ ID NO. 111
source                  1..680
                        mol_type = protein
                        organism = Zea mays
SEQUENCE: 136
MGIDLNAVGE DDPAGAVCAE LWHACAGAGV ALPRRGSAVV YLPQAHLAAG GCDGGGMSAP    60
APPRVPPHVV CRVVDVELRA DAATDEVYAR LALVAMDTMF GRNINDGETE EKNGEEEDGD   120
GEKKHASHMF CKTLTASDTS THGGFSVPRR AAEDCFPPLD YEQLRPSQEL IAKDLHGMKW   180
RFRHIYRGQP RRHLLTTGWS SFINKKKLVS GDAVLFLRGN DGELRLGVRR AVQLKNEALL   240
EAVNCTDSKL LMLSAVANSL DNRSIFHICF NPRVGASEFI VPYCKFLKSL NYPFSVGTRF   300
KVGCENEDAN ERSFGLIIGI SEVDPIHWPG SKWKSLLIKW DGATKYSHQN RVSPWDIEGV   360
GSSVSVTHRL SSSVSKRTKL CFPPSDLDTP ILDGNGRPDS VETERFHRVL QGQELVHSSI   420
HGAACSHSSD SPRCQGSYGR RFSADAWNCK MNDVMSGPRH LNATGFAYQP LGFSESVKFS   480
EVLQGQEMSQ AVPSFMRSAF NSGTQNGRVR PFDYVQRSDA TQGYALQQFN LPATEVHSPS   540
SVLMFNQTMV PHAELDGATN REEVHGSRYL SSNAIGREAE PWPSMEQQRA SVNGSEPLDT   600
TEASAPARNA ESGSVGRGVG RSSCKLFGFS LTEKILATDG GGVKEGNYEV DRQTPRVLDL   660
FGHGSTPGAL HALCAAPLGI                                              680

SEQ ID NO: 137          moltype = AA  length = 655
FEATURE                 Location/Qualifiers
REGION                  1..655
                        note = misc_feature - Public GI ID no.125527740
REGION                  1..655
                        note = misc_feature - Bit score of 1060.7 for hmm based on
                          sequences of FIGURE 5.
REGION                  114..219
                        note = misc_feature - Pfam Name: B3 Pfam Description: B3
                          DNA binding domain
REGION                  241..322
                        note = misc_feature - Pfam Name: Auxin_resp Pfam
                          Description: Auxin response factor
REGION                  1..655
                        note = misc_feature - Is Acted Upon By Ceres SEEDLINE ID
```

```
                        no. ME00572 at SEQ ID NO. 111
source                  1..655
                        mol_type = protein
                        note = subspecies = indica
                        organism = Oryza sativa
SEQUENCE: 137
MGIDLNYTAS GGEEDAPAPA PVCRDLWHAC AGPVVSLPRR GSAVVYLPQG HLSAAGAGGR    60
IRGEVAVALP PHVACRVVDV ELCVFERNLH GGGIEREDDM EDGDEERKSR MLHMFCKTLT   120
ASDTSTHGGF SVPRRAAEDC FPPLDHKQLR PSQELVAKDL HGAKWRFRHI YRGQPRRHLL   180
TTGWSSFVNK KKLVSGDAVL FLRGDDGELR LGVRRATQLK NEAIFKAFSS ESSKMRTLSA   240
VADSLKHGSV FHICYNPRAT ASEYVVPYWK FVKSFNHPVC IGMRFKFPHYE SEDVNERRSG  300
MIAGVSEVDP IRWPGSKWRS LLVRWEDATD CNSQNRVSPW EIEIVGGSIS VAHSLSASSS   360
KRTKLCPQGN LDVPALYGNG RPDSVETEKF PRVLQGQELM GSRTHRVTCS PQSIDITKSK   420
SFDAWRFLTD TRSCMLGSST SRLPVQYSGY THQSVSFGES IGFPEVLQGQ EISQTVPPIQ   480
GMLPDACSAK SRYELKNYVC TPATMNGLSS ANEGYCLSLS TVPPSPPSSL MLYQTGVPQL   540
ELASKNNDKS GNDSQPALRQ HKLLSETSWD QFKIGKASTP GNATKPGNGG REVDRTSCRL   600
FGFSLTEKII PTDKDGEKEV SYETDCQNPR MLDLFGYNCS TPGALHALCA APLGI        655

SEQ ID NO: 138          moltype = AA  length = 719
FEATURE                 Location/Qualifiers
REGION                  1..719
                        note = misc_feature - Public GI ID no.125553314
REGION                  1..719
                        note = misc_feature - Bit score of 1618.5 for hmm based on
                           sequences of FIGURE 5.
REGION                  141..246
                        note = misc_feature - Pfam Name: B3 Pfam Description: B3
                           DNA binding domain
REGION                  268..349
                        note = misc_feature - Pfam Name: Auxin_resp Pfam
                           Description: Auxin response factor
REGION                  1..719
                        note = misc_feature - Is Acted Upon By Ceres SEEDLINE ID
                           no. ME00572 at SEQ ID NO. 111
source                  1..719
                        mol_type = protein
                        note = subspecies = indica
                        organism = Oryza sativa
SEQUENCE: 138
MTGIDLNTVE EDEEEAAEEV AANGSSPAPA RAGAVCLELW HACAGPVAPL PRKGGVVVYL    60
PQGHLEHLGD APAAAAAAAA VPPHVFCRVV DVTLLADAAT DEVYAQLSLV PEKEEVARRA   120
DDGEGEDGDG MKQRFARMPH MFCKTLTASD TSTHGGFSVP RRAAEDCFPP LDYSQQRPSQ   180
ELVAKDLHGT EWRFRHIYRG QPRRHLLTTG WSAFVNKKKL VSGDAVLFLR GDDGELRLGV   240
RRAAQLKNGS AFPALYNQCS NLGTLANVAH AVATESVFNI YYNPRLSQSE FIVPYWKFMK   300
SLSQPPFSVGL RFKMRYESED ASERRYTGII TGSGDTDPMW HGSKWKCLLV RWDDDAEFRR   360
PNRVSPWEIE LTSSVSGSHL STPHSKRLKP CLPHVNPEYM VPRGGGCPDF AESAQFHKVL   420
QGQELLGFKS HGGTAAATSQ PCEARHLQYI DERSCSSDAS NSILGVPRLG DRAPLGNPGF   480
SYHCSGFGES QRLQKVLQGQ ELFRPYRGTL VDASMGSNGF HQQDSPRAPG VVVNKWQAQLH  540
GRAAFHGPPA LALPSQSSSP PSVLMFQQAN SKMPRLEFGH GQLDKHENDR RVRFGPSEGI   600
ERREQRIPLQ PYPTSGEVID GQVTEKSHS PGRHGKDGPD NKAVGTNSCK IFGISLTEKV   660
PAREELDDGD ANYSLQSLKQ VPKSLGNSCA TMVAEYQGDG GTDDSIFIL DVGVGALIM    719

SEQ ID NO: 139          moltype = AA  length = 788
FEATURE                 Location/Qualifiers
REGION                  1..788
                        note = misc_feature - Ceres LOCUS ID no. At5g60450
REGION                  1..788
                        note = misc_feature - Bit score of 808.3 for hmm based on
                           sequences of FIGURE 5.
REGION                  176..281
                        note = misc_feature - Pfam Name: B3 Pfam Description: B3
                           DNA binding domain
REGION                  302..384
                        note = misc_feature - Pfam Name: Auxin_resp Pfam
                           Description: Auxin response factor
REGION                  1..788
                        note = misc_feature - Is Acted Upon By Ceres SEEDLINE ID
                           no. ME00572 at SEQ ID NO. 111
source                  1..788
                        mol_type = protein
                        organism = Arabidopsis thaliana
SEQUENCE: 139
MEFDLNTEIA EVEEEENDDV GVGVGGGTRI DKGRLGISPS SSSSCSSGSS SSSSSTGSAS    60
SIYSELWHAC AGPLTCLPKK GNVVVYFPQG HLEQDAMVSY SSPLEIPKFD LNPQIVCRVV   120
NVQLLANKDT DEVYTQVTLL PLQEFSMLNG EGKEVKELGG EEERNGSSSV KRTPHMFCKT   180
LTASDTSTHG GFSVPRRAAE DCFAPLDYKQ QRPSQELIAK DLHGVEWKFR HIYRGQPRRH   240
LLTTGWSIFV SQKNLVSGDA VLFLRDEGGE LRLGIRRAAR PRNGLPDSII EKNSCSNILS   300
LVANAVSTKS MFHVFYSPRA THAEFVIPYE KYITSIRSPV CIGTRFRMRF EMDDSPERRC   360
AGVVTGVCDL DPYRWPNSKW RCLLVRWDES FVSDHQERVS PWEIDPSVSL PHLSIQSSPR   420
```

```
PKRPWAGLLD TTPPGNPITK RGGFLDFEES VRPSKVLQGQ ENIGSASPSQ GFDVMNRRIL  480
DFAMQSHANP VLVSSRVKDR FGEFVDATGV NPACSGVMDL DRFPRVLQGQ EICSLKSFPQ  540
FAGFSPAAAP NPFAYQANKS SYYPLALHGI RSTHVPYQNP YNAGNQSSGP PSRAINFGEE  600
TRKFDAQNEG GLPNNVTADL PFKIDMMGKQ KGSELNMNAS SGCKLFGFSL PVETPASKPQ  660
SSSKRICTKV HKQGSQVGRA IDLSRLNGYD DLLMELERLF NMEGLLRDPE KGWRILYTDS  720
ENDMMVVGDD PWHDFCNVVW KIHLYTKEEV ENANDDNKSC LEQAALMMEA SKSSSVSQPD  780
SSPTITRV                                                         788

SEQ ID NO: 140          moltype = DNA  length = 2064
FEATURE                 Location/Qualifiers
misc_feature            1..2064
                        note = Ceres ANNOT ID no.1515383
misc_feature            1..2064
                        note = Encodes the peptide sequence at SEQ ID NO. 141
source                  1..2064
                        mol_type = other DNA
                        organism = Populus balsamifera
                        sub_species = trichocarpa
SEQUENCE: 140
atggaaattg atctgaatca tccagtgact gaggtggaga agaattcatt ttgtaccaat   60
ggggactctt catgttcttc taattcatct tcatctccag tttcctcttc aatttacttg  120
gagctttggc atgcttgtgc tggtcctctc acttctctcc ctaagaaagg gaatgtggtt  180
gtctacttcc ctcaaggcca cttggagcag cttgcctctt cctctccttt ctctcatagg  240
gacatgccca attttgatct ccacccacaa atattttgca aagttgtaaa tgtgcagcta  300
cttgccaata gggaaaatga tgaggtctac actcggctta ctttgcttcc tcaaccagag  360
gtggtaggac aggatttaga aggcaaagag cttcaagagt taggcgtgga tggagaggat  420
gacgacgcat caccaacaaa atcaacccca cacatgtttt gcaaaacact cacagccttc  480
gatactagca cccatggagg gttttccgtt cctcgaagag ctgccgaaga ctgtttccct  540
tcactggatt ataaacagca gagaccctct caagagcttt tggccaaaga cttgcatgga  600
gttgaatgga gatttcgtca tatttacaga ggtcaaccaa gaaggcatct tctaactacg  660
ggatggagta tttttgtgag tcaaaagaat cttgtttcag gggatgcagt gctatttctg  720
aggggcgaag tgtgagagtt gagactgggg atcagacgag ctgctcgacc tagaaatggt  780
cttcctgatt ctgttactgg caagcagaat tcacttccca gtgctctctc cttggtgtct  840
aatgcaatat ccaccaagag cgtgttcact gtttcatata gtccaagggc cactcatgca  900
gtgtttgttg tacccctacca aaagtatata aaaagcatca ccaatgcagt ttgcatcggg  960
acaagattca aaatgagatt tgaaatggat gattctcctg aaagaaggtg tagcggtgta 1020
gtaactggaa cagctgactt ggatcccctat aagtggccca actcaaaatg gaggtgctta 1080
atggttagat gggatgaaga tgtcatcagt gatcatcaag aacgagtttc cccatggaa  1140
attgacgctt ctgtttcact cccacccttg attattcaat cttccaccaag gttgaagaaa 1200
ctgcggactg ggctgcaagc agccccacct gataagccca tagctgcagg gggtgggttt 1260
ttggatttca aggagtctgt aagatcctcc aaggtcttgc aaggtcaaga aatatgctcg 1320
ttgagttctg ttggtgcttt gggaaagccc aatactggac gcagttcttt ccagatgtat 1380
ccaggaccaa gacccgcttt ctatcctgta gcagcagaaa gcttagaag tatgtacttt 1440
ccctatggag atgtatacaa aaatggtcaa gatcccagaa cacaatctta tgctatcttc 1500
tctagagaaa atgcccattt caatacatct tctattcaga cttgtgtggt tagggaagaa 1560
gttagaaagc ctaatcaatc aagcgagtat aagacacaag aaagtatttc tgctgcaccg 1620
gctttatgtg caaatctaag aaaccaaaag gatgacttgt ttaatgggaa tgctactggc 1680
tgcaaacttt ttgggttctc cttgaatgca gaaacatctc caaattcgca gaacactagt 1740
aagaggagtt gcacaaaggt tcacaagcaa ggtagcttgg tcggaagagc tattgatctt 1800
tcaaggctga atggctatag tgatctcttg aatgaactag agcgactatt tagcatggag 1860
ggtcttttac gaaatcctga ggaaggatgg cgaatcttgt atactgacag tgagaatgat 1920
gttatggttg tcggagatga cccatggctt gagttctgta atgtggcaac caagatccat 1980
atatataccc aagaagaagt ggagaagatg accgttggaa ttactgggga cgatactcaa 2040
agttgtttgg atcaagccct gtga                                       2064

SEQ ID NO: 141          moltype = AA  length = 687
FEATURE                 Location/Qualifiers
REGION                  1..687
                        note = misc_feature - Ceres ANNOT ID no.1515383
REGION                  1..687
                        note = misc_feature - Bit score of 794.3 for hmm based on
                          sequences of FIGURE 5.
REGION                  152..257
                        note = misc_feature - Pfam Name: B3 Pfam Description: B3
                          DNA binding domain
REGION                  279..361
                        note = misc_feature - Pfam Name: Auxin_resp Pfam
                          Description: Auxin response factor
REGION                  1..687
                        note = misc_feature - Is Acted Upon By Ceres SEEDLINE ID
                          no. ME00572 at SEQ ID NO. 111
source                  1..687
                        mol_type = protein
                        note = subspecies = trichocarpa
                        organism = Populus balsamifera
SEQUENCE: 141
MEIDLNHPVT EVEKNSFCTN GDSSCSSNSS SSPVSSSIYL ELWHACAGPL TSLPKKGNVV   60
VYFPQGHLEQ LASSSPFSHR DMPNFDLHPQ IFCKVVNVQL LANRENDEVY TRLTLLPQPE  120
VVGQDLEGKE LQELGVDGEG DDASPTKSTP HMFCKTLTAS DTSTHGGFSV PRRAAEDCFP  180
```

```
SLDYKQQRPS QELLAKDLHG VEWRFRHIYR GQPRRHLLTT GWSIFVSQKN LVSGDAVLFL  240
RGEGGELRLG IRRAARPRNG LPDSVTGKQN SLPSALSLVS NAISTKSVFT VSYSPRATHA  300
VFVVPYQKYI KSITNAVCIG TRFKMRFEMD DSPERRCSGV VTGTADLDPY KWPNSKWRCL  360
MVRWDEDVIS DHQERVSPWE IDASVSLPPL IIQSSPRLKK LRTGLQAAPP DKPIAGGGGF  420
LDFKESVRSS KVLQGQEICS LSSVGALGKP NTGRSSFQMY PGPRPAFYPV AAESLRSMYF  480
PYGDVYKNGQ DPRTQSYAIF SRENAHFNTS SIQTCVVREE VRKPNQSSEY KTQESISAAP  540
ALCANLRNQK DDFFNGNATG CKLFGFSLNA ETSPNSQNTS KRSCTKVHKQ GSLVGRAIDL  600
SRLNGYSDLL NELERLFSME GLLRNPEEGW RILYTDSEND VMVVGDDPWL EFCNVATKIH  660
IYTQEEVEKM TVGITGDDTQ SCLDQAL                                     687

SEQ ID NO: 142         moltype = DNA  length = 2722
FEATURE                Location/Qualifiers
misc_feature           1..2722
                       note = Ceres CLONE ID no.462443
misc_feature           1..2722
                       note = Encodes the peptide sequence at SEQ ID NO. 143
source                 1..2722
                       mol_type = other DNA
                       organism = Zea mays
SEQUENCE: 142
agacaaccaa acgaaccctc ccggagcagc aaagcatagg cgctcgagcg ctccctcccg   60
agctcctccg cctcacggtc acgcctcgtg tcccccccacc cctcctcct cctcctcggc  120
cggccgcctc acgccgtcac ctccgctcgg cgagtctcgg ctccgaccgc tgccgccacg  180
tgcgacctcc cctactcctg agagatctgc ggggctcggc atggggtgac cagatcgggc  240
cgctgctcgg tgctttccag ctgaattttg cccgcagctc gtgtcggagg cagcgaagat  300
ggcggaggcc ggcgtggcac gcggctcagg gagcgctgcg gatgctttgt tcagggaact  360
ctggcatgct tgtgctgggc cgttggtcac agtgcctcgc caaggcgagc tggtttatta  420
cttcccccag ggtcatatgg aacagcttga agcgtctaca gatcaacaac ttgatcagca  480
cttgcctttg tttaatctac cgcacaagat cctctgcaag gtggtcaatg tagaacttag  540
agctgaaact gattctgatg aagtttatgc tcaaattatg ctgcaaccac aaacagagca  600
aagtgagccc accagcccag atcctgaacc acctgagcct gaaagatgca acattcattc  660
cttctgcaag accttgactg cttcagatac aagtacccat ggtctctctg tcctcaggag  720
gcatgctgaa gaatgtttgc cccaactgga catgactcag aatccaccgt ggcaagaact  780
agtggctcaaa gatctccatg gaaatgaatg gcatttccgt cacatctttc gagggcaacc  840
aaggaggcat ctacttacga caggctggag tgttttttgtt agctcaaaaa gattggttgc  900
gggtgacgcg tttatcttct tgagaggtga gaacggagag ctgcgagtcg gggtaaggag  960
gctcatgaga caactaaaata acatgccgtc ttcggttatc tcaagccaca gcatgcatct 1020
tggagtccta gcaactgcat ctcatgccat ctccactgga actctatttt ctgttttcta 1080
caaacccaga acaagtagat ctgaattttgt cgttagtgta aacaagtacc tcgaagctaa 1140
gaatcacaag atgtctgttg gtatgaggtt taaaatgaga tttgagggtg atgaatcccc 1200
tgaaagaaga ttcagtggga taattattgg tatgggatgc atgccagcta actcaacatc 1260
tccatgggct aactctgaat ggagatcatt gaaggtccaa tgggacgagc cttctgctat 1320
tctgcgtcca gatagagttt caccatggga agtagaccca cttaatcgaa caaatccaca 1380
gccacctcaa cctcctttac ggaataagcg agcacggcct cctgcttcac cttcgattgc 1440
tccagaactt gctccagttt ttggttttttg gaagtccca gctgagcctg cccaagcttt 1500
ctcattctca ggactgcagc gaactcagga gctataccat tcaagcccca gttcaatgtt 1560
ctcatcgtcg ttgaatgtgg gattcaatcc aaagtacgag ggtcccactc caaacaccaa 1620
ccatttgtac tggacaatga gagagacaag aactgaatcc tactccgcta gcatcaacaa 1680
agctccaact gaaaagaagc aagaatccac tacttctggc tgcagattgt tcggtatcga 1740
gataggttct tctgcagtgt cacccgtggt tactgttgct agcgtcgggc atgatcctcc 1800
gccacctgct ctctcagtag acgctgaatc tgaccagctg tcacagccgt ccatgccaa 1860
caaagcaacg gatgccccag cggcaagcag cgatcgctct cctaacgaga cagagagccg 1920
gcaagccagg agctgcacca aggtaatcat gcaaggggtg gcggttggca gggcggtgga 1980
cttgacgagg ctagatgggt acgatgacct ccgccgcaag ttggaggaga tgttcgatat 2040
cccgggagag ctttccgcca gcctcaataa atggaaggtg atctacacag atgacgagga 2100
cgatatgatg ctggtcgggg acgatccatg gagtgaattt gcaggatgg taaaaaggat 2160
atacatttat tcctacgagg aggccaagtc tttgactccc aaggcgaagc tgccggccat 2220
cggtggtgac accggcgtca agccggaccc aagtaaactg tcagcagaat ctgacgtgcc 2280
acagagcgac tccgacaaca gtgctcccgt ttctgctgat aaggactgat ggacgctagc 2340
tcggccgtac cttctctttta tgttggccat gggaggccag tgcagtgccc atgctccttg 2400
agactgctaa gaattgatca tctgttccat ctgcctcggc ttggaccagc gaggatggcc 2460
gggagggagt gcatgccgct ccgtgcgtgt ttcgtttgcc gtgtttggta ggagccatgg 2520
cttgttgccg gctacttggg ttctgtagac tgttacactg actgctgccg tctcacctgg 2580
ccgtcggcgc gggccgcccc ctctcacctc tctagtaata tactagggct tatgtacaca 2640
cagctgtttt ggtagtgcga tatgtatatc gtcggtcatg ttgcttgcga catttagcat 2700
cctccgtagc tgctatttcc tc                                         2722

SEQ ID NO: 143         moltype = AA  length = 676
FEATURE                Location/Qualifiers
REGION                 1..676
                       note = misc_feature - Ceres CLONE ID no.462443
REGION                 1..676
                       note = misc_feature - Bit score of 1504.3 for hmm based on
                        sequences of FIGURE 5.
REGION                 121..225
                       note = misc_feature - Pfam Name: B3 Pfam Description: B3
                        DNA binding domain
REGION                 247..332
                       note = misc_feature - Pfam Name: Auxin_resp Pfam
```

```
                        Description: Auxin response factor
REGION                  1..676
                        note = misc_feature - Is Acted Upon By Ceres SEEDLINE ID
                         no. ME00572 at SEQ ID NO. 111
source                  1..676
                        mol_type = protein
                        organism = Zea mays
SEQUENCE: 143
MAEAGVARGS GSAGDALFRE LWHACAGPLV TVPRQGELVY YFPQGHMEQL EASTDQQLDQ    60
HLPLFNLPHK ILCKVVNVEL RAETDSDEVY AQIMLQPQTE QSEPTSPDPE PPEPERCNIH   120
SFCKTLTASD TSTHGLSVLR RHAEECLPQL DMTQNPPWQE LVAKDLHGNE WHFRHIFRGQ   180
PRRHLLTTGW SVFVSSKRLV AGDAFIFLRG ENGELRVGVR RLMRQLNNMP SSVISSHSMH   240
LGVLATASHA ISTGTLFSVF YKPRTSRSEF VVSVNKYLEA KNHKMSVGMR FKMRFEGDES   300
PERRFSGIII GMGCMPANST SPWANSEWRS LKVQWDEPSA ILRPDRVSPW EVEPLNRTNP   360
QPPQPPLRNK RARPPASPSI APELAPVFGF WKSPAEPAQA FSFSGLQRTQ ELYHSSPSSM   420
FSSSLNVGFN PKYEGPTPNT NHLYWTMRET RTESYSASIN KAPTEKKQES TTSGCRLFGI   480
EIGSSAVSPV VTVASVGHDP PPPALSVDAE SDQLSQPSHA NKATDAPAAS SDRSPNETES   540
RQARSCTKVI MQGVAVGRAV DLTRLDGYDD LRRKLEEMFD IPGELSASLN KWKVIYTDDE   600
DDMMLVGDDP WSEFCRMVKR IYIYSYEEAK SLTPKAKLPA IGGDTGVKPD PSKLSAESDV   660
PQSDSDNSAP VSADKD                                                  676

SEQ ID NO: 144          moltype = DNA  length = 329
FEATURE                 Location/Qualifiers
misc_feature            1..329
                        note = Public GI No. 21403834
misc_feature            1..329
                        note = Homolog Of Ceres SEEDLINE ID no. ME00572 at SEQ ID
                         NO. 111
misc_feature            1..329
                        note = FRAGMENT
source                  1..329
                        mol_type = other DNA
                        organism = Arabidopsis thaliana
SEQUENCE: 144
tatctgagct tttagtcgga ttttttcttt tcaattattg tgttttatct agatgatgca    60
tttcattatt ctcttttctt tgaccttgta aggccttttc ttgaccttgt aagacccccat  120
ctctttctaa acgttttatt attttctcgt tttacagatt ctattctatc tcttctcaat  180
atagaataga tatctatctc tacctctaat tcgttcgagt cattttctcc taccttgtct  240
atccctcctg agctaatctc cacatatatc ttttgtttgt tattgatgta tggttgacat  300
aaattcaata aagaagttga cgttttttcc                                   329

SEQ ID NO: 145          moltype = DNA  length = 350
FEATURE                 Location/Qualifiers
misc_feature            1..350
                        note = Public GI No. 158087544
misc_feature            1..350
                        note = Homolog Of Ceres SEEDLINE ID no. ME00572 at SEQ ID
                         NO. 111
misc_feature            1..350
                        note = FRAGMENT
source                  1..350
                        mol_type = other DNA
                        organism = Solanum lycopersicum
SEQUENCE: 145
cctaacgatg agtgtcgcat cctcatctta atctcggtgc tatcctacct gagcttttc    60
tcaccgcttt ttttttttctg ttgtgtattc tctttttga cttgttgcct ttcgttcctc  120
tacctaccc attcttcttg accttgtaag acctttttctt gaccttgtaa gacccgtgt   180
tatctcttac gtctttatgt tttgtttttt tgcaaatctt acgtcatgac ttcttcatgt  240
aagctttgtt tggtctcctt cttctttcct actcaactct cgttctcctt ccttgtctat  300
ccctcctgag ctgttgattt tattccatgt acaattgaac acaacaaaaa              350

SEQ ID NO: 146          moltype = DNA  length = 197
FEATURE                 Location/Qualifiers
misc_feature            1..197
                        note = Public GI No. 110797273
misc_feature            1..197
                        note = Homolog Of Ceres SEEDLINE ID no. ME00572 at SEQ ID
                         NO. 111
misc_feature            1..197
                        note = FRAGMENT
source                  1..197
                        mol_type = other DNA
                        organism = Brassica rapa
SEQUENCE: 146
aaaaaatttc tttctcccac tgaatgattt tttattttct tgaccttgta aggccttttc    60
ttgaccttgt aagaccccat cccttttctaa gtgtttcctt cttctatcat cttacagatt  120
ttctttttatc tcttttttggt gtaagatatg tatgtatatc taccctagt ttgtctgagt   180
catcttctcc taccttg                                                  197
```

```
SEQ ID NO: 147           moltype = DNA  length = 207
FEATURE                  Location/Qualifiers
misc_feature             1..207
                         note = Public GI No. 118566241
misc_feature             1..207
                         note = FRAGMENT
misc_feature             1..207
                         note = Homolog Of Ceres SEEDLINE ID no. ME00572 at SEQ ID
                            NO. 111
source                   1..207
                         mol_type = other DNA
                         organism = Medicago truncatula
SEQUENCE: 147
gagcttttt ttcacctttc tcttttctta actttttttt tactctactt gtgtcttctt     60
gaccttgtaa gacctttct tgaccttgta agacctcact ctgtgtcggt tttcttgtt    120
tttgcttttg tggaagacgc tatatcgaaa tttgttgata tagagtttcg tctccgtttt   180
tcccttttac cacccaactc attctct                                       207

SEQ ID NO: 148           moltype = DNA  length = 188
FEATURE                  Location/Qualifiers
misc_feature             1..188
                         note = Public GI No. 147857869
misc_feature             1..188
                         note = FRAGMENT
misc_feature             1..188
                         note = Homolog Of Ceres SEEDLINE ID no. ME00572 at SEQ ID
                            NO. 111
source                   1..188
                         mol_type = other DNA
                         organism = Vitis vinifera
SEQUENCE: 148
cccggttgtg tttcctttg ttcgggtcat tacttcttct tgaccttgta agaccttttc     60
ttgaccttgt aagaccccgg gcaaaatccg ctatccttat tatatcagtc gagaaggact   120
tcctattaga cactactgat aaagagttca ataatcaata cttgatgtcc ccaacctact   180
cgtcatct                                                            188

SEQ ID NO: 149           moltype = DNA  length = 182
FEATURE                  Location/Qualifiers
misc_feature             1..182
                         note = Public GI No. 58530789
misc_feature             1..182
                         note = FRAGMENT
misc_feature             1..182
                         note = Homolog Of Ceres SEEDLINE ID no. ME00572 at SEQ ID
                            NO. 111
source                   1..182
                         mol_type = other DNA
                         organism = Oryza sativa
SEQUENCE: 149
aaaacctcaa catcactttg tgtgggaatt aaaaggaatt ggtcttcttg accttgcaag    60
acctttcttt gaccttgtaa gacccaacat cgttgtgttg tttttcttgt ttcttatttt   120
tcaatttcat ccacctcttc tttctaccct ccatctttct cctagttctt gccttctctc   180
tc                                                                  182

SEQ ID NO: 150           moltype = DNA  length = 232
FEATURE                  Location/Qualifiers
misc_feature             1..232
                         note = Public GI No. 21212701
misc_feature             1..232
                         note = FRAGMENT
misc_feature             1..232
                         note = Homolog Of Ceres SEEDLINE ID no. ME00572 at SEQ ID
                            NO. 111
source                   1..232
                         mol_type = other DNA
                         organism = Zea mays
SEQUENCE: 150
ccaagccagc tagcaactca aaggaggaag actagaagat atatagcctt ctccttgtgt    60
gacactcata aataaactgt tagcagcttg cgagcactgc aagatctttc tgctggcatc   120
tgaatagtca gctgctggca tctatccggg cacctctcga ccagccagag gcaggatacc   180
tggatcccaa actagctggc caacatggcg aacgatgacc ctgtggacga cg           232

SEQ ID NO: 151           moltype = DNA  length = 549
FEATURE                  Location/Qualifiers
misc_feature             1..549
                         note = Public GI No. 119010892
misc_feature             1..549
                         note = Homolog Of Ceres SEEDLINE ID no. ME00572 at SEQ ID
                            NO. 111
```

```
                            -continued source                  1..549
                        mol_type = other DNA
                        organism = Manhiot esculenta
SEQUENCE: 151
ttttttttttt ctcttcttct ccttctcctt tccttctca tctctctctc tctctctctc       60
tctctcagca tgaaagagag aggaaagcat tcagaggtga aactcaggca taagtttctt      120
caaggcattc atgaagttaa aatcatgaac aacgccacca tctgcaacgc ttccagtggt      180
gggttttttgg ctggcttctc gtttggggct aaaagtccct ttggaatggt ggttggttca     240
tgttgatggg gtgctatcct acctgagctt tttctattat tttcctttt atttttttc        300
ttactttttgt ttttaatctt cttgaccttg taagaccttt tcttgacctt gtaagacccc     360
ttttatgtt tatttatctt aattttgta ttgtcataaa ttctatatca aaattttttg        420
atatagaatt tcatgtttat ttttttctgt ttttgcccaa ctcatattct ccttccttgt      480
ctatccctcc tgagctattt gaataaaatt attatgctaa ttattcagaa aaaaaaaaa       540
aaaaaatcg                                                              549

SEQ ID NO: 152          moltype = DNA   length = 168
FEATURE                 Location/Qualifiers
misc_feature            1..168
                        note = 000POPULUS
misc_feature            1..168
                        note = Homolog Of Ceres SEEDLINE ID no. ME00572 at SEQ ID
                         NO. 111
source                  1..168
                        mol_type = other DNA
                        organism = Populus balsamifera
                        sub_species = trichocarpa
SEQUENCE: 152
gtttttttttt ttgttttttt ttcttgacct tgtaagacct tttcttgacc ttgtaagacc      60
ccattttttg ttctttgttt ctatagcatc cctcttgcca cccaactcat catctccttc      120
tctgtctatc cctcctgagc tatttcgatc acaccgcaag atcacatt                   168

SEQ ID NO: 153          moltype = DNA   length = 167
FEATURE                 Location/Qualifiers
misc_feature            1..167
                        note = 000THEOBROMA
misc_feature            1..167
                        note = Homolog Of Ceres SEEDLINE ID no. ME00572 at SEQ ID
                         NO. 111
misc_feature            69
                        note = n is a, c, t, g, unknown, or other
misc_feature            71
                        note = n is a, c, t, g, unknown, or other
source                  1..167
                        mol_type = other DNA
                        organism = Theobroma cacao
SEQUENCE: 153
ttcttcttc ttttcttatc ttccttgacct tgtaagacct tttcttgacc ttgtaagacc       60
ccgttcggng ntcettggtt ttgcttctac cccattcccg ccaacttttc ttctcccttc      120
cttgctatcc ctcctgagct ggttgaatta gcctagccta gctatag                    167

SEQ ID NO: 154          moltype = DNA   length = 168
FEATURE                 Location/Qualifiers
misc_feature            1..168
                        note = 000MALUS
misc_feature            1..168
                        note = Homolog Of Ceres SEEDLINE ID no. ME00572 at SEQ ID
                         NO. 111
source                  1..168
                        mol_type = other DNA
                        organism = Malus x domestica
SEQUENCE: 154
cgcatcgatc ccttcccttt ttcttgacct tgtaagacct tttcttgacc ttgtaagatg       60
tcatgccagg tctgttgtct ttggttcctc atcgttavvg vvvaattcat cttctcccttc    120
cttgtctatc cctcctgagc tgttccacaa ttacctcaaa ctacaagc                   168

SEQ ID NO: 155          moltype = DNA   length = 168
FEATURE                 Location/Qualifiers
misc_feature            1..168
                        note = 000GLYCINE
misc_feature            1..168
                        note = Homolog Of Ceres SEEDLINE ID no. ME00572 at SEQ ID
                         NO. 111
source                  1..168
                        mol_type = other DNA
                        organism = Glycine max
SEQUENCE: 155
gtttttccct tggagtcttc ttcttgacct tgtaagacct tttcttgacc ttgtaagacc       60
tcacacccta tctcttctct ttgttctttc ccgttacca cccaactcat actttccttc      120
cttgtctatc cctcctgagc tgttccaatt taattaattt ggcctacc                   168
```

```
SEQ ID NO: 156           moltype = DNA  length = 168
FEATURE                  Location/Qualifiers
misc_feature             1..168
                         note = 000LOTUS
misc_feature             1..168
                         note = Homolog Of Ceres SEEDLINE ID no. ME00572 at SEQ ID
                           NO. 111
source                   1..168
                         mol_type = other DNA
                         organism = Lotus japonicus
SEQUENCE: 156
ccttgtttcc cctccggtc ttcttgacct tgtaagacct tttcttgacc ttgtaagacc    60
tcacgccgtg tctgttttct tcagtctttc cccgttaccg tccaactcat cctctccttc   120
cttgtctatc cctcctgagc tatttcaatt ttggccaagc atgccaca               168

SEQ ID NO: 157           moltype = AA  length = 165
FEATURE                  Location/Qualifiers
REGION                   1..165
                         note = misc_feature - Ceres Annot ID no. 8670388
REGION                   1..165
                         note = misc_feature - Truncated
REGION                   1..165
                         note = misc_feature - Bit score of 420.2 for hmm based on
                           sequences of FIGURE 4.
REGION                   1..165
                         note = misc_feature - Functional Homolog Of SEQ ID NO. 93
source                   1..165
                         mol_type = protein
                         organism = Sorghum bicolor
SEQUENCE: 157
MIDTMIPLMK HSPYGARIVN VSSRLGRANG RRNRIGDASL RDRLLKDDCL SEQLVDEMIT    60
KFLEQVKQGT WSSNEWPQMY TDYSISKLAV NVYTRLMARR LSDRPEGQKI YINCFCPGWV   120
NTAMTGWEGN ISAEEGADTG VWLALLPQEP PTNGKFFAER CEISF                  165

SEQ ID NO: 158           moltype = AA  length = 165
FEATURE                  Location/Qualifiers
REGION                   1..165
                         note = misc_feature - Public GI ID no. 194696386
REGION                   1..165
                         note = misc_feature - Truncated
REGION                   1..165
                         note = misc_feature - Bit score of 411.4 for hmm based on
                           sequences of FIGURE 4.
REGION                   1..165
                         note = misc_feature - Functional Homolog Of SEQ ID NO. 93
source                   1..165
                         mol_type = protein
                         organism = Zea mays
SEQUENCE: 158
MIDAMIPLMK RSAYGARIVN VSSRLGRANG RRNRIGDVSL RDRLLKDDCL SEQLIDEMIT    60
KFLEQAKQGT WSLNEWPQMY TDYSISKLAV NAYTRLMARR LSDRPEGQKI YINCFCPGWV   120
KTAMTGWEGN VSAEEGADTG IWLALLPQET DTNGKFFAER CEISF                  165

SEQ ID NO: 159           moltype = AA  length = 163
FEATURE                  Location/Qualifiers
REGION                   1..163
                         note = misc_feature - Ceres Clone ID no. 1906273
REGION                   1..163
                         note = misc_feature - Truncated
REGION                   1..163
                         note = misc_feature - Bit score of 400.6 for hmm based on
                           sequences of FIGURE 4.
REGION                   1..163
                         note = misc_feature - Functional Homolog Of SEQ ID NO. 93
source                   1..163
                         mol_type = protein
                         organism = Panicum virgatum
SEQUENCE: 159
MLTEALLPLF RQSPATSRIL NISSQLGLLN KVSDSSLKAL LLDEETLTEA AIDAMVSRFL    60
AQVKDGTWGA QGWPKVWTDY SVSKLALNAY SRLLARRLQA RGARVSVNCF CPGFTRTDMT   120
RGWGKRTAEE VADVGARLAL LPPGELPTGA FFKWCTPQLY SKL                    163

SEQ ID NO: 160           moltype = AA  length = 161
FEATURE                  Location/Qualifiers
REGION                   1..161
                         note = misc_feature - Ceres Clone ID no. 100894176
REGION                   1..161
                         note = misc_feature - Truncated
```

| | | |
|---|---|---|
| REGION | 1..161 | |
| | note = misc_feature - Bit score of 364.2 for hmm based on sequences of FIGURE 4. | |
| REGION | 1..161 | |
| | note = misc_feature - Functional Homolog Of SEQ ID NO. 93 | |
| source | 1..161 | |
| | mol_type = protein | |
| | organism = Zea mays | |

SEQUENCE: 160
```
MLTEALLPLF RQSSATSRIL NISSQLGLLN KVGDPSLKAL LLDEERLTEA GIEAMVSRFL   60
AQVKDGTWGE QGWPKVWTDY SVSKLALNAY SRLLARRLEA RGVSVNCFCP GFTRTDMTRG  120
WGKRTAGEEA DVGARLALLP PTELPTGTFF KWRTPQLYSK L                    161
```

| | | |
|---|---|---|
| SEQ ID NO: 161 | moltype = AA   length = 164 | |
| FEATURE | Location/Qualifiers | |
| REGION | 1..164 | |
| | note = misc_feature - Ceres Annot ID no. 8459736 | |
| REGION | 1..164 | |
| | note = misc_feature - Truncated | |
| REGION | 1..164 | |
| | note = misc_feature - Bit score of 361.8 for hmm based on sequences of FIGURE 4. | |
| REGION | 1..164 | |
| | note = misc_feature - Functional Homolog Of SEQ ID NO. 93 | |
| source | 1..164 | |
| | mol_type = protein | |
| | organism = Solanum lycopersicum | |

SEQUENCE: 161
```
MIKALTPLMR PSPAGSRIVS VTSRLGRLNS KRNGISNVAV REQLENVDTL SEEVIDKTMH   60
TFLEQVKDGT WESAGWPHVF TDYSLSKLAV NAYTRLMARI FEERPEGEKI YINCYCPGWV  120
KTAMTGWAGH VTIEEAADTA VWLALLPDQF VSGKFFAERR EINF                  164
```

| | | |
|---|---|---|
| SEQ ID NO: 162 | moltype = DNA   length = 975 | |
| FEATURE | Location/Qualifiers | |
| misc_feature | 1..975 | |
| | note = Ceres Annot ID no. 8670388 | |
| misc_feature | 1..975 | |
| | note = Encodes the peptide sequence at SEQ ID NO. 163 | |
| source | 1..975 | |
| | mol_type = other DNA | |
| | organism = Sorghum bicolor | |

SEQUENCE: 162
```
atggggaaga aagggaagga ggcggcgcgg gagcggcgcg agcagcgccg ccgcgaggtc   60
accctcctcc gggctctccc ctacgagccc caccagcgat ggtgggaccg cctggcgccg  120
cgggccgtgg cggtggtcac gggcgccaac cgcgggatag gcttcgaggc cgcccgccag  180
ctcgcgctcc acgccctgca cgtcgtgctc gcctcccgcg acgccgccaa gggccaggac  240
gccgcgggga ggatcctggc ggaggctccc gatggcgcgg tcgtcagcgt ggagtcccgg  300
cagcttgacg tggcggacgc cgcgtccgtg gaggccttcg cggcctgggc ggtgaaaacc  360
cacggcggca tccatgtcct tgttaacaat gcaggtgtaa acttcaacaa aggagcagat  420
aattctgttg agtttgctga gcaagttatc aagacaaatt actatggcac aaagcggatg  480
attgatacta tgataccact aatgaaacac tccccgtactg gtgctcggat agtgaatgtc  540
agctcaaggc ttggtagagc caatggcaga cggaatagaa ttggtgatgc gagtctaaga  600
gatcgtctgt tgaaagatga ttgttttatca gagcagctag ttgatgagat gatcacgaaa  660
tttctcgaac aagtcaagca aggtacttgg tcctccaatg agtggccaca gatgtacacg  720
gactattcga tctcaaagct tgctgttaat gtttatcaac gactgatggc aaggaggctc  780
tcggatcgac ctgaaggcca aaagatatac attaactgtt tctgccctgg ctgggtaaat  840
actgccatga ctggttggga agggaatatt tctgccgaag aaggtgctga cacaggtgta  900
tggctcgcct tattacctga gaaccaccac acaaatggga agttcttcgc tgagagatgt  960
gagataagct tctaa                                                  975
```

| | | |
|---|---|---|
| SEQ ID NO: 163 | moltype = AA   length = 324 | |
| FEATURE | Location/Qualifiers | |
| REGION | 1..324 | |
| | note = misc_feature - Ceres Annot ID no. 8670388 | |
| REGION | 1..324 | |
| | note = misc_feature - Bit score of 760.0 for hmm based on sequences of FIGURE 3. | |
| REGION | 42..195 | |
| | note = misc_feature - Pfam Name: adh_short Pfam Desc: short chain dehydrogenase | |
| REGION | 1..324 | |
| | note = misc_feature - Functional Homolog Of SEQ ID NO. 74 | |
| source | 1..324 | |
| | mol_type = protein | |
| | organism = Sorghum bicolor | |

SEQUENCE: 163
```
MGKKGKEAAR ERREQRRREV TLLRALPYEP HQRWWDRLAP RAVAVVTGAN RGIGFEAARQ   60
LALHGLHVVL ASRDAAKGQD AAGRILAEAP DGAVVSESR QLDVADAASV EAFAAWAVET  120
HGGIHVLVNN AGVNFNKGAD NSVEFAEQVI KTNYYGTKRM IDTMIPLMKH SPYGARIVNV  180
```

```
                                          -continued
SSRLGRANGR  RNRIGDASLR  DRLLKDDCLS  EQLVDEMITK  FLEQVKQGTW  SSNEWPQMYT   240
DYSISKLAVN  VYTRLMARRL  SDRPEGQKIY  INCFCPGWVN  TAMTGWEGNI  SAEEGADTGV   300
WLALLPQEPP  TNGKFFAERC  EISF                                             324

SEQ ID NO: 164          moltype = AA   length = 313
FEATURE                 Location/Qualifiers
REGION                  1..313
                        note = misc_feature - Public GI ID no. 147853829
REGION                  1..313
                        note = misc_feature - Bit score of 757.9 for hmm based on
                          sequences of FIGURE 3.
REGION                  37..185
                        note = misc_feature - Pfam Name: adh_short Pfam Desc: short
                          chain dehydrogenase
REGION                  1..313
                        note = misc_feature - Functional Homolog Of SEQ ID NO. 74
source                  1..313
                        mol_type = protein
                        organism = Vitis vinifera
SEQUENCE: 164
MGRKERAEER  RKQRQQEISL  FRTIPYSDHQ  RWWNSETIAV  VTGANRGIGF  EIARQLCGHG    60
LTVILTSRDS  AIGREAASVL  QEGGFNAVSH  QLDVLDPSSI  EQFAEWVQQN  YGFVDILINN   120
AGVNYNMGSE  NSVENAENVI  ATNYFGTKNV  IKAMVPLMKP  SASGARIVNV  SSRLGRINGR   180
RNKIEDSALR  GQLEDVDSLS  EEVIDQMVHT  FVEQVKDGTW  TSAGWPQTFT  DYSVSKLAVN   240
CYTRIMAKVL  SDRPEGEKIF  INCYCPGWVK  TAMTGWAGNV  SVEEGADTGV  WLALLPDQSV   300
TGKIFAERRE  VHF                                                          313

SEQ ID NO: 165          moltype = AA   length = 324
FEATURE                 Location/Qualifiers
REGION                  1..324
                        note = misc_feature - Public GI ID no. 194696386
REGION                  1..324
                        note = misc_feature - Bit score of 755.3 for hmm based on
                          sequences of FIGURE 3.
REGION                  42..195
                        note = misc_feature - Pfam Name: adh_short Pfam Desc: short
                          chain dehydrogenase
REGION                  1..324
                        note = misc_feature - Functional Homolog Of SEQ ID NO. 74
source                  1..324
                        mol_type = protein
                        organism = Zea mays
SEQUENCE: 165
MGKKGKEAAR  ERREQRRREV  ALLRSLPYEP  HQRWWDRLAP  RAVAVVTGAN  RGIGFEAARQ    60
LALHGLHVVL  ACRDAAKGQD  AAERILAEAP  DDTVVSVESR  KLDVADAASV  EAFAAWAVET   120
YGGIHVLVNN  AGVNFNKGAD  NSVEFAEQVI  ETNYYGTKRM  IDAMIPLMKR  SAYGARIVNV   180
SSRLGRANGR  RNRIGDVSLR  DRLLKDDCLS  EQLIDEMITK  FLEQAKQGTW  SLNEWPQMYT   240
DYSISKLAVN  AYTRLMARRL  SDRPEGQKIY  INCFCPGWVK  TAMTGWEGNV  SAEEGADTGI   300
WLALLPQETD  TNGKFFAERC  EISF                                             324

SEQ ID NO: 166          moltype = DNA   length = 942
FEATURE                 Location/Qualifiers
misc_feature            1..942
                        note = Ceres Annot ID no. 8459736
misc_feature            1..942
                        note = Encodes the peptide sequence at SEQ ID NO. 167
source                  1..942
                        mol_type = other DNA
                        organism = Solanum lycopersicum
SEQUENCE: 166
atggataaaa  aggaaagggc  aaaggaaaaa  aaggagaaaa  gacgccagga  gatctcccttt    60
ctacgtacta  ttccctattc  tgatcaccaa  agatggtggt  catctgaaac  aattgcggtt   120
gttacgggcg  caaatagagg  cattggattt  gaaattgctc  atcagcttgc  atcacatggc   180
gttactgttg  ttctcacgtc  gcgagagaca  gctgttgaga  aagaagcagt  gaaagtcttt   240
caggaaggag  gtctaaatgt  ggcatttcat  caattggata  ttgtggatcc  tgtatcaatt   300
caaacatttt  gtgattggat  taagaaaaca  tatggtggcc  tagatatact  gatcaacaat   360
gcaggagtca  atttcaattg  cggaaaagat  aattctgttg  aattttctga  aatggtaatc   420
caagttaact  attttggcac  caaaaacatg  atcaaagcac  ttactccgtt  gatgaggcct   480
tcccctgctg  gctctcgtat  tgttagtgtc  acctcgcgat  tgggtagact  taatagcaat   540
cgaaatggaa  tttcaaatgt  agcagtgaga  gaacaattag  aaaacgtgga  tacgctatct   600
gaggaagtta  tcgataaaac  tatgcacaca  ttttggagc   aagtaaaaga  tggaacttgg   660
gaatcagcag  gatggcctca  tgtgttcaca  gactactcat  tgtcaaagct  agcagttaat   720
gcctacacaa  ggttaatggc  aaggatattc  gaggaacgac  cagaaggtga  aaaaatatac   780
ataaatgtt   attgctcggg  atgggtgaaa  actgctctga  ctggctgggc  agggcatgtt   840
actattgaag  aagctgctga  tactgctgta  tggcttgctt  tgctccctga  tcaatttgtg   900
agtggtaagt  tcttcgctga  gaggcgcgaa  attaacttt   aa                       942

SEQ ID NO: 167          moltype = AA   length = 313
FEATURE                 Location/Qualifiers
```

```
REGION                  1..313
                        note = misc_feature - Ceres Annot ID no. 8459736
REGION                  1..313
                        note = misc_feature - Bit score of 744.3 for hmm based on
                          sequences of FIGURE 3.
REGION                  37..193
                        note = misc_feature - Pfam Name: adh_short Pfam Desc: short
                          chain dehydrogenase
REGION                  1..313
                        note = misc_feature - Functional Homolog Of SEQ ID NO. 74
source                  1..313
                        mol_type = protein
                        organism = Solanum lycopersicum
SEQUENCE: 167
MDKKERAKEK KEKRRQEISL LRTIPYSDHQ RWWSSETIAV VTGANRGIGF EIAHQLASHG    60
VTVVLTSRET AVGEEAVKVF QEGGLNVAFH QLDIVDPVSI QTFCDWIKET YGGLDILINN   120
AGVNFNCGKD NSVEFSEMVI QVNYFGTKNM IKALTPLMRP SPAGSRIVSV TSRLGRLNSK   180
RNGISNVAVR EQLENVDTLS EEVIDKTMHT FLEQVKDGTW ESAGWPHVFT DYSLSKLAVN   240
AYTRLMARIF EERPEGEKIY INCYCPGWVK TAMTGWAGHV TIEEAADTAV WLALLPDQFV   300
SGKFFAERRE INF                                                     313

SEQ ID NO: 168          moltype = DNA  length = 1198
FEATURE                 Location/Qualifiers
misc_feature            1..1198
                        note = Ceres Clone ID no. 1906273
misc_feature            1..1198
                        note = Encodes the peptide sequence at SEQ ID NO. 169
source                  1..1198
                        mol_type = other DNA
                        organism = Panicum virgatum
SEQUENCE: 168
agtcagccac ccccgcgct ccccgctcgt ctccagctcg atggactatt cgagcaccaa     60
ggagttgcct ccggccgggg cctggtggtc gagggagacg gtggccgtgg tgacgggcgc   120
gaaccggggc atcgggcacg ccctcgccgc gcgcctggcc gagcacgggc tcaccgtggt   180
gctcacggca cgggacgcg cggcgcggga ggcgcgggcg gcccgcgctcc gcgcgcgggg   240
gctcgccgtc gccttccgca ggctcgacgt ctccgacgcc gcctccgtcg ccgagttcgc   300
cgcctggctc cgcgacgccg tcggcggcct cgacatcctg gtgaacaacg cggccgtgtc   360
cttcaacgag atcgacacca actcggtgga gcacgccgag acagtcctca ggaccaactt   420
ccacggcgcc aagatgctca cggaagcgct gctgccgctc ttccggcagt ccccggccac   480
cagcaggatc ctcaacatca gctcgcagct tggccttctc aacaaggtga gcgactcgtc   540
cctgaaggcc ctgctcctgg acgaggagac cctgacggag gcggcgatcg acgccatggt   600
gtcgcggttc ctggcgcagg tgaaggacgg gacgtgggc gctcagggct ggcccaaggt    660
gtggacggac tactcggtct ccaagctggc cctgaacgcc tactcccgcc tgctggccgcg   720
gcggctgcag gcgcgcggcg cccgcgtgag cgtcaactgc ttctgcccgc ggttcacgcg   780
caccgacatg accaggggct gggggaagcg caccgccgag gaggtggccg acgtcggcgc   840
gcggctcgcg ctgctgccgc ccggcgagct ccccacgggg gccttcttca gtggtgcac   900
gccgcagctc tactccaagc tgtgacctgc cgggagctag ccacgccgcc ggccggccgg   960
ccccggccat ggcggcagtg ggagtatatg tatgtagcgt tggtttagct gctcctagtg  1020
acttgactcc ccatgcaaac aagaagtcga tcgagtagtt agtgcctctg gcagtctggc  1080
tttctgccaa ggtgctatgg ttgaagcaat gcaacctaac catgtcagca atcaatgtac  1140
tatgcctagt tagccgtgta agatttaaag ttaacttctg aacatgggaa gaatcatg    1198

SEQ ID NO: 169          moltype = AA  length = 294
FEATURE                 Location/Qualifiers
REGION                  1..294
                        note = misc_feature - Ceres Clone ID no. 1906273
REGION                  1..294
                        note = misc_feature - Bit score of 656.4 for hmm based on
                          sequences of FIGURE 3.
REGION                  20..173
                        note = misc_feature - Pfam Name: adh_short Pfam Desc: short
                          chain dehydrogenase
REGION                  1..294
                        note = misc_feature - Functional Homolog Of SEQ ID NO. 74
source                  1..294
                        mol_type = protein
                        organism = Panicum virgatum
SEQUENCE: 169
MDYSSTKELP PAGWWSRET VAVVTGANRG IGHALAARLA EHGLTVVLTA RDGARGEAAA    60
APLRARGLAV AFRRLDVSDA ASVAEFAAWL RDAVGGLDIL VNNAAVSFNE IDTNSVEHAE   120
TVLRTNFHGA KMLTEALLPL FRQSPATSRI LNISSQLGLL NKVSDSSLKA LLLDEETLTE   180
AAIDAMVSRF LAQVKDGTWG AQGWPKVWTD YSVSKLALNA YSRLLARRLQ ARGARVSVNC   240
FCPGFTRTDM TRGWGKRTAE EVADVGARLA LLPPGELPTG AFFKWCTPQL YSKL         294

SEQ ID NO: 170          moltype = AA  length = 319
FEATURE                 Location/Qualifiers
REGION                  1..319
                        note = misc_feature - Public GI ID no. 198285679
REGION                  1..319
```

|   |   |
|---|---|
|   | note = misc_feature - Bit score of 219.9 for hmm based on sequences of FIGURE 2. |
| REGION | 252..296 |
|   | note = misc_feature - Pfam Name: CCT Pfam Desc: CCT motif |
| REGION | 1..46 |
|   | note = misc_feature - Pfam Name: zf-B_box Pfam Desc: B-box zinc finger |
| REGION | 1..319 |
|   | note = misc_feature - Functional Homolog Of SEQ ID NO. 20 |
| source | 1..319 |
|   | mol_type = protein |
|   | organism = Olea europaea |

SEQUENCE: 170
```
MWVCEACERA PAAFLCKADA ASLCITCDSD IHSAQPLARR HQRVPILPIP GMLCGTPSAP   60
YPSGLVMGPT GVAAKIEFLT QDEDQTIHEE EDEDEAASWP LFNHVKNICN QSNNIGRFFG  120
GEVDEYLDLD EYNSYQDNQF SNQDNNQLQP YDVSQKSYGS DNVVPIQYGK SKDQIHNHGF  180
QLGREYEASK NVYDNPASIS HTVSFSSLDV GVVPESTTES VSVPHPRPPK GTIDLFSSPP  240
IPMPTQLSPM DREARVLRYR EKKKARKFEK TIRYASRKAY AETRPRIKGR FAKRTDVRAN  300
QMFSSTLIEE GGYGIVPSF                                             319
```

|   |   |
|---|---|
| SEQ ID NO: 171 | moltype = DNA length = 982 |
| FEATURE | Location/Qualifiers |
| misc_feature | 1..982 |
|   | note = Ceres Clone ID no. 7088 |
| misc_feature | 1..982 |
|   | note = Encodes the peptide sequence at SEQ ID NO. 172 |
| source | 1..982 |
|   | mol_type = other DNA |
|   | organism = Arabidopsis thaliana |

SEQUENCE: 171
```
atagagagaa gaaaagaag aggtttagag agagaaaaat ggcgtcaaag ctctgcgatt    60
cgtgcaaatc agcgacggcg gcgttatact gccgaccaga cgcagcgttt ctatgcttaa  120
gctgcgattc aaaagtccac gcggcgaaca aactcgcgtc acgacacgcg cgcgtgtgga  180
tgtgtgaagt gtgcgagcaa gcaccggcac acgtcacgtg caaagcagac gcggccgcgt  240
tatgcgtcac gtgcgaccgt gatatccact cggctggtcc gttactcgc cgtcacgaac  300
gcgttcccgt tactccgttt tacgattccg tctctagtga cggttccgtt aaacacaccg  360
ccgttaattt ccttgacgac tgttacttct ccgatataga tggtaacgga agccgtgaag  420
aagaggagga agaagctgct tcgtggctgt tacttcccaa tccaaagact acaacgacgg  480
cgacggcggg gatcgttgct gttacttcag ctgaggaagt tccgggagat agtccggaga  540
tgaacactgg tcaacagtat ttgttctcgg atccggatcc gtatctggat ctggattatg  600
gaaatgttga tccgaaggtg gaatcgttag agcagaatag ctccggtact gatggtgttg  660
ttccggtgga gaatcggacg gttagaatcc cgacggtgaa cgagaattgc tttgaaatgg  720
attttaccgg aggatctaaa ggcttttgctt atggaggtgg ttacaattgc atcagtcaca  780
gcgtgtcatc atcgtcgatg gaagtgggag tggtgccaga tggtggtcg gtggctgatg  840
tatcgtatcc ttacggtggt cctgcaacca gtggagctga tccggggaca cagcgggctg  900
ttccgctgac ttcagctgag agagaagcga gggtaatgag gtacagagag aagaggaaga  960
acaggaagtt tgagaagact at                                          982
```

|   |   |
|---|---|
| SEQ ID NO: 172 | moltype = AA length = 314 |
| FEATURE | Location/Qualifiers |
| REGION | 1..314 |
|   | note = misc_feature - Ceres Clone ID no. 7088 |
| REGION | 1..314 |
|   | note = misc_feature - Bit score of 334.7 for hmm based on sequences of FIGURE 2. |
| REGION | 1..48 |
|   | note = misc_feature - Pfam Name: zf-B_box Pfam Desc: B-box zinc finger |
| REGION | 295..314 |
|   | note = misc_feature - Pfam Name: CCT Pfam Desc: CCT motif |
| REGION | 1..314 |
|   | note = misc_feature - Functional Homolog Of SEQ ID NO. 20 |
| source | 1..314 |
|   | mol_type = protein |
|   | organism = Arabidopsis thaliana |

SEQUENCE: 172
```
MASKLCDSCK SATAALYCRP DAAFLCLSCD SKVHAANKLA SRHARVWMCE VCEQAPAHVT   60
CKADAAALCV TCDRDIHSAN PLARRHERVP VTPFYDSVSS DGSVKHTAVN FLDDCYFSDI  120
DGNGSREEEE EEAASWLLLP NPKTTTTATA GIVAVTSAEE VPGDSPEMNT GQQYLFSDPD  180
PYLDLDYGNV DPKVESLEQN SSGTDGVVPV ENRTVRIPTV NENCFEMDFT GGSKGFAYGG  240
GYNCISHSVS SSSMEVGVVP DGGSVADVSY PYGGPATSGA DPGTQRAVPL TSAEREARVM  300
RYREKRKNRK FEKT                                                  314
```

|   |   |
|---|---|
| SEQ ID NO: 173 | moltype = AA length = 350 |
| FEATURE | Location/Qualifiers |
| REGION | 1..350 |
|   | note = misc_feature - Public GI ID no. 118489345 |
| REGION | 1..350 |
|   | note = misc_feature - Bit score of 491.6 for hmm based on |

```
                            sequences of FIGURE 2.
REGION                      1..48
                            note = misc_feature - Pfam Name: zf-B_box Pfam Desc: B-box
                             zinc finger
REGION                      287..331
                            note = misc_feature - Pfam Name: CCT Pfam Desc: CCT motif
REGION                      1..350
                            note = misc_feature - Functional Homolog Of SEQ ID NO. 20
source                      1..350
                            mol_type = protein
                            organism = Populus x generosa
SEQUENCE: 173
MASKLCDSCK SATATLFCRA DSAFLCISCD SKIHAANKLA SRHARVSVCE VCEQAPAHFT    60
CKADAAALCV TCDRDIHSAN PLASRHERVP ITPFFDSSST VHGGGAAVNL LEDRYFDEVD   120
GGRGDVSREE AEAESWLLPN PGGGTAKGVD SMDLNTGQYV FGSEMDPYLD LDPYVDPKVE   180
VQEQNSSGTT DGVVPVQSNK LGFQAPALVN DNCCYELDFS TGSKSFGGGY GYNSLSHSVS   240
SSSLDVGVVP DGSGSTLTDI SNPYCSRSVS NGMESANQTV QLSAVDREAR VLRYREKRKN   300
RKFEKTIRYA SRKAYAETRP RIKGRFAKRT DTEVEVDRSS LYGFGVVPSF              350

SEQ ID NO: 174              moltype = DNA  length = 1549
FEATURE                     Location/Qualifiers
misc_feature                1..1549
                            note = Ceres Clone ID no. 1769510
misc_feature                1..1549
                            note = Encodes the peptide sequence at SEQ ID NO. 175
source                      1..1549
                            mol_type = other DNA
                            organism = Panicum virgatum
SEQUENCE: 174
ctccctccac tacgccgcgc gcgctccctc ccacccctcc cctccaccac cacaagcacc    60
gcgtcgacac cacctgccat cgccgcgccg agctcagcct ctagctagct gcgccaggag   120
ggcgcccgcc tcgctccctc cctgccgacg ccagtgcgat ggagctgcat aagtactggg   180
gcgtgggggg ccggcggtgc ggcgactgcg aggcggcccc ggcggcggtg cactgccgct   240
cgtgccccgc caccgccggg ggcgcgttcc tctgcgctgc gtgcgacgcg cgcccggggc   300
acgcgcggct gggccacgag cgcgtgtgga tgtgcgaggt ctgcgagctg gcccccgccg   360
ccgtcacctg caaggccgac gccgccgtgc tctgcgccgc ctgcgacgcc gacatccacg   420
acgccaaccc gctggcgcgc cgccatgcgc gcgtccccgt cgcgcccatc gggtccgagg   480
ccgccgcctc cgccgtcgag gccatgctgt tcgggaccgg cgacgcgac ccggccgcgc    540
ccgaggccga ggagccgcag gacgcggccg ccgggcacgg gcacgggcag ctccagcacc   600
accaccagca cgcgctgaac ctcaacgtgg aggccaagga catgaagctg gactacctct   660
tctccgacct ggaccctac ctcagcgtcg acatcccgcg cttccagcac gccgacagcg    720
tcgtcccag cggcgtcggc gccggagccg ccgccgcgc cgtcgagctg gacttcacgt     780
gcggcatcgg cgtcaagccc tcctcgtaca gctcctacag gcaacatcc ttcgcccaca    840
gcggctcctc ctctgaggtc ggcgtggtgc cggaggcctt ctgcggcggc ggcgccggga   900
ccttcgagct cgacttcacc cggcccaagc tcaagcccta catgccgtac accgcgactc   960
ctcagagcca cagcgtgtcg tcggtggacg tggaggtggc ggcggcggag cggggggaca  1020
tggccgggc gaggccggtg ccgctggtgg gggagagccg ggaggcgccg ctgatgcgct   1080
accgggagaa gcggaagaac cggcggttcg agaagaccat ccggtacgcg tcccggaagg  1140
cctacgccga cgcgccg cggatcaagg gccggttcgc caagcgcgcc gaccacgacg     1200
ccgacgacgc cgaggccgag gccgccgtgc cgtcgccggc gtcgtacgtg ctcgacttcg  1260
gctacggcgt cgtgcccagc ttctgatcga tcgacgacgg tccggcggc ggcggcgcc   1320
ctgacccggc actggcgcgc gcgccttgtg tacttgtatc gatgcatgat gtataggga   1380
ggaatagtaa atcccatgta ctactctctt tttggagctg tgctagcctt gcgcacgcta  1440
gtgatgtata atttgtatac tacgcgctgc tacttactac tagcatgttc ttgctggaat  1500
tagccccggc tattttgaa tcaaatctat gcaagaaatt tgtaacggt                1549

SEQ ID NO: 175              moltype = AA  length = 375
FEATURE                     Location/Qualifiers
REGION                      1..375
                            note = misc_feature - Ceres Clone ID no. 1769510
REGION                      1..375
                            note = misc_feature - Bit score of 695.5 for hmm based on
                             sequences of FIGURE 2.
REGION                      301..345
                            note = misc_feature - Pfam Name: CCT Pfam Desc: CCT motif
REGION                      54..101
                            note = misc_feature - Pfam Name: zf-B_box Pfam Desc: B-box
                             zinc finger
REGION                      1..375
                            note = misc_feature - Functional Homolog Of SEQ ID NO. 20
source                      1..375
                            mol_type = protein
                            organism = Panicum virgatum
SEQUENCE: 175
MELHKYWGVG GRRCGDCEAA PAAVHCRSCP ATAGGAFLCA ACDARPGHAR LGHERVWMCE    60
VCELAPAAVT CKADAAVLCA ACDADIHDAN PLARRHARVP VAPIGSEAAA SAVEAMLFGT   120
GDGDPAAPEA EEPQDAAAGH GHGQLQHHHQ HALNLNVEAK DMKLDYLFSD LDPYLSVDIP   180
RFQHADSVVP SGVGAGAAAG AVELDFTCGI GVKPSSYSSY TATSFAHSGS SSEVGVVPEA   240
FCGGGAGTFE LDFTRPKPQA YMPYTATPQS HSVSSVDVEV AAAERGDMAA ARPVPLVGES   300
```

```
REARLMRYRE KRKNRRFEKT IRYASRKAYA ETRPRIKGRF AKRADHDADD AEAEAAVPSP    360
ASYVLDFGYG VVPSF                                                    375

SEQ ID NO: 176          moltype = AA  length = 336
FEATURE                 Location/Qualifiers
REGION                  1..336
                        note = misc_feature - Public GI ID no. 170779038
REGION                  1..336
                        note = misc_feature - Bit score of 411.9 for hmm based on
                          sequences of FIGURE 2.
REGION                  13..60
                        note = misc_feature - Pfam Name: zf-B_box Pfam Desc: B-box
                          zinc finger
REGION                  267..311
                        note = misc_feature - Pfam Name: CCT Pfam Desc: CCT motif
REGION                  1..336
                        note = misc_feature - Functional Homolog Of SEQ ID NO. 20
source                  1..336
                        mol_type = protein
                        organism = Chenopodium rubrum
SEQUENCE: 176
MMKKEVPGGD NNSWARVCDT CRSAPCTVYC KEDSAFLCTS CDARIHAVNQ VASRHERVWV    60
CEACEREPAA FLCKADAASL CATCDADIHS ANPLARRHHR VPIMPVGCVY GPSDGRMSEE    120
GFLDLPDGDD QTTDHEGDED EAASWLLLNP GADNQFCEQY SQQQEFSVPE KNCGGDSVVP    180
VQCREVKDHQ IQYQKFLFGM ECETKSEYNY NTSISHSVSV SSLDVGVVPE STMSDMSVSH    240
SRPPKGTIDL FSSPPMQVPT QLSPLDREAR VMRYREKKKN RKFEKTIRYA SRKAYAETRP    300
RIKGRFAKRT DVEAEMDQMF TNSLMSDGGY GIVPSF                             336

SEQ ID NO: 177          moltype = DNA  length = 1357
FEATURE                 Location/Qualifiers
misc_feature            1..1357
                        note = Ceres Clone ID no. 1996408
misc_feature            1..1357
                        note = Encodes the peptide sequence at SEQ ID NO. 178
source                  1..1357
                        mol_type = other DNA
                        organism = Panicum virgatum
SEQUENCE: 177
aaaaacaccc ccgaggccaa ccatttccga cgcaaaaccc cccggaatcc gtgacacccg    60
cccggaggag agcagagcag aggcaccagg catggacgcc gcggtggagc tggagctgga    120
gcagaagccg gcggtggggt actgggggctt ggccggcgcg cggccctgcg acgcgtgcgc    180
cgcggaggcg gcgcggctgc actgccgcgc ggacggcgcg ttcctgtgcc ccgggtgcga    240
cgcccgcgtc cacggcgccg ggtcgcgcca cgcgcgcgtc tgtctctgcg aggtctgcga    300
gcacgcccc gccgccgtca cgtgccgcgc cgacgccgc gcgctctgcg cggcctgcga    360
cgccgacatc cactcggcca acccgctcgc gcgccgccac gagcggctcc ccgtcgcgcc    420
cttcttcggc gcgctcgccg acgcgccgca gccgttcccg tcctcagcct tcgccgccgc    480
gggggtccag gcccagggg acgcgccgtc ggacgacgac gggagcaacg aggccgaggc    540
cgcctcgtgg ctcctccccg agcccgacaa ctgccacgag gacagcgccg ccgcaccga    600
cgccttcttc gctgactccg acgcgtacct cggcgtcgac ctcgacttcg cccggtccat    660
ggacggcatc aaggccatcg gcgtgccggt cgcgccgccc gagctggaca tggccaccgg    720
cggttactac tacccgaac actccatgaa ccacagcgtc tcgtcgtcgg aggtggcgg    780
tgtgccggac gcgctggcgg gcggcgcccc ggccgcgccg gcggtgccgg cggcgagccg    840
gggaaggag cgggaggcgc ggctgatgcg gtaccgcgag aagcgcaaga ccggcgggtt    900
cgacaagacc atccggtacg cgtcccgcaa ggcgtacgcc gagacgcggc cgcgcatcaa    960
gggccgcttc gccaagcgct gctcctccgc ggaggccgag gccgaggacg aggcgctgct    1020
ggagcacgag gaagcggcgt gcttctcgcc cgcggcgtcg gcgccccgcg cctcctcgga    1080
cggcgtcgtc ccgtcctgct gaggggacac gacggggcgg cccgcgcct cctcctcca    1140
ggctccccgg cggcgacccc ttaattttgc cgactctgaa tcgatcccaa cgcatgcgaa    1200
catgcgatgc gatgcgcgct ccgtgcagca catgaataat tgtacagtag ttccacgaac    1260
tcgatcgtgg tcgcacggaa tcgcatgtaa tcctcctcac cgtccttgta atccagcctt    1320
gtacattacc gtctagaggt gtttgtgctt ctctcgc                             1357

SEQ ID NO: 178          moltype = AA  length = 336
FEATURE                 Location/Qualifiers
REGION                  1..336
                        note = misc_feature - Ceres Clone ID no. 1996408
REGION                  1..336
                        note = misc_feature - Bit score of 649.8 for hmm based on
                          sequences of FIGURE 2.
REGION                  254..298
                        note = misc_feature - Pfam Name: CCT Pfam Desc: CCT motif
REGION                  21..65
                        note = misc_feature - Pfam Name: zf-B_box Pfam Desc: B-box
                          zinc finger
REGION                  1..336
                        note = misc_feature - Functional Homolog Of SEQ ID NO. 20
source                  1..336
                        mol_type = protein
                        organism = Panicum virgatum
```

```
SEQUENCE: 178
MDAAVELELE QKPAVGYWGL AGARPCDACA AEAARLHCRA DGAFLCPGCD ARAHGAGSRH    60
ARVCLCEVCE HAPAAVTCRA DAAALCAACD ADIHSANPLA RRHERLPVAP FFGALADAPQ   120
PFPSSAFAAA GVQAQGDAAA DDDGSNEAEA ASWLLPEPDN CHEDSAAATD AFFADSDAYL   180
GVDLDFARSM DGIKAIGVPV APPELDMATG GYYYPEHSMN HSVSSSEVAV VPDALAGGAP   240
AAPAVPAASR GKEREARLMR YREKRKNRRF DKTIRYASRK AYAETRPRIK GRFAKRCSSA   300
EAEAEDEALL EHEEAACFSP AASAPAASSD GVVPSC                            336

SEQ ID NO: 179            moltype = DNA  length = 990
FEATURE                   Location/Qualifiers
misc_feature              1..990
                          note = Ceres Annot ID no. 8701721
misc_feature              1..990
                          note = Encodes the peptide sequence at SEQ ID NO. 180
source                    1..990
                          mol_type = other DNA
                          organism = Sorghum bicolor
SEQUENCE: 179
atggagggcg acgagaagtc ggcgggcggg gccccggcgt actggggcct gggcgcgcgg    60
ccctgcgacg cgtgcggcgc cgatgcggcg cgcctctact gccgcgcgga ctcggcgttc   120
ctgtgcgccg ggtgcgacgc gcgggcgcac ggggccgggt cgcccaacgc gcgggtctgg   180
ctctgcgagg tctgcgagca cgcgccggcg gcggtcacgt gccgcgccga cgccgccgcg   240
ctctgcgcct cctgcgacgc cgacatccac tcgccaacc cgctggcgcg acgccacgag   300
cgcctccccg tggcgccctt cttcggcgcg ctggccgacg cgcccaagcc cttcgcctcg   360
tcggcggcgg ccgtgccgcc caagcgacg gccggggccg acgacgacgg gagcagcgag   420
gccgaggcgc cgtcgtggct cctccccgag cccgaccacg ggcacaaaga agaaggcgcc   480
accacggagg tgttcttcgc ggactccgac ccgtacctcg acctcgactt cgcgcgttcc   540
atggacgaca tcaagaccat cggcgtccag ggcgggccac cagagctcga cctcaacggc   600
gccaagctct tctactccga ccactccatg aaccacagtg tgtcatcgtc ggaggcagcg   660
gtggtgcccg acgcggcggc tggcgcggcg cccgtggtcg cagtggtcag caggggccgg   720
gagcgggagg cgcggctgat gcggtaccgc gagaagcgca agagcaggcg gttcgagaag   780
acgatccggt acgcgtcccg caaggcgtac gcggagacgc ggccgcgcat caagggccgg   840
ttcgccaagc gcacgccggg ggctggggag acccgctgg aggagcacga ggagatgtac   900
tcctcggccg cggcggccgt ggctgcgctc atggcccccg gcggagccga cgcggactac   960
ggcgtcgacg gcgtcgtgcc cacatattga                                   990

SEQ ID NO: 180            moltype = AA  length = 329
FEATURE                   Location/Qualifiers
REGION                    1..329
                          note = misc_feature - Ceres Annot ID no. 8701721
REGION                    1..329
                          note = misc_feature - Bit score of 640.1 for hmm based on
                            sequences of FIGURE 2.
REGION                    242..286
                          note = misc_feature - Pfam Name: CCT Pfam Desc: CCT motif
REGION                    57..104
                          note = misc_feature - Pfam Name: zf-B_box Pfam Desc: B-box
                            zinc finger
REGION                    1..329
                          note = misc_feature - Functional Homolog Of SEQ ID NO. 20
source                    1..329
                          mol_type = protein
                          organism = Sorghum bicolor
SEQUENCE: 180
MEGDEKSAGG APAYWGLGAR PCDACGADAA RLYCRADSAF LCAGCDARAH GAGSPNARVW    60
LCEVCEHAPA AVTCRADAAA LCASCDADIH SANPLARRHE RLPVAPFFGA LADAPKPFAS   120
SAAAVPPKAT AGADDDGSSE AEAASWLLPE PDHGHKEEGA TTEVFFADSD PYLDLDFARS   180
MDDIKTIGVQ GGPPELDLNG AKLFYSDHSM NHSVSSSEEA VVPDAAAGAA PVVAVVSRGL   240
EREARLMRYR EKRKSRRFEK TIRYASRKAY AETRPRIKGR FAKRTPGAGE DPLEEHEEMY   300
SSAAAAVAAL MAPGGADADY GVDGVVPTY                                    329

SEQ ID NO: 181            moltype = AA  length = 343
FEATURE                   Location/Qualifiers
REGION                    1..343
                          note = misc_feature - Public GI ID no. 197726026
REGION                    1..343
                          note = misc_feature - Bit score of 521.0 for hmm based on
                            sequences of FIGURE 2.
REGION                    1..48
                          note = misc_feature - Pfam Name: zf-B_box Pfam Desc: B-box
                            zinc finger
REGION                    282..326
                          note = misc_feature - Pfam Name: CCT Pfam Desc: CCT motif
REGION                    1..343
                          note = misc_feature - Functional Homolog Of SEQ ID NO. 20
source                    1..343
                          mol_type = protein
                          organism = Prunus persica
SEQUENCE: 181
```

```
MASKLCDSCK  SATATLFCRA  DSAFLCVNCD  SKIHAANKLA  SRHARVWLCE  VCEQAPAHVT   60
CKADDAALCV  TCDRDIHSAN  PLSRRHERVP  VTPFYDSGNS  AANSAPVVKS  VVNFLDDRYF  120
SDVDGQDAET  EVSREEAEAA  SWLLPNPKAM  ENPDLNSGEY  FLPEMDPYLD  LDYGHVDPKL  180
EDAQEQNSCG  TDGVVPVQSK  SVQPQLVNDH  SFEIDFSAAS  KPYVYGFHAQ  CLSQSVSSSS  240
MDVSVVPDGN  TTMTDVCDPY  TKSMSAAVES  THQAVQISSA  DREARVLRYR  EKRKNRKFEK  300
TIRYASRKAY  AETRPRIKGR  FAKRTEVEIE  AERLCRYGVV  PSF                    343

SEQ ID NO: 182           moltype = AA  length = 343
FEATURE                  Location/Qualifiers
REGION                   1..343
                         note = misc_feature - Public GI ID no. 194244824
REGION                   1..343
                         note = misc_feature - Bit score of 289.3 for hmm based on
                           sequences of FIGURE 2.
REGION                   7..54
                         note = misc_feature - Pfam Name: zf-B_box Pfam Desc: B-box
                           zinc finger
REGION                   281..325
                         note = misc_feature - Pfam Name: CCT Pfam Desc: CCT motif
REGION                   1..343
                         note = misc_feature - Functional Homolog Of SEQ ID NO. 20
source                   1..343
                         mol_type = protein
                         organism = Brassica nigra
SEQUENCE: 182
MLKQESNWAQ  ACDTCRSAAC  TVYCRADSAY  LCTSCDAQIH  AANRLASRHE  RVRVCESCER   60
APAAFFCKAD  AASLCTACDS  QIHSANPLAR  RHQRVPILPI  SGCVATNHHS  SETTEPENIV  120
VVGQEEEDEA  EAASWLLPSS  VKNCGDNNNN  NSENNRFSVG  EEYLDLVDYS  SSMDKRFTGQ  180
ANQYQQDYNV  PQRSYVADGV  VPLQVGVSKG  HMHHEQHNFQ  FGFTNVSSEA  HQISNGSPIH  240
MVSLVPESVT  SDATVSHQRS  PKSGTEELPE  APVQMLSPME  RKARVLRYRE  KKKTRKFEKR  300
IRYASRKEYA  EKRPRIKGRF  AKRNEVDADQ  AFPTVVMFDT  GYG                    343

SEQ ID NO: 183           moltype = AA  length = 398
FEATURE                  Location/Qualifiers
REGION                   1..398
                         note = misc_feature - Public GI ID no. 158866355
REGION                   1..398
                         note = misc_feature - Bit score of 329.2 for hmm based on
                           sequences of FIGURE 2.
REGION                   327..371
                         note = misc_feature - Pfam Name: CCT Pfam Desc: CCT motif
REGION                   27..74
                         note = misc_feature - Pfam Name: zf-B_box Pfam Desc: B-box
                           zinc finger
REGION                   1..398
                         note = misc_feature - Functional Homolog Of SEQ ID NO. 20
source                   1..398
                         mol_type = protein
                         organism = Zea mays
SEQUENCE: 183
MDYNFDTSVL  DEDVAGRGGR  EGSCPPAWAR  ACDGCRAAPS  VVYCHADTAY  LCASCDSRVH   60
AANRVASRHE  RVRVCEACEC  APAVLACRAD  AAALCAACDA  QVHSANPLAG  RHQRVPVLPL  120
PAAAVPAASV  LAEAAATAAA  VAGDKDEEVD  SWLLLTKDPD  DDDKNHNCSS  NNNNNNNISS  180
NTSTFYADVD  EYFDLVGYSS  YCDNHINSNT  KQYGMQEQQL  LLHKEFGDKE  GSEYVVPSQV  240
GQQQSGYHRV  IGTEQAASMT  PGVSAYTDSI  SNSISFSSSM  EVGIVPDNMA  TTDMPSSGIL  300
LTPAGAISLF  SSGPPLQMPL  HLASMDREAR  VLRYREKKKS  RKFEKTIRYA  TRKTYAEARP  360
RIKGRFAKRS  SDMDVEVDQM  FSAAALSSDG  SYGTVPWF                           398

SEQ ID NO: 184           moltype = DNA  length = 1320
FEATURE                  Location/Qualifiers
misc_feature             1..1320
                         note = Ceres Clone ID no. 472076
misc_feature             1..1320
                         note = Encodes the peptide sequence at SEQ ID NO. 185
source                   1..1320
                         mol_type = other DNA
                         organism = Glycine max
SEQUENCE: 184
tcttcactct cagaacacta actcccccaa tgttggaggg ccaagcaaca acgcccacgt        60
ggccgcgcat gtcgacacg tgccgctccg tccctccac cgtcttctgc cgctcccaca       120
ccgcctttct ctgcgccacg tgcgacactc gcctccacgt ctcgctcacg tggcacgagc     180
gcgtgtgggt gtgcgaggcg tgcgagcgcg ccccggcggc gttcctctgc aaggccgacg     240
ccgcctcccc ctgcgcctcc tgcgacgccg acatccacgc cgccaacccc ctcgccagcc     300
gccaccaccg cgtcccaatc ctcccatcg cgccgccaa caacaacaac aacgacgacg       360
acgacgttgc tgacgttgac gacgaagacg aaaccgcttc atggctcttg ctcaaccta      420
tcaagagtgc tactgtccct aacaccaata acaataacaa taatcacggg ttcttgtata     480
acggtgaggt tgatgagtat ttggaccttg ttgataattg taactcttgt ggtgataata     540
atcacttcgc ttcagctgct gctactactg atcattacgc tcagcaccaa catttcgctg     600
gtgttctctca gaagagttat gctggggaca gttgtgttcc ggttcagcaa caccagcatt   660
```

```
ttcagcttgg gttggacttt gacaactcca aacctgcctt cagttacaat ggttctgtta    720
gtcaaagtgt ttcagtttca tcaatggata ttggtgttgt acctgaatca ccaatgaggg    780
atgtctcaat tgcccataca agaccccca aagggacaat tgacctattt tctggacctc    840
caattcaggt gccttccat tttctccaa tggacaggga ggccagagtc ctaaggtaca      900
gggagaaaaa gaagatgaga aaatttgaga agacaatcag gtatgcctca aggaaggcct    960
atgcagagac tagacctcgt ataaaaggtc gatttgccaa gagaacagat gtagaagctg   1020
aagtggatca gatgttctcg acaacactaa ttacagaagt tggatatgga attgttccct   1080
ctttctgaat atgctgtgta gaacaaatgg ccagaagaca ttgaagatgc tagaggatca   1140
tgattaatag aaatggaaac cacttgtgta ctaagttatt ctgctgataa tgtattttt    1200
atgtaatcta attgcttgca gttgtactaa tcggatgtta tattattttg tttattgtct   1260
tttgaatgaa acttgtattt gtaaatacag tccttgtatt aaattattaa attacagtcg   1320

SEQ ID NO: 185         moltype = AA  length = 352
FEATURE                Location/Qualifiers
REGION                 1..352
                       note = misc_feature - Ceres Clone ID no. 472076
REGION                 1..352
                       note = misc_feature - Bit score of 378.3 for hmm based on
                         sequences of FIGURE 2.
REGION                 283..327
                       note = misc_feature - Pfam Name: CCT Pfam Desc: CCT motif
REGION                 50..97
                       note = misc_feature - Pfam Name: zf-B_box Pfam Desc: B-box
                         zinc finger
REGION                 1..352
                       note = misc_feature - Functional Homolog Of SEQ ID NO. 20
source                 1..352
                       mol_type = protein
                       organism = Glycine max
SEQUENCE: 185
MLEGQATTPT WPRMCDTCRS VPSTVFCRSH TAFLCATCDT RLHVSLTWHE RVWVCEACER     60
APAAFLCKAD AASLCASCDA DIHAANPLAS RHHRVPILPI AAANNNNNDD DDVADVDDED    120
ETASWLLLNP IKSATVPNTN NNNNNNGFLY NGEVDEYLDL VDNCNSCGDN NHFASAAATT    180
DHYAQHQHFA GVSQKSYAGD SVVPVQQHQH FQLGLDFDNS KPAFSYNGSV SQSVSVSSMD    240
IGVVPESPMR DVSIAHTRPP KGTIDLFSGP PIQVPSHFSP MDREARVLRY REKKKMRKFE    300
KTIRYASRKA YAETRPRIKG RFAKRTDVEA EVDQMFSTTL ITEVGYGIVP SF            352

SEQ ID NO: 186         moltype = AA  length = 321
FEATURE                Location/Qualifiers
REGION                 1..321
                       note = misc_feature - Public GI ID no. 33943521
REGION                 1..321
                       note = misc_feature - Bit score of 284.1 for hmm based on
                         sequences of FIGURE 2.
REGION                 252..296
                       note = misc_feature - Pfam Name: CCT Pfam Desc: CCT motif
REGION                 46..93
                       note = misc_feature - Pfam Name: zf-B_box Pfam Desc: B-box
                         zinc finger
REGION                 1..321
                       note = misc_feature - Functional Homolog Of SEQ ID NO. 20
source                 1..321
                       mol_type = protein
                       note = subspecies = campestris
                       organism = Brassica rapa
SEQUENCE: 186
MLKEESNESG GTRACDTCRS AACTIYREAD STYLCTTCDA RVHAAKRVRV CDSCESAPAA     60
FFCKADAASL CTACDAEIHS ANPLARRHQR VPITSNSCGS MATDGDNNVM MVSEEKEDAD    120
EVASWLMLNP GKNNQNNGFL FGVEYLDLVD YSSSIDNQFE DQYSKYHRSF GGGEDGVVPL    180
QLEESSTSHM QQSQHNFHLG VNYGYSTEPQ YSYVSVVPES LSDTTVQHAK ETIDQVCGPP    240
TQMVQQLTPA DREARVLRYR EKKKRRKFEK TIRYASRKAY AEVRPRIKGR FAKRIDMEAD    300
AEQLFSTSVM SNTSYGIVPS F                                             321

SEQ ID NO: 187         moltype = AA  length = 348
FEATURE                Location/Qualifiers
REGION                 1..348
                       note = misc_feature - Public GI ID no. 186911830
REGION                 1..348
                       note = misc_feature - Bit score of 348.6 for hmm based on
                         sequences of FIGURE 2.
REGION                 6..53
                       note = misc_feature - Pfam Name: zf-B_box Pfam Desc: B-box
                         zinc finger
REGION                 313..348
                       note = misc_feature - Pfam Name: CCT Pfam Desc: CCT motif
REGION                 1..348
                       note = misc_feature - Functional Homolog Of SEQ ID NO. 20
source                 1..348
                       mol_type = protein
```

```
                                    note = subspecies = vulgaris
                                    organism = Beta vulgaris
SEQUENCE: 187
MGGGLMAAKL  CDSCKSATAT  IFCRADTAYL  CISCDAKIHA  ANKLASRHAR  VWVCEVCEHA   60
PATVTCKADA  AHLCATCDRD  IHSANPLARR  HERVPLTPFY  DPLSPPNTTN  NNNDDSDSSA  120
TAAAAKSAA   INKLFGDEYY  SDADEAEAAS  WLLPNPNKTD  EPKSIDYLFS  SSGNDGDDID  180
PYLDLDFGAE  AKPDPDLSSD  GVVPDPDQKG  VHHHHLTTLQ  HPAASMFSLS  SYHHHHHHHH  240
VSNNNGHFDG  FENSSAACKP  FALSSYHTQP  SLSHSVSSSS  LDFGVVPDAS  NITDVASTGF  300
DKQQQMKIIG  MDREARVLRY  REKRKNRKFE  KTIRYASRKA  YAETRPRI                348

SEQ ID NO: 188            moltype = DNA  length = 1077
FEATURE                   Location/Qualifiers
misc_feature              1..1077
                          note = Ceres Annot ID no. 8457547
misc_feature              1..1077
                          note = Encodes the peptide sequence at SEQ ID NO. 189
source                    1..1077
                          mol_type = other DNA
                          organism = Solanum lycopersicum
SEQUENCE: 188
atgggaacgg  agaattggag  tttaacggcg  aagttatgtg  actcatgcaa  aacgtcgccg    60
gcgacggtgt  tctgccgggc  agattcagca  ttttctctgct taggatgtga  ctgcaaaatc   120
cacgcagcga  acaagttagc  gtcacgtcac  gcgcgtgtct  gggtttgtga  agtgtgtgag   180
caagctccgg  cgagtgtcac  gtgtaaagcg  gatgccgctg  ctctctgcgt  tacgtgtgac   240
cgtgatattc  attcagcaaa  tccgttagct  cgtcgccatg  agcgttttcc  ggtagttccg   300
ttctatgatt  tcgccgtcgc  gaaatctcac  ggcggtggta  taccgatgc   cgatgctgtt   360
gatgatgaga  agtactttga  tagtactaat  gagaatgcct  tctcaaccaga ggaagaagct   420
gaagcagcgt  cgtggatact  tccgacgccg  aagaaggaa   ctgatcagta  taaatctgct   480
gattacttgt  ttaatgatat  ggattcatat  ttagatatag  atctaatgtc  atgtgagcaa   540
aaaccacata  ttcttcatca  tcaacagcat  caacacaacc  attacagctc  cgacggagtt   600
gtaccagtac  agaacaacaa  cgaaactact  catttacccg  gtccagtcgt  tgatggattc   660
cctacatacg  aactcgattt  cactggatct  aaaccttata  tgtacaattt  cacctctcaa   720
tcgatcagcc  aaagtgtttc  atcatcatct  cttgacgtcg  gagttgtacc  agaccacagc   780
acaatgacaa  atgtatcaaa  cacttttgtg  atgaactcat  cttccggtgc  tattgccggc   840
gccggcgcca  acgttgtacc  gaatgcagtt  tccggtttag  acagagaagc  aagggtaatg   900
aggtacagag  agaagaggaa  gaatagaaag  ttcgagaaga  cgattcgata  tgcttctaga   960
aaagcttatg  ctgagactcg  gcccagaatc  aaagggagat  cgctaaacg   tactgaaact  1020
gaaatcgatt  cactcatcac  cgtcgatgca  tcatacggtg  tcgttccatc  gttttaa     1077

SEQ ID NO: 189            moltype = AA   length = 358
FEATURE                   Location/Qualifiers
REGION                    1..358
                          note = misc_feature - Ceres Annot ID no. 8457547
REGION                    1..358
                          note = misc_feature - Bit score of 531.8 for hmm based on
                            sequences of FIGURE 2.
REGION                    8..55
                          note = misc_feature - Pfam Name: zf-B_box Pfam Desc: B-box
                            zinc finger
REGION                    295..339
                          note = misc_feature - Pfam Name: CCT Pfam Desc: CCT motif
REGION                    1..358
                          note = misc_feature - Functional Homolog Of SEQ ID NO. 20
source                    1..358
                          mol_type = protein
                          organism = Solanum lycopersicum
SEQUENCE: 189
MGTENWSLTA  KLCDSCKTSP  ATVFCRADSA  FLCLGCDCKI  HAANKLASRH  ARVWVCEVCE   60
QAPASVTCKA  DAAALCVTCD  RDIHSANPLA  RRHERFPVVP  FYDFAVAKSH  GGGDTDADAV  120
DDEKYFDSTN  ENPSQPEEEA  EAASWILPTP  KEGTDQYKSA  DYLFNDMDSY  LDIDLMSCEQ  180
KPHILHHQQH  QHNHYSSDGV  VPVQNNNETT  HLPGPVVDGF  PTYELDFTGS  KPYMYNFTSQ  240
SISQSVSSSS  LDVGVVPDHS  TMTDVSNTFV  MNSSSGAIAG  AGADVVPNAV  SGLDREARVM  300
RYREKRKNRK  FEKTIRYASR  KAYAETRPRI  KGRFAKRTET  EIDSLITVDA  SYGVVPSF    358

SEQ ID NO: 190            moltype = AA   length = 369
FEATURE                   Location/Qualifiers
REGION                    1..369
                          note = misc_feature - Public GI ID no. 188484477
REGION                    1..369
                          note = misc_feature - Bit score of 209.9 for hmm based on
                            sequences of FIGURE 2.
REGION                    300..344
                          note = misc_feature - Pfam Name: CCT Pfam Desc: CCT motif
REGION                    22..69
                          note = misc_feature - Pfam Name: zf-B_box Pfam Desc: B-box
                            zinc finger
REGION                    1..369
                          note = misc_feature - Functional Homolog Of SEQ ID NO. 20
source                    1..369
```

```
                            mol_type = protein
                            organism = Lolium perenne
SEQUENCE: 190
MLMNCDFNCD  LFEQEAKRRS  YPWARPCDGC  HAAPSAVYCH  ADAAYLCASC  DTQVHSANRL   60
ASSHERVRVC  VSCESAAAVL  ECHADSAALC  TTCDAQVHSA  NPIAQRHQRV  PVLPLPALAI  120
PAASVFAEAE  AATTVYGDKE  EGEEVDSWLL  LERDSDDNNC  TNNIDQYFNL  FGYDMYYDKF  180
SCNPGPGEEY  RLQEQDVQNM  YRENEVCEFA  VPSQVGMASE  QPESSYGMIG  AEQDASMTAG  240
TSTYTASISN  GIPFSSMEVG  IIPDNTRPDV  SNTNIQRTSE  AMELAGHSLQ  MPVHFSSMDR  300
DARVLRYKEK  KQARTFQKTI  RYATRKAYAE  ARPRIKGRFA  KRSDIEHELD  QMLTIPALPD  360
SGHATVLWF                                                               369

SEQ ID NO: 191          moltype = DNA   length = 1131
FEATURE                 Location/Qualifiers
misc_feature            1..1131
                        note = Ceres Annot ID no. 8743875
misc_feature            1..1131
                        note = Encodes the peptide sequence at SEQ ID NO. 192
source                  1..1131
                        mol_type = other DNA
                        organism = Sorghum bicolor
SEQUENCE: 191
atggagctgc acaagtactg gggcgtgggt ggccggcggt gcggcagctg cgaggcggcg   60
ccggcggcgg tgcactgccg cacgtgcgtc ggcgggtcgt cgtcgttcct ctgcacgacg  120
tgcgacgcgc gccccgcgca cgcgcgcctg gcccacgagc gcgtgtgggt gtgcgaggtc  180
tgcgagctgg ccccgccgc cgtcacgtgc aaggccgacg ccgccgtgct ctgcgccgcc  240
tgcgacgccg acatccacga cgccaacccg ctggccgacg gccacgcgcg ggtccccgtc  300
gcgcccatcg gctccgaggc cgccgccgcg gccgtcgagg ccatgctgtt cgggaccggc  360
gacgcggccg aggccgacga ccagcacaac aacgcggcgg cggcggccga gcagcatcag  420
catcagcacc acgctcacca cgcgcacgcg ctgaacctca cgtgaggc gaaggacatg   480
aagctggact acctcttctc tgagctggat cctacctca cccgcgcttc   540
caccacgccg acagcgtcgt ccccaacggc gccggcgctg ccggcgccgt cgagctcgac   600
ttcacgtgcg gcatcggcgt caagcactcc tcctacagct cctacaccgc cacctccctc   660
gatctcgcgc atagcggctc ctcgtcggag gtcggcgtgg tgccagaggc cttcggcggc   720
ggcggcggc gcggcggcgg gagctttgag ctcgacttca caaggccaaa gcctcaggcc   780
tacatgccat acacggcgac tccccagagc cacagcgtgt cgtccgtgga cgtggaggtg   840
gtgccggagc ggggagactt gccggcggtg aggccggtgc cgctgatggg ggagagccgg   900
gaggcgcggc tgatgcggta ccgtgagaag aggaagaacc ggcggttcga aagaccatc   960
cggtacgcgt cccggaaggc ctacgccgag acgcggccgc ggatcaaggg gaggtttgcc  1020
aagcgccgcg accacgacgg cgacggcgac gccgacgacg ccgaggccga ggccgccgtg  1080
ccgtcgtcgt acgtgctcga cttcggctac ggcgtcgtgc cgagcttctg a           1131

SEQ ID NO: 192          moltype = AA   length = 376
FEATURE                 Location/Qualifiers
REGION                  1..376
                        note = misc_feature - Ceres Annot ID no. 8743875
REGION                  1..376
                        note = misc_feature - Bit score of 743.4 for hmm based on
                         sequences of FIGURE 2.
REGION                  300..344
                        note = misc_feature - Pfam Name: CCT Pfam Desc: CCT motif
REGION                  53..100
                        note = misc_feature - Pfam Name: zf-B_box Pfam Desc: B-box
                         zinc finger
REGION                  1..376
                        note = misc_feature - Functional Homolog Of SEQ ID NO. 20
source                  1..376
                        mol_type = protein
                        organism = Sorghum bicolor
SEQUENCE: 192
MELHKYWGVG  GRRCGSCEAA  PAAVHCRTCV  GGSSSFLCTT  CDARPAHARL  AHERVWVCEV   60
CELAPAAVTC  KADAAVLCAA  CDADIHDANP  LARRHARVPV  APIGSEAAAA  AVEAMLFGTG  120
DAAEADDQHN  NAAAAAEQHQ  HQHHAHHAHA  LNLNVEAKDM  KLDYLFSELD  PYLSVEIPRF  180
HHADSVVPNG  AGAAGAVELD  FTCGIGVKHS  SYSSYTATSL  DLAHSGSSSE  VGVVPEAFGG  240
GGGGGGGSFE  LDFTRPKPQA  YMPYTATPQS  HSVSSVDVEV  VPERGDLPAV  RPVPLMGESR  300
EARLMRYREK  RKNRRFEKTI  RYASRKAYAE  TRPRIKGRFA  KRADHDGDGD  ADDAEAEAAV  360
PSSYVLDFGY  GVVPSF                                                     376

SEQ ID NO: 193          moltype = AA   length = 444
FEATURE                 Location/Qualifiers
REGION                  1..444
                        note = misc_feature - Public GI ID no. 193735598
REGION                  1..444
                        note = misc_feature - Bit score of 405.5 for hmm based on
                         sequences of FIGURE 2.
REGION                  377..421
                        note = misc_feature - Pfam Name: CCT Pfam Desc: CCT motif
REGION                  79..126
                        note = misc_feature - Pfam Name: zf-B_box Pfam Desc: B-box
                         zinc finger
```

```
REGION                  1..444
                        note = misc_feature - Functional Homolog Of SEQ ID NO. 20
source                  1..444
                        mol_type = protein
                        organism = Picea abies
SEQUENCE: 193
MVKEEDKDWH TVEDLHRGSH VDHKEFLRGI GGWRMSMPKL CDVCQVSNSV LYCRAHTAQL    60
CLVCDVKIHG GSKASLCHER VWVCEVCEQA PAVVTCKADA AALCVSCDTD IHSANPLASR   120
HERAPVIPFY ECPNMPNNNT ATNANNDNLD CNVLLNEDGG GDDPLKHDYV DDDYDDYDDD   180
ENDHNNLLNH QEDDNDAEIC CAEEAATASW LIPEANRNNL TNINGGNSEG EDKMVKDKLK   240
FKAYMQSIDF LQDVENYVDL EYLGTTTTIT TPTTPTAHMG ADSMVPVHTP EVIEHSSTKV   300
SVETARSLDV DAASKCNYVY RTTSLNHCVS SSSIDVGIVP DSNTTTDIST PYHDPRGVFE   360
IPPRVVHPGG HVEVMGREAR VLRYREKRKN RRFEKTIRYA SRKAYAETRP RIKGRFAKRT   420
EVEVEQIYSS SLLPDQGYGV VPSY                                         444

SEQ ID NO: 194          moltype = AA   length = 384
FEATURE                 Location/Qualifiers
REGION                  1..384
                        note = misc_feature - Public GI ID no. 116787635
REGION                  1..384
                        note = misc_feature - Bit score of 467.1 for hmm based on
                        sequences of FIGURE 2.
REGION                  23..70
                        note = misc_feature - Pfam Name: zf-B_box Pfam Desc: B-box
                        zinc finger
REGION                  320..364
                        note = misc_feature - Pfam Name: CCT Pfam Desc: CCT motif
REGION                  1..384
                        note = misc_feature - Functional Homolog Of SEQ ID NO. 20
source                  1..384
                        mol_type = protein
                        organism = Picea sitchensis
SEQUENCE: 194
MVKEEDCKVP KEAGIVKEFQ AWTMPKPCNV CRIASASLYC RADSAYLCSG CDVKVHGANK    60
LASRHERVWL CEVCEQAPAA VTCKADAASL CVSCDADIHS ANPLARRHDR VPIVPFYECA   120
SVAKTFLPPP PPPPTSSLQD SDVVGTLDYE DHDDDDEIYA AEAASWLLPN PKSSAEGTKN   180
CDDGGSCFGV DAGPPVNKAA GGYFSVVDLF PDVDPYLDLD YASPLEATGG TDSVVPVQSN   240
VSSQDGAVST PSDCFDTEKV TYSYTTTTSL SHSVSSSSLD VGVVPDATLS DMPRPLNRGV   300
FELANPGVVN VGIQYVQLDR EARVLRYKEK RKNRKFEKTI RYASRKAYAE TRPRIKGRFA   360
KRVDADVAQM YTSAELSYGL VPSF                                         384

SEQ ID NO: 195          moltype = AA   length = 383
FEATURE                 Location/Qualifiers
REGION                  1..383
                        note = misc_feature - Public GI ID no. 169807976
REGION                  1..383
                        note = misc_feature - Bit score of 230.7 for hmm based on
                        sequences of FIGURE 2.
REGION                  314..358
                        note = misc_feature - Pfam Name: CCT Pfam Desc: CCT motif
REGION                  19..66
                        note = misc_feature - Pfam Name: zf-B_box Pfam Desc: B-box
                        zinc finger
REGION                  1..383
                        note = misc_feature - Functional Homolog Of SEQ ID NO. 20
source                  1..383
                        mol_type = protein
                        organism = Triticum aestivum
SEQUENCE: 195
MNCVSNGTVY EEAVGREGSW ARLCDGCCTV PSVVYCRADS AYLCASCDAQ IHAANRVASR    60
HERVLLSEAY KHAPVVLECH ADAAALCAAY EAQVHYANLL ATMHQRVPVV SHPVAAIPAA   120
SLFAEAAATA PVLGSKEEDA SWLLLSKDSD NHNHSGNHSS SSSSSRYFGE VDQYFDLVGY   180
NSYYDSHMNN QEQYVMQEQQ HLQQMQKEYA EQQMQKEYVE KEGSECIVPS QSAIVSRPHQ   240
SGYAPLVRAE QAASVTAGVS AYTDSVNNSI SFSMEAGIVP DNTVQSSILR PAGAIGHFSS   300
PSLQTPLHFS SKEREARVLR YKEKKKSRKF EKTTRYATRK AYAEEARPRIK GRFAKRSDAD   360
MEVDQTFSTA ALSDSSYSTV PWF                                          383

SEQ ID NO: 196          moltype = AA   length = 397
FEATURE                 Location/Qualifiers
REGION                  1..397
                        note = misc_feature - Public GI ID no. 157422228
REGION                  1..397
                        note = misc_feature - Bit score of 334.9 for hmm based on
                        sequences of FIGURE 2.
REGION                  326..370
                        note = misc_feature - Pfam Name: CCT Pfam Desc: CCT motif
REGION                  27..74
                        note = misc_feature - Pfam Name: zf-B_box Pfam Desc: B-box
                        zinc finger
```

| | | |
|---|---|---|
| REGION | 1..397 | |
| | note = misc_feature - Functional Homolog Of SEQ ID NO. 20 | |
| source | 1..397 | |
| | mol_type = protein | |
| | organism = Zea mays | |
| SEQUENCE: 196 | | |

```
MDYNFDTSVL DEDVAGRGGR EGSCPPAWAR ACDGCRAAPS VVYCHADTAY LCASCDSRVH   60
AANRVASRHE RVRVCEACEC APAVLACRAD AAALCAACDA QVHSANPLAG RHQRVPVLPL  120
PAAAVPAASV LAEATATAAS VAGDKDEEVD SWLLLTKDPD DDDKNHNCSS NNNNNNISSN  180
TSTFYADVDE YFDLVGYSSY CDNHINSNTK QYGMQEQQLL LHKEFGDKEG SEYVVPSQVG  240
QQQSGYHRVI GTEQAASMTP GVSAYTDSIS NSISYSSSME VGIVPDNMAT TDMPSSGILL  300
TPAGAISLFS SGPPLQMPLH LASMDREARV LRYREKKKSR KFEKTIRYAT RKTYAEARPR  360
IKGRFAKRSS DMDDEVDQMF SAAALSSDGS YGTVPWF                          397
```

| | | |
|---|---|---|
| SEQ ID NO: 197 | moltype = DNA length = 1423 | |
| FEATURE | Location/Qualifiers | |
| misc_feature | 1..1423 | |
| | note = Ceres Clone ID no. 1755159 | |
| misc_feature | 1..1423 | |
| | note = Encodes the peptide sequence at SEQ ID NO. 198 | |
| source | 1..1423 | |
| | mol_type = other DNA | |
| | organism = Panicum virgatum | |
| SEQUENCE: 197 | | |

```
gcgcgctccc tcccctcccc tcctcccacc agcccaccac caccacaagc accgcgtcgt    60
ccacaccacc tgccattgcc gcgccgagct cagcctctag ctgcgccagg agggcgcccg   120
cctccctccc tgccgacgcc ggtgtgatgg agctgcacaa gtactggggc gtgggggcc    180
gccggtgcgg cggctgcgag gcggcccggc cggcggtgca ctgccgctcg tgccccgccg   240
ggggcgcgtt cctctgcacg gcgtgcgacg cgcgcccggg gcacgcgcat ctgggccacg   300
agcgcgtgtg gatgtgcgag gtctgcgagc tggcgcccgc cgccgtcacg tgcaaggccg   360
acgccgccgt gctctgcgcc gcctgcgacg ccgacatcca cgacgccaac ccgctggccg   420
gccgccacgc acgcgtcccc gtcgcgccca tcggctcgga ggccgcggcc gccgccgtgg   480
aggccatgct gttcgggacc ggcgagccgg ccgcgtccga ggccgaggag ccgcagaacg   540
cggcggccag gcacaaccac cagcacgcgc tgaacctcaa cgtggaggcc aaggacatga   600
agctggacta cctcttttcc gacctggacc cctacctcag cgtcgatatc ccgcgcttcc   660
agcacgccga cagcgtcgtc cccagcggcg tcggcgccgg agcagccggc gccgtcgagc   720
tggacttcac gtgcggcatc ggcgtcgagc cctcctcata cagctcctac acggcaacat   780
ccctcgccca cagcggctcc tcttctgagg tcggcgtggt gccagaggcc ttctgcgccg   840
ggggcgggag cttcgagctc gacttcacaa ggccaagcc tcaagcctac atgccgtaca   900
ccgcgactcc tcaaagtcac agcgtgtcgt cggtgacgt ggaggtggtg ccggagcggg   960
gggacatgat ggcggcggcg aggccggtgc cgctggtggg ggagagccgg gaggcgcggc  1020
tgatgcgcta ccgggagaag cggaagaacc ggcggttcga gaagaccatc cggtacgcgt  1080
cccggaaggc ctacgccgag atgcggccgc ggatcaaggg ccggttcgcc aagcgcgcgg  1140
accacgacgc cgacgccgac gacaccgagg ccgaggccga ggccgccgtg ccgtcgccgg  1200
cgtcgtacgt gctcgacttc ggctacgcgg tcgtgcccag cttctgatcg acgacgatcg  1260
tctcgctcgt tccacgcgcg gcgcgcttga cccggcccgg cgcgcgcgcc ttgtacttgt  1320
atcgatgcat gtatagggga ggaatagtaa tcccatgtac tctcgtcttg gagctgcgct  1380
agccctgcgt acgtacgcta gtgatgtata atttgtacaa ccc                   1423
```

| | | |
|---|---|---|
| SEQ ID NO: 198 | moltype = AA length = 366 | |
| FEATURE | Location/Qualifiers | |
| REGION | 1..366 | |
| | note = misc_feature - Ceres Clone ID no. 1755159 | |
| REGION | 1..366 | |
| | note = misc_feature - Bit score of 709.8 for hmm based on sequences of FIGURE 2. | |
| REGION | 288..332 | |
| | note = misc_feature - Pfam Name: CCT Pfam Desc: CCT motif | |
| REGION | 52..99 | |
| | note = misc_feature - Pfam Name: zf-B_box Pfam Desc: B-box zinc finger | |
| REGION | 1..366 | |
| | note = misc_feature - Functional Homolog Of SEQ ID NO. 20 | |
| source | 1..366 | |
| | mol_type = protein | |
| | organism = Panicum virgatum | |
| SEQUENCE: 198 | | |

```
MELHKYWGVG GRRCGGCEAA PAAVHCRSCP AGGAFLCTAC DARPGHAHLG HERVWMCEVC   60
ELAPAAVTCK ADAAVLCAAC DADIHDANPL ARRHARVPVA PIGSEAAAAA VEAMLFGTGE  120
PAASEAEEPQ NAAARHNHQH ALNLNVEAKD MKLDYLFSDL DPYLSVDIPR FQHADSVVPS  180
GVGAGAAGAV ELDFTCGIGV EPSSYSSYTA TSLAHSGSSS EVGVVPEAFC GGGGSFELDF  240
TRPKPQAYMP YTATPQSHSV SSVDVEVVPE RGDMMAAARP VPLVGESREA RLMRYREKRK  300
NRRFEKTIRY ASRKAYAEMR PRIKGRFAKR ADHDADADDT EAEAEAAVPS PASYVLDFGY  360
GVVPSF                                                            366
```

| | | |
|---|---|---|
| SEQ ID NO: 199 | moltype = AA length = 362 | |
| FEATURE | Location/Qualifiers | |
| REGION | 1..362 | |
| | note = misc_feature - Public GI ID no. 170779036 | |

```
REGION                      1..362
                            note = misc_feature - Bit score of 423.2 for hmm based on
                              sequences of FIGURE 2.
REGION                      13..60
                            note = misc_feature - Pfam Name: zf-B_box Pfam Desc: B-box
                              zinc finger
REGION                      297..341
                            note = misc_feature - Pfam Name: CCT Pfam Desc: CCT motif
REGION                      1..362
                            note = misc_feature - Functional Homolog Of SEQ ID NO. 20
source                      1..362
                            mol_type = protein
                            organism = Chenopodium rubrum
SEQUENCE: 199
MMKKEVPGGD NNSWARVCDT CRSAPCTVYC KEDSAFLCTS CDARIHAVNQ MASRHERVWV     60
CEACEREPAA FLCKADAASL CATCDADIHS ANPLARRHHR VPIMPVGCVY GPSDGRMSED    120
GFLDLPDRDD QTTDHEGDED EAASWLLLNP GKNSNNQTTN GFLTGGGEVD EYLDLFEYNS    180
GADNQFCEQY NQQQEFSVPE KNCGGDSVVP VQCREVKDHQ IQYQNLFLGM ECETKSEYTY    240
NTSISHSVSV SSLDVGVVPE STMSDMSVSH SRPPKGTIDL FSSTPMQVPT QLSPLDREAR    300
VMRYREKKKN RKFEKTIRYA SRKAYAETRP RIKGRFAKRT DVEAERTNSL MSDGGYGIVP    360
SF                                                                  362

SEQ ID NO: 200              moltype = DNA  length = 1116
FEATURE                     Location/Qualifiers
misc_feature                1..1116
                            note = Ceres Annot ID no. 1731456
misc_feature                1..1116
                            note = Encodes the peptide sequence at SEQ ID NO. 201
source                      1..1116
                            mol_type = other DNA
                            organism = Oryza sativa
SEQUENCE: 200
atgatggagt tgcgcaagta ctggggcgtc ggcgggcggc ggtgcggtgc gtgcgaggcg     60
tcgccggcgg ccgtgcactg ccgcggctgc ggcggggtgt acctgtgcac ggcgtgcgac    120
gcgcgccogg gccacgcgcg ggcggcgcac gagcggggtg gggtgtgcga ggtctgcgag    180
gtggcgcccg ccgccgtcac ctgcaaggcc gacgccgcgg tgctctgcgc cgcctgcgac    240
gccgacatcc acgacgccaa cccgctggcc cgccgccacg cgcgcgtccc cgtcgcgccc    300
atcggctccg ccgccgccgc cgccgtggcc gccgaggcca tgctgttcgg cgtcgccgcc    360
gccggggccg aggccgaggc ggtggaggat aaggccgcag ccgagcacca ccaccaccag    420
cagcggcagc agcacggcgc gctcaacctc aacgtggagg cgaaggacat gaagctcgac    480
tacctcttct ccgacctcga cccttacctc aacgtcgagt tcgcccgctt cccccacgcc    540
gacagcgtcg tccccaacgg cgccggcgcc ggcgccgcca tagagctcga cttcacctgc    600
ggcctaggcg tcggcgtcgg cggcgccaag cagtcctaca gctcctacac cgccaccgac    660
ctcgctcaca gcggctcgtc gtcggaggtg ggcgtggtgc cggaggccat gtgcggcggc    720
ggcggcgcca tcgatctcga cttcacgagg ccgaagcctc aaccctacat gccgtacacg    780
gcgactcctc ctccgagcca cagcgtagta agcgcgcaga tgtcgtcgtc ggtggtcgac    840
gtgggcgtgg tgccggaagc ggcggcggcg atgggggaag ggaggaggc gaggctgatg    900
aggtacaggg agaagcggaa gaaccggcgg ttcgagaaga cgatccggta cgcgtcgcgc    960
aaggcctacg ccgagacgcg ccccccggatc aagggccgct cgccaagcg cgccgaccac   1020
gacgccgacg acgccgacgc cgacgccgac gaccccgccg ccgtcccatc ctcctacatg   1080
ctcgacttcg gctacggcgt cgtcccgtcc ttctga                             1116

SEQ ID NO: 201              moltype = AA  length = 371
FEATURE                     Location/Qualifiers
REGION                      1..371
                            note = misc_feature - Ceres Annot ID no. 1731456
REGION                      1..371
                            note = misc_feature - Bit score of 611.8 for hmm based on
                              sequences of FIGURE 2.
REGION                      295..339
                            note = misc_feature - Pfam Name: CCT Pfam Desc: CCT motif
REGION                      51..98
                            note = misc_feature - Pfam Name: zf-B_box Pfam Desc: B-box
                              zinc finger
REGION                      1..371
                            note = misc_feature - Functional Homolog Of SEQ ID NO. 20
source                      1..371
                            mol_type = protein
                            organism = Oryza sativa
SEQUENCE: 201
MMELRKYWGV GGRRCGACEA SPAAVHCRGC GGVYLCTACD ARPGHARAAH ERVWVCEVCE     60
VAPAAVTCKA DAAVLCAACD ADIHDANPLA RRHARVPVAP IGSAAAAVA AEAMLFGVAA    120
AGAEAEAVED KAAAEHHHHQ QRQQHGALNL NVEAKDMKLD YLFSDLDPYL NVEFARFPHA    180
DSVVPNGAGA GAAIELDFTC GLGVGVGGAK QSYSSYTATD LAHSGSSSEV GVVPEAMCGG    240
GGAIDLDFTR PKPQPYMPYT ATPPPSHSVV SAQMSSSVVD VGVVPERAAA MGEGREARLM    300
RYREKRKNRR FEKTIRYASR KAYAETRPRI KGRFAKRADH DADDADADAD DPAAVPSSYM    360
LDFGYGVVPS F                                                        371

SEQ ID NO: 202              moltype = DNA  length = 1251
```

-continued

```
FEATURE                 Location/Qualifiers
misc_feature            1..1251
                        note = Ceres Clone ID no. 1770031
misc_feature            1..1251
                        note = Encodes the peptide sequence at SEQ ID NO. 203
source                  1..1251
                        mol_type = other DNA
                        organism = Panicum virgatum
SEQUENCE: 202
agcgagctcc cggcgcgcga taatggaggg tgacgagaag tcggcaggcg gggcccggc      60
cccggcctac tggggcctgg gcgcgcggcc ctgcgacgcg tgcggcgacg aggcggcgag    120
gctctactgc cgcgcggacg cggcgttcct ctgcgccggg tgcgacgcgc gcgcgcacgg    180
cgccgggtcg cgccacgccc gcgtctggct ctgcgaggtc tgcgagcacg cgccggccgc    240
ggtcacgtgc cgcgcggacg ccgcgcgct tgcgcagcca acatccactc                300
cgccaacccg ctcgcgcgcc gccacgagcg ccaggccgtg gcgcccttct acggcgcgct    360
ggccgacgcg cccaagccct tcgcctcgtc ggcggccgtg cccaaagcgg ccgacgacga    420
cgggagcaac gaggccgagg cggcgtcgtg gctcctcccc gagcccgacc acgggctcaa    480
ggaaggcgcc acgacggagg tgttcttcgc ggactccgac ccgtacctcg acctcgactt    540
cgcgcgcacc atgacgacaa tcaaggccat cggcgtccag aacggccccg ccgagctcga    600
cctcaccggc gccaagctct ctactccga ccactccatg aaccacagcg tgtcgtcatc     660
ggaggcagca gtggtgcccg acgcggcggc gggcgcggcg cccgtggttc cagtggtgag    720
caggggctctg gagcgggagg cccggctgat gcggtaccgg gagaagcgca agagccgactt  780
gttcgagaag acgatccggt acgcgtcccg caaggcgtac gcggagacgc ggccgcgcat    840
caagggccgg ttcgccaagc gcaccccgg gccggcggc gcggacgggg aggacccgct      900
ggaggagcac gaggaggaga tgtactcctc cgccgcggca gccgtggccg cgctcatggt    960
ccccggcggc gccgacgccg actacggcgt cgtgcccacg tattgatcgg cgccggcctg   1020
ttgtaacact agccagcctc gacctcgccg ccggggctgt aatttttgct gcatgccctg   1080
catgcaaagc tgccgtgtag cattaattac ctgtaatatg attccacgga agccatcagg   1140
ccggacttcc aagctattct tcctcccta tcattccgcc atgtatgtat attattatga    1200
gtaaattgca ctcatcatac aataaattga cagatagata caaattgatc c            1251

SEQ ID NO: 203          moltype = AA length = 327
FEATURE                 Location/Qualifiers
REGION                  1..327
                        note = misc_feature - Ceres Clone ID no. 1770031
REGION                  1..327
                        note = misc_feature - Bit score of 643.2 for hmm based on
                          sequences of FIGURE 2.
REGION                  238..282
                        note = misc_feature - Pfam Name: CCT Pfam Desc: CCT motif
REGION                  19..63
                        note = misc_feature - Pfam Name: zf-B_box Pfam Desc: B-box
                          zinc finger
REGION                  1..327
                        note = misc_feature - Functional Homolog Of SEQ ID NO. 20
source                  1..327
                        mol_type = protein
                        organism = Panicum virgatum
SEQUENCE: 203
MEGDEKSAGG APAPAYWGLG ARPCDACGDE AARLYCRADA AFLCAGCDAR AHGAGSRHAR     60
VWLCEVCEHA PAAVTCRADA AALCASCDAD IHSANPLARR HERQAVAPFY GALADAPKPF    120
ASSAAVPKAA DDDGSNEAEA ASWLLPEPDH GLKEGATTEV FFADSDPYLD LDFARTMDDI    180
KAIGVQNGPA ELDLTGAKLF YSDHSMNHSV SSSEAAVVPD AAAGAAPVVP VVSRGLEREA    240
RLMRYREKRK SRRFEKTIRY ASRKAYAETR PRIKGRFAKR TPGPGGADGE DPLEEHEEEM    300
YSSAAAAVAA LMVPGGADAD YGVVPTY                                       327

SEQ ID NO: 204          moltype = AA length = 345
FEATURE                 Location/Qualifiers
REGION                  1..345
                        note = misc_feature - Public GI ID no. 194244874
REGION                  1..345
                        note = misc_feature - Bit score of 278.5 for hmm based on
                          sequences of FIGURE 2.
REGION                  7..54
                        note = misc_feature - Pfam Name: zf-B_box Pfam Desc: B-box
                          zinc finger
REGION                  283..327
                        note = misc_feature - Pfam Name: CCT Pfam Desc: CCT motif
REGION                  1..345
                        note = misc_feature - Functional Homolog Of SEQ ID NO. 20
source                  1..345
                        mol_type = protein
                        organism = Brassica nigra
SEQUENCE: 204
MLKQESNWAQ ACDTCRSAAC TVYCRADSAY LCTSCDAQIH AANRLASRHE RVRVCESCER     60
APAAFFCKAD AASLCTACDS QIHSANPLAR RHQRVPILPI SGCVATNHSS KTTEPENIVV    120
VGQEEEDEAE AASWLLPSSV KNCGDNNNNN NNNSENNRFS VGEEYLDLVD YSSSIDKRFT    180
GQSNQYQQDY NVPQRSYVAD GVVPLQVGVA NGHMHHEQHN FQFGFTNVSS EAHQISNGSP    240
IHMVSLVPES VTSDATVSHP RSPKAGTEEL PEAPVQMLSP MERKARVLRY REKKKTRKFE    300
```

```
KRIRYASRKE YAEKRPRIKG RFAKRNEVDA DHALSTMVVF DTGYG              345

SEQ ID NO: 205            moltype = AA  length = 384
FEATURE                   Location/Qualifiers
REGION                    1..384
                          note = misc_feature - Public GI ID no. 150014754
REGION                    1..384
                          note = misc_feature - Bit score of 466.3 for hmm based on
                            sequences of FIGURE 2.
REGION                    23..70
                          note = misc_feature - Pfam Name: zf-B_box Pfam Desc: B-box
                            zinc finger
REGION                    320..364
                          note = misc_feature - Pfam Name: CCT Pfam Desc: CCT motif
REGION                    1..384
                          note = misc_feature - Functional Homolog Of SEQ ID NO. 20
source                    1..384
                          mol_type = protein
                          organism = Picea abies
SEQUENCE: 205
MVKEEDCKVP KEAGIVKEFQ AWTMPKPCNV CRIASASLYC RADSAYLCSG CDVKVHGANK   60
LASRHERVWL CEVCEQAPAA VTCKADAASL CVSCDADIHS ANPLARRHDR VPIVPFYECA  120
SVAKTFLPPP PPPPTSSLQD SDVVGTLDYE DDDEDDEIYA AEAASWLLPN PKSSAEGAKN  180
CDDGGSCFGV DAGPPVNKAA GGYFSVVDLF PDVDPYLDLD YASPLEATGG TDSVVPVQSN  240
VSSQDGAVST PSDCFDTEKA TYSYTTTTSL SHSVSSSSLD VGVVPDATLS DMSRPLNRGV  300
FELANPGVVN VGIQYVQLDR EARVLRYKEK RKNRKFEKTI RYASRKAYAE TRPRIKGRFA  360
KRVDADVAQM YTSAELSYGL VPSF                                        384

SEQ ID NO: 206            moltype = AA  length = 340
FEATURE                   Location/Qualifiers
REGION                    1..340
                          note = misc_feature - Public GI ID no. 194244844
REGION                    1..340
                          note = misc_feature - Bit score of 276.3 for hmm based on
                            sequences of FIGURE 2.
REGION                    7..54
                          note = misc_feature - Pfam Name: zf-B_box Pfam Desc: B-box
                            zinc finger
REGION                    280..324
                          note = misc_feature - Pfam Name: CCT Pfam Desc: CCT motif
REGION                    1..340
                          note = misc_feature - Functional Homolog Of SEQ ID NO. 20
source                    1..340
                          mol_type = protein
                          organism = Brassica nigra
SEQUENCE: 206
MLKQESNWAQ ACDTCRSAAC TVYCRADSAY LCTSCDAQIH AANRLASRHE RVRVCESCER   60
APAAFFCKAD AASLCTACDS QIHSANPLAR RHQRVPILPI SGCVATNHHS SETTEPENIV  120
VVGQEEEDEA EAASWLLPSS VKNCGDNNNN TENNRFSVGE EYLDLVDYSS SIDKRFTGQT  180
NQYQQDYNVP QRSYVADGVV PLQVGVSKGH MHHEQHNFQF GFTNVSSEAH QISNGSPIHM  240
VSLVPESVTS DATVSHQRSP KAGTEELPEA PVQMLSPMER KARVLRYREK KKTRKFEKRI  300
RYASRKEYAE KRPRIKGRFA KRNEVDADQA FPTVVMFDTG                        340

SEQ ID NO: 207            moltype = AA  length = 340
FEATURE                   Location/Qualifiers
REGION                    1..340
                          note = misc_feature - Public GI ID no. 189014382
REGION                    1..340
                          note = misc_feature - Bit score of 510.4 for hmm based on
                            sequences of FIGURE 2.
REGION                    1..48
                          note = misc_feature - Pfam Name: zf-B_box Pfam Desc: B-box
                            zinc finger
REGION                    279..323
                          note = misc_feature - Pfam Name: CCT Pfam Desc: CCT motif
REGION                    1..340
                          note = misc_feature - Functional Homolog Of SEQ ID NO. 20
source                    1..340
                          mol_type = protein
                          organism = Malus x domestica
SEQUENCE: 207
MALKLCDSCK SATGTLFCRA DSAFLCVNCD SKIHAANKLA SRHARVWLCE VCEQAPAHVT   60
CKADDAALCV TCDRDIHSAN PLSRRHERVP VTPFYDSVNS ATDSVPAVKS AVNFLNDRYF  120
SDVDGEIEAR REEAEAASWL LPNPKAMENP DLNSGQYLFP EMDPYMDLDY GHVDPKLEDA  180
QEQNSCITDG VVPEQSKNMQ PQLVNDHSFE IDFSAASKPF VYGYHHAQCL RQSVSSSSMD  240
VSIVPDDNAM TDDSNPYNKS MTSAVESSHP AVQLSSADRE ARVLRYREKR KNRKFEKTIR  300
YASRKAYAET RPRIKGRFAK RTEVEIEAEP MCRYGIVPSF                        340

SEQ ID NO: 208            moltype = AA  length = 386
```

```
FEATURE                 Location/Qualifiers
REGION                  1..386
                        note = misc_feature - Public GI ID no. 186915025
REGION                  1..386
                        note = misc_feature - Bit score of 486.0 for hmm based on
                         sequences of FIGURE 2.
REGION                  307..351
                        note = misc_feature - Pfam Name: CCT Pfam Desc: CCT motif
REGION                  22..63
                        note = misc_feature - Pfam Name: zf-B_box Pfam Desc: B-box
                         zinc finger
REGION                  1..386
                        note = misc_feature - Functional Homolog Of SEQ ID NO. 20
source                  1..386
                        mol_type = protein
                        organism = Solanum lycopersicum
SEQUENCE: 208
MGIFREAPNC FPGGWNIGAA ARMAKSCEYC HLAAALVFCR TDNTFVCLSC DTRLHARHER      60
VWVCEVCEQA AASVTCRADA AALCVACDRD IHSANPLARR HERVPVVPFY DPVESVVKST     120
AATLLVSING TTTTATTTAT ITPELGKVDT CIGHHENNND PWIPPNTITS KLPLNTEMKG     180
MDFIFTDSEN FLDFDYPACV DTQSQPHYNS SNDSVVPVQA NTPIKSLPFH HQEKHFEIDF     240
TQSHIKSYNT PSLSVSSSSL DVGIVPDGSS ISEISYPYIR TMNNSNSSID LSNSANHQGE     300
KLLGLDREAR VLRYREKKKN RKFEKTIRYA SRKAYAETRP RIKGRFAKRT DGSAGAGEFD     360
DVDGIFSGTD FIAAESRYGV VPSFLT                                         386

SEQ ID NO: 209          moltype = DNA  length = 772
FEATURE                 Location/Qualifiers
misc_feature            1..772
                        note = Ceres Clone ID no. 100941305
misc_feature            1..772
                        note = Encodes the peptide sequence at SEQ ID NO. 210
source                  1..772
                        mol_type = other DNA
                        organism = Zea mays
SEQUENCE: 209
gatggagggt gacgagaagt cggcggggcgg ggccctgct tactggggcc tgggcgcgcg      60
gccctgcgac gcgtgcggcg ccgaggcggc gcgcctctac tgccgcgcgg acgcggcgtt     120
cctgtgcgcc gggtgcgacg cgcgggcgca cggcgccggg tcgcgccacg cgcgggtctg     180
gctctgcgag gtctgcgagc acgcgccggc ggccgtcacg tgccgcgcga acgctgccgc     240
gctctgcgcc tcctgcgacg ccgacatcca ctcggcgaac ccgctcgcgc gccgccacga     300
gcgcctccac gtggcgccct tcttcggcgc gctggccgac gcgcccaagc ccttcgcctc     360
ggcggcgccg cccaaagcaa ccgacgacga cgggagcaac gaggacgagg cggcgtcgtg     420
gctcctcccc gagcccgacc acgggcagaa agaaggcgcc acgacggagg tgttcttcgc     480
ggactctgac ccgtacctcg acctcgactt cgcgcgttcc atggacgaaa tcaagaccat     540
cggcgtccag cagagcgggt caccagagct cgacctcgcc ggcaccaagc tcttctactc     600
cgatcactcc gtgaaccaca gtgtgtcatc gtcgaggca gcgttgtgc ccgacgcggc     660
gtctggcatg gcgcccatgg tggcagtggt cagcaggggc ctggagcgag aggcgcggct     720
gatgcggtac cgggagaagc gcaagagcag gcggttcgag aagacgatcc gg            772

SEQ ID NO: 210          moltype = AA  length = 257
FEATURE                 Location/Qualifiers
REGION                  1..257
                        note = misc_feature - Ceres Clone ID no. 100941305
REGION                  1..257
                        note = misc_feature - Bit score of 429.2 for hmm based on
                         sequences of FIGURE 2.
REGION                  17..61
                        note = misc_feature - Pfam Name: zf-B_box Pfam Desc: B-box
                         zinc finger
REGION                  236..257
                        note = misc_feature - Pfam Name: CCT Pfam Desc: CCT motif
REGION                  1..257
                        note = misc_feature - Functional Homolog Of SEQ ID NO. 20
source                  1..257
                        mol_type = protein
                        organism = Zea mays
SEQUENCE: 210
MEGDEKSAGG APAYWGLGAR PCDACGAEAA RLYCRADAAF LCAGCDARAH GAGSRHARVW      60
LCEVCEHAPA AVTCRADAAA LCASCDADIH SANPLARRHE RLHVAPFFGA LADAPKPFAS     120
AAPPKATDDD GSNEDEAASW LLPEPDHGQK EGATTEVFFA DSDPYLDLDF ARSMDEIKTI     180
GVQQSGSPEL DLAGTKLFYS DHSVNHSVSS SEAAVVPDAA SGMAPMVAVV SRGLEREARL     240
MRYREKRKSR RFEKTIR                                                   257

SEQ ID NO: 211          moltype = AA  length = 358
FEATURE                 Location/Qualifiers
REGION                  1..358
                        note = misc_feature - Public GI ID no. 157341339
REGION                  1..358
                        note = misc_feature - Bit score of 452.0 for hmm based on
```

```
                            sequences of FIGURE 2.
REGION                      289..333
                            note = misc_feature - Pfam Name: CCT Pfam Desc: CCT motif
REGION                      18..65
                            note = misc_feature - Pfam Name: zf-B_box Pfam Desc: B-box
                              zinc finger
REGION                      1..358
                            note = misc_feature - Functional Homolog Of SEQ ID NO. 20
source                      1..358
                            mol_type = protein
                            organism = Vitis vinifera
SEQUENCE: 211
MLKDEGCNAD AAAGGGGWA RVCDTCRSAA CTIYCRADSA YLCAGCDARI HAANRVASQH    60
ERVWVCESCE RAPAAFVCKA DAASLCATCD ADIHSANPLA RRHHRVPVLP IAGCLYGPPA   120
TDPGGTVTID EEDEDEAASW LLLNPVKNNN GSSNNQNNGL LFGGEVDEYL DLVEYNSCPE   180
NQFSDQYNQQ QPPPHYSVPH KNYGGDRVVP VQCGEAKGQL HQQHQQQGFH LGMDHSVSVS   240
SMDVGVVPEA TTMSDISISI SHPRPPKGTI DLFSGPPIQM PTQLTPMDRE ARVLRYREKK   300
KTRKFEKTIR YASRKAYAET RPRIKGRFAK RTDVEVEVDQ MFSTTLMAES GYGIVPSF     358

SEQ ID NO: 212              moltype = AA  length = 338
FEATURE                     Location/Qualifiers
REGION                      1..338
                            note = misc_feature - Public GI ID no. 157327254
REGION                      1..338
                            note = misc_feature - Bit score of 612.5 for hmm based on
                              sequences of FIGURE 2.
REGION                      1..48
                            note = misc_feature - Pfam Name: zf-B_box Pfam Desc: B-box
                              zinc finger
REGION                      271..315
                            note = misc_feature - Pfam Name: CCT Pfam Desc: CCT motif
REGION                      1..338
                            note = misc_feature - Functional Homolog Of SEQ ID NO. 20
source                      1..338
                            mol_type = protein
                            organism = Vitis vinifera
SEQUENCE: 212
MASKLCDSCK SAPPTLFCRA DSAFLCVACD SKVHAANKLA SRHARVWMCE VCEQAPAHVT    60
CKADAAALCV TCDRDIHSAN PLARRHERVP VVPFYDSAAA AAKSNAVNLL VDDRYYSDPD   120
GDASREEAEA ASWLLPNPNP KLAESSDLNS SHYMFSDIDP YLDLDYPSMD PKLQSQQQQQ   180
SSGTDGVVPV QNKSVQAPLV NDNCFDMDFS GSKSFYNGQS LSQSVSSSSL EVGVVPDGNA   240
MVDVTNPFGR SMNTGSESAN QTAQISSGID REARVLRYRE KRKNRKFEKT IRYASRKAYA   300
ETRPRIKGRF AKRSEIEVDY SSSGALTADS GYGVVPSF                          338

SEQ ID NO: 213              moltype = AA  length = 395
FEATURE                     Location/Qualifiers
REGION                      1..395
                            note = misc_feature - Public GI ID no. 187830112
REGION                      1..395
                            note = misc_feature - Bit score of 326.8 for hmm based on
                              sequences of FIGURE 2.
REGION                      324..368
                            note = misc_feature - Pfam Name: CCT Pfam Desc: CCT motif
REGION                      27..74
                            note = misc_feature - Pfam Name: zf-B_box Pfam Desc: B-box
                              zinc finger
REGION                      1..395
                            note = misc_feature - Functional Homolog Of SEQ ID NO. 20
source                      1..395
                            mol_type = protein
                            organism = Zea mays
SEQUENCE: 213
MDYNFDTSVL DEDVAGRGGR EGSCPPAWAR ACDGCRAAPS VVYCHADTAY LCASCNSRVH    60
AANRVASRHE RVRVCEACEC APAVLACRAD AAALCAACDA QVHSANPLAG RHQRVPVLPL   120
PAAAVPAASV LAEAAATAAA VAGDKDEEVD SWLLLTKDPD DDDKNHNCSS NNNNISSNTS   180
TFYADVDEYF DLVGYSSYCD NHINSNTKQY GMQEQQLLLH KEFGDKEGSE YVVPSQVGQQ   240
QSGYHRVIGT EQAASMTPGV SAYTDSISNS ISFSSSMEVG IVPDNMATTD MPSSGILLTP   300
AGAISLFSSG PPLQMPLHLA SMDREARVLR YREKKKSRKF EKTIRYATRK TYAEARPRIK   360
GRFAKRSSDM DVEVDQMFSA AALSSDGSYG TVPWF                             395

SEQ ID NO: 214              moltype = AA  length = 317
FEATURE                     Location/Qualifiers
REGION                      1..317
                            note = misc_feature - Public GI ID no. 110277457
REGION                      1..317
                            note = misc_feature - Bit score of 385.4 for hmm based on
                              sequences of FIGURE 2.
REGION                      1..48
                            note = misc_feature - Pfam Name: zf-B_box Pfam Desc: B-box
```

```
                          zinc finger
REGION                    256..300
                          note = misc_feature - Pfam Name: CCT Pfam Desc: CCT motif
REGION                    1..317
                          note = misc_feature - Functional Homolog Of SEQ ID NO. 20
source                    1..317
                          mol_type = protein
                          organism = Medicago sativa
SEQUENCE: 214
MATKLCDSCK SSKATLFCRS DSAFLCLTCD SNIHAANKLA SRHHRVTLCQ VCEQAPAHVT    60
CKADAAALCI SCDHDIHSAN PLARRHERVP LTTFHHHNNN SQQQSFFSEN DHDATNEEAG   120
AASWLLQTPS NPKFPDLNYS HYSYPEIDDF VTVNAKTDTP EQNSPGTTAD GVVPVQSQSK   180
TTTEHQHEHY SDINIDFSNS KPFTYNFNHT VSSPSMEVGV VPDGNVMTEI SYCGYQTTAT   240
ETAPMTVAVP MTAVEREARV SRYREKRKNR KFEKTIRYAS RKAYAETRPR IKGRFAKRSD   300
LNMNLIAEDE YGVVPSC                                                  317

SEQ ID NO: 215            moltype = DNA  length = 1290
FEATURE                   Location/Qualifiers
misc_feature              1..1290
                          note = Ceres Annot ID no. 8736698
misc_feature              1..1290
                          note = Encodes the peptide sequence at SEQ ID NO. 216
source                    1..1290
                          mol_type = other DNA
                          organism = Sorghum bicolor
SEQUENCE: 215
atggcaaagg atctgccgat gatgcaaagg aggagtctgg aagctgccgg tcgttatgtg    60
gaggagtttc gctccaacgc tctcgacgag gaggaggtcg ctggaagagg cggggaagga   120
gggagctgcg ccgcagcacc agcatgggcc aggccctgcg acgggtgccg ggcggcgccc   180
agcgtggtgt actgccacgc cgacgcggcg tacctgccgg cgtcgtgcga cgtgcgggtg   240
cacgccgcca accgcgttgc gtcgcgccac gagcgcgtgc gcgtgtgcga ggcctgcgag   300
cgcgcgccag cagtgctggc gtgcgcgcgc gacgccgccg cgctctcgcg cgtctgcgac   360
gcgcaggtcc actccgcgaa cccgctggcc gggaggcacc agcgcgtgcc cgtgctgccg   420
ctccccgtcg cggccatccc ggctgcttcc gtgctcgccg aggctgcggc caccgccgtg   480
gccgtgggtg acaagcagga agaggaggtg gactcgtggc tgctgctcac caacaccaag   540
gatccagttt cagacaacaa caactgcaac tgcagcagca gcagcaacaa caacatcagc   600
agcagcaaca ccagcacctt ctacgcggat gttgatgagt actttgatct cgtgggctac   660
aattcctact gtgacaacca catcaacagc aacccaaagc agtacgggat gcaagaacga   720
cagcaacagc agcagctgct gctgcaaaag gaatttgaag acaaggaggg aagcgagcac   780
gttgtgcctg cttcacaggt cgcgatggca aatgagcagc agcagagtgg ttatggagtt   840
attggggtag agcaggctgc ctccatgact gccgcggtca gtgcttacac agattccatc   900
actaacagca tatctttctc atcatcaatg gaggtgggta tagtcccaga caacatggca   960
acgacgacag acatgccaaa ctccggcatc tgtctgaccc ctgctgaggc catcagcctc  1020
ttctcgtcag gttcttcgct tcagatgcca ctccacttga cctccatgga cagagaggcc  1080
agggtcctca ggtacaagga gaagaagaag agcagaaagt tcgcgaagac catacgtatt  1140
gcgacgagga agacatatgc agaagcaagg ccgaggatca agggccgctt cgccaagaga  1200
tcttctgata tggaaatcga agtggaccag atgttctcat ctgcagctct gtcgtctgat  1260
ggtagctacg gtacggttct atggttctga                                   1290

SEQ ID NO: 216            moltype = AA  length = 429
FEATURE                   Location/Qualifiers
REGION                    1..429
                          note = misc_feature - Ceres Annot ID no. 8736698
REGION                    1..429
                          note = misc_feature - Bit score of 297.5 for hmm based on
                             sequences of FIGURE 2.
REGION                    358..402
                          note = misc_feature - Pfam Name: CCT Pfam Desc: CCT motif
REGION                    48..95
                          note = misc_feature - Pfam Name: zf-B_box Pfam Desc: B-box
                             zinc finger
REGION                    1..429
                          note = misc_feature - Functional Homolog Of SEQ ID NO. 20
source                    1..429
                          mol_type = protein
                          organism = Sorghum bicolor
SEQUENCE: 216
MAKDLPMMQR RSLEAAGRYV EEFRSNALDE EEVAGRGGEG GSCAAAPAWA RPCDGCRAAP    60
SVVYCHADAA YLCASCDVRV HAANRVASRH ERVRVCEACE RAPAVLACRA DAAALCVVCD   120
AQVHSANPLA GRHQRVPVLP LPVAAIPAAS VLAEAAATAV AVGDKQEEEV DSWLLLTNTK   180
DPVSDNNNCN CSSSSNNNIS SSNTSTFYAD VDEYFDLVGY NSYCDNHINS NPKQYGMQER   240
QQQQQLLLQK EFGDKEGSEH VVPASQVAMA NEQQQSGYGV IGVEQAASMT AAVSAYTDSI   300
TNSISFSSSM EVGIVPDNMA TTTDMPNSGI LLTPAEAISL FSSGSSLQMP LHLTSMDREA   360
RVLRYKEKKK SRKFAKTIRY ATRKTYAEAR PRIKGRFAKR SSDMEIEVDQ MFSSAALSSD   420
GSYGTVLWF                                                           429

SEQ ID NO: 217            moltype = DNA  length = 1125
FEATURE                   Location/Qualifiers
misc_feature              1..1125
```

```
                         note = Ceres Annot ID no. 8671780
misc_feature             1..1125
                         note = Encodes the peptide sequence at SEQ ID NO. 218
source                   1..1125
                         mol_type = other DNA
                         organism = Sorghum bicolor
SEQUENCE: 217
atggaggccc tggtggcggg gaggtactgg ggtgtcgggg gacggcggtg cgaggcgtgc    60
gggggctcgc cggcggcggt gcactgccgg acgtgcccgc gcggcggggc gtacctgtgc   120
gcggggtgcg acgcggggca cgcgcgggcc gggcacggga gggtgtgggt gtgcgaggtg   180
tgcgagcgcg cgccggccgc cgtcacgtgc cgcgccgacg cggccgcgct ctgcgccgcg   240
tgcgacgccg acatccacga cgcgaacccg ctggcgcgcc gccacgagcg cgtgccggtg   300
cagcccatcg gcgcggccgc ggccgcgccc gccgcggaga cgctgctgtt cggcgccgcc   360
gcggaagaga atcaggacga cgacgacggc gccgccgcgg cggctaaggt cgtcggcgtc   420
gacgccggta agctggcgga cttcctgttc gcggacgtca tggacccgtt cttcggccaa   480
gacttcactg gtggcaccag gttcccgcac gccgacagcg ttgtgcctaa ccagggatcc   540
tgcggcgccg tcgctgccaa gccgtcctac agctcctaca ccgcggcgtc gctcggccac   600
agcggctcgt cgtcggaggt cggcctggtc ccagacgcga tgtgcggccg cggcgggagc   660
gtgaccggcg gcgtcatcga gctcgacttc gcgcagtcca aggccgccta cctgccttac   720
gctgcaactc cgacccacag tatgtcatct ttggacgtgg gtgcggtgcc ggaacgcggt   780
gacggggtca tggcgggcag ggtcgcgacg ccgccggcgg cggcggccgc ggagagcagg   840
gaggccggct gatgcggta ccgcgagaag cggaagaacc ggcggttcga gaagacgatc   900
cgctacgcgt cccggaaggc ctacgcggag tcgcggccgc gcatcaaggg ccgcttcgcg   960
aagcgcgcgg acgacaacga cgccgacgcc gacgccgact cgacttcga cgcgggtgcc  1020
gcggcggcga cggcgccggc gcggtcgcgg tcgcagcagc agcagccatc gtacccctat  1080
gtgctcgact tcgccgccgg ctacggcgtc gtgcccacat tctga                  1125

SEQ ID NO: 218          moltype = AA  length = 374
FEATURE                 Location/Qualifiers
REGION                  1..374
                        note = misc_feature - Ceres Annot ID no. 8671780
REGION                  1..374
                        note = misc_feature - Bit score of 474.1 for hmm based on
                          sequences of FIGURE 2.
REGION                  280..324
                        note = misc_feature - Pfam Name: CCT Pfam Desc: CCT motif
REGION                  53..100
                        note = misc_feature - Pfam Name: zf-B_box Pfam Desc: B-box
                          zinc finger
REGION                  1..374
                        note = misc_feature - Functional Homolog Of SEQ ID NO. 20
source                  1..374
                        mol_type = protein
                        organism = Sorghum bicolor
SEQUENCE: 218
MEALVAGRYW GVGGRRCEAC GGSPAAVHCR TCPGGGAYLC AGCDAGHARA GHERVWVCEV    60
CERAPAAVTC RADAAALCAA CDADIHDANP LARRHERVPV QPIGAAAAAP AAETLLFGAA   120
AEENQDDDDG AAAAAKVVGV DAGKLADFLF ADVMDPFFGQ DFTGGTRFPH ADSVVPNQGS   180
CGAVAAKPSY SSYTAASLGH SGSSSEVGLV PDAMCGRGGS VTGGVIELDF AQSKAAYLPY   240
AATPTHSMSS LDVGAVPERG DGVMAGRVAT PPAAAAESR EARLMRYREK RKNRRFEKTI   300
RYASRKAYAE SRPRIKGRFA KRADDNDADA DADFDFDAGA AAATAPARSR SQQQQPSYPY   360
VLDFAAGYGV VPTF                                                    374

SEQ ID NO: 219          moltype = AA  length = 367
FEATURE                 Location/Qualifiers
REGION                  1..367
                        note = misc_feature - Public GI ID no. 186911828
REGION                  1..367
                        note = misc_feature - Bit score of 434.9 for hmm based on
                          sequences of FIGURE 2.
REGION                  13..60
                        note = misc_feature - Pfam Name: zf-B_box Pfam Desc: B-box
                          zinc finger
REGION                  298..342
                        note = misc_feature - Pfam Name: CCT Pfam Desc: CCT motif
REGION                  1..367
                        note = misc_feature - Functional Homolog Of SEQ ID NO. 20
source                  1..367
                        mol_type = protein
                        note = subspecies = vulgaris
                        organism = Beta vulgaris
SEQUENCE: 219
MMKEEVSGSD TNSWARVCDT CRAAPCTVYC RADSAFLCTS CDARIHAANQ VASRHERVWV    60
CEACERAPAA FLCKADAASL CATCDAEIHS ANPLARRHQR VPIMPVAGCV YGPQGGRMSE   120
DRFLTLPEGD DHTTDHEGDE DEAASWLLLN PVKNSNNQNT NGFLTGGGEV DEYLDLLEYN   180
SGADNQLCEQ YNQQEFKVP EKNCGGDSVV PVQCREAKDH QIQYQNFLFG MECETKSGYT    240
YNTSISQSVS VSSMDVGVVP ESAMSDISMS HPRPPKGTID LFSSPPMQVP TQLSPLDREA   300
RVMRYREKKK NRKFEKTIRY ASRKAYAETR PRIKGRFAKR TDVEAEMDQM FTNSLMADSG   360
YGIVPSY                                                            367
```

```
SEQ ID NO: 220          moltype = AA  length = 368
FEATURE                 Location/Qualifiers
REGION                  1..368
                        note = misc_feature - Public GI ID no. 168062896
REGION                  1..368
                        note = misc_feature - Bit score of 368.4 for hmm based on
                          sequences of FIGURE 2.
REGION                  301..345
                        note = misc_feature - Pfam Name: CCT Pfam Desc: CCT motif
REGION                  1..47
                        note = misc_feature - Pfam Name: zf-B_box Pfam Desc: B-box
                          zinc finger
REGION                  1..368
                        note = misc_feature - Functional Homolog Of SEQ ID NO. 20
source                  1..368
                        mol_type = protein
                        note = subspecies = patens
                        organism = Physcomitrella patens
SEQUENCE: 220
MPKSCDACQA SSAVVYCRAD AAYLCLGCDG KVHGANKLAS RHERLWMCEV CEVAAAVVTC    60
KADAASLCVS CDTDIHSANP LAQRHERVPV QPLFDCVSQF RGTHFSVLAP KNECNNNLLK   120
GDEDPAVAEA VSWLLPHPKT LSSAILRGIA AADEAPAFPF RERPFSPKLK KLKVEQAADI   180
YSDVDPFLVL DGGNGTGFQP DSMVPVHIPE GPDDSPSLAN STAPSSAINF RASQKSGCSY   240
GTSTLTHSMS CSSVDAAVVP DSSLSDISTP YSKALDSQDS QDLSGALVPH QASKPIDTVD   300
REARVMRYKE KRQKRKFEKT IRYASRKAYA ESRPRIKGRF TKRTDSDVEQ MFSSCTADSG   360
FGVVPSSC                                                            368

SEQ ID NO: 221          moltype = AA  length = 342
FEATURE                 Location/Qualifiers
REGION                  1..342
                        note = misc_feature - Public GI ID no. 194244852
REGION                  1..342
                        note = misc_feature - Bit score of 286.3 for hmm based on
                          sequences of FIGURE 2.
REGION                  7..54
                        note = misc_feature - Pfam Name: zf-B_box Pfam Desc: B-box
                          zinc finger
REGION                  280..324
                        note = misc_feature - Pfam Name: CCT Pfam Desc: CCT motif
REGION                  1..342
                        note = misc_feature - Functional Homolog Of SEQ ID NO. 20
source                  1..342
                        mol_type = protein
                        organism = Brassica nigra
SEQUENCE: 221
MLKQESNWAQ ACDTCRSAAC TVYCRADSAY LCTSCDAQIH AANRLASRHE RVRVCESCER    60
APAAFFCKAD AASLCTACDS QIHSANPLAR RHQRVPILPI SGCVATNHHS SETTEPENIV   120
VVGQEEEDEA EAASWLLPSS VKNCGDNNNN TENNRFSVGE EYLDLVDYSS SIDKRFTGQT   180
NQYQQDYNVP QRSYVADGVV PLQVGVSKGH MHHEQHNFQF GFTNVSSEAH QISNGSPIHM   240
VSLVPESVTS DATVSHQRSP KAGTEELPEA PVQMLSPMER KARVLRYREK KKTRKFEKRI   300
RYASRKEYAE KRPRIKGRFA KRNEVDADQA FPTVVMFDTG YG                      342

SEQ ID NO: 222          moltype = DNA  length = 1011
FEATURE                 Location/Qualifiers
misc_feature            1..1011
                        note = Ceres Annot ID no. 8680182
misc_feature            1..1011
                        note = Encodes the peptide sequence at SEQ ID NO. 223
source                  1..1011
                        mol_type = other DNA
                        organism = Sorghum bicolor
SEQUENCE: 222
atggacaccg cggtggagct ggagctggag cagaagccgg cggtgggtta ctggagcgtg    60
gtgggcgccc ggccctgcga cgcgtgcgcc gcggagccgg cgcggctgca ctgccgcgag   120
gacggcgcgt tcctgtgccc cggctgcgac gcccgggcgc acggcgcgg gtcccgccac   180
gcgcgcgtct ggctgtgcga ggtctgcgag cacgcccccg ccgccgtcac ctgccgcgcc   240
gacgccgccg cgctctgcgc cgcctgcgac gccgacatcc actcggcaa cccgctcgcg   300
cgccgccacg agcgcctccc cgtcgcgccc ttcttcggcg cgctcgctga cgcgcccag   360
cccttcccgt ccccggcctt cgccgccgct gccgcagcgg ggggccaggc tcagggggaa   420
gccgcggcgg cggacaacga cgacgacgac gggagcaacg aggccgaggc ggcgtcgtgg   480
ctgctcgccg agcccgacaa cagccacgag acagcgccg ccgccaccgc cgccgacacg   540
ttgttcgcgg aatcggacgc gtacctcggc gtcgacctgg acttcgcccg gtgcatggac   600
ggctcaaagg ccatccgcgt gccggtcgtg ccgcccgagc tggacatcgc tgccggcagc   660
ttttctacc ccgaacactc catgaaccac agtttgtcgt cgtcggaggt ggcggtggtc   720
ccggacgcgg aggcggccgg cgtgccggcg gtggtgagca ggggaagga gcggaggcg    780
cggctgatgc ggtaccgtga gaagcgcaag aaccgccggt tcgacaagac catccgctac   840
gcgtcccgca aggcgtacgc cgagacgcgg ccgcgcatca agggccgctt cgccaagcgc   900
tgcctccgcgg aggccgacga cgacgcgctg gagcacgacg aaggcgcgtg cttctcgccc   960
```

-continued

```
gcggggtcgg cgcacgcggc gtcggacggc gtcgtcccgt ccttctgttg a           1011
```

| SEQ ID NO: 223 | moltype = AA   length = 336 |
|---|---|
| FEATURE | Location/Qualifiers |
| REGION | 1..336 |
| | note = misc_feature - Ceres Annot ID no. 8680182 |
| REGION | 1..336 |
| | note = misc_feature - Bit score of 634.7 for hmm based on sequences of FIGURE 2. |
| REGION | 258..302 |
| | note = misc_feature - Pfam Name: CCT Pfam Desc: CCT motif |
| REGION | 21..65 |
| | note = misc_feature - Pfam Name: zf-B_box Pfam Desc: B-box zinc finger |
| REGION | 1..336 |
| | note = misc_feature - Functional Homolog Of SEQ ID NO. 20 |
| source | 1..336 |
| | mol_type = protein |
| | organism = Sorghum bicolor |

SEQUENCE: 223

```
MDTAVELELE QKPAVGYWSV VGARPCDACA AEPARLHCRE DGAFLCPGCD ARAHGAGSRH    60
ARVWLCEVCE HAPAAVTCRA DAAALCAACD ADIHSANPLA RRHERLPVAP FFGALADAPQ   120
PFPSPAFAAA AAAGGQAQGE AAAADNDDDD GSNEAEAASW LLAEPDNSHE DSAAATAADT   180
LFAESDAYLG VDLDFARCMD GVKAIGVPVA PPELDIAAGS FFYPEHSMNH SLSSSEVAVV   240
PDAQAAGVPA VVSRGKEREA RLMRYREKRK NRRFDKTIRY ASRKAYAETR PRIKGRFAKR   300
CSAEADDDAL EHDEGACFSP AGSAHAASDG VVPSFC                            336
```

| SEQ ID NO: 224 | moltype = DNA   length = 2463 |
|---|---|
| FEATURE | Location/Qualifiers |
| misc_feature | 1..2463 |
| | note = Ceres Annot ID no. 8457344 |
| misc_feature | 1..2463 |
| | note = Encodes the peptide sequence at SEQ ID NO. 225 |
| source | 1..2463 |
| | mol_type = other DNA |
| | organism = Solanum lycopersicum |

SEQUENCE: 224

```
atggctactt ctgagaattg ccggaacgct gccggcgccg gaaaagttga tgctgagaaa     60
gcgttgtaca cggagctatg gcgagcatgt gcaggtccgc ttgtgacagt gccatgtgaa   120
ggcgagctgg tgttctattt cccacaaggt catattgaac aggttgaagc atcaacaaac   180
caagcttcag accagcagat gccagtatat aatcttcctt ctaagatcct ctgtcgtgtg   240
attaacgtcc tgctgaaggc tgaacccgat acagatgagg tgtatgcaca agtgactttg   300
ttgccagaac caaatcaaga tgagaatgtg gtatcaaagg aaccgatgcc ctctccgacg   360
ccacgattcc atgtgcactc tttttgtaag acattaacag cctctgatac cagcactcat   420
ggaggatttt ctgtcttgag acggcatgct gatgaatgcc tccgcctct ggatatgtct    480
cggcagcctc aacacaggta gttggtgcc aaagatttgc atgcaaatga gtggcgcttc     540
aggcacatat tccggggcca gcctaggagg caccttcttc agagtggttg gagtgtcttt   600
gttagttcga aaaggcttgt tgcagggat gcattcatat ttcttagagg tgagaatggg     660
gagcttcgtg ttggagtccg acgtgccatg agacagcagg gtaatgctcc atcatcagtg   720
atatccagtc atagcatgca tcttggtgtc cttgctacag cttggcatgc tattcagacg   780
aaaacactga cgagccctgc tgactttata gttccatatg atcagtatat ggagtctctg   840
aaaaacaatt actccatcgg gatgaggttt aaaatgaggt ttgaaggtga agaagctcca   900
gaacagaggt ttactggaac tatagttggc attgaaaatg ctgacctcaa aggtggcct    960
gagtcaaaat ggagatgcct gaaggttcga tgggatgaaa cttctgctat tcctaggcca  1020
gaccgagttt caccctggaa agtagagcca gctcttagcc ctcctgcact taatccactt  1080
ccaataccaa ggcagaaaag gccgcgatca aatgttctgc cctcgtctcc tgattcttct  1140
gtacttacta gggaaggttc atccaaagta gttgtagaca cttcacaagc cagtgggttt  1200
tcaagagttt gcaaggtca agaaatatca accttgagag caattttgt agaaaataac    1260
gagtcggact cttctgagaa gccacctata tggcaaccat tactgatga cgaaaggct    1320
gatgttcatt ctgcgtcaag gaaatgtata tcagataaac ggcttccttt agggaggcct  1380
gaatcatctt ttacagatct tttatcaggt tttgggggc aatctagttc atctcatgga   1440
ttccattcac ccactggggg ccaaacagca cctgctagct gggttaagcg acaagctctg   1500
gataaggaaa ctgatttcag cttactggca aaacaatggt ctctagtgtc ttctggtctc  1560
tcacttaatc tgatggaatc aggattgaag ggtgcagata ctctgtatca aatgcgggga  1620
acatctcgac tcaattgttt taacgagtat ccaaccttcc ctggtcatag acctgacaat  1680
cagcaggaa attggttaat gccccgtcc gtgctgcctt atattcagat gtccgctcat   1740
tctgagaaa ttatgcctaa acccatggct tcaccacagc ccgaagccat gaaacccaaa   1800
gaagggaact gcaaactatt tggcattccc cttgtaagta aatgtgccac catgatcct   1860
gtcatgttgc ggaaaaattc cccgattcac tcaacaagta acatgcactt tggtatacat  1920
ccacatcaat tccctataat tgaatctgat caaaggtctg agcaatcaaa gggatcaaag  1980
ctaccagatg atggcttcat agttcatgat caggaagaac aattccaaac ctctcatcct  2040
ggtactcgag atagagaggg caaaggcctt gttcattcaa caaggagttg caccaaggtt  2100
cataaacagg gtacagccct tggaaggtct gttgatcttg caaagttcaa caactatgaa  2160
gaattgatag ctgaactgga tcacattttt gatttttaatg gtgagctcaa ggctcgtaac  2220
aagaactgcc tggttgtata tactgatgat gagggtgaca tgatgcttgt tggagatgat  2280
ccatgggaat tttgtggtat ggttcggaag atttttatct acacgaaaga tgaggtgcag  2340
cggatgaacc ctgggactct caattcaaaa ggcgaggaca attcttctgt tgcagaaggc  2400
tctgatgcta aagaagtgaa gaatctacag cttcacattg attccagtcc ggaagattct  2460
tag                                                                 2463
```

```
SEQ ID NO: 225          moltype = AA  length = 820
FEATURE                 Location/Qualifiers
REGION                  1..820
                        note = misc_feature - Ceres Annot ID no. 8457344
REGION                  1..820
                        note = misc_feature - Bit score of 1560.8 for hmm based on
                          sequences of FIGURE 5.
REGION                  254..328
                        note = misc_feature - Pfam Name: Auxin_resp Pfam Desc:
                          Auxin response factor
REGION                  127..232
                        note = misc_feature - Pfam Name: B3 Pfam Desc: B3 DNA
                          binding domain
REGION                  1..820
                        note = misc_feature - Is Acted Upon By Ceres SEEDLINE ID
                          no. ME00572 at SEQ ID NO. 111
source                  1..820
                        mol_type = protein
                        organism = Solanum lycopersicum
SEQUENCE: 225
MATSENCRNA AGAGKVDAEK ALYTELWRAC AGPLVTVPCE GELVFYFPQG HIEQVEASTN        60
QASDQQMPVY NLPSKILCRV INVLLKAEPD TDEVYAQVTL LPEPNQDENV VSKEPMPSPP       120
PRFHVHSFCK TLTASDTSTH GGFSVLRRHA DECLPPLDMS RQPPTQELVA KDLHANEWRF       180
RHIFRGQPRR HLLQSGWSVF VSSKRLVAGD AFIFLRGENG ELRVGVRRAM RQQGNAPSSV       240
ISSHSMHLGV LATAWHAIQT KTLTSPADFI VPYDQYMESL KNNYSIGMRF KMRFEGEEAP       300
EQRFTGTIVG IENADLKRWP ESKWRCLKVR WDETSAIPRP DRVSPWKVEP ALSPPALNPL       360
PIPRQKRPRS NVLPSSPDSS VLTREGSSKV VVDTSQASGF SRVLQGQEIS TLRGNFVENN       420
ESDSSEKPPI WQPLLDDEKA DVHSASRKCI SDKRLPLGRP ESSFTDLLSG FGGQSSSSHG       480
FHSPTGGQTA PASWVKRQAL DKETDFSLLA KQWSLVSSGL SLNLMESGLK GADTLYQMRG       540
TSRLNCFNEY PTFPGHRPDN QQGNWLMPPS VLPYIQMSAH SGEIMPKPMA SPQPEAMKPK       600
EGNCKLFGIP LVSKCATIDP VMLRKNSPIH STSNMHFGIH PHQFPIIESD QRSEQSKGSK       660
LPDDGFIVHD QEEQFQTSHP GTRDREGKGL VHSTRSCTKV HKQGTALGRS VDLAKFNNYE       720
ELIAELDHIF DFNGELKARN KNWLVVYTDD EGDMMLVGDD PWEFCGMVRK IFIYTKDEVQ       780
RMNPGTLNSK GEDNSSVAEG SDAKEVKNLQ LHIDSSPEDS                            820

SEQ ID NO: 226          moltype = AA  length = 563
FEATURE                 Location/Qualifiers
REGION                  1..563
                        note = misc_feature - Public GI ID no. 157327120
REGION                  1..563
                        note = misc_feature - Bit score of 794.2 for hmm based on
                          sequences of FIGURE 5.
REGION                  202..281
                        note = misc_feature - Pfam Name: Auxin_resp Pfam Desc:
                          Auxin response factor
REGION                  75..180
                        note = misc_feature - Pfam Name: B3 Pfam Desc: B3 DNA
                          binding domain
REGION                  1..563
                        note = misc_feature - Is Acted Upon By Ceres SEEDLINE ID
                          no. ME00572 at SEQ ID NO. 111
source                  1..563
                        mol_type = protein
                        organism = Vitis vinifera
SEQUENCE: 226
MEQLQASTNQ GVDQRIPLFN LPSKILCRVV HTRLLAEQET DEVYAQITLQ PEADQTEPKS        60
PDSCPDEAPK QTVHSFCKIL TASDTSTHGG FSVLRKHANE CLPPLDMSQA TPTQELVARD       120
LHGYEWRFKH IFRGQPRRHL LTTGWSTFVT SKRLVAGDAV VFLRGDNGEL RVGVRRLARQ       180
QSPMPSSVIS SQSMHLGVLA TASHAVTTQT LFVVYYKPRT SQFIISLNKY LEAVNYGFAV       240
GMRFKMRFEG EDSPERRFTG TIVGIGDISP QWSNSKWRSL KIQWDEPATI QRPERVSSWD       300
IEPFVASASL NLTQPPVKIK RPRPLDLPVA VPSPFWYAGS SPSHELTQLD SKTVSTRSIL       360
SGYNTSLSSR PNNGLISDQV EKGKRIEASI GCRLFGIDLT NNSKATALLE MIQNLDVSKS       420
SNEQKQVVPE ASQKETQGRQ SCTPSSRTRT KKVQMQGVAV GRAVDLTALE GYDELISELE       480
KMFEIKGELC PRNKWEVVFT DDEGDMMLVG DDPWQEFCKM VRKIFIYSSE EVKKMSPRCK       540
LSTSSLDGEG TVISLDSELR TEP                                             563

SEQ ID NO: 227          moltype = AA  length = 737
FEATURE                 Location/Qualifiers
REGION                  1..737
                        note = misc_feature - Public GI ID no. 157358702
REGION                  1..737
                        note = misc_feature - Bit score of 957.5 for hmm based on
                          sequences of FIGURE 5.
REGION                  278..360
                        note = misc_feature - Pfam Name: Auxin_resp Pfam Desc:
                          Auxin response factor
REGION                  151..256
                        note = misc_feature - Pfam Name: B3 Pfam Desc: B3 DNA
```

```
                         binding domain
REGION                   1..737
                         note = misc_feature - Is Acted Upon By Ceres SEEDLINE ID
                         no. ME00572 at SEQ ID NO. 111
source                   1..737
                         mol_type = protein
                         organism = Vitis vinifera
SEQUENCE: 227
MIDLNTVDDD ETPSSGSSSS SSSSASASAS TVCGSLLSAA SSVCLELWHA CAGPLISLPK    60
KGSLVVYFPQ GHLEQLSDYP AVAYDLPPHV FCRVVDVKLH AEVVTDEVYA QVSLVPETKQ   120
IKQKLQEGEI EADGGEEEDI EGSIKSMTPH MFCKTLTASD TSTHGGFSVP RRAAEDCFPP   180
LDYKQQRPSQ ELVAKDLHGF EWRFRHIYRG QPRRHLLTTG WSAFVNKKKL VSGDAVLFLR   240
GGDGELRLGI RRAAQIKGSS PFPALCSQQL NLNTLTAVVN AISTRSVFNI CYNPRASSSE   300
FIIPLRKFSK SIDHSFSAGM RFKMRVETED AAERRYTGLI TGISDMDPVR WPGSKWRCLL   360
VRWDDIEANR HNRVSPWEIE LSGSLSGSGS LTVPGSKRTR IGLPGTRPDF SVPNGMGVSD   420
FGESSRFQKV LQGQEIFGFN TPYDGVDTQD HHPSEIRCFP GSSCSGIAAI GNGVRNPLGN   480
SDISYKGIGF GESFRFHKVL QGGQETFPSPP CGRALSANQA HENGSFGIFD GVQVPTSRNG   540
WPALVQGYNA HTHLSTPSVQ VSSPSSVLMF QQASTAAPNI YSMHSANNQE KEQEISNRSS   600
FDIPEVYGEK LTPSRCELSV RGGGQGGMNF FGLLNEHNQL AVPHPLVTQS AFRGSQDLVP   660
TCKSSCRLFG FSLTEERSIG NKVDNPTPVT SSLIPGTSFL PQQLHSEPPV MTKAIGSNCT   720
KVSDFYAVRD MLFDIAL                                                 737

SEQ ID NO: 228           moltype = DNA  length = 2922
FEATURE                  Location/Qualifiers
misc_feature             1..2922
                         note = Ceres Clone ID no. 1892720
misc_feature             1..2922
                         note = Encodes the peptide sequence at SEQ ID NO. 229
source                   1..2922
                         mol_type = other DNA
                         organism = Panicum virgatum
SEQUENCE: 228
aaaaaaaaaa cccaacgcct cggctccaag ccagccagcc aaccaacccg ccccgggcag     60
caaagcacag gcgcacgagc tcccacagct ccccagctcc cgcctcctc ctcgcgctc     120
ccgccatcct ctcctccgcc gcgcgccttc ccgcccgccg agcctttggg gtggttccgg    180
agtcgcggcc gcgcgcgcga gagcgagacc ctccccctgct gccgagcgta atctgccga    240
gctcggcatg gggtgaccag atcggggcgc ggctcggtgc tctacggctg aattccgctc    300
gaggagggggg gtttgccttg cctagaagag gccgcgggga tggcgaacgc cggcgtggcc    360
gtcggctcag ggggtgttag ccatgctttg ttcagggaac tctgccatgc ttgtgctggg    420
ctgttggtca cggtgcctcg ccaaggcgag ctggtttact acttcccgca aggtcatatg    480
gaacagcttg aagcatctac agatcagcaa cttgaccagc acttaccttt gtttaatcta    540
ccatccaaga tcctgtgcaa ggtggtaaat gtagaactca gagctgaaac tgattccgat    600
gaagttttatg ctcaaattat gctgcaacca gaagcagtc aaagtgagcc caccagccca    660
gctcctgagc taccagagcc agaaaggtgc aatgtccatt cctctgcaa gactttgact    720
gcttcagaca cgagcacca tggtggtttc tctgtcctca ggagacatgc tgaagaatgt    780
ttgccccaat tggatatgac tcagaaccca ccgtggcaag aactggtggc taaagatctc    840
catggaaatg aatggcattt ccgtcacatc tttcgaggtc aaccaaggag gcatctactt    900
acaacaggtt ggagtgtttt tgttagctca aaaagattgg ttgccggtga tgcatttatc    960
ttttgagag gtgagaatgg agagctacga gtcggggtaa gaaggctcat gaggcaagta   1020
aataacatgc catcatcagt tatctcaagc cacagcatgc atcttggagt cctcgcaact   1080
gcatctcatg ccatctccac tggaactctc tttttctgttt tctacaaacc cagaacaggt   1140
cgatcggagt tgttgtgag cgtaaacaag taccttgaag ctaagaatca caagatgtct   1200
gtcggtatga ggtttaaat gagatttgag ggtgatgaat ctcctgaaag aagatttagt   1260
ggaacaatta ttggtctggg aagcatgcca gctaactcaa catctccgtg ggctgactct   1320
gattggagat ctttgaaggt ccaatgggat gagccttctg ctgttgtccg tccagataga   1380
gtttcaccat gggaactaga accccttgat gcaactaaca cacaaccgcc tcagcctcct   1440
ttacggagta agcgtgcacg gcctcctgct tcaccttcta ttgctccaga acttcctcca   1500
gcttttggtt tttggaaatc cccacctgag cctacccatg ctttctcatt tcgggactg   1560
cagcgaaccc aggaactata ccattcaaat cccaattcga tctttttcatc atcgttgaat   1620
gtgggattta attcaaagaa cgagcattct actccaacca caatcatttt gtattggcca   1680
attcgagaca ctagaacgga atcctactct gctagcatta caaaacttcc acctgaaagg   1740
aagcaagaat tcactattgc tggctgcaga ttgtttggta ttgagttaag taatgcagta   1800
tcaccagtgg ttgctgttgc tagtgctggt caagaccaac cacctgttgt gtcagtagat   1860
gttgagcctg atcagctgtc acagccatcc caagcgcaaca aaacggatgc cccagcagca   1920
agcagtgagc gctctcctca tgagactgag agccggcaag tcaggagctg caccaaggta   1980
atcatgcaag gaatgcggt tggcagggca gtgacttga cgaggctaga agggtatgat   2040
gatcttctcc acaagttgga ggagatgttt gatatccagg gggagctttc tgctagcctc   2100
aagaaatgga aggttattta cacggatgat gaggatgata tgatgctggt tggggatgat   2160
ccgtggcctg aattttgcgg catggtgaaa aggatataca tttactccta tgaggaggcc   2220
aagtctcttga ctcccaaggt gaagctgccg gtcattggtg acaccactaa actgaaccta   2280
gacaaattgt caccagaatc tgacatgccg cagagtgact caaacaacat cgctctggtt   2340
gccgccgata aggactgatg gatgctaact tggtgcttta ccttttcttc ccttttttgga   2400
tgtttgggag gcaatgccca tgctccttga gactgctaag agttatctgt ttgttgcgct   2460
ggtcccca aggacgttgc cccacaatct gcctgactgc tggttttggg aatggctgaa   2520
gtaggaccac tggtggtcct ctgccagcaa ggacgactgg aacgtaatgg caagcaggct   2580
gcgtgcgcgc cgttccctgt ggcaccaacc tgtgttttgt ttgccggtgtt tggtaggagg   2640
catggcgaat tgccggctgc ttggttttgg agactgccac tgactgctgc cgtcgcgttg   2700
gtcgacgtcg gccggcaggc cgcgccctc acctccagta aataggactt catgtacaac   2760
tagtttggta gtagcagtag tggtttatgt atatcagcgt catgttcctt gctacctata   2820
```

```
taagcatcat catctgtagc tgctgctccc accttgcatt gtattctacc cccggcttgg    2880
taccgaatga tctggtgcaa aaaagtctca gcttgctgtt cc                       2922

SEQ ID NO: 229          moltype = AA   length = 672
FEATURE                 Location/Qualifiers
REGION                  1..672
                        note = misc_feature - Ceres Clone ID no. 1892720
REGION                  1..672
                        note = misc_feature - Bit score of 1319.2 for hmm based on
                          sequences of FIGURE 5.
REGION                  248..333
                        note = misc_feature - Pfam Name: Auxin_resp Pfam Desc:
                          Auxin response factor
REGION                  121..226
                        note = misc_feature - Pfam Name: B3 Pfam Desc: B3 DNA
                          binding domain
REGION                  1..672
                        note = misc_feature - Is Acted Upon By Ceres SEEDLINE ID
                          no. ME00572 at SEQ ID NO. 111
source                  1..672
                        mol_type = protein
                        organism = Panicum virgatum
SEQUENCE: 229
MANAGVAVGS GGVSHALFRE LWHACAGLLV TVPRQGELVY YFPQGHMEQL EASTDQQLDQ      60
HLPLFNLPSK ILCKVVNVEL RAETDSDEVY AQIMLQPEAD QSEPTSPAPE LPEPERCNVH     120
SFCKTLTASD TSTHGGFSVL RRHAEECLPQ LDMTQNPPWQ ELVAKDLHGN EWHFRHIFRG     180
QPRRHLLTTG WSVFVSSKRL VAGDAFIFLR GENGELRVGV RRLMRQVNNM PSSVISSHSM     240
HLGVLATASH AISTGTLFSV FYKPRTSRSE FVVSVNKYLE AKNHKMSVGM RPKMRFEGDE     300
SPERRFSGTI IGLGSMPANS TSPWADSDWR SLKVQWDEPS AVVRPDRVSP WELEPLDATN     360
TQPPQPPLRS KRARPPASPS IAPELPPAFG FWKSPPEPTH AFSFSGLQRT QELYHSNPNS     420
IFSSSLNVGF NSKNEHSTPT NNHLYWPIRD TRTESYSASI NKLPPERKQE FTIAGCRLFG     480
IELSNAVSPV VAVASAGQDQ PPVVSVDVEP DQLSQPSQAN KTDAPAASSE RSPHETESRQ     540
VRSCTKVIMQ GMAVGRAVDL TRLEGYDDLL HKLEEMFDIQ GELSASLKKW KVIYTDDEDD     600
MMLVGDDPWP EFCGMVKRIY IYSYEEAKSL TPKVKLPVIG DTTKLNLDKL SPESDMPQSD     660
SNNIALVAAD KD                                                        672

SEQ ID NO: 230          moltype = DNA   length = 2076
FEATURE                 Location/Qualifiers
misc_feature            1..2076
                        note = Ceres Annot ID no. 8667998
misc_feature            1..2076
                        note = Encodes the peptide sequence at SEQ ID NO. 231
source                  1..2076
                        mol_type = other DNA
                        organism = Sorghum bicolor
SEQUENCE: 230
atggcgggca ttgacctcaa caccgtggag gaggaggacg aggaggaggc ggaggcggag      60
gcgccgcctg tggccgccag ggccggtggt ggcgccgtgt gtctggagct gtggcacgcg     120
tgcgcgggcc ccgtcgcgcc gctgccgcgc aagggcagcg ccgtcgtgta cctgccgcag     180
ggccacctcg agcacatcgg cggcgacgct gacgcggcgg gagcagcggt gccgccacac     240
gtgctctgcc gcgtcgtcga cgtcaccctc cacgcggcgc gcgccaccga cgaggtgtac     300
gcgcgggtgt cgctgctgcc cgaggacgag gaggcggaga ggcgggcgcg ggcgcgggtt     360
cgggaggacg aggacgcgga tcgcgacggc gaggacgggg ccgccatgaa gccgctcgca     420
cggacgccgc acatgttctg caagacgctc acggcctctg acaccagcac gcacggcggc     480
ttctccgtgc cgcgccgcgc cgcggacgtg tgcttcccgc cgctggacta cagccagcag     540
aggccgtctc aggagctcgt ggccaaggat ctacaccgca cggagtggaa gttccgacat     600
atctaccgag gccagccacg aaggcatctc ttaaccactg gatggagtgc atttgttaat     660
aagaagaagc ttgtttctgg cgatgcagtt ctgttccttc gaggtgaaga tggagtgctt     720
cgactgggag tgcgccgagc agcccagcta aaaattgtaa ctcctattcc tgcactgcat     780
aaccagtgct caagccagac cactctggga aatgttgcac aagctgtggc cacgaggact     840
gttttccaca tttactacaa tcccaggtta agtcaatctg aattcattgt acctattgg      900
aagttcacca gaagcttgaa tcaaccaatt tctgttggaa tgagatgcag aatgcgatat     960
gaaagtgacg atgcttctga agaaggtgc actgggataa taattggaag cagagaagct    1020
gagcctattt ggtatggttc aaaatgaaa tgcttgttgg ttagatggta tgatggtata    1080
gagtgccatt ggcccaatag ggtatctcct tgggagattg aggtcacagg atcagtttca    1140
ggatctcata tgtgcgctcc caattcaaaa cgtctgaaac catgcctccc tcaagttaat    1200
ccggagattg tgcttccaaa tggaagcgtt tcttcagatt ttgcgggatc tgtcagattc    1260
cacaaggtct tgcaaggtca agaattgttg ggtttgaaca cccatgacgg tactgctatt    1320
tctgcttttc aggcaactga agcaagtaat ttgcagtaca gtgatgaacg tagtaacatg    1380
agtaacaata tcttagggat cccaaggctc ggtgttagat ctccaaatgg aatccctgga    1440
tttccctacc attgctcagg ctttgggaa tctcaaagat tccaaaaggt cttgcaaggt    1500
caagaagtgt tcgtccttt ccgaggagga tgtttggctg atggccatat aagaactgct    1560
ggcatgtatc aacctaaatg gcctgcacca caagggtgtg atttccaca gccagcaaaa    1620
ccggtacttg tgttgcaagc atcctcccca tcatctgtcg tgatgtttcc acaaactgtt    1680
tctaagataa ctccattgga atatgagtac agctgcctgg ataaggatga agatggtaga    1740
tttgatagga ctgtccctac tcaagatatg ggaaagaaca atcaaacatt atctctttgg    1800
cctcatcttg tttccggcga agcaataaga gaatgtactg gaactgagaa tatgcactct    1860
tctgtcagtg gtgcagagca tgaatcaaac aatgagagta cagttgaaaa tggctgcaaa    1920
atctttggta tctcattggc tgaaaagatc cgatcatgtg atgaagcaga ctcttgtagt    1980
```

```
gcaaaacgta attctgggct ccagccttcg aggtcacaaa tactaggcag ctgttgggcc    2040
acttttgcct gtaattttca agaccgaatc ttttga                              2076
```

| SEQ ID NO: 231 | moltype = AA   length = 691 |
|---|---|
| FEATURE | Location/Qualifiers |
| REGION | 1..691 |
| | note = misc_feature - Ceres Annot ID no. 8667998 |
| REGION | 1..691 |
| | note = misc_feature - Bit score of 955.7 for hmm based on sequences of FIGURE 5. |
| REGION | 272..353 |
| | note = misc_feature - Pfam Name: Auxin_resp Pfam Desc: Auxin response factor |
| REGION | 145..250 |
| | note = misc_feature - Pfam Name: B3 Pfam Desc: B3 DNA binding domain |
| REGION | 1..691 |
| | note = misc_feature - Is Acted Upon By Ceres SEEDLINE ID no. ME00572 at SEQ ID NO. 111 |
| source | 1..691 |
| | mol_type = protein |
| | organism = Sorghum bicolor |

SEQUENCE: 231

```
MAGIDLNTVE EEDEEEAEAE APPVAARAGG GAVCLELWHA CAGPVAPLPR KGSAVVYLPQ     60
GHLEHIGGDA DAAGAAVPPH VLCRVVDVTL HADGATDEVY ARVSLLPEDE EAERRARARV    120
REDEDADRDG EDGAAMKPLA RTPHMFCKTL TASDTSTHGG FSVPRRAAED CFPPLDYSQQ    180
RPSQELVAKD LHGTEWKFRH IYRGQPRRHL LTTGWSAFVN KKKLVSGDAV LFLRGEDGVL    240
RLGVRRAAQL KIVTPIPALH NQCSSQTTLG NVAQAVATRT VPHIYYNPRL SQSEFIVPYW    300
KFTRSLNQPI SVGMRCRMRY ESDDASERRC TGIIIGSREA EPIWYGSKWK CLVVRWDDGI    360
ECHWPNRVSP WEIEVTGSVS GSHMCAPNSK RLKPCLPQVN PEIVLPNGSV SSDFAGSVRF    420
HKVLQGQELL GLKTHDGTAI SAFQATEASN LQYSDERSNM SNNILGIPRL GVRSPNGIPG    480
FPYHCSGFGE SQRFQKVLQG QEVFRPFRGG CLADGHIRTA GMYQPKWPAP QGCDFPQPAK    540
PVLVLQASSP SSVLMFPQTG SKITPLEYEY SCLDKDEDGR FDRTVPTQDM GRNNQTLSLW    600
PHLVSGEAIE ECTGTENMHS SVSGAEHESN NESTVENGCK IFGISLAEKI RSCDEADSCS    660
AKRNSGLQPS RSQILGSCWA TFACNFQDRI F                                  691
```

| SEQ ID NO: 232 | moltype = DNA   length = 2439 |
|---|---|
| FEATURE | Location/Qualifiers |
| misc_feature | 1..2439 |
| | note = Ceres Annot ID no. 8721170 |
| misc_feature | 1..2439 |
| | note = Encodes the peptide sequence at SEQ ID NO. 233 |
| source | 1..2439 |
| | mol_type = other DNA |
| | organism = Sorghum bicolor |

SEQUENCE: 232

```
atggcggcgg ctgcaccggc ggccggcggc ggcggtggtg cggaagcggg atgcggagga     60
ggcggaggga aggacccgct gttcgtcgag ctgtggaagg cctgcgcggg gccgctgtct    120
agcgtgccgc cgctcgggga gaaggtctac tacttcccgc agggccacat cgagcaggtg    180
gaggcatcga cgaaccagat tgctgagcag cagggcacgc ccctctacaa cctgccatgg    240
aagattccat gcaagctcat gaacatcgag ctgaaggctg agccggatac tgatgaggtg    300
tacgcccagc tcaccctgct ccctgataag aagcaagatg agaatacatc tacaacagtg    360
gagaatgagg aggcagagga ggaggtggtg cctcatgcgc caccaacaaa tgagggacct    420
cggatccatt ccttttgcaa gacattgact gcctcagaca caagcacgca tggtggtttc    480
tcagtgttgc gccggcatgc agatgagtgc ctcccaccat tggatatgag tcaacaccct    540
ccaaatcaag aattggtggc caaggacctg catgggattg agtggcggtt ccgtcacatc    600
tttcgaggtc agccacggag acacctcctt cagagtggtt ggagtgtttt tgttagcgcc    660
aagcgtcttg ttgcagggga tgccttcata tttctcagag gtgagaatgg ggagttacgt    720
gttggggttc ggcgtgcact gaggcaccaa accactatcc catcttcagt catatcaagc    780
cacagtatgc atcttggtgt tcttgcgaca gcatggcatg cagtcaacac tgggagtatg    840
ttcactgtct actacaagcc aaggactagt ccagctgaat tgtggtctc gcagataggg    900
tactatgaat cactgaaacg aaattattca ataggggatga gatttaagat gagatttgaa    960
ggtgaagaag cagcagagca aagattcact ggcacaatag ttggaatagg tgcttctgat   1020
ccatctggtt gggctgactc aaaatggcgt tcccttaagg tgagatggga tgaagcttct   1080
tctgttcctc gtcctgaaag agtttctcct tggcaaatga aacctgctat tagcccatct   1140
cctgtgaacc ctcttccagt cagattcaag aggtctcgtt caagtgttaa tgcttcacca   1200
tctgacgtgc ctactgtatc cagagaaggt cgataccatg atagcagtga tgtgaagact   1260
gctcaggatc ttaccatgtg tgcttcagga actgagcagc agagaaacaa tattgctgcc   1320
cagacaaagc gaagtctgga gggatggacg caatctagaa ctcctgaagg ttacaatcag   1380
ctgttctcgg catttcaacc actgaaagat acacataatc cactttgtac tttcccctagt   1440
caaatatctg ggactcgctc aaatacctgg gacacagccg atgctcgtta ccagcccaa    1500
caagccaatc acaacatgtt acatggcaca tggccttttta tgcctcatag cagtggtttt   1560
aggacgaatc aacagaatta tctagtgatg cctgaagctg caaagtttac tgggaaatca   1620
gcttttcactt cacttcaggg ccatggcact gatcagtgct ccacaggctg gttggacat    1680
attgagtcaa gttcccgcac agaccatgca tcgtcaagtt cgatcaggcc ccagcctttg   1740
gttattggta atgatgttca gaaaaccaaa ggcacttcat tcaaactatt tgggattcct   1800
cttggcagcc cggaaaaatc tgaacctctg gtatccccac caagtgtcgc atatgacggg   1860
aaacttcaaa cttctccatc agaaaaaggg aatcagctag acatagttgg agtggataat   1920
tgttctgatc cttcgaagac tgtgaagcca tttgatggtc tcaatcaga ttcgattaca    1980
```

```
gagaataatc agccttgtcc agaagctacc cagaatattc agaacaaagt gcaaagtagt    2040
tccaccagaa gctgcaagaa ggtccataag caaggcagtg ccctcggcag atcgattgat    2100
ctaacaaagt tcacttgcta cgatgagctg attgctgaac tggatcagat gtttgacttt    2160
gatggtgagc tgaagaatcc atgcaaaaat tggctggttg tctacactga caatgaaggc    2220
gatataatgc tggttggcga tgaccctgg aatgaattct gcgacatgt ccacaagatc    2280
ttcatctaca caagggagga agtgaaagg atgaacccag gtgccctaaa ctcaaggtcc    2340
gaggatagtc tgtctgactc gcagggaaga gggttggctt ccaaagagcc gccccgaggt    2400
ggcccgtcta cttcgactcc caattccgag agctgctaa                          2439
```

| | |
|---|---|
| SEQ ID NO: 233 | moltype = AA  length = 812 |
| FEATURE | Location/Qualifiers |
| REGION | 1..812 |
| | note = misc_feature - Ceres Annot ID no. 8721170 |
| REGION | 1..812 |
| | note = misc_feature - Bit score of 1310.2 for hmm based on sequences of FIGURE 5. |
| REGION | 271..353 |
| | note = misc_feature - Pfam Name: Auxin_resp Pfam Desc: Auxin response factor |
| REGION | 144..249 |
| | note = misc_feature - Pfam Name: B3 Pfam Desc: B3 DNA binding domain |
| REGION | 1..812 |
| | note = misc_feature - Is Acted Upon By Ceres SEEDLINE ID no. ME00572 at SEQ ID NO. 111 |
| source | 1..812 |
| | mol_type = protein |
| | organism = Sorghum bicolor |

```
SEQUENCE: 233
MAAAAPAAGG GGGAEAGCGG GGGKDPLFVE LWKACAGPLS SVPPLGEKVY YFPQGHIEQV    60
EASTNQIAEQ QGTPLYNLPW KIPCKLMNIE LKAEPDTDEV YAQLTLLPDK KQDENTSTTV   120
ENEEAEEEVV PHAPPTNEGP RIHSFCKTLT ASDTSTHGGF SVLRRHADEC LPPLDMSQHP   180
PNQELVAKDL HGIEWRFRHI FRGQPRRHLL QSGWSVFVSA KRLVAGDAFI FLRGENGELR   240
VGVRRALRHQ TTIPSSVISS HSMHLGVLAT AWHAVNTGSM FTVYYKPRTS PAEFVVSRDR   300
YYESLKRNYS IGMRFKMRFE GEEAAEQRFT GTIVGIGASD PSGWADSKWR SLKVRWDEAS   360
SVPRPERVSP WQIEPAISPS PVNPLPVRFK RSRSSVNASP SDVPTVSREG RYHDSSDVKT   420
AQDLTMWSSG TEQQRNNIAA QTKRSLEGWT QSRTPEGYNQ LFSAFQPLKD THNPLCTFPS   480
QISGTRSNTW DTADARYPAQ QANHNMLHGT WPFMPHSSGF RTNQQNYLVM PEAAKFTGKS   540
AFTSLQGHGT DQCSTGWFGH IESSSRTDHA SSSSIRPQPL VIGNDVQKTK GTSFKLFGIP   600
LGSPEKSEPL VSPPSVAYDG KLQTSPSEKG NQLDIVGVDN CSDPSKTVKP FDGPQSDSIT   660
ENNQPCPEAT QNIQNKVQSS STRSCKKVHK QGSALGRSID LTKFTCYDEL IAELDQMFDF   720
DGELKNPCKN WLVVYTDNEG DIMLVGDDPW NEFCDMVHKI FIYTREEVER MNPGALNSRS   780
EDSLSDSQGR GLASKEPPRG GPSTSTPNSE SC                                 812
```

| | |
|---|---|
| SEQ ID NO: 234 | moltype = DNA  length = 2007 |
| FEATURE | Location/Qualifiers |
| misc_feature | 1..2007 |
| | note = Ceres Annot ID no. 8679636 |
| misc_feature | 1..2007 |
| | note = Encodes the peptide sequence at SEQ ID NO. 235 |
| source | 1..2007 |
| | mol_type = other DNA |
| | organism = Sorghum bicolor |

```
SEQUENCE: 234
atggcggacg ccggcgtggc gcgcggccca gggagtgctg gcgatgctct gttcagggaa     60
ctctggcatg cttgtgctgg gccgttggtc acagtgcctc gccaaggcga gctggtttac    120
tacttccgc agggtcatat ggaacagctt gaagcatcta cagatcaaca acttgatcag    180
cacttacctc tgtttaatct accacccaag atcctctgca aggtggtcaa tgtagaactt    240
agagctgaaa ctgattccga tgaagtttat gctcagatta tgctacaaac cgaagcagag    300
caaaatgagc ccaccagccc agatgctgag ccaccgagc ctgaaagatg caacgtccat    360
tccttctgca agaccttgac tgcttccgat acaagtaccc atggtggatt ctctgtcctc    420
aggaggcatg ctgaagaatg tctgccccaa ctggacatga ctcagaatcc accatggcaa    480
gaactggtgg ctaaagatct ccatggaaat gaatggcatt tccgtcacat ctttcgaggg    540
caaccaagga ggcatctact tacgacaggc tggagtgttt ttgttagctc gaaaagattg    600
gttgctggtg acgcgtttat ctttttgaga ggtgagaatg gagagctgcg agtcgggtg    660
aggaggctca tgaggcaact aaacaacatg ccatcttcgg ttatctcaag ccacagcatg    720
catcttggag tccttgcaac tgcatctcat gccatctcca ctggaactct cttttctgtt    780
ttctacaaac ccagaacaag tcgatcagaa tttgtcgttc gtgtaaacaa gtaccttgaa    840
gctaagaatc acaagatgtc tgttggtatg aggtttaaaa tgagatttga gggtgacgaa    900
tctcctgaaa aagattcag tggacaatt attggtctgg aagcatgcc agctaactca    960
acatctccgt gggctaactc tgagtggaga tctttgaagg tccaatggga cgagccttct   1020
gctattctgc gtcagatag agtttcacca tgggaactag aaccccttga tgcaactaat   1080
ccacaaccac ctcaacctcc tttacggaat aagcgtgcgc ggcctcctgc ttcaccttcc   1140
attgctccag aacttcctcc tgttttttggt ttttggaatc cccagctga gctgcccaa   1200
gctttctcat tttcaggact gcagcgaact caggaattat accattcaa ccccaattca   1260
atcttctcgt catcgttgaa tgtaggattc aattcaaaga atgagcgttc tactccaaac   1320
aacaatcatt tgtactggac aatgagagag acaagaactg aatcctactc tgctagcatt   1380
aacaaagctc tactgaaaa gaagcaagaa tctgctactt ctggctgcag attgtttggt   1440
attgagatag gttctgcagt atcaccagtg gttactgttg ctagtgttgg tcaggatcca   1500
```

```
ccacctgctc tctcagtaga tgttgaatct gatcagctgt cacaaccatc ccatgccaac   1560
aaaacggatg ccccagcggc aagcagtgag cgctctccta atgaaacaga gagccgacaa   1620
gtcaggagct gcaccaaggt aatcatgcaa ggaatggcgg ttggcagggc agtggacttg   1680
acgaggttaa atgggtatga tgatcttcac cgcaagttgg aggagatgtt tgatatccat   1740
ggagagcttt ctgccaacct caggaaatgg aaggttgttt acacagatga tgaggatgac   1800
atgatgctgg tcggggacga tccatggaag atggtaaaaa ggatatatat ttactcttac   1860
gaggaggcca aatctttgac tcccaaagcg aagctgccag tcattggtga caccatcaag   1920
ccagacccaa acaaattgtc accggaatct gacatgccac agagtgacac aaacagcaat   1980
gctcccgttg ctgctgataa ggattga                                      2007
```

```
SEQ ID NO: 235              moltype = AA   length = 668
FEATURE                     Location/Qualifiers
REGION                      1..668
                            note = misc_feature - Ceres Annot ID no. 8679636
REGION                      1..668
                            note = misc_feature - Bit score of 1385.0 for hmm based on
                              sequences of FIGURE 5.
REGION                      248..333
                            note = misc_feature - Pfam Name: Auxin_resp Pfam Desc:
                              Auxin response factor
REGION                      121..226
                            note = misc_feature - Pfam Name: B3 Pfam Desc: B3 DNA
                              binding domain
REGION                      1..668
                            note = misc_feature - Is Acted Upon By Ceres SEEDLINE ID
                              no. ME00572 at SEQ ID NO. 111
source                      1..668
                            mol_type = protein
                            organism = Sorghum bicolor
SEQUENCE: 235
MADAGVARGP GSAGDALFRE LWHACAGPLV TVPRQGELVY YFPQGHMEQL EASTDQQLDQ    60
HLPLFNLPPK ILCKVVNVEL RAETDSDEVY AQIMLQPEAE QNEPTSPDAE PPEPERCNVH   120
SFCKTLTASD TSTHGGFSVL RRHAEECLPQ LDMTQNPPWQ ELVAKDLHGN EWHFRHIFRG   180
QPRRHLLTTG WSVFVSSKRL VAGDAFIFLR GENGELRVGV RRLMRQLNNM PSSVISSHSM   240
HLGVLATASH AISTGTLFSV FYKPRTSRSE FVVSVNKYLE AKNHKMSVGM RFKMRFEGDE   300
SPERRFSGTI IGLGSMPANS TSPWANSEWR SLKVQWDEPS AILRPDRVSP WELEPLDATN   360
PQPPQPPLRN KRARPPASPS IAPELPPVFG FWKSPAEPAQ AFSFSGLQRT QELYHSNPNS   420
IFSSSLNVGF NSKNERSTPN NNHLYWTMRE TRTESYSASI NKAPTEKKQE SATSGCRLFG   480
IEIGSAVSPV VTVASVGQDP PPALSVDVES DQLSQPSHAN KTDAPAASSE RSPNETESRQ   540
VRSCTKVIMQ GMAVGRAVDL TRLDGYDDLH RKLEEMFDIH GELSANLRKW KVVYTDDEDD   600
MMLVGDDPWK MVKRIYIYSY EEAKSLTPKA KLPVIGDTIK PDPNKLSPES DMPQSDTNSN   660
APVAADKD                                                           668
```

```
SEQ ID NO: 236              moltype = DNA   length = 2415
FEATURE                     Location/Qualifiers
misc_feature                1..2415
                            note = Ceres Annot ID no. 8670373
misc_feature                1..2415
                            note = Encodes the peptide sequence at SEQ ID NO. 237
source                      1..2415
                            mol_type = other DNA
                            organism = Sorghum bicolor
SEQUENCE: 236
atggcgctgc cgtcccaggc cccgtctaac tcaggggatc cgctgtaccc ggagctctgg     60
cgccgctgcg ccggcccgct cgtcaccgtc cctcgcgtcg gcgacctcgt cttctactt    120
ccccagggac acatcgagca ggtggaggcg tccatgaacc aggtcgccgg gaaccagatg    180
cgcctctacg atctgccctc caagctgctc tgccgcgtgc tcaacgtcga gcttaaggcg    240
gagacggaca ccgacgaggt ctacgcgcag atcatgctca tgccagagcc cgagcaaacc    300
gatgtggcgg ctgagaaggc gagttctgcg tccgctgcgt cgccgaggcc agcagtgagg    360
tccttctgca agacgctcac cgctcccgac accagcacac acggaggctt ctctgtgctg    420
cgccgccacg cagacgagtg cctcccacca ctggatatga cgcagtcgcc tcccacacag    480
gagctggtgg cgaaggatct gcatggcatg agtggcgct tccgcacat ctttcgcggg     540
caacccagga ggcatctcct tcagagtggt tggagtgttt tgttagttc caaaaggctt    600
gttgctggag acgccttcat tttcctcaga ggagaaatg gtgaacttcg ggttggtgtt    660
aggcgggcta tgaggcagtt gtctaatgta ccttcttcag tcatatctag ccaaagcatg    720
cacctcgagt tccttgcgac tgcatggcac gccatcaaca ccaaatccat gttcactgtc    780
tactacaagc ctaggacgag cccttcagag ttcatcatac catatgatca atatatgag    840
tcagtgaaaa ataactattc aattgggatg agattcagaa tgaggtttga aggggaagag    900
gcaccagagc agaggtttac tggtacaatc gttggctgtg aaaatcttga cccactatgg    960
cctgattcca gttggagata cttgaaggtg cgctgggatg agccttctac tatcccacga   1020
ccagataggg tctctccttg gaagatagag cctgcttcat cacctccagt taatccactc   1080
ccgctttctt ctagagtaaa aagacctaga caaaatgctc ctccaccttc acctgaagca   1140
tctgttctca caaaagaaag tgcagccaag atcgatattg actctgctca aacacaacat   1200
caaaattcgg tcttgcaagg tcaagagcaa gggaacaaat gacaccaagc gactgaaagc   1260
aacgactctg attccactgt tcaaaagcg atgatgtggt cccatcacc caatgggaaa    1320
gcccacacta actttcagca gagacctgct atggatagtt ggatgccaat gggaggcgt    1380
gaaacggact tcaaggactc acgttccgcc ttcaaggatg cccgcactgc ctctcaatca   1440
tttagagata cacaggggtt cttcatgcaa gcttatgatg acaatcatca ccgtctttct   1500
ttcaacaacc agtttcagga tcaggggttca gctcatcgct ttgcggatcc atacttctat   1560
```

-continued

```
atggcccaac aaccttctct gactgttgaa tcaagcacaa ggacacaaac agcaaacaac  1620
gacttgcgtt tctggggcga ccagaattcg atctatggta atccaggtga tcaacagcag  1680
cagggtttca gctttggaca aaacccatca agttggttga accagccatt tccccaggtt  1740
gaacagccac gagtggttag gcctcatgca acagttgctc catttgattt ggaaaagacc  1800
agagaaggca gcgggttcaa gatctttggg ttccaagttg atacaaccag tccatctcct  1860
gcccagttga gctctccatt atgtgctatc cgggagcatg tggtacaaac ccgaccatcg  1920
gcaccagtga atgaattgca acctgtcaa aatgagtgct tgcctgaggg atctgtaagc  1980
actgctggaa ctgcaactga gaacgagaaa acattcagc aagcccagcc aagttcaaaa  2040
gatattcaaa gcaagtccca gggtgcttcg acaaggagct gcacaaagt tcataagcaa  2100
ggggttgcgc ttggcagatc tgtgacctc tcaaaattca ctgactacga tgaactcaaa  2160
gcagaattag acaagatgtt tgaattcaat ggcgaattag tatctgccaa cagaagctgg  2220
cagatcgttt atactgacaa tgagggtgac atgatgcttg ggggatga cccgtgggaa  2280
gagttctgta gcatagtgcg caagatctac atctatacga aggaggaggt ccagaagatg  2340
aactcaaaat catctgcgcc aaggaaggag gagcctctaa cagtgggtga aggatgcgcc  2400
gccacaaatg agtag                                                   2415

SEQ ID NO: 237          moltype = AA  length = 804
FEATURE                 Location/Qualifiers
REGION                  1..804
                        note = misc_feature - Ceres Annot ID no. 8670373
REGION                  1..804
                        note = misc_feature - Bit score of 1526.4 for hmm based on
                          sequences of FIGURE 5.
REGION                  248..329
                        note = misc_feature - Pfam Name: Auxin_resp Pfam Desc:
                          Auxin response factor
REGION                  121..226
                        note = misc_feature - Pfam Name: B3 Pfam Desc: B3 DNA
                          binding domain
REGION                  1..804
                        note = misc_feature - Is Acted Upon By Ceres SEEDLINE ID
                          no. ME00572 at SEQ ID NO. 111
source                  1..804
                        mol_type = protein
                        organism = Sorghum bicolor
SEQUENCE: 237
MALPSQAPSN SGDPLYPELW RACAGPLVTV PRVGDLVFYF PQGHIEQVEA SMNQVAGNQM   60
RLYDLPSKLL CRVLNVELKA ETDTDEVYAQ IMLMPEPEQT DVAAEKASSA SAASPRPAVR  120
SFCKTLTASD TSTHGGFSVL RRHADECLPP LDMTQSPPTQ ELVAKDLHGM EWRFRHIFRG  180
QPRRHLLQSG WSVFVSSKRL VAGDAFIFLR GENGELRVGV RRAMRQLSNV PSSVISSQSM  240
HLGVLATAWH AINTKSMFTV YYKPRTSPSE FIIPYDQYME SVKNNYSIGM RFRMRFEGEE  300
APEQRFTGTI VGCENLDPLW PDSSWRYLKV RWDEPSTIPR PDRVSPWKIE PASSPPVNPL  360
PLSSRVKRPR QNAPPPSPEA SVLTKESAAK IDIDSAQTQH QNSVLQGQEQ MTLRNNLTES  420
NDSDSTVQKP MMWSPSPNGK AHTNFQQRPA MDSWMPMGRR ETDFKDSRSA FKDARTASQS  480
FRDTQGFFMQ AYDDNHHRLS FNNQFQDQGS AHRFADPYFY MAQQPSLTVE SSTRTQTANN  540
DLRFWGDQNS IYGNPGDQQQ QGFSFGQNPS SWLNQPFPQV EQPRVVRPHA TVAPFDLEKT  600
REGSGFKIFG FQVDTTSPSP AQLSSPLCAI REHVVQTRPS APVNELQPVQ NECLPEGSVS  660
TAGTATENEK NIQQAQPSSK DIQSKSQGAS TRSCTKVHKQ GVALGRSVDL SKFTDYDELK  720
AELDKMFEFN GELVSANRSW QIVYTDNEGD MMLVGDDPWE EFCSIVRKIY IYTKEEVQKM  780
NSKSSAPRKE EPLTVGEGCA ATNE                                        804

SEQ ID NO: 238          moltype = DNA  length = 2565
FEATURE                 Location/Qualifiers
misc_feature            1..2565
                        note = Ceres Annot ID no. 8690553
misc_feature            1..2565
                        note = Encodes the peptide sequence at SEQ ID NO. 239
source                  1..2565
                        mol_type = other DNA
                        organism = Sorghum bicolor
SEQUENCE: 238
atgacttcgg cggcggccgc ggcccaggcg gcgggagggg gtggaggagg aggaggagtc   60
tgcgaggggg atgccgctgc cgcggcgcga ggcgaggcg gaggcggaac ggaggacggc  120
atgtacacgg agctctggag cctctgcgcc ggccggctgg tcacggtgcc caggtcggg  180
gacaaggtct actacttccc acagggccat atcgagcagg tggaggcatc gaccaaccag  240
gtggctgagc agcacatgca actttacaat ctcccatgga gatcctgtg tgaggtcatg  300
aatgttgaat gaaggctga gccggacaat gatgaggttt atgcccagct cactctgcta  360
cctgaatcga agccagagga gaatggctct agtcaggagg agatgcctgc tgcacctcct  420
gctgcacttg caaggccacg tgtgcactcc ttctgcaaga cattgacagc ctctgacacg  480
agcacacatg gtggtttctc ggtgctgcgt cgccatgcag atgaatgcct tccaccgctg  540
gatatgagtc gtcaacctcc aacacaagag cttgtggcca aggatctgca tggtgtggaa  600
tggcgctttc gtcacatatt cagaggtcaa cccggaaggc ttttttgca gagtggctgg  660
agtgtttttg ttagtgcaaa gcgtcttgtt gctggggatg ccttcatctt tctgagaggt  720
gataagggga gctgcgtgt gggagtcagg cgtgccatga aaatgttccg  780
tcttcagtaa tatcaagcca cagcatgcat cttggtgttc ttgctactgc atggcatgct  840
gttaacactg gaccatgtt cactgtctac tacaaaccta ggacaagtcc agctgagttt  900
gttgtccccct gtgatcgcta tacggagtca ctgaacgaa attacccctat agggatgaga  960
tttaaaatga ggtttgaagg tgaagaggct ccagagcaaa ggttcactgg acgattgtt  1020
ggaaatgtgg atcctgaaca agctggatgg gctgaatcta aatggcgtta cctcaaggtg  1080
```

-continued

```
aggtgggatg aagcttcctc cattccacgt cctgaaaggg tttctccttg gcaaatagaa  1140
cctgcagtca gccctccccc tgtcaatcca cttccagtac acaggcccaa gaggcctcgc  1200
tctaatgctg tagcttctct ggctgagtct tcagctccaa caaaagaagc tgctccgaag  1260
gtcacattag agactcaaca acatgccctg caaaggccct tgcagaccca ggataatgcg  1320
gccccaaaaa gtggttttgg tgataacagt gagttggacg ctgctcataa gtcagccctg  1380
cgaccatcag ggtttgatct agagaagaac accattggca tgcagaggaa gctgggttca  1440
gatagttgga tgcatatgaa cagacctgaa ggatacaatg aaatgttatc tggatatcaa  1500
caacctaata aagatgtaca gaatccacag ggtttctgtt ctttacctga tcagattgct  1560
gccggtcgtc ctaatttctg gcacaccgta aatgctcatt atcaagacca gcaaggcaat  1620
cacaatctat tccctggttc atggtccatg atgccttcaa gtactggctt tgggttgaac  1680
agacagagct atccaatgat gcaggaagtt ggtgggttgt ctcagagtgc tacgaacacc  1740
aagtttggga tggagctta tgctgcacta cctggtcatg gcattgatca atactcttct  1800
ggatggtttg gcacatgat acctggtgct cgcatggacg atgtccagcc acgcgtgatt  1860
aagcctcaac ctttggtcct tgctcatggt gaagctcaga aaatgaaagg caattcatgc  1920
aagcttttg gaattcacct tgatagccca gccaaatctg aacctttgaa atctccacca  1980
agtgttgcct atgatgggat gccacaaact ccagcagcag ctgaatggcg gatggttgat  2040
tcaattgaag cagacagatg ttctgatcca cttaagatgc caaagcaact cgatgctaca  2100
caggtcgatc ctgttccaga gaaatgttca caagtttcaa gaggcacaca gtgcaaatca  2160
caaggtggat caactaggag ctgcaagaag gtccacaagc aaggaatcgc acttggcagg  2220
tctgtggatc ttacaaagtt caatggctac acggaattga ttgctgagct ggatgagatg  2280
tttgacttca tggggagct gaaaggttct aacaaggaat ggatggttgt gtacaccgac  2340
aatgaaggtg atatgatgct ggttggggat gatccctgga atgagttctg caacatggtc  2400
cacaagatct tcatctacac aagggaggag gtccagagga tgaatccggg cacccctgaat  2460
tcaaggtccg aggacagcct tgctaattca atggaaaggg gctctactgc tagggagaca  2520
cctggcagcc tatccgcctc ttcccttgac tctgagaact gctaa              2565

SEQ ID NO: 239          moltype = AA   length = 854
FEATURE                 Location/Qualifiers
REGION                  1..854
                        note = misc_feature - Ceres Annot ID no. 8690553
REGION                  1..854
                        note = misc_feature - Bit score of 1661.5 for hmm based on
                          sequences of FIGURE 5.
REGION                  277..359
                        note = misc_feature - Pfam Name: Auxin_resp Pfam Desc:
                          Auxin response factor
REGION                  150..255
                        note = misc_feature - Pfam Name: B3 Pfam Desc: B3 DNA
                          binding domain
REGION                  1..854
                        note = misc_feature - Is Acted Upon By Ceres SEEDLINE ID
                          no. ME00572 at SEQ ID NO. 111
source                  1..854
                        mol_type = protein
                        organism = Sorghum bicolor
SEQUENCE: 239
MTSAAAAAQA AGGGGGGGGV CEGDAAAAAR GGGGGGTEDG MYTELWSLCA GPLVTVPRVG    60
DKVYYFPQGH IEQVEASTNQ VAEQHMQLYN LPWKILCEVM NVELKAEPDN DEVYAQLTLL   120
PESKPEENGS SQEEMPAAPP AALARPRVHS FCKTLTASDT STHGGFSVLR RHADECLPPL   180
DMSRQPPTQE LVAKDLHGVE WRFRHIFRGQ PGRLFLQSGW SVFVSAKRLV AGDAFIFLRG   240
DNGELRVGVR RAMRQQANVP SSVISSHSMH LGVLATAWHA VNTGTMFTVY YKPRTSPAEF   300
VVPCDRYTES LKRNYPIGMR FKMRFEGEEA PEQRFTGTIV GNVDPEQAGW AESKWRYLKV   360
RWDEASSIPR PERVSPWQIE PAVSPPPVNP LPVHRPKRPR SNAVASLAES SAPTKEAAPK   420
VTLETQQHAL QRPLQTQDNA APKSGFGDNS ELDAAHKSAL RPSGFDLEKN TIGMQRKLGS   480
DSWMHMNRPE GYNEMLSGYQ QPNKDVQNPQ GFCSLPDQIA AGRPNFWHTV NAHYQDQQGN   540
HNLFPGSWSM MPSSTGFGLN RQSYPMMQEV GGLSQSATNT KFGNGAYAAL PGHGIDQYSS   600
GWFGHMIPGA RMDDVQPRVI KPQPLVLAHG EAQKMKGNSC KLFGIHLDSP AKSEPLKSPP   660
SVAYDGMPQT PAAAEWRMVD SIEADRCSDP LKMPKQLDAT QVDPVPEKCS QVSRGTQCKS   720
QGGSTRSCKK VHKQGIALGR SVDLTKFNGY TELIAELDEM FDFNGELKGS NKEWMVVYTD   780
NEGDMMLVGD DPWNEFCNMV HKIFIYTREE VQRMNPGTLN SRSEDSLANS MERGSTARET   840
PGSLSASSLD SENC                                                    854

SEQ ID NO: 240          moltype = DNA   length = 2924
FEATURE                 Location/Qualifiers
misc_feature            1..2924
                        note = Ceres Clone ID no. 1744705
misc_feature            1..2924
                        note = Encodes the peptide sequence at SEQ ID NO. 241
source                  1..2924
                        mol_type = other DNA
                        organism = Panicum virgatum
SEQUENCE: 240
agccagccaa cctacccgcc ccggacagca agcacaggc gcacgagccc ccccagctcc    60
acgcctcctc ctcctccctc ccctctccc gccatcctcc tccgcgcgc gccttcccgc   120
ccgccgagcc tttaggaggg ggtttccgga gtcgcggacg cgcgtgcgag accccttccc   180
ctgccgcgca gcgcaagtaa gatctccggc ctccgccctc gcgcgctccg ggcgcctcct   240
ctctcccctg aattgcccgg gctcggggc tctaacggct gccccggtgg cgctgcgcgc   300
gcagatctgc cgagctcggc atgggtgac cagatcgggc gcggctcgg ggctctacgg   360
ctgaattccg ctcggtgagg agggagctgg tctcggagag gccgggggga tggcgaacgc   420
```

-continued

```
cggcgcggcc gtcggtccag ggggtgctag cgatgctttg ttcagggaac tctggcatgc    480
ttgtgctggg ccgttggtca cggtgcctcg ccaaggcgag ctggtttact acttcccgca    540
aggtcatatg aacagcttg  aagcatctac agatcagcaa cttgaccagc acttaccttt    600
gtttaatcta ccatccaaga tcctgtgcaa agtggtaaat gtagaactca gagctgaaac    660
tgattccgat gaagtttatg ctcaaattat gctgcaacca gaagcagatc aaaatgagcc    720
cactggccca gatcctgagc caccagagcc agaaaggtgc aatgtccatt ccttctgcaa    780
gactttgact gcttcagaca cgagcaccca tggtggtttc tctgtcctca ggagacatgc    840
tgaagaatgt ttgccccaat tggatatgac tcagaatcca ccatggcaag aactggtggc    900
taaagatctc catggaaatg aatggcattt ccgtcacatc tttcgaggtc aaccaaggag    960
gcatctactt acaacaggct ggagtgtttt tgttagctca aaaagattgg ttgctggtga   1020
tgcatttatc ttttttgagag gtgataatgg agagctacga gtcggggtaa gaaggctcat   1080
gaggcaacta aataacatgc catcatcagt tatctcaagc catagcatgc atcttggagt   1140
cctcgcaaca gcatctcatg ccatctccac tggaactctc ttttctgttt tctacaaacc   1200
cagaacaagt cgatcggagt ttgttgtgca cgtaaacaag taccttgaag ctaagaatca   1260
caagatgtct gtcggtatga ggtttaaaat gagagtttgag ggtaatgaat ctcctgaaag   1320
aagatttagt gggacaatta ttggtctggg aagcatgcca gctaactcaa catctccgtg   1380
ggctgactct gattggagat cttttgaaggt ccaatgggat gagccttctg ctgttgtccg   1440
tccagataga gtttcaccat gggaactaga accccttgca gcaactaaca caaaccgcc    1500
tcagcctcct ttacggaata agcgtgcacg gcctcctgct tcaccttcta ttgctccaga   1560
acttcctcca gcttttggtt tttggaaatc cccagctgag cctacccatc ctttctcatt   1620
ttcgggactg cagcgaactc aggaattata ccattcaaac cccaattcaa tcttttcatc   1680
atcgttgaat gtgggatta attcaaagaa tgaacattct actccaacca acaatcattt   1740
gtactggcca attcgagaca ctagaacgga atcctactct gctagcatta acaaacttct   1800
acctgaaagg aagcaagaat ccgctactgc tggctgcaga ttgtttggta ttgagataag   1860
taatgcagta tcaccagtgg ttactgttgc tagtgttggt caagaccagc cacctgttga   1920
gtcagtagat gttgagtctg atcagctgtc acagccatcc caagccaaca aacagatgc    1980
tccagcagca agcagtgagc gctcctccta tgagactgag agccggcaag tcaggagctg   2040
caccaaggta atcatgcaag aatggcggt tggcagggca gtggacttga cgaggctaga   2100
aggatatgat gatcttctcc acaagttgga ggagatgttt gatatccagg gggagctttc   2160
tgctagcctc aagaaatgga aggttattta cacggatgat gaggatgaa tgatgctggt   2220
cggggatgat ccgtggcctg aatttttgcag catggtgaaa aggatataca tttactccta   2280
tgaggaggcc aagtctttga ctcccaaggc gaagctgccg gtcattggtg ataccactaa   2340
accgaaccca gacaagttgt caccggaatc tgacatgccg cagagtgact caaacaacag   2400
cgctctggtt gctgccgata aggactgatg gatgctaact tggcgctcta cctttaattc   2460
ccgttttgga tgtttgggag gcaatgccca tactccttga gactgctgag agttatctgt   2520
ttgttgcgct gtgggcccga aggacgttgc cccacaatct gcctgactgc cttggtttgg   2580
aatggctgat gtaggaccag tggtggtcct ctgccagcaa ggtcgactgg aatgtaatgg   2640
caagcaggcc gcattgcgcg ccgttccctg tgccaccaac ctgtgtttg  tttgccgtgt   2700
ttggtaggag gcatggcgta tcgctggcct cacctccaga gtaaatagga cttttatgtac   2760
aactattttg gtagtagcag tagcggttta tgtatatcag cgtcatgttc cttgctacct   2820
atataagcat tatcatctgt agctgctgtt cccacctgca ttgtattcta cccccggctt   2880
ggtaccggat gctctggtgc aaaaatgtct ctgcttgctg ttcc                   2924

SEQ ID NO: 241           moltype = AA  length = 672
FEATURE                  Location/Qualifiers
REGION                   1..672
                         note = misc_feature - Ceres Clone ID no. 1744705
REGION                   1..672
                         note = misc_feature - Bit score of 1346.5 for hmm based on
                           sequences of FIGURE 5.
REGION                   248..333
                         note = misc_feature - Pfam Name: Auxin_resp Pfam Desc:
                           Auxin response factor
REGION                   121..226
                         note = misc_feature - Pfam Name: B3 Pfam Desc: B3 DNA
                           binding domain
REGION                   1..672
                         note = misc_feature - Is Acted Upon By Ceres SEEDLINE ID
                           no. ME00572 at SEQ ID NO. 111
source                   1..672
                         mol_type = protein
                         organism = Panicum virgatum
SEQUENCE: 241
MANAGAAVGP GGASDALFRE LWHACAGPLV TVPRQGELVY YFPQGHMEQL EASTDQQLDQ     60
HLPLFNLPSK ILCKVVNVEL RAETDSDEVY AQIMLQPEAD QNEPTGPDPE PPEPERCNVH    120
SFCKTLTASD TSTHGGFSVL RRHAEECLPQ LDMTQNPPWQ ELVAKDLHGN EWHFRHIFRG    180
QPRRHLLTTG WSVFVSSKRL VAGDAFIFLR GDNGELRVGV RRLMRQLNNM PSSVISSHSM    240
HLGVLATASH AISTGLFSV  FYKPRTSRSE FVVSVNKLYLE AKNHKMSVGM RPKMRFEGNE   300
SPERRFSGTI IGLGSMPANS TSPWADSDWR SLKVQWDEPS AVVRPDRVSP WELEPLNATN    360
TQPPQPPLRN KRAPPASPS  IAPELPPAFG FWKSPAEPTH PFSFSGLQRT QELYHSNPNS    420
IFSSSLNVGF NSKNEHSTPT NNHLYWPIRD TRTESYSASI NKLLPERKQE SATAGCRLFG    480
IEISNAVSPV VTVASVGQDQ PPVESVDVES DQLSQPSQAN KTDAPAASSE RSPHETESRQ    540
VRSCTKVIMQ GMAVGRAVDL TRLEGYDDLL HKLEEMFDIQ GELSASLKKW KVIYTDDEDD    600
MMLVGDDPWP EFCSMVKRIY IYSYEEAKSL TPKAKLPVIG DTTKPNPDKL SPESDMPQSD    660
SNNSALVAAD KD                                                       672

SEQ ID NO: 242           moltype = AA  length = 670
FEATURE                  Location/Qualifiers
REGION                   1..670
```

```
                            note = misc_feature - Public GI ID no. 140053546
REGION                      1..670
                            note = misc_feature - Bit score of 1133.4 for hmm based on
                              sequences of FIGURE 5.
REGION                      250..332
                            note = misc_feature - Pfam Name: Auxin_resp Pfam Desc:
                              Auxin response factor
REGION                      119..228
                            note = misc_feature - Pfam Name: B3 Pfam Desc: B3 DNA
                              binding domain
REGION                      1..670
                            note = misc_feature - Is Acted Upon By Ceres SEEDLINE ID
                              no. ME00572 at SEQ ID NO. 111
source                      1..670
                            mol_type = protein
                            organism = Medicago truncatula
SEQUENCE: 242
MCFSITFTGS TNDALYKELW HACAGPLVTL PREGERVYYF PQGHMEQLEA SMNQGLEQQM    60
PSFNLPSKIL CKVVNIHLRA EPETDEVYAQ ITLLPETDQS EVTSPDDPLP EPPRCTVHSF   120
CKTLTASDTS THGGFSVLRR HADDCLPPLD MTQQPPWQEL VATDLHGNEW HFRHIFRGQP   180
RRHLLTTGWS VFVSSKKLVA GDAFIFLRQV VLGENGELRV GVRRLMRQQS NMPSSVISSH   240
SMHLGVLATA SHAISTGTLF SVFYKPRTSR SEFIVSINKY LEARNHKLSV GMRFKMRFEG   300
DEVPERRFSG TIVGVEDNKS SVWADSEWRS LKVQWDEPSS ILRPDRVSPW ELEPLVSTPP   360
ANSQPTQRNK RSRPPILPST MTDSSLQGIW KSPADSPPFP YRDPQHGRDL YPSPRFSSTA   420
TSFLGFGGNS PASNKSMYWS SRLENSTEPF SPVALEESGE KRQGTGNGCR LFGIQLLENS   480
NAEESLQTAP LSGRVGDDRS VPSLDVESDQ HSEPSNVNRS DIPSVSCDAD KSCLRSPQES   540
QSRQIRSCTK VHMQGMAVGR AVDLTRFDGY EDLLRKLEEM FDIEGELCGA TKKWLVVYTD   600
NEDDMMMVGD DPWLEFCSVV RKMFIYTPEE VKKLSPKIGL PSNEEGKPSK LDSEAVVNPE   660
DRSSIVGPGC                                                         670

SEQ ID NO: 243              moltype = DNA  length = 2031
FEATURE                     Location/Qualifiers
misc_feature                1..2031
                            note = Ceres Annot ID no. 8733583
misc_feature                1..2031
                            note = Encodes the peptide sequence at SEQ ID NO. 244
source                      1..2031
                            mol_type = other DNA
                            organism = Sorghum bicolor
SEQUENCE: 243
atggggattg atctcaacag cgtggaggag gacgagcagg cgccggcggg cgcggtgtgc     60
tgcggggagc tgtggcacgc gtgcgcgggg gctggggtgg cgctgccgcg gcggggcagc    120
gccgtggtgt acctgcctca ggcgcacctc gcggccgggc gcgacggtgg ggagctgccg    180
gcccttgcgg cggcgccgcg cgtgccgccg cacgtggtgt gtcgcgtcgt cgacgtcgag    240
ctacgcgcgg atgcggcgac ggacgaggtc tatgcgcggc ttgcgctggt ggcggaggat    300
aagatgtttg gccgaaacat ccatgatggt gaaactgaag agaaggatgg tgagaaagag    360
gatggtgatg gagaaaagct cacatcgcac atgttctgca agacactcac agcttctgat    420
acaagcactc atgggggatt ctctgttcct cggcgggctg cagaggactg ctttccacca    480
ttggactatg agcagcttag gccttcccaa gagcttattg ccaaggattt gcatggcatg    540
aaatggaggt tccgtcatat ctatagaggt caacctcgta ggcatcttct gacaactgga    600
tggagttcat ttattaataa gaagaaacta gtctcaggag atgcagtctt gtttctgaga    660
ggtagtgatg gcgagctaag attgggtgtg aggagagcag ttcaactgaa aaatgaagct    720
ctacttggaa ctgtcaactg tactgattcg aagctactta tgctgctgc tgtgccagt     780
tctttggaca atagaagtat atttcacatc tgtttcaacc caaggattgg tgcatcagaa    840
tttattgtgc catattgcaa gtttttgaag ggcttgaact atccttttc aattggaacc    900
agatttaaag ttggctgcaa gaatgaagat gctaacgaga ggtccttggg attgatctca    960
ggtattagtg aagttgatcc catacgctgg cctggatcaa aatggaaatc tctcttggta   1020
aagtgggatg gtgataccaa gtacagccac cagaatagag tatctccatg ggacatcgag   1080
agagttggca gctcagtttc agttactcac tgtctttcat cttgtgtttc gaagcgaatg   1140
aagttgtgct tcccccaagg caatttggac gctccaattc tagatggaaa tggtcgtcca   1200
gactctgtgg gaactgaagg tttccaccag gtcttgcaag gtcaagaatt ggtgagggtt   1260
catggtgctg catgctctca ttcatcagat acccccagat gtcaaggctc ttatggaagg   1320
agattctctg ccgatgtgtg gaactgcaag atgaatgatg gacacctaaa taccactggg   1380
tttgcttacc agcccctagg cttcagtgaa tctgtcaaat tctcagaggt cttgcaaggt   1440
caagaaatgt ctcaggtggc agccccttcc ttcatgagag atgctttcag tgctggcaca   1500
cagaatggca gggttcgatc atttgattat gtgcagagat cagctgcaac tcaaggatat   1560
gctctccagc aatttaatct gccagcaaca gaagtgcatt caccgtcttc tgttcttatg   1620
tttaaccaaa ccatggtacc acagcctgag ttagatggtc tgaccaaccg tgaagaagca   1680
tatgccagcg ggtactcatc cattgcaata cagagagaag ctgaaccatg gccatccacg   1740
cagcagcaaa gagtgcgcga aaatggaagc gagcctctcg acacaactga agcctcagct   1800
cctgcaagga tcgcaaaatc tggatcggtg gacaggggcg tcgggggaag cagctgtaag   1860
cttttttggtt tctccttgac tgagaagatc cttggaacag agggagttgg tgggaaagaa   1920
gggaactacg aagcggatcg gcagactccc gggttctag acttgcttgg gcacggccat   1980
tctacgcccg tgctctgca tgctctttgc gctgctccct gggaatatg a              2031

SEQ ID NO: 244              moltype = AA  length = 676
FEATURE                     Location/Qualifiers
REGION                      1..676
                            note = misc_feature - Ceres Annot ID no. 8733583
```

```
REGION                  1..676
                        note = misc_feature - Bit score of 1288.5 for hmm based on
                         sequences of FIGURE 5.
REGION                  258..339
                        note = misc_feature - Pfam Name: Auxin_resp Pfam Desc:
                         Auxin response factor
REGION                  131..236
                        note = misc_feature - Pfam Name: B3 Pfam Desc: B3 DNA
                         binding domain
REGION                  1..676
                        note = misc_feature - Is Acted Upon By Ceres SEEDLINE ID
                         no. ME00572 at SEQ ID NO. 111
source                  1..676
                        mol_type = protein
                        organism = Sorghum bicolor
SEQUENCE: 244
MGIDLNSVEE DEQAPAGAVC CGELWHACAG AGVALPRRGS AVVYLPQAHL AAGGDGGELP    60
ALAAAPRVPP HVVCRVVDVE LRADAATDEV YARLALVAED KMFGRNIHDG ETEEKDGEKE   120
DGDGEKLTSH MFCKTLTASD TSTHGGFSVP RRAAEDCFPP LDYEQLRPSQ ELIAKDLHGM   180
KWRFRHIYRG QPRRHLLTTG WSSFINKKKL VSGDAVLFLR GSDGELRLGV RRAVQLKNEA   240
LLEAVNCTDS KLLMLSAVAS SLDNRSIFHI CFNPRIGASE FIVPYCKFLK GLNYPFSIGT   300
RFKVGCKNED ANERSFGLIS GISEVDPIRW PGSKWKSLLV KWDGDTKYSH QNRVSPWDIE   360
RVGSSVSVTH CLSSCVSKRM KLCFPQGNLD APILDGNGRP DSVGTEGFHQ VLQGQELVRV   420
HGAACSHSSD TPRCQGSYGR RFSADVWNCK MNDGHLNTTG FAYQPLGFSE SVKFSEVLQG   480
QEMSQVAAPS FMRDAFSAGT QNGRVRSFDY VQRSAATQGY ALQQFNLPAT EVHSPSSVLM   540
FNQTMVPQPE LDGLTNREEA YGSGYSSIAI QREAEPWPST QQQRVRENGS EPLDTTEASA   600
PARIAKSGSV DRGVGGSSCK LFGFSLTEKI LGTEGVGGKE GNYEADRQTP RVLDLLGHGH   660
STPGALHALC AAPLGI                                                   676

SEQ ID NO: 245          moltype = DNA  length = 1974
FEATURE                 Location/Qualifiers
misc_feature            1..1974
                        note = Ceres Annot ID no. 8700968
misc_feature            1..1974
                        note = Encodes the peptide sequence at SEQ ID NO. 246
source                  1..1974
                        mol_type = other DNA
                        organism = Sorghum bicolor
SEQUENCE: 245
atggacgcgc ccaaccctgc agcggctgct ggctcaggag gaatgcctag tgacgccctg     60
taccgagagc tgtggcatgc gtgtgccggc ccgttggtca cagtacctag acaaggcgag    120
cgcgtctatt acttcccccca gggccatatg gagcagcttg aggcgtctac acaccagcag   180
cttgatcagt acttaccgat gttcaatcta ccacccaagc tcctatgcag tgtagtcaac    240
gtggaactac gggccgaagc tgattcagat gaagtttatg ctcaaattat gttgcaacca    300
gaagctgatc aaaacgaact caccagcctg gaccctgaac acaagaaacc tgaaaaatgc    360
actgcccatt ccttctgcaa gacactgaca gcttcagata cgagcactca cggcggtttt    420
tctgttcttc ggaggcatgc tgaagaatgt cttcctcagc tggacatgtc tctaaatcca    480
ccttgccaag aactggttgc caaagatctc catggcactg aatggcattt tcgacacatt    540
tttcgagggc aacccaagag gcatctcctt acaactggct ggagtgtctt tgttagctca    600
aagagattgg ttgcggggga tgcatttatc ttcatgagag gtgaaaatgg tgagctacgg    660
gttggtgtaa ggaggctcat gagacaagta aatagcagcc cgtcatctgt catatcaagc    720
cacagcatgc atcttggagt cttggccaca gcctcccatg ccatctccac tggaaccctc    780
ttttccgttt tctacaaacc aagaactagc cgatctgatt ttattgtgag tgttaacaag    840
taccttgaag ctaagaagca gaaaatatct gttggaatga ggtttaagat gagatttgaa    900
ggtgatgagg ctcctgaaag aaggttcagt ggaacaatta ttggcattgg cagtttgccg    960
gcaatgtcaa aatctctgtg ggcagattct gactggagat ctctaaaggt tcaatgggac   1020
gaaccttcat ccattcttcg tccagataga atctccacct gggaagtgga gcccctggat   1080
gctgctaatc cacaatcccc tcaacctcca ccaaggccta agcgtccacg acccccagct   1140
tcaccttgta tggtttcaga actgccttca ggttttggac tctgaaaatc cccaacagaa   1200
tcatcccgta cactctcatt ttcggaacct caacgggctc gagagttatt tccttcaatt   1260
cccacatcaa ccttctcatc ttcatcaaac gtcagtttca attcaaagaa tgagccatcc   1320
atgctaacca cacagttcta ctggtcagca agggatacaa gagctgactc ctgcgctgct   1380
agcaccaaca cagtcatagt tgaaaagaag caagagccaa gttctggtgg ttgcagattg   1440
tttggaattg atatatgctc agctgaggaa gaagtattac ctgtggttac tgctccaagt   1500
gttggttatg agcagactgc tgcctctgta gagttgaact cggataagct ctcacaggga   1560
tctgatgtca acaattctga tgccccagca gctagcagtg agcgttcacc tcttgaatcc   1620
caaagccggc aagtgaggag ctgcaccaag gtaattatgc aaggaatggc agttggaagg   1680
gctgtagacc tgacaaagct tagtggctac agtgatcttt gccagaagtt ggaggagatg   1740
tttgacatcc acggggacgt aggttgcaca ctcaagaaat ggcgggtcat tttcactgat   1800
gatgaggatg acatgatgct tgttggggat gatccttggg atgagttttg cagaatggtg   1860
aaaaggattt acatttacac atatgaggag gcgaagaaac tgacatccaa gtcaaagtta   1920
cctgttagca gtgacagcag caagctgagt gctgtaaact cactgtctga atga          1974

SEQ ID NO: 246          moltype = AA  length = 657
FEATURE                 Location/Qualifiers
REGION                  1..657
                        note = misc_feature - Ceres Annot ID no. 8700968
REGION                  1..657
                        note = misc_feature - Bit score of 1132.7 for hmm based on
```

```
                           sequences of FIGURE 5.
REGION                     251..336
                           note = misc_feature - Pfam Name: Auxin_resp Pfam Desc:
                           Auxin response factor
REGION                     124..229
                           note = misc_feature - Pfam Name: B3 Pfam Desc: B3 DNA
                           binding domain
REGION                     1..657
                           note = misc_feature - Is Acted Upon By Ceres SEEDLINE ID
                           no. ME00572 at SEQ ID NO. 111
source                     1..657
                           mol_type = protein
                           organism = Sorghum bicolor
SEQUENCE: 246
MDAPNPAAAA GSGGMPSDAL YRELWHACAG PLVTVPRQGE RVYYFPQGHM EQLEASTHQQ    60
LDQYLPMFNL PPKILCSVVN VELRAEADSD EVYAQIMLQP EADQNELTSL DPEPQEPEKC   120
TAHSFCKTLT ASDTSTHGGF SVLRRHAEEC LPQLDMSLNP PCQELVAKDL HGTEWHFRHI   180
FRGQPKRHLL TTGWSVFVSS KRLVAGDAFI FMRGENGELR VGVRRLMRQV NSMPSSVISS   240
HSMHLGVLAT ASHAISTGTL FSVFYKPRTS RSDFIVSVNK YLEAKKQKIS VGMRFKMRFE   300
GDEAPERRFS GTIIGIGSLP AMSKSLWADS DWRSLKVQWD EPSSILRPDR ISPWEVEPLD   360
AANPQSPQPP PRPKRPRPPA SPCMVSELPS GFGLWKSPTE SSRTLSFSEP QRARELFPSI   420
PTSTFSSSSN VSFNSKNEPS MLTTQFYWSA RDTRADSCAA STNTVIVEKK QEPSSGGCRL   480
FGIDICSAEE EVLPVVTAPG VGYEQTAASV ELNSDKLSQG SDVNNSDAPA ASSERSPLES   540
QSRQVRSCTK VIMQGMAVGR AVDLTKLSGY SDLCQKLEEM FDIHGELGCT LKKWRVIFTD   600
DEDDMMLVGD DPWDEFCRMV KRIYIYTYEE AKKLTSKSKL PVSSDSSKLS AVNSLSE      657

SEQ ID NO: 247             moltype = AA  length = 831
FEATURE                    Location/Qualifiers
REGION                     1..831
                           note = misc_feature - Public GI ID no. 147770011
REGION                     1..831
                           note = misc_feature - Bit score of 909.6 for hmm based on
                           sequences of FIGURE 5.
REGION                     280..362
                           note = misc_feature - Pfam Name: Auxin_resp Pfam Desc:
                           Auxin response factor
REGION                     153..258
                           note = misc_feature - Pfam Name: B3 Pfam Desc: B3 DNA
                           binding domain
REGION                     1..831
                           note = misc_feature - Is Acted Upon By Ceres SEEDLINE ID
                           no. ME00572 at SEQ ID NO. 111
SITE                       606
                           note = misc_feature - Xaa is any aa, unknown, or other
source                     1..831
                           mol_type = protein
                           organism = Vitis vinifera
SEQUENCE: 247
MVAMIDLNTV DDDETPSSGS SSSSSSSASA SASTVCGSLL SAASSVCLEL WHACAGPLIS    60
LPKKGSLVVY FPQGHLEQLS DYPAVAYDLP PHVFCRVVDV KLHAEVVTDE VYAQVSLVPE   120
TKIKQKLQEG EIEADGGEEE DIEGSIKSMT PHMFCKTLTA SDTSTHGGFS VPRRAAEDCE   180
PPLDYKQQRP SQELVAKDLH GFEWRFRHIY RGQPRRHLLT TGWSAFVNKK KLVSGDAVLF   240
LRGGDGELRL GIRRAAQIKG SSPFPALCSQ QLNLNTLTAV VNAISTRSVF NICYNPRASS   300
SEFIIPLRKF SKSIDHSFSA GMRFKMRVET EDAAERRYTG LITGISDMDP VRWPGSKWRC   360
LLLHHSHGSE CVLLPCLPYY SDSATFFDLS LQVRWDDIEA NRHNRVSPWE IELSGSLSGS   420
GSLTVPGSKR TRIGLPGTRP DFSVPNGMGV SDFGESSRFQ KVLQGQEIFG FNTPYDGVDT   480
QDHHPSEIRC FPGSSCSRIA AIGNGVRNPL GNSDISYKGI GFGESFRFHK VLQGQTEFPS   540
PPCGRALSAN QAHENGSFGI FDGVQVPTSR NGWPALVQGY NAHTHLSTPS VQVSSPSSVL   600
MRRSKXLSNR SSFDIPEVYG EKLTPSRCEL SVRGGGQGGM NFFGLLNEHN QLAVPHPLVT   660
QSAFRGSQDL VPTCKSSCRL FGFSLTEERS IGNKVDNPTP VTSSLIPGTS FLPQQLHSEP   720
PVMTKAIGSN CTKRTAVVRS KLQPHKLGSV VDQAINRWKL DRHDDLICAL KHLFDMEGGL   780
LHGEGNDMHL SLTPAFYSPK SGLAEIQNGY PFANSYVRPV FPENRILDII I            831

SEQ ID NO: 248             moltype = DNA  length = 2049
FEATURE                    Location/Qualifiers
misc_feature               1..2049
                           note = Ceres Annot ID no. 8668727
misc_feature               1..2049
                           note = Encodes the peptide sequence at SEQ ID NO. 249
source                     1..2049
                           mol_type = other DNA
                           organism = Sorghum bicolor
SEQUENCE: 248
atgggaatcg atctcaacat ggtgggcggc gagggccacg atcgccgccc gccgccgccg    60
gtgagccggg agctgtggca cgcgtgcgcg gggcccgtgg tcgcgctacc gcggcggggg   120
agcctggtcg tgtacctgcc gcagggccac ctagccgcgg cggcggcgg ggacgtcgct    180
gcggacctgc cgccgcacgt ggtgtgccgc gtcgcggatg tcgagctatg cgcggatgcg   240
gcgacggacg aggtgtacgc gcggctgcg ctggttgcg aaggcgaggc atttggagat    300
aatctgcacg gcggcggagc tgaagggggac gatgacatgg aggatttgga tgctgaaagg   360
```

```
aagtcccgga tgttgcacat gttctgcaaa acgcttacag cctctgacac aagcacgcat    420
ggagggttct ctgttcctcg ccgtgctgct gaggactgtt tcccgcctct ggattataat    480
cagctcaggc cttctcaaga gctggttgcc aaggatttgc atggaactaa atggaagttt    540
cgtcatatat atagggggtca gcctcgtagg catctcttga ctactggatg gagttcattt    600
gtcaataaaa agaaactggt ttcagggggat gctgtgttat ttctccgagg tgatgatggt    660
gaactaaggc ttggtgtacg gagagccatt cagcttaaaa atgaggccct ttttgaagat    720
ttcagtagtg acagtacaaa gcggcataca ttgtcggctg tagctgattc cttgaagcac    780
agaagtgttt ttcacatttc ttacaatcca agagctactg cttcagaata tattattcca    840
taccataagt tcctgaagag cctcaatcat ccagtctgtg ttggagcaag gatcaacttt    900
cagtgccata atgaagatgt tagtgaaagg cgatctggaa tggttgttcg cattagtgaa    960
atagatccca tgaaatggcc tggctcgaag tggagaagcc tgctggtaag atgggaggat   1020
ggtgctgaat gtaacggcca agatagagta tctccatggg agatcgaggt agctggtggt   1080
tctgtctctg ttgctcattc tctgtccgca tctagttcta aaagaaccaa gttgtgtgct   1140
cagggaaatt tggacgttcc aacaatgtgg aatggttgta ctgatccgtc ggaaactgga   1200
aagttaccca gggtcttgca aggtcaagaa ttgatgggtt ttaggactcg tcatgttccg   1260
tgtgctcctc aaactgctga ggctgcaaaa cttcaatctt ctgatgctag taggtttctt   1320
agtaatgcac gtgactgcgc attgagtgct ccaacaagca gactcgcagt gcataactct   1380
ggttttacct accaatcgt aggcttcaat gaatctattg gattctcaga gttcttgcaa   1440
ggtcaagaaa tttctcgggc agttcctatg ttccaaggaa tgatgtctga ggcttgttca   1500
ctgaaaggcg gatatgggct acatagttat atgcataccc cagttgctgt taatggatta   1560
tcagccccag ctcaagaatg ttgtctgaca ctatctactc cgccaggagc acaagtgccc   1620
tctctctacc ctgataatat tttaaccga actgtggttc cgcagcttgg actggcaagc   1680
aagtttggtg gtggaggtac aaatggccag cagtctggcc catttgatag gcggagggaa   1740
atttggacca agccacagca tgaaacacct gatcaaatga acttggatca gtttgagact   1800
agaagagctt cagcacctgg agatgctggt aagcttgggt ctggtggagg ggaggttcgc   1860
aaaactagct gcagacttttt tggtttctcc ttgactgaga agatcttgcc agcagatgat   1920
gatggcgtca aggaagtgag ctatgagcct gagtgccaga acccacggat gctggatctg   1980
tttgggtaca actgctcaac cccgagtgct gctcttccgg ctctgtgtgc tgcccccatt   2040
ggaatgtga                                                           2049

SEQ ID NO: 249           moltype = AA  length = 682
FEATURE                  Location/Qualifiers
REGION                   1..682
                         note = misc_feature - Ceres Annot ID no. 8668727
REGION                   1..682
                         note = misc_feature - Bit score of 1041.4 for hmm based on
                           sequences of FIGURE 5.
REGION                   127..232
                         note = misc_feature - Pfam Name: B3 Pfam Desc: B3 DNA
                           binding domain
REGION                   254..335
                         note = misc_feature - Pfam Name: Auxin_resp Pfam Desc:
                           Auxin response factor
REGION                   1..682
                         note = misc_feature - Is Acted Upon By Ceres SEEDLINE ID
                           no. ME00572 at SEQ ID NO. 111
source                   1..682
                         mol_type = protein
                         organism = Sorghum bicolor
SEQUENCE: 249
MGIDLNMVGG EGHDRRPPPP VSRELWHACA GPVVALPRRG SLVVYLPQGH LAAAGGGDVA     60
ADLPPHVVCR VADVELCADA ATDEVYARLA LVAEGEAFGR NLHGGAEGD DDMEDLDAER    120
KSRMLHMFCK TLTASDTSTH GGFSVPRRAA EDCFPPLDYN QLRPSQELVA KDLHGTKWKF   180
RHIYRGQPRR HLLTTGWSSF VNKKKLVSGD AVLFLRGDDG ELRLGVRRAI QLKNEALFED   240
FSSDSTKRHT LSAVADSLKH RSVFHISYNP RATASEYIIP YHKFLKSLNH PVCVGARINF   300
QCHNEDVSER RSGMVVRISE IDPMKWPGSK WRSLLVRWED GAECNGQDRV SPWEIEVAGG   360
SVSVAHSLSA SSSKRTKLCA QGNLDVPTMW NGCTDSVETG KLPRVLQGQE LMGFRTRHVP   420
CAPQTAEAAK LQSSDASRFL SNARDCALSA PTSRLAVHNS GFTYQSVGFN ESIGFSEVLQ   480
GQEISRAVPM PQGMMSEACS LKGGYGLHSY MHTPVAVNGL SAPAQECCLT LSTPPGAQVP   540
SLYPDNIFNR TVVPQLGLAS KFGGGGTNGQ QSGPFDRRRE IWTKPQHETP DQMNLDQFET   600
RRASAPGDAG KLGSGGGEVR KTSCRLFGFS LTEKILPADD DGVKEVSYEP ECQNPRMLDL   660
FGYNCSTPSA ALPALCAAPI GM                                            682

SEQ ID NO: 250           moltype = AA  length = 670
FEATURE                  Location/Qualifiers
REGION                   1..670
                         note = misc_feature - Public GI ID no. 157354310
REGION                   1..670
                         note = misc_feature - Bit score of 1095.7 for hmm based on
                           sequences of FIGURE 5.
REGION                   246..329
                         note = misc_feature - Pfam Name: Auxin_resp Pfam Desc:
                           Auxin response factor
REGION                   119..224
                         note = misc_feature - Pfam Name: B3 Pfam Desc: B3 DNA
                           binding domain
REGION                   1..670
                         note = misc_feature - Is Acted Upon By Ceres SEEDLINE ID
                           no. ME00572 at SEQ ID NO. 111
```

```
source                  1..670
                        mol_type = protein
                        organism = Vitis vinifera
SEQUENCE: 250
MTCCCLLGAP CDALYKELWH ACAGPLVTVP REGERVYYFP QGHMEQLEAS TTHQGLDQQM   60
PSFNLPSKIL CKVVHVQLRA EPETDEVYAQ VTLLPEPDQS EITSPDPPLP EPQRCTVHSF  120
CKTLTASDTS THGGFSVLRR HADDCLPPLD MSQQPPWQEL VAADLHGNEW HFRHIFRGQP  180
RRHLLTTGWS VFVSSKKLVA GDAFIFLRGE NGELRVGVRR LMRQLSNMPS SVISSHSMHL  240
GVLATASHAI STGTLFSVFY KPRTSRSEFI VSLNKYLEAR NHKLSVGMRF KMRFEGEEVP  300
ERRFSGTIVG VGDKNTSSGW ADSEWRSLKV QWDEPASIFR PERVSAWELE PLVAAAAPTN  360
LQPAQRNKRA RPPVLPSATP DLSVLGMWKS SVESPSGFPY CDPHRGRDLY PSPKFSSITK  420
TNSFSFSGNS SPAAVSSNSM YWSNRMETAT ESFAPAVNKE SGEKRRDTGS GCRLFGFQLL  480
DNSTLEETLP VLTVGEDQPV PSLDVESDQH SEPSNINRSD IPSVSCEPDK LSLRSPQESQ  540
SRQIRSCTKV HMQGIAVGRA VDLTRFDRYE DLLKKLEEMF DIQGELCGLT SIWQVVYTDD  600
EDDMMMVGDD PWLEFCSMVR KIFIYTAEEV KRLSPKIKLP AMEEIKPGKL DSDVAVAGTD  660
DQSSVVGPGC                                                        670

SEQ ID NO: 251          moltype = DNA  length = 2721
FEATURE                 Location/Qualifiers
misc_feature            1..2721
                        note = Ceres Clone ID no. 1769972
misc_feature            1..2721
                        note = Encodes the peptide sequence at SEQ ID NO. 252
source                  1..2721
                        mol_type = other DNA
                        organism = Panicum virgatum
SEQUENCE: 251
attaatgggg tgctcatcct cctgacctcc tcgtcctccc cctcctctcc tcctcccgc    60
cgggtcgcgc tcggctccgc cttttaaccg ccttgccctg gaggggggccg agcggcggac  120
cgcacggacg cacgaccgcg gggggaccgg agcaggaccg ggaaccctag tggcggccgc  180
gcgcgccatg gcatcgatc tcaacatggt ggacggcgag ggcgaggagc ggcgcccccc   240
gccgccggtg tgccgggacc tgtggcacgc gtgcgcgggg cccgtagtcg cgctgccgcg  300
gcggggcagc ctcgtcgtgt acctgccgca gggccacctc gctgcggctg gcggcgggga  360
cgtcgcggcc gacctgccgc cgcacgtggt gtgccgcgtc gcggacatcg agctatgcgc  420
ggatgcggcg acggacgagg tgtacgcacg gctggccgtc gtggcggagg tgaggcatt   480
tgggagaaat gtgcgtgttg gtggagttga aggggacgag gacatggagg attttgatgc  540
tgaaaggaag tccggatgc tgcacatgtt ctgcaaaacg ctcactgcct ctgacacaag    600
cacgcatgga gggttctctg ttcctcgtcg agctgctgag gactgtttcc caccgctgga  660
ctataatcaa ctcaggcctt ctcaagagct tgttgccaag gatttgcatg gagccaagtg  720
gaagtttcgt catatttata ggggtcagcc tcgtaggcat ctcttaacaa ctggatggag  780
ttcatttgtc aataaaaaga aactggtttc aggggatgca gtcttatttc tccgaggtga  840
tgatggtgaa ctaagactgg tgtaaggag agctgttcag cttaaaaatg aggccctttt   900
tgaagaattc agtagcgaca gtgcaaagcg acatacgttg tctgctgtat ataattcctt  960
gaaacataaa agtgtctttc acatttctta caatccaaga gttgctgctt cagaatatat  1020
aattccttac cggaagttcc ttaagagcct caaccatcca gtctgtattg gagcgaggat  1080
caacttccaa tgccagaatg aagatgttag tgaaaggcga tctggaatgg ttgttggcaa  1140
tagtgaagta gatcccatga aatggcctgg ctcaaagtgg agaagcctgc tggtaagatg  1200
ggaggatggt tctgaatgca atggccaaga tagagtatct ccatgggaga tcgatatagt  1260
tggtggctca gtctctgctg cccattctct gtccgcatct agttctaaaa gaaccaagtt  1320
atgccctccg ggaaatttgg acgttccaac aatgtggaat ggttgtactg actccgtgga  1380
aactggaaag ttacccaggg tcttgcaagg tcaagaattg atgggttta ggactcatcg   1440
tgttacgtgt gctcctcaaa cagctgaggt tgcaaaattt caatcttctg atgctagtag  1500
gttccttact aatgcacgaa gctgcatgtt agtggtccaa acaggcagac ttgcagtaca  1560
gaactctggc tttacctacc aatctctggg cttcagtgaa tctattggat ctcagaggt   1620
cttgcaaggt caagaaattt ctcaggcagt cctatgttc caaggaataa tatctgcggc   1680
atgttcactg aagggcggat atgggctgcg tggttatgtg catacccag ctgctgttaa    1740
tggattatca gccacagctc aagaatgttc tctcacacta tgtactccac ctgcagcaca  1800
agtgccccct cctcatccca atcatatgtt taaccaaact gtgtcgtccc agcttggatt  1860
gggaaacaag tctgctggcg aagttgcaaa tggcagtcag cctcgcccat ttgatatgtc  1920
gtgggaagct cagaccaggc cacagcatga aatacctgct caaattagct tggatcaatt  1980
tgaggctagg agagcttcag cacctggaga tgctgctaaa attgggtctg tgggaaggga  2040
ggtgcgcaaa actagctgca ggcttttggg tttctcattg actgagaaga tcttgccagc  2100
tgatgatgat ggcgtgaagg aagtgagtta tgaggctgag tgccagaatc acggatgcc   2160
ggacttgttc gggtacaact gctccaccccc aagtgctgct cttccgctc tctgtgccgc   2220
cccttcgga atgtgatgct acttttagta tcttttcaag tattttcaag cactcagatt  2280
agacgtactt tccagtacc ccagtgtgtg cataagctgt cttttgacct cattccctcc   2340
attgcctgc tcatgttaat cagtcatctg cacgagtcaa ggaaggatga ttggtgaacc   2400
attcctctgc atggctcacc tggccaccca aagtatttatg gttgtgtatc gtgatatgca  2460
ccattgtaac tttgtggct atccttcaga cccattgtgc gatgaagcta acgatgtgcc   2520
ctaaaagtac ttcgctcaca gatttggatt catgggaagg tctgtcagct tgatgtacc   2580
ggttatgtgt ctttaactga gctcctgtat gactttgta gctcagtcat gagccgtgtt   2640
tgcactggtg cctaggtcgt gtgattgtat cagtatgtaa gactattgct tcgtttcaag  2700
atatgttgct tatggacctt t                                            2721

SEQ ID NO: 252          moltype = AA  length = 682
FEATURE                 Location/Qualifiers
REGION                  1..682
                        note = misc_feature - Ceres Clone ID no. 1769972
REGION                  1..682
```

```
                    note = misc_feature - Bit score of 1072.6 for hmm based on
                       sequences of FIGURE 5.
REGION              127..232
                    note = misc_feature - Pfam Name: B3 Pfam Desc: B3 DNA
                       binding domain
REGION              254..335
                    note = misc_feature - Pfam Name: Auxin_resp Pfam Desc:
                       Auxin response factor
REGION              1..682
                    note = misc_feature - Is Acted Upon By Ceres SEEDLINE ID
                       no. ME00572 at SEQ ID NO. 111
source              1..682
                    mol_type = protein
                    organism = Panicum virgatum
SEQUENCE: 252
MGIDLNMVDG EGEERRPPPA VCRDLWHACA GPVVALPRRG SLVVYLPQGH LAAAGGGDVA    60
ADLPPHVVCR VADIELCADA ATDEVYARLA LVAEGEAFGR NVRVGGVEGD EDMEDFDAER   120
KSRMLHMFCK TLTASDTSTH GGFSVPRRAA EDCFPPLDYN QLRPSQELVA KDLHGAKWKF   180
RHIYRGQPRR HLLTTGWSSF VNKKKLVSGD AVLFLRGDDG ELRLGVRRAV QLKNEALFEE   240
FSSDSAKRHT LSAVYNSLKH KSVFHISYNP RVAASEYIIP YRKFLKSLNH PVCIGARINF   300
QCQNEDVSER RSGMVVGNSE VDPMKWPGSK WRSLLVRWED GSECNGQDRV SPWEIDIVGG   360
SVSAAHSLSA SSSKRTKLCP PGNLDVPTMW NGCTDSVETG KLPRVLQGQE LMGFRTHRVT   420
CAPQTAEVAK FQSSDASRFL TNARSCMLSG PTGRLAVQNS GFTYQSLGFS ESIGFSEVLQ   480
GQEISQAVPM FQGMISAACS LKGGYGLRGY VHTPAAVNGL SATAQECSLT LCTPPAAQVP   540
PPHPNHMFNQ TVSSQLGLGN KSAGEVANGS QPRPFDMSWE AQTRPQHEIP AQISLDQFEA   600
RRASAPGDAA KIGSGGREVR KTSCRLFGFS LTEKILPADD DGVKEVSYEA ECQNPRMLDL   660
FGYNCSTPSA ALPALCAAPF GM                                           682

SEQ ID NO: 253             moltype = DNA  length = 2421
FEATURE                    Location/Qualifiers
misc_feature               1..2421
                           note = Ceres Annot ID no. 8460878
misc_feature               1..2421
                           note = Encodes the peptide sequence at SEQ ID NO. 254
source                     1..2421
                           mol_type = other DNA
                           organism = Solanum lycopersicum
SEQUENCE: 253
atggctactt ctgagaattg ccggaacgct gccggcgccg gaaaagttga tgctgagaaa    60
gcgttgtaca cggagctatg gcgagcatgt gcaggtccgc ttgtgacagt gccatgtgaa   120
ggcgagctgg tgttctattt cccacaaggt catattgaac aggttgaagc atcaacaaac   180
caagcttcag accagcagat gccagtatat aatcttcctt ctaagatcct ctgtcgtgtg   240
attaacgtcc tgctgaaggc tgaacccgat acagatgagg tgtatgcaca agtgacttta   300
ttgccagaac caaatcaaga tgagaatgtg gtatcaaagg aaccgatgcc ctctccgcca   360
ccacgattcc atgtgcactc tttttgtaag acattaacag cctctgatac cagcactcat   420
ggaggatttt ctgtcttgag acggcatgct gatgaatgcc tccgcctct ggttagaaag    480
aattctttct caatacagtt atggtgcctg tatttgata atcctccaac acaggagttg   540
gtggccaaag atttgcatgc aaatgagtgg cgcttcaggc acatattccg gggccagcct   600
aggaggcacc ttcttcagag tggttggagt gtctttgtta gttcgaaaag gcttgttgca   660
ggggatgcat tcatatttct tagaggtgag aatggggagc ttcgtgttgg agtccgacgt   720
gccatgagac agcagggtaa tgctccatca tcagtgatat ccagtcatag catgcatctt   780
ggtgtccttg ctacagcttg gcatgctatt cagacgaaaa cactgacgag ccctgctgac   840
tttatagttc catatgatca gtatatggag tctctgaaaa acaattactc catcgggatg   900
aggttttaaa tgaggtttga aggtgaagaa gctccagaac agaggtttac tggaactata   960
gttggcattg aaaatgctga cctcaaaagg tggcctgagt caaaatggaa atgcctgaag  1020
gttcgatggg atgaaacttc tgctattcct aggccagacc gagtttcacc ctggaaagta  1080
gagccagctc ttagccctcc tgcacttaat ccacttccaa taccaaggca gaaaaggccg  1140
cgatcaaatg ttctgccctc gtctcctgat tcttctgtac ttactaggga aggttcatcc  1200
aaagtagttg tagacacttc acaagccagt gggttttcaa gagttttgca aggtcaagaa  1260
atatcaaacct tgagaggcaa ttttgtagaa aataacgagt cggactcttc tgaagagcca  1320
cctatatggc aaccattact ggatgacgag aaggctgatg ttcattctgc gtcaaggaaa  1380
tgtatatcag ataaacggct tccttttaggg aggcctgaat catcttttac agatcttta   1440
tcaggttttg gggggcaatc tagttcatct catggattcc attcacccac tgggggccaa  1500
acagcacctg ctagctgggt taagcgacaa gctctggata aggaaactga tttcagctta  1560
ctggcaaaac aatggtctct agtgtcttct ggtctctcac ttaatctgat ggaatcagga  1620
ttgaagggtg cagatactct gtatcaaatg cgggaacat ctcgactcaa ttgttttaac    1680
gagtatccaa ccttccctgg tcatagacct gacaatcagc agggaaattg gttaatgccc  1740
ccgtccgtgc tgccttatat tcagatgtcc gctcattctg gagaaattat gcctaaaccc  1800
atggcttcac cacagcccga agccatgaaa cccaaagagg ggaactgcaa actatttggc  1860
attccccttg taagtaaatg tgccaccata gatcctgtca tgttgcggaa aaattccccg  1920
attcactcaa caagtaacat gcactttggt atacatccac atcaattccc tataattgaa  1980
tctgatcaaa ggtctgagca atcaaaggga tcaaagctac cagatgatgg cttcatagtt  2040
catgatcagg aagaacaatt ccaaacctct catcctggta ctcgagatag agagggcaaa  2100
ggccttgttc attcaacaag gagttgcacc aaggttcata aacagggtac agccccttga  2160
aggtctgttg atcttgcaaa gttcaacaac tatgaagaat tgatagctga actggatcac  2220
attttttgatt ttaatggtga gctcaaggct cgtaacaaga actggctgat ttttatctac  2280
acgaaagatg aggtgcagcg gatgaaccct gggactctca attcaaaagg cgaggacaat  2340
tcttctgttg cagaaggctc tgatgctaaa gaagtgaaga atctacagct tcacattgat  2400
tccagtccgg aagattctta g                                            2421
```

```
SEQ ID NO: 254          moltype = AA   length = 806
FEATURE                 Location/Qualifiers
REGION                  1..806
                        note = misc_feature - Ceres Annot ID no. 8460878
REGION                  1..806
                        note = misc_feature - Bit score of 1407.8 for hmm based on
                           sequences of FIGURE 5.
REGION                  266..340
                        note = misc_feature - Pfam Name: Auxin_resp Pfam Desc:
                           Auxin response factor
REGION                  127..244
                        note = misc_feature - Pfam Name: B3 Pfam Desc: B3 DNA
                           binding domain
REGION                  1..806
                        note = misc_feature - Is Acted Upon By Ceres SEEDLINE ID
                           no. ME00572 at SEQ ID NO. 111
source                  1..806
                        mol_type = protein
                        organism = Solanum lycopersicum
SEQUENCE: 254
MATSENCRNA AGAGKVDAEK ALYTELWRAC AGPLVTVPCE GELVFYFPQG HIEQVEASTN   60
QASDQQMPVY NLPSKILCRV INVLLKAEPD TDEVYAQVTL LPEPNQDENV VSKEPMPSPP  120
PRFHVHSFCK TLTASDTSTH GGFSVLRRHA DECLPPLVRK NSFSIQLWCL YFDNPPTQEL  180
VAKDLHANEW RFRHIFRGQP RRHLLQSGWS VFVSSKRLVA GDAFIFLRGE NGELRVGVRR  240
AMRQQGNAPS SVISSHSMHL GVLATAWHAI QTKTLTSPAD FIVPYDQYME SLKNNYSIGM  300
RFKMRFEGEE APEQRFTGTI VGIENADLKR WPESKWRCLK VRWDETSAIP RPDRVSPWKV  360
EPALSPPALN PLPIPRQKRP RSNVLPSSPD SSVLTREGSS KVVVDTSQAS GFSRVLQGQE  420
ISTLRGNFVE NNESDSSEKP PIWQPLLDDE KADVHSASRK CISDKRLPLG RPESSFTDLL  480
SGFGGQSSSS HGFHSPTGGQ TAPASWVKRQ ALDKETDFSL LAKQWSLVSS GLSLNLMESG  540
LKGADTLYQM RGTSRLNCFN EYPTFPGHRP DNQQGNWLMP PSVLPYIQMS AHSGEIMPKP  600
MASPQPEAMK PKEGNCKLFG IPLVSKCATI DPVMLRKNSP IHSTSNMHFG IHPHQFPIIE  660
SDQRSEQSKG SKLPDDGFIV HDQEEQFQTS HPGTRDREGK GLVHSTRSCT KVHKQGTALG  720
RSVDLAKFNN YEELIAELDH IFDFNGELKA RNKNWLIFIY TKDEVQRMNP GTLNSKGEDN  780
SSVAEGSDAK EVKNLQLHID SSPEDS                                      806

SEQ ID NO: 255          moltype = AA   length = 862
FEATURE                 Location/Qualifiers
REGION                  1..862
                        note = misc_feature - Public GI ID no. 157343873
REGION                  1..862
                        note = misc_feature - Bit score of 1864.9 for hmm based on
                           sequences of FIGURE 5.
REGION                  289..371
                        note = misc_feature - Pfam Name: Auxin_resp Pfam Desc:
                           Auxin response factor
REGION                  162..267
                        note = misc_feature - Pfam Name: B3 Pfam Desc: B3 DNA
                           binding domain
REGION                  1..862
                        note = misc_feature - Is Acted Upon By Ceres SEEDLINE ID
                           no. ME00572 at SEQ ID NO. 111
source                  1..862
                        mol_type = protein
                        organism = Vitis vinifera
SEQUENCE: 255
MASSEVSIKG NCGHGRGESF TSGYSEPNDG GVSRSVAEGQ KGHSSVSGAG KDFETALYTE   60
LWHACAGPLV TVPRERERVF YFPQGHIEQV EASTNQVSDQ QMPVYDLPSK ILCRVINVQL  120
KAEPDTDEVF AQVTLLPEPN QDETAQEKEP LPPPPPRPHV HSFCKTLTAS DTSTHGGFSV  180
LRRHADECLP QLDMSRQPPT QELVAKDLHG NEWRFRHIFR GQPRRHLLQS GWSVFVSSKR  240
LVAGDAFIFL RGENGELRVG VRRAMRQQGN VPSSVISSHS MHLGVLATAW HAKSTGTMFT  300
VYYKPRTSPA EFIVPFDQYM ESVKNNYSIG MRFKMRFEGE EAPEQRFTGT IVGIEDADPK  360
RWRDSKWRCL KVRWDETSTI PRPDRVSPWK IEPAVTPPAL NPLPVPRPKR PRSNMVPSUI  420
DSSVLTREGS SKVTVDPSPA SGFSRVLQGQ EFSTLRGTFA ESNESDTAEK SVVWPPLLDD  480
EKIDVVSTSR RFGSDNWMHL VRHEPTCTDL LSGFGARTDS SHGFSSFVDQ NDVAANTMKK  540
HLEHESKFNL LAGPWSMMPS GLSLNLLESS IKVPVQGSDM PYQTRGDARF GGFSEYPTLH  600
GHRVELQQGN WLMPPPAQSH FENFAHSREL MPKPILVQKQ EAVKPKDGNC KLFGIPLIGN  660
PVISEPAMSY RSMTNEPAGH LHLAPSAFDS DQKSEQSKGA KSTDNPLAVS EQEKPCQTSL  720
PLSRDVQGKV QSVSTRSCTK VHKQGIALGR SVDLTKFNNY DELIAELDQL FEFGGELMAP  780
KKNWLIVYTD DEGDMMLVGD DPWQEFCGMV RKIYIYTREE VQRMNPGTLN SKNDDNPSVA  840
EGMDAKEVKR QPVPLTSNLE NC                                          862

SEQ ID NO: 256          moltype = AA   length = 946
FEATURE                 Location/Qualifiers
REGION                  1..946
                        note = misc_feature - Public GI ID no. 147791931
REGION                  1..946
                        note = misc_feature - Bit score of 1795.4 for hmm based on
                           sequences of FIGURE 5.
```

| | | |
|---|---|---|
| REGION | 289..371 | |
| | note = misc_feature - Pfam Name: Auxin_resp Pfam Desc: Auxin response factor | |
| REGION | 162..267 | |
| | note = misc_feature - Pfam Name: B3 Pfam Desc: B3 DNA binding domain | |
| REGION | 1..946 | |
| | note = misc_feature - Is Acted Upon By Ceres SEEDLINE ID no. ME00572 at SEQ ID NO. 111 | |
| source | 1..946 | |
| | mol_type = protein | |
| | organism = Vitis vinifera | |

SEQUENCE: 256
```
MASSEVSIKG NCGHGRGESF TSGYSEPNDG GVSRSVAEGQ KGHSSVSGAG KDFETALYTE   60
LWHACAGPLV TVPRERERVF YFPQGHIEQV EASTNQVSDQ QMPVYDLPSK ILCRVINVQL  120
KAEPDTDEVF AQVTLLPEPN QDETAQEKEP LPPPPPRFHV HSFCKTLTAS DTSTHGGFSV  180
LRRHADECLP QLDMSRQPPT QELVAKDLHG NEWRFRHIFR GQPRRHLLQS GWSVFVSSKR  240
LVAGDAFIFL RGENGELRVG VRRAMRQQGN VPSSVISSHS MHLGVLATAW HAKSTGTMFT  300
VYYKPRTSPA EFIVPPFDQYM ESVKNNYSIG MRFKMRFEGE EAPEQRFTGT IVGIEDADPK  360
RWRDSKWRCL KVRWDETSTI PRPDRVSPWK IEPAVTPPAL NPLPVPRPKR PRSNMVPSSP  420
DSSVLTREGS SKVTVDPSPA SGFSRVLQGQ EFSTLRGTFA ESNESDTAEK SVVWPPLLDD  480
EKIDVVSTSR RFGSDNWMHL VRHEPTCTDL LSGFGARTDS SHGFSSFVDQ NDVAANTMKK  540
HLEHESKFNL LAGPWSMMPS GLSLNLLESS IKVPVQGSDM PYQTRGDARF GGFSEYPTLH  600
GHRVELQQGN WLMPPPAQSH FENFAHSREL MPKPILVQKQ EAVKPKDGNC KLFGIPLIGN  660
PVISEPAMSY RSMTNEPAGH LHLAPSAFDS DQKSEQSKGA KSTDNPLAVS EQEKPCQTSL  720
PLSRDVQGKV QSVSTRSCTK VCIHSLDGCW FLNNEYEIWK MLAGYKIVPQ ICFIAVSCLM  780
SIGNLVHKQG IALGRSVDLT KFNNYDELIA ELDQLFEFGG ELMAPKKNWL IVYTDDEGDM  840
MLVGDDPWQE FCGMVRKIYI YTREEVQRMN PGTLNSKNDD NPSVAEGMDA KEVKQKLAMV  900
VLVGRAIELI EMHKSLLPLL DRFLNGCTFG WFLFSGLWEA PVDDGF                 946
```

| | | |
|---|---|---|
| SEQ ID NO: 257 | moltype = DNA  length = 2124 | |
| FEATURE | Location/Qualifiers | |
| misc_feature | 1..2124 | |
| | note = Ceres Annot ID no. 8734042 | |
| misc_feature | 1..2124 | |
| | note = Encodes the peptide sequence at SEQ ID NO. 258 | |
| source | 1..2124 | |
| | mol_type = other DNA | |
| | organism = Sorghum bicolor | |

SEQUENCE: 257
```
atggcgggga tcgacctcaa cgacaccgtg gaggaggacg aggaggaggc ggagcccggc   60
aaccccgcct gctcccagca aagccggacc agctccgcgg ccacgccccc accccgccg  120
ctgaccccgc tgctccagcc gaggccgggc gccgccggt gcctcgagct ctggcacgcc  180
tgcgccggcc ccgtcgcgcc gctgccgcgg aaagggaccg tcgtcgtcta cctcccgcag  240
ggacacctgg agcacctcgg tgacgccgcc gcggccgcag ccgaggcgc gccggcgccc  300
gccgccctgc cgccccacgt cttctgccgc gtcgtcgacg tcactctcca tgcggacgcg  360
tccacgacgg aggtgtacgc ccagctcgcc ctcgtccgcg agaacgagga tgtcgcgagg  420
cggctgcgcg gagggtccga ggacgggagc gctgggggacg gcgacgacgg ggaggccgtg  480
aagcagcggt tctcgcggat gccgcacatg ttcctgcaaga gctcacggc ctccgacacc  540
agcacgcacg gcggcttctc cgtgccgcgc cgcgccgccg aggactgctt cccgcctctg  600
gactcagcc agcagcggcc gtcgcaggag ctttgtcgca aggatttgca cggaaccgag  660
tggaggttcc gccacattta cgaggccaa ccccgcaggc ccttttaac cactggatgg  720
agtgcatttg tcaacaagaa gaagcttgtc tcaggggacg ctgtactatt tttgagaggt  780
gatgatgggg agctaagact tggagtgcgc cgtgcagctc agcttaaaaa tggatctgct  840
tttccagctc ttttataatca gtgttctaat cttggttcac tagctaacgt agcacatgct  900
gtggccacaa aaagcgtgtt ccacatctac tacaacccca gattaagcca atctgaattc  960
attataccgt attcaaagtt tatgaagagc ttcagtcaac aatttctgc tggtttgagg 1020
ttcaaaatga gatatgagag tgatgatgct tctgaaagaa gatgcactgg ggtaatagca 1080
ggaattggtg atgctgaccc catgtggcgt ggttcgaagt ggaaatgttt gatgatccga 1140
tgggatgctg atgtagattt tcgtcgaccg aacaggattt ctccttggga gattgagctg 1200
actagttcag tttcaggatc ccatctgtct gcaccaaatg caaagagact caaaccatgt 1260
cttccccccgg actacctagt tccaaatgga agtggttgtc ctgattttgc ggaatctgcc 1320
caattccaca aggtcttgca aggtcaagaa ttattgggt atagaactcg tgacaatgct 1380
gctgtttgcaa cttctcaaac accactagga aaccctaggt tttcctacca ttgctcaggc 1440
tttgggagt ctccaagatt ccaaaaggtc ttgcaaggtc aagaagtatt caacccctac 1500
cgaggaactc tagtcgatcc aagtttgaga aatagtggct tcatcagca agatggttct 1560
catgtgccta ctcaagcgaa taagtggcat ccacagcttc atgggtgtgc ttttcgtggg 1620
acacaagcac cagctattcc atctcaatcc tcatcgccac catctgtcct aatgtttcaa 1680
cgagataatc caaagatgtc ccctttgaa tttgggcatt gtcacatgga taagaatgag 1740
gatatgcgtg caatgtttgg ccatgctgga ggtattggaa gaactgagca acaatgatg 1800
ctccaggctc ataatgtttc tggaggaatg ggaaatagag atgtgaccgt tgagaaattt 1860
cagccacact tgctgttgg aagggatgga tcagacaaca gggaagttac caaaaatagt 1920
tgcaaaatat ttggcatatc tttgactgag aaggttccag caatcaaaga aaggactgt 1980
ggtgatacca actatcctcc ccctcctcg tctctttgaagc aacacgtgcc aaaatcgctg 2040
ggcaacagtt gtgccactat tcatgagcag aggcctgttg ttggtagggt gattgatgtt 2100
tcaacagtgg atatgatgat ctga                                        2124
```

| | | |
|---|---|---|
| SEQ ID NO: 258 | moltype = AA  length = 707 | |
| FEATURE | Location/Qualifiers | |

-continued

```
REGION                  1..707
                        note = misc_feature - Ceres Annot ID no. 8734042
REGION                  1..707
                        note = misc_feature - Bit score of 1084.7 for hmm based on
                          sequences of FIGURE 5.
REGION                  297..378
                        note = misc_feature - Pfam Name: Auxin_resp Pfam Desc:
                          Auxin response factor
REGION                  170..275
                        note = misc_feature - Pfam Name: B3 Pfam Desc: B3 DNA
                          binding domain
REGION                  1..707
                        note = misc_feature - Is Acted Upon By Ceres SEEDLINE ID
                          no. ME00572 at SEQ ID NO. 111
source                  1..707
                        mol_type = protein
                        organism = Sorghum bicolor
SEQUENCE: 258
MAGIDLNDTV EEDEEEAEPG NPACSQQSRT SSAATPPPPP LTPLLQPRPG AAVCLELWHA   60
CAGPVAPLPR KGTVVVYLPQ GHLEHLGDAA AAAAGGAPAP AALPPHVFCR VVDVTLHADA  120
STDEVYAQLA LVAENEDVAR RLRGGSEDGS AGDGDDGEAV KQRFSRMPHM FCKTLTASDT  180
STHGGFSVPR RAAEDCFPPL DYSQQRPSQE LVAKDLHGTE WRFRHIYRGQ PRRHLLTTGW  240
SAFVNKKKLV SGDAVLFLRG DDGELRLGVR RAAQLKNGSA FPALYNQCSN LGSLANVAHA  300
VATKSVPHIY YNPRLSQSEF IIPYSKFMKS FSQQFSAGLR FKMRYESDDA SERRCTGVIA  360
GIGDADPMWR GSKWKCLMVR WDDDVDFRRP NRISPWEIEL TSSVSGSHLS APNAKRLKPC  420
LPPDYLVPNG SGCPDFAESA QFHKVLQGQE LLGYRTRDNA AVATSQTPLG NPRFSYHCSG  480
FGESPRFQKV LQGQEVFQPY RGTLVDPSLR NSGFHQQDGS HVPTQANKWH PQLHGCAFRG  540
TQAPAIPSQS SSPPSVLMFQ RDNPKMSPFE FGHCHMDKNE DMRAMFGHAG GIGRTEQTMM  600
LQAHNVSGGM GNRDVTVEKF QPTVAVGRDG SDNREVTKNS CKIFGISLTE KVPAIKEKDC  660
GDTNYPSPFL SLKQHVPKSL GNSCATIHEQ RPVVGRVIDV STVDMMI                707

SEQ ID NO: 259          moltype = AA  length = 687
FEATURE                 Location/Qualifiers
REGION                  1..687
                        note = misc_feature - Public GI ID no. 158564103
REGION                  1..687
                        note = misc_feature - Bit score of 984.1 for hmm based on
                          sequences of FIGURE 5.
REGION                  259..340
                        note = misc_feature - Pfam Name: Auxin_resp Pfam Desc:
                          Auxin response factor
REGION                  132..237
                        note = misc_feature - Pfam Name: B3 Pfam Desc: B3 DNA
                          binding domain
REGION                  1..687
                        note = misc_feature - Is Acted Upon By Ceres SEEDLINE ID
                          no. ME00572 at SEQ ID NO. 111
source                  1..687
                        mol_type = protein
                        note = subspecies = japonica
                        organism = Oryza sativa
SEQUENCE: 259
MGIDLNTVEE EAEEGAAAAV CGELWHACAG PGVALPRRGS ALVYLPQAHL AADGGGGEVP   60
PAGAAAVPPH VACRVVGVEL RADAATDEVY ARLAVAEGE MLQRNFREGG GEDGAGEMEG  120
CDAEKKPRMP HMFCKTLTAS DTSTHGGFSV PRRAAEDCEFP PLDYKTVRPS QELIAVDLHG  180
TQWKFRHIYR GQPRRHLLTI GWSSFVNRKK LVSGDAVLFL RGDDGQLRLG VRRAVQLRNE  240
ALFEPVNSSD SKLRILSSVA SSLENKSVPH ICFNPRSGAS EFIVPYWRLL KSLNHPFSIG  300
MRFRVCYESE DANERSAGLI SGISEVDPIR WPGSRWKCLL VRWDDSTDSS HQNRVSPWEI  360
ERVGGSVSVT HSLSSGSKRT KLHFPQGSLD TPFLNGNGHP DSMGTENFHR VLQGQEFRGS  420
RSHGVVCSES PGVPNFQSPD NRRFSADMRG YMMPASGPPQ RNTEFTYQPI GFSESLGFPE  480
VLQGQEMSQV VPLFRGATFG ARTQNDRVVS ANSVHRSAAQ SGLLASTLGH PISQFTLSSS  540
KVSSPSSVLM FNQATAPNHE TVSGTNNKGM HVSQFASQEM LSETVTWPGT QRQTPSEITS  600
NQFALARIPA PPSGAESGLP KRDAGRSSCR LFGFSLTGNM LGEDGEGLDD GAIEAGCENP  660
PVLELFGHSH STPGALHALC AAAPLGM                                      687

SEQ ID NO: 260          moltype = AA  length = 653
FEATURE                 Location/Qualifiers
REGION                  1..653
                        note = misc_feature - Public GI ID no. 157360302
REGION                  1..653
                        note = misc_feature - Bit score of 952.6 for hmm based on
                          sequences of FIGURE 5.
REGION                  243..322
                        note = misc_feature - Pfam Name: Auxin_resp Pfam Desc:
                          Auxin response factor
REGION                  116..221
                        note = misc_feature - Pfam Name: B3 Pfam Desc: B3 DNA
                          binding domain
REGION                  1..653
```

```
                    note = misc_feature - Is Acted Upon By Ceres SEEDLINE ID
                       no. ME00572 at SEQ ID NO. 111
     source          1..653
                    mol_type = protein
                    organism = Vitis vinifera
SEQUENCE: 260
MMVGFGGEGD  DLYAELWKAC  AGPLVDVPRR  GERVFYFPQG  HVEQLEASTN  QELSQRIPLF   60
NLPSKILCRV  IHIQLRAEQE  TDEVYAQITL  LPEPDQAEPR  SPDPCTPEPP  RPTVHSFCKV  120
LTASDTSTHG  GFSVLRKHAN  ECLPQLDMNQ  ATPTQELVAK  DLHGYEWRFK  HIFRGQPRRH  180
LLTTGWSTFV  TSKRLVAGDS  FVFLRGDNGE  LRVGVRRLAR  QQSTMPTSVI  SSQSMHLGVL  240
ATASHAVATQ  TLFIVYYKPR  TSQFIIGLNK  YLEAVSNGFA  VGMRFKMRFE  GEDSPERRFS  300
GTIVGGEDFS  PEWKDSEWRS  LKVQWDEPAS  IPRPEKVSPW  EIEHYVSSVP  QGLAPPGVLK  360
NKRPRSNESP  VPGSAAASAV  WHLGLTQSHD  LTQMSSTAEG  KRSENHQADI  GAIPPTEGSW  420
LSSSHVSASQ  HQFQDATEDS  KSVSAWPALS  GYSTLHSSKL  TSDTIIDPNG  NGKKAVAEMA  480
TSCRLFGFEL  MNHSSSPPVG  KAHGHSISSD  LSKASKEQKQ  GQSHVSPKEI  QSKQNCYSNT  540
RSRTKVQMQG  IAVGRAVDLT  ALEGYDELID  ELEEMFEIKG  ELRPRYKWEI  VFTDDEGDMM  600
LVGDDPWPEF  CNMVRRIFIC  SSQDVKKMSP  GSKLPISSME  GEGTTISLDS  TEN         653
```

NUCLEOTIDE SEQUENCES AND POLYPEPTIDES ENCODED THEREBY USEFUL FOR MODIFYING PLANT CHARACTERISTICS IN RESPONSE TO COLD

CROSS REFERENCE TO RELATED APPLICATIONS

This application is a divisional of application Ser. No. 16/829,740, filed on Mar. 25, 2020 (now U.S. Pat. No. 11,542,521), which application is a divisional of application Ser. No. 14/273,492, filed on May 8, 2014 (now issued as U.S. Pat. No. 10,689,661), which application is a Continuation of application Ser. No. 12/863,773, filed on Nov. 23, 2010 (now abandoned). Application Ser. No. 12/863,773 is the U.S. National Phase Application of International No. PCT/US2009/031609, filed on Jan. 21, 2009, which claims priority under 35 U.S.C. 119(c) to U.S. Provisional Application No. 61/022,786, filed on Jan. 22, 2008. The entire contents of all applications listed above are hereby incorporated by reference.

INCORPORATION-BY-REFERENCE OF SEQUENCE LISTING OR TABLE

The material in the accompanying sequence listing is hereby incorporated by reference into this application. The accompanying file, named 2007-11-27_2750-1707PUS1_Sequence Listing.txt was created on Nov. 27, 2007 and is 459 KB. The file can be accessed using Microsoft Word on a computer that uses Windows OS.

TECHNICAL FIELD

This document relates to methods and materials involved in modulating cold tolerance in plants, including growth levels in plants grown under low or chilling temperature stress conditions (a.k.a. "cold stress"). For example, this document provides plants having increased growth rate, vegetative growth, seedling vigor and/or biomass under cold stress conditions as compared to wild-type plants grown under similar conditions, as well as materials and methods for making plants and plant products having increased growth levels under cold stress conditions.

BACKGROUND

Plants are constantly exposed to a variety of biotic (i.e. pathogen infection and insect herbivory) and abiotic (i.e. high or low temperature, drought, flood and salinity) stresses. To survive these challenges to their sessile life, plants have developed elaborate mechanisms to perceive external signals and to manifest adaptive responses with proper physiological and morphological changes (Bohnert et al. 1995). Plants exposed to cold or chilling conditions typically have low yields of biomass, seeds, fruit and other edible products. The term "chilling sensitivity" is used for the description of physiological and developmental damages in the plant caused by low, but above freezing, temperatures. Important agricultural crop plants such as corn, soybean, rice and cotton have tropical ancestors that make them chilling sensitive. In some countries or agricultural regions of the world chilling temperatures are a significant cause of crop losses and a primary factor limiting the geographical range and growing season of many crop species. Another example is that chilling conditions can cause significant concern in early spring planting of corn or canola. Poor germination and reduced growth of chilling sensitive crops in the spring results in less ground coverage, more erosion and increased occurrence of weeds leading to less nutrient supply for the crop.

Typically, chilling damage includes wilting, necrosis or ion leakage from cell membranes, especially calcium leakage, and decreased membrane fluidity, which consequently impacts membrane dependent processes such as: photosynthesis, protein synthesis, ATPase activity, uptake of nitrogen, etc. (see Levitt J (1980) Chilling injury and resistance. In Chilling, Freezing, and High Temperature Stresses: Responses of Plant to Environmental Stresses, Vol 1., T T Kozlowsky, ed, Academic Press, New York, pp 23-64; Graham and Patterson (1982) *Annu Rev Plant Physiol* 33: 347-372; Guy (1990) *Annu Rev Plant Physiol Plant Mol Biol* 41: 187-223; and Nishida and Murata (1996) *Annu Rev Plant Physiol Plant Mol Biol* 47: 541-568.). In addition, cold temperatures are often associated with wet conditions. The combination of cold and wet can result in hypoxic stress on the roots, causing an even more severe reduction of growth rate but, more critically, can be lethal to the plants, especially sensitive plant species such as corn and cotton.

Yet it has been observed that environmental factors, such as low temperature, can serve as triggers to induce cold acclimation processes allowing plants responding thereto to survive and thrive in low temperature environments. It would, therefore, be of great interest and importance to be able to identify genes that regulate or confer improved cold acclimation characteristics to enable one to create transformed plants (such as crop plants) with improved cold tolerance characteristics such as faster germination and/or growth and/or improved nitrogen uptake under cold conditions to improve survival or performance under low or chilling temperatures.

In the fields of agriculture and forestry, efforts are constantly being made to produce plants with an increased growth potential in order to feed the ever-increasing world population and to guarantee the supply of reproducible raw materials. This is done conventionally through plant breeding. The breeding process is, however, both time-consuming and labor-intensive. Furthermore, appropriate breeding programs must be performed for each relevant plant species.

Progress has been made in part by the genetic manipulation of plants; that is by introducing and expressing recombinant nucleic acid molecules in plants. Such approaches have the advantage of not usually being limited to one plant species, but instead being transferable among plant species. There is a need for generally applicable processes that improve forest or agricultural plant growth potential. Therefore, the present invention relates to a method for increasing growth potential, decreasing chilling damage, and/or increasing levels of cold acclimation in plants under low temperature, chilling or cold conditions, characterized by expression of recombinant DNA molecules stably integrated into the plant genome.

SUMMARY

This document provides methods and materials related to plants having modulated levels of cold tolerance. For example, this document provides transgenic plants and plant cells having increased levels of cold tolerance, nucleic acids (i.e. isolated polynucleotides), polypeptides encoded thereby used to generate transgenic plants and plant cells having increased levels of cold tolerance, and methods for making plants and plant cells having increased levels of cold tolerance. Such plants and plant cells having increased biomass levels may be useful in producing biomass for conversion to a liquid fuel or other chemicals, or may be useful as a thermochemical fuel.

Methods of producing a plant and/or plant tissue are provided herein. In one aspect, a method comprises growing a plant cell comprising an exogenous nucleic acid. The exogenous nucleic acid comprises a regulatory region operably linked to a nucleotide sequence encoding a polypeptide. The Hidden Markov Model (HMM) bit score of the amino acid sequence of the polypeptide is greater than about 130, 180, 650, or 315, using an HMM generated from the amino acid sequences depicted in one of FIG. 1, 2, 3, or 4, respectively. The plant and/or plant tissue has a difference in the level of cold tolerance as compared to the corresponding level of cold tolerance of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence encoding a polypeptide having 80 percent or greater sequence identity to an amino acid sequence set forth in SEQ ID NOs: 2, 20, 74, or 93. A plant and/or plant tissue produced from the plant cell has a difference in the level of cold tolerance as compared to the corresponding level of cold tolerance of a control plant that does not comprise the exogenous nucleic acid.

In another aspect, a method comprises growing a plant cell comprising an exogenous nucleic acid. The exogenous nucleic acid comprises a regulatory region operably linked to a nucleotide sequence having 80 percent or greater sequence identity to a nucleotide sequence or at a fragment thereof set forth in SEQ ID NO: 1, 19, 92, 97, or 111. A plant and/or plant tissue produced from the plant cell has a difference in the level of cold tolerance as compared to the corresponding level of cold tolerance of a control plant that does not comprise the exogenous nucleic acid.

Methods of modulating the level of cold tolerance in a plant are provided herein. In one aspect, a method comprises introducing into a plant cell an exogenous nucleic acid, that comprises a regulatory region operably linked to a nucleotide sequence encoding a polypeptide. The HMM bit score of the amino acid sequence of the polypeptide is greater than about 130, 180, 650, 315 or 790 using an HMM generated from the amino acid sequences depicted in any one of FIG. 1, 2, 3, 4 or 5, respectively. A plant and/or plant tissue produced from the plant cell has a difference in the level of cold tolerance as compared to the corresponding level of cold tolerance of a control plant that does not comprise the exogenous nucleic acid.

In certain embodiments, the amino acid sequence of the polypeptide has an HMM score greater than about 180, using an HMM generated from the amino acid sequences depicted in FIG. 2, wherein the polypeptide comprises an CCT motif domain having 80 percent or greater sequence identity to amino acid residues 285 to 329 of SEQ ID NO: 20, residues 291 to 335 of SEQ ID NO: 22, residues 235 to 279 of SEQ ID NO: 24, residues 217 to 261 of SEQ ID NO: 26, residues 311 to 355 of SEQ ID NO: 28, residues 285 to 329 of SEQ ID NO: 29, residues 281 to 325 of SEQ ID NO: 30, residues 302 to 346 of SEQ ID NO: 32, residues 289 to 333 of SEQ ID NO: 34, residues 295 to 339 of SEQ ID NO: 36, residues 261 to 305 of SEQ ID NO: 38, residues 284 to 328 of SEQ ID NO: 40, residues 288 to 332 of SEQ ID NO: 42, residues 261 to 305 of SEQ ID NO: 43, residues 239 to 283 of SEQ ID NO: 44, residues 294 to 338 of SEQ ID NO: 45, residues 279 to 323 of SEQ ID NO: 46, residues 261 to 305 of SEQ ID NO: 47, residues 239 to 283 of SEQ ID NO: 48, residues 294 to 338 of SEQ ID NO: 49, residues 261 to 305 of SEQ ID NO: 50, residues 298 to 342 of SEQ ID NO: 51, residues 241 to 285 of SEQ ID NO: 52, residues 268 to 312 of SEQ ID NO: 53, residues 245 to 289 of SEQ ID NO: 54, residues 238 to 282 of SEQ ID NO: 56, residues 245 to 289 of SEQ ID NO: 58, residues 279 to 323 of SEQ ID NO: 59, residues 236 to 280 of SEQ ID NO: 60, residues 250 to 294 of SEQ ID NO: 61, residues 322 to 366 of SEQ ID NO: 62, residues 297 to 341 of SEQ ID NO: 63, residues 348 to 392 of SEQ ID NO: 64, residues 312 to 356 of SEQ ID NO: 65, residues 340 to 384 of SEQ ID NO: 68, residues 307 to 351 of SEQ ID NO: 69, or residues 253 to 297 of SEQ ID NO: 71.

In certain embodiments, the amino acid sequence of the polypeptide has an HMM score greater than about 180, using an HMM generated from the amino acid sequences depicted in FIG. 2, wherein the polypeptide comprises a B-box zinc finger domain having 80 percent or greater sequence identity to amino acid residues 56 to 103 of SEQ ID NO: 20, residues 62 to 109 of SEQ ID NO: 22, residues 64 to 106 of SEQ ID NO: 24, residues 34 to 81 of SEQ ID NO: 26, residues 63 to 110 of SEQ ID NO: 28, residues 56 to 103 of SEQ ID NO: 29, residues 56 to 103 of SEQ ID NO: 30, residues 60 to 107 of SEQ ID NO: 32, residues 56 to 103 of SEQ ID NO: 34, residues 51 to 98 of SEQ ID NO: 36, residues 70 to 112 of SEQ ID NO: 38, residues 51 to 98 of SEQ ID NO: 40, residues 52 to 99 of SEQ ID NO: 42, residues 72 to 114 of SEQ ID NO: 43, residues 62 to 104 of SEQ ID NO: 44, residues 50 to 97 of SEQ ID NO: 45, residues 55 to 102 of SEQ ID NO: 46, residues 72 to 114 of SEQ ID NO: 47, residues 62 to 104 of SEQ ID NO: 48, residues 50 to 97 of SEQ ID NO: 49, residues 27 to 71 of SEQ ID NO: 50, residues 60 to 107 of SEQ ID NO: 51, residues 1 to 48 of SEQ ID NO: 52, residues 1 to 48 of SEQ ID NO: 53, residues 1 to 48 of SEQ ID NO: 54, residues 62 to 104 of SEQ ID NO: 56, residues 64 to 106 of SEQ ID NO: 58, residues 1 to 48 of SEQ ID NO: 59, residues 61 to 103 of SEQ ID NO: 60, residues 70 to 112 of SEQ ID NO: 61, residues 52 to 99 of SEQ ID NO: 62, residues 51 to 98 of SEQ ID NO: 63, residues 77 to 119 of SEQ ID NO: 64, residues 59 to 106 of SEQ ID NO: 65, residues 59 to 106 of SEQ ID NO: 68, residues 34 to 66 of SEQ ID NO: 69, or residues 64 to 106 of SEQ ID NO: 71.

In certain embodiments, the amino acid sequence of the polypeptide has an HMM score greater than about 650, using an HMM generated from the amino acid sequences depicted in FIG. 3, wherein the polypeptide comprises an short-chain dehydrogenase domain having 80 percent or greater sequence identity to amino acid residues 38 to 173 of SEQ ID NO: 74, residues 37 to 174 of SEQ ID NO: 76, residues 23 to 160 of SEQ ID NO: 77, residues 7 to 168 of SEQ ID NO: 79, residues 43 to 179 of SEQ ID NO: 81, residues 49 to 188 of SEQ ID NO: 82, residues 48 to 187 of SEQ ID NO: 83, residues 37 to 172 of SEQ ID NO: 85, residues 35 to 170 of SEQ ID NO: 86, residues 20 to 160 of SEQ ID NO: 88, or residues 37 to 174 of SEQ ID NO: 90.

In certain embodiments, the amino acid sequence of the polypeptide has an HMM score greater than about 790, using an HMM generated from the amino acid sequences depicted in FIG. 5, wherein the polypeptide comprises a B3 DNA binding domain and an auxin response factor.

In another aspect, a method comprises introducing into a plant cell an exogenous nucleic acid that comprises a regulatory region operably linked to a nucleotide sequence encoding a polypeptide having 80 percent or greater sequence identity to an amino acid sequence set forth in SEQ ID NO: 2, 20, 74, 93 or 112. A plant and/or plant tissue produced from the plant cell has a difference in the level of cold tolerance as compared to the corresponding level of cold tolerance of a control plant that does not comprise the exogenous nucleic acid.

In another aspect, a method comprises introducing into a plant cell an exogenous nucleic acid, that comprises a regulatory region operably linked to a nucleotide sequence having 80 percent or greater sequence identity to a nucleotide sequence set forth in SEQ ID NO: 1, 19, 92, 97, or 111, or a fragment thereof. A plant and/or plant tissue produced from the plant cell has a difference in the level of cold tolerance as compared to the corresponding level of cold tolerance of a control plant that does not comprise the exogenous nucleic acid.

Methods of modulating the level of cold tolerance in a plant are provided herein. In one aspect, a method comprises introducing into a plant cell an exogenous nucleic acid, that comprises a regulatory region operably linked to a nucleotide sequence encoding a trans-activating small-interfering RNA (tasiRNA) that acts upon, e.g. suppresses expression of, an auxin responsive factor (ARF) polypeptide. The HMM bit score of the amino acid sequence of the ARF polypeptide is greater than about 790, using an HMM generated from the amino acid sequences depicted in FIG. 5. A plant and/or plant tissue produced from the plant cell has a difference in the level of cold tolerance as compared to the corresponding level of cold tolerance of a control plant that does not comprise the exogenous nucleic acid.

Plant cells comprising an exogenous nucleic acid are provided herein. In one aspect, the exogenous nucleic acid comprises a regulatory region operably linked to a nucleotide sequence encoding a tasiRNA. In some embodiments, the nucleotide sequence comprises a tasiRNA coding region having 80 percent or greater sequence identity to a nucleic acid sequence selected from the group consisting of residues 305 to about 346 of SEQ ID NO: 111, residues 21 to about 62 of SEQ ID NO: 66, residues 20 to about 61 of SEQ ID NO: 67, residues 21 to about 62 of SEQ ID NO: 72, residues 21 to about 62 of SEQ ID NO: 73, residues 77 to about 118 of SEQ ID NO: 144, residues 292 to about 313 of SEQ ID NO: 145, residues 37 to about 78 of SEQ ID NO: 146, residues 56 to about 97 of SEQ ID NO: 147, residues 37 to about 78 of SEQ ID NO: 148, residues 45 to about 86 of SEQ ID NO: 149, residues 46 to about 98 of SEQ ID NO: 150, residues 476 to about 497 of SEQ ID NO: 151, residues 21 to about 62 of SEQ ID NO: 152, residues 21 to about 62 of SEQ ID NO: 153, residues 21 to about 62 of SEQ ID NO: 154, residues 21 to about 62 of SEQ ID NO: 155, and residues 21 to about 62 of SEQ ID NO: 156, wherein a plant produced from said plant cell has a difference in the level of cold tolerance as compared to the corresponding level of cold tolerance of a control plant that does not comprise said nucleic acid. Transgenic plants comprising such plant cells are provided herein. In some embodiments, the transgenic plant comprises an exogenous nucleic acid having a sequence selected from the group consisting of SEQ ID NO: 66, 67, 72, 73, 111, 144, 145, 146, 147, 148, 149, 150, 151, 152, 153, 154, 155, and 156.

Methods of producing a plant and/or plant tissue are provided herein. In one aspect, a method comprises introducing into a plant cell an exogenous nucleic acid, said exogenous nucleic acid comprising a regulatory region operably linked to a nucleotide sequence encoding a gene suppressing tasiRNA, said nucleotide sequence comprising a tasiRNA coding region having 80 percent or greater sequence identity to a nucleic acid sequence selected from the group consisting of residues 305 to about 346 of SEQ ID NO: 111, residues 21 to about 62 of SEQ ID NO: 66, residues 20 to about 61 of SEQ ID NO: 67, residues 21 to about 62 of SEQ ID NO: 72, residues 21 to about 62 of SEQ ID NO: 73, residues 77 to about 118 of SEQ ID NO: 144, residues 292 to about 313 of SEQ ID NO: 145, residues 37 to about 78 of SEQ ID NO: 146, residues 56 to about 97 of SEQ ID NO: 147, residues 37 to about 78 of SEQ ID NO: 148, residues 45 to about 86 of SEQ ID NO: 149, residues 46 to about 98 of SEQ ID NO: 150, residues 476 to about 497 of SEQ ID NO: 151, residues 21 to about 62 of SEQ ID NO: 152, residues 21 to about 62 of SEQ ID NO: 153, residues 21 to about 62 of SEQ ID NO: 154, residues 21 to about 62 of SEQ ID NO: 155, and residues 21 to about 62 of SEQ ID NO: 156, wherein a plant produced from said plant cell has a difference in the level of cold tolerance as compared to the corresponding level of cold tolerance of a control plant that does not comprise said nucleic acid. In certain embodiments, the expression of a target ARF gene is suppressed in a plant. In some embodiments, the ARF gene encodes a polypeptide having 80 percent or greater sequence identity to an amino acid sequence selected from the group consisting of SEQ ID NO: 112, 114, 116, 117, 118, 119, 120, 121, 122, 123, 124, 125, 126, 127, 128, 130, 131, 132, 134, 136, 137, 138, 139, 141, and 143. In other embodiments, the ARF gene encodes a polypeptide and the HMM bit score of the amino acid sequence of said polypeptide is greater than about 790, said HMM based on the amino acid sequences depicted in FIG. 5. In other embodiments, the gene suppressing tasiRNA or its complement is complementary to RNA transcribed from said target ARF gene. In other embodiments, the nucleotide sequence encoding a gene suppressing tasiRNA comprises a microRNA recognition site having 80 percent or greater sequence identity to a nucleic acid sequence selected from the group consisting of residues 109 to about 129 of SEQ ID NO: 66, residues 114 to about 135 of SEQ ID NO: 67, residues 119 to about 139 of SEQ ID NO: 72, residues 108 to about 128 of SEQ ID NO: 73, residues 234 to about 254 of SEQ ID NO: 144, residues 135 to about 176 of SEQ ID NO: 145, residues 173 to about 189 of SEQ ID NO: 147, residues 154 to about 170 of SEQ ID NO: 148, residues 134 to about 157 of SEQ ID NO: 149, residues 154 to about 198 of SEQ ID NO: 150, residues 319 to about 360 of SEQ ID NO: 151, residues 121 to about 141 of SEQ ID NO: 152, residues 120 to about 140 of SEQ ID NO: 153, residues 121 to about 141 of SEQ ID NO: 154, residues 121 to about 141 of SEQ ID NO: 155, residues 121 to about 141 of SEQ ID NO: 156, and residues 462 to about 483 of SEQ ID NO: 111.

Plant cells comprising an exogenous nucleic acid are provided herein. In one aspect, the exogenous nucleic acid comprises a regulatory region operably linked to a nucleotide sequence encoding a polypeptide. The HMM bit score of the amino acid sequence of the polypeptide is greater than about 130, using an HMM based on the amino acid sequences depicted in one of FIG. 1, 2, 3, or 4. The plant and/or plant cells has a difference in the level of cold tolerance as compared to the corresponding level of cold tolerance of a control plant that does not comprise the exogenous nucleic acid. In another aspect, the exogenous nucleic acid comprises a regulatory region operably linked to a nucleotide sequence encoding a polypeptide having 80 percent or greater sequence identity to an amino acid sequence selected from the group consisting of SEQ ID NO: 2, 20, 93, or 74. A plant and/or plant tissue produced from the plant cell has a difference in the level of cold tolerance as compared to the corresponding level of cold tolerance of a control plant that does not comprise the exogenous nucleic acid. In another aspect, the exogenous nucleic acid comprises a regulatory region operably linked to a nucleotide sequence having 80 percent or greater sequence identity to a nucleotide sequence selected from the group consisting of SEQ ID NO: 1, 19, 92, 97, or 111. A plant and/or plant tissue produced from the plant cell has a difference in the level of cold tolerance as compared to the corresponding level of cold tolerance of a control plant that does not comprise the exogenous nucleic acid. A transgenic plant comprising such a plant cell is also provided. Also provided is a seed product. The product comprises embryonic tissue from a transgenic plant.

Isolated nucleic acids are also provided. In one aspect, an isolated nucleic acid comprises a nucleotide sequence having 80% or greater sequence identity to the nucleotide sequence set forth in SEQ ID NO: 3, 5, 7, 9, 11, 14, 16, 21, 23, 25, 27, 33, 35, 37, 39, 41, 55, 57, 70, 75, 80, 84, 87, 91, 92, 97, 105, 113, 115, 129, 133, 140, or 142.

In another aspect, an isolated nucleic acid comprises a nucleotide sequence encoding a polypeptide having 80% or greater sequence identity to the amino acid sequence set forth in SEQ ID NO: 4, 6, 8, 10, 12, 22, 24, 26, 28, 36, 38, 40, 42, 71, 74, 85, 88, 93, 105, 114, 116, 130, 134, 136, 141, or 143.

In another aspect, methods of identifying a genetic polymorphism associated with variation in the level of cold tolerance are provided. The methods include providing a population of plants, and determining whether one or more genetic polymorphisms in the population are genetically linked to the locus for a polypeptide selected from the group consisting of the polypeptides depicted in FIGS. 1, 2, 3, and 4 and functional homologs thereof, such as, but not limited to, those identified in the Sequence Listing. The correlation between variation in the level of cold tolerance in a tissue in plants of the population and the presence of the one or more genetic polymorphisms in plants of the population is measured, thereby permitting identification of whether or not the one or more genetic polymorphisms are associated with such variation.

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 is an alignment of Ceres SEEDLINE ID no. ME00327 with homologous and/or orthologous amino acid sequences Ceres SEEDLINE ID no. ME00327 (SEQ ID NO: 2), Ceres CLONE ID no. 1915941 (SEQ ID NO: 8), Ceres ANNOT ID no. 1461830 (SEQ ID NO: 10), Ceres CLONE ID no. 1080942 (SEQ ID NO: 15), and Ceres CLONE ID no. 1073190 (SEQ ID NO: 17). In all the alignment figures shown herein, a dash in an aligned sequence represents a gap, i.e., a lack of an amino acid at that position. Identical amino acids or conserved amino acid substitutions among aligned sequences are identified by boxes. FIG. 1 and the other alignment figures provided herein were generated using the program MUSCLE version 3.52.

Figure 2:
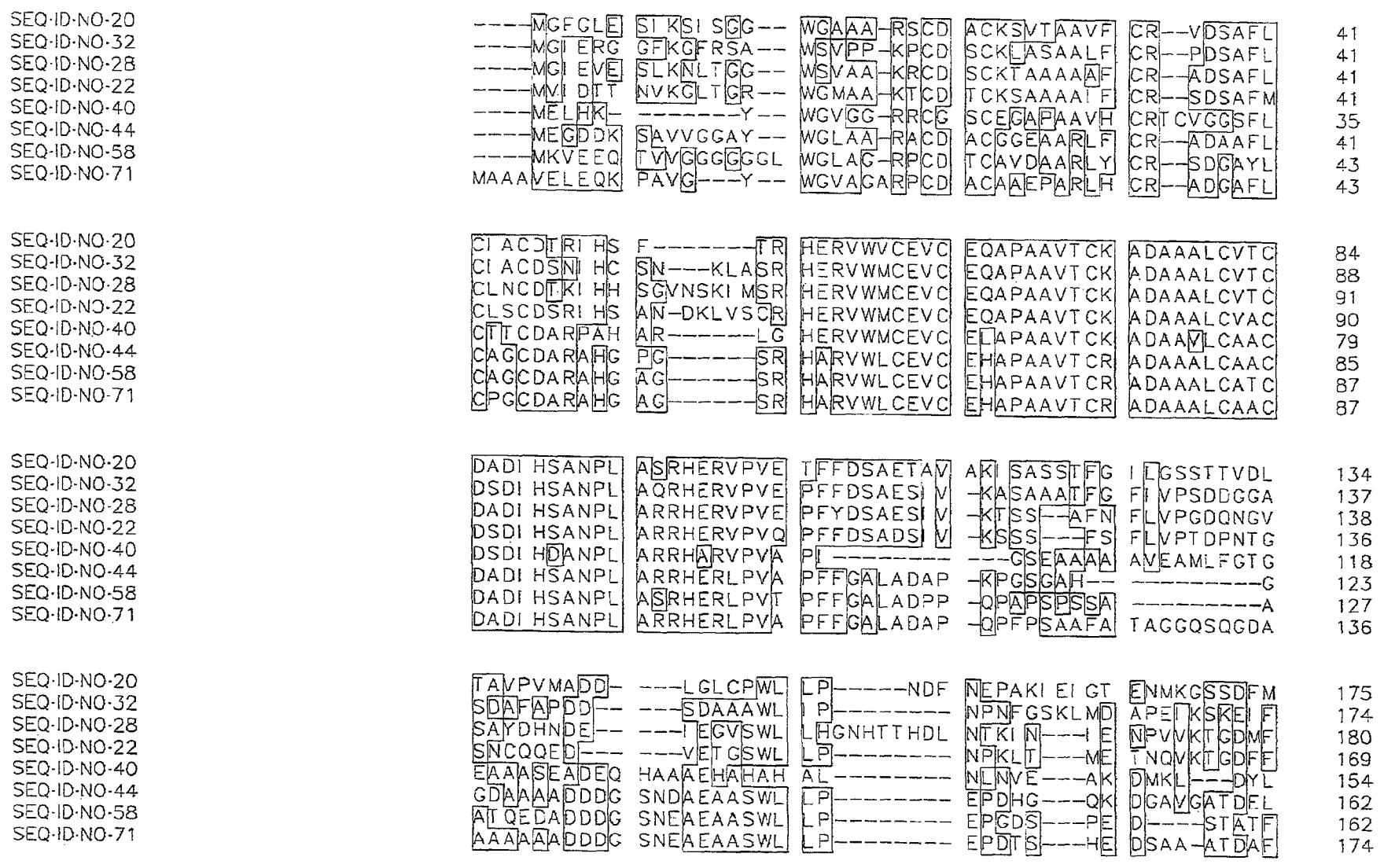
Figure 2:
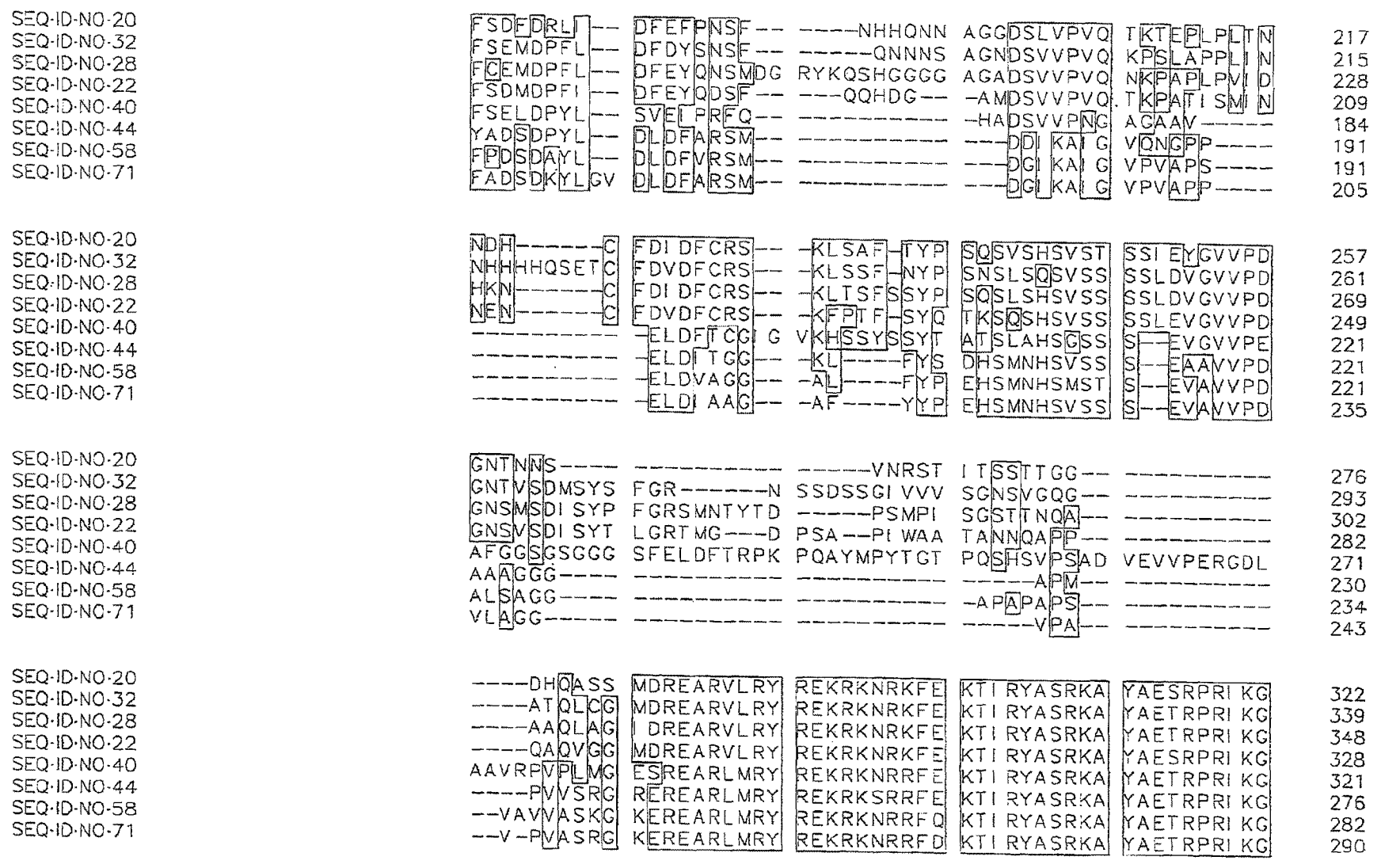

FIG. 2 is an alignment of Ceres SEEDLINE ID no. ME04315 (SEQ ID NO: 20) with homologous and/or orthologous amino acid sequences Ceres CLONE ID no. 1842825 (SEQ ID NO: 22), Ceres ANNOT ID no. 1482536 (SEQ ID NO: 28), Ceres CLONE ID no. 463157 (SEQ ID NO: 32), Ceres CLONE ID no. 1674443 (SEQ ID NO:40), GI ID no. 116310719 (SEQ ID NO: 44), Ceres CLONE ID no. 907473 (SEQ ID NO: 58), and Ceres CLONE ID no. 1755065 (SEQ ID NO: 71).

FIG. 3 is an alignment of full length homologous and/or orthologous amino acid sequences of Ceres SEEDLINE ID no. ME17294 (SEQ ID NO: 93), including Ceres CLONE ID no. 473040 (SEQ ID NO: 79), Ceres CLONE ID no. 922223 (SEQ ID NO: 81), GI ID no. 125528967 (SEQ ID NO: 82), GI ID no. 125573200 (SEQ ID NO: 83), Ceres ANNOT ID no. 1527409 (SEQ ID NO: 85), GI ID no. 92871098 (SEQ ID NO: 86), Ceres CLONE ID no. 1831117 (SEQ ID NO: 88), and Ceres ANNOT ID no. 857222 (SEQ ID NO: 90).

FIG. 4 is an alignment of a truncated version of Ceres SEEDLINE ID no. ME17294 (SEQ ID NO: 93) with homologous and/or orthologous amino acid truncated sequences, Ceres CLONE ID no. 1831117 (SEQ ID NO: 95), Ceres CLONE ID no. 1844076 (SEQ ID NO: 98), Ceres CLONE ID no. 473040 (SEQ ID NO:104), Ceres CLONE ID no. 922223 (SEQ ID NO: 106), and GI ID no. 125528967 (SEQ ID NO:107).

FIG. 5 is an alignment of functional homologs of the ARF (Auxin Response Factor) genes ARF2, ARF3, and ARF4, including LOCUS ID no. AT5G62000 (SEQ ID NO: 112), Ceres ANNOT ID no. 1527370 (SEQ ID NO: 114), Ceres ANNOT ID no. 1473961 (SEQ ID NO: 116), GI ID no. 62319853 (SEQ ID NO: 117), GI ID no. 62319903 (SEQ ID NO:118), GI ID no. 47716275 (SEQ ID NO: 119), GI ID no. 125534572 (SEQ ID NO:120), GI ID no. 26251300(SEQ ID NO:121), GI ID no. 115441981 (SEQ ID NO:123), GI ID no. 23893346 (SEQ ID NO:124), GI ID no. 115485689 (SEQ ID NO:125), GI ID no. 108864435 (SEQ ID NO:126), GI ID no. 50511471 (SEQ ID NO:127), LOCUS ID no. At2g33860 (SEQ ID NO:128), GI ID no. 2245390 (SEQ ID NO:131), GI ID no. 3228517 (SEQ ID NO:132), Ceres CLONE ID no. 827306 (SEQ ID NO: 134), Ceres CLONE ID no. 1598488 (SEQ ID NO: 136), GI ID no. 125553314 (SEQ ID NO:138), and Ceres CLONE ID no. 462443 (SEQ ID NO:143).

DETAILED DESCRIPTION

The invention features methods and materials related to modulating cold tolerance levels in plants. In some embodiments, the cold tolerance plants of the invention, under cold stress and/or cold flux conditions, have modulated levels of growth, cold acclimation, and/or cold damage. The methods can include transforming a plant cell with a nucleic acid encoding a cold tolerance modulating polypeptide, wherein expression of the polypeptide results in a modulated level of cold tolerance. Plant cells produced using such methods can be grown to produce plants having an increased cold tolerance. Such plants, and the seeds of such plants, may be used to produce, for example, plants and/or plant tissues having increased biomass.

I. DEFINITIONS

"Amino acid" refers to one of the twenty biologically occurring amino acids and to synthetic amino acids, including D/L optical isomers.

"Cell type-preferential promoter" or "tissue-preferential promoter" refers to a promoter that drives expression preferentially in a target cell type or tissue, respectively, but may also lead to some transcription in other cell types or tissues as well.

"Cold." Plant species vary in their capacity to tolerate low temperatures. Chilling-sensitive plant species, including many agronomically important species, can be injured by cold, above-freezing temperatures. At temperatures below the freezing-point of water most plant species will be damaged. Thus, "cold" can be defined as the temperature at which a given plant species will be adversely affected as evidenced by symptoms such as decreased photosynthesis and membrane damage (measured by electrolyte leakage). Since plant species vary in their capacity to tolerate cold, the precise environmental conditions that cause cold stress cannot be generalized. However, cold tolerant plants are characterized by their ability to retain their normal appearance, recover quickly from low temperature conditions, exhibit normal or increased growth under low temperature conditions, and/or have improved cold acclimation. Such cold tolerant plants produce higher biomass and/or yield than plants that are not cold tolerant. Differences in physical appearance, recovery and yield can be quantified and statistically analyzed using well known measurement and analysis methods.

"Control plant" refers to a plant that does not contain the exogenous nucleic acid present in a transgenic plant of interest, but otherwise has the same or similar genetic background as such a transgenic plant. A suitable control plant can be a non-transgenic wild type plant, a non-transgenic segregant from a transformation experiment, or a transgenic plant that contains an exogenous nucleic acid other than the exogenous nucleic acid of interest.

"Domains" are groups of substantially contiguous amino acids in a polypeptide that can be used to characterize protein families and/or parts of proteins. Such domains have a "fingerprint" or "signature" that can comprise conserved primary sequence, secondary structure, and/or three-dimensional conformation. Generally, domains are correlated with specific in vitro and/or in vivo activities. A domain can have a length of from 10 amino acids to 400 amino acids, e.g., 10 to 50 amino acids, or 25 to 100 amino acids, or 35 to 65 amino acids, or 35 to 55 amino acids, or 45 to 60 amino acids, or 200 to 300 amino acids, or 300 to 400 amino acids.

"Down-regulation" refers to regulation that decreases production of expression products (mRNA, polypeptide, or both) relative to basal or native states.

"Exogenous" with respect to a nucleic acid indicates that the nucleic acid is part of a recombinant nucleic acid construct, or is not in its natural environment. For example, an exogenous nucleic acid can be a sequence from one species introduced into another species, i.e., a heterologous nucleic acid. Typically, such an exogenous nucleic acid is introduced into the other species via a recombinant nucleic acid construct. An exogenous nucleic acid can also be a sequence that is native to an organism and that has been reintroduced into cells of that organism. An exogenous nucleic acid that includes a native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. It will be appreciated that an exogenous nucleic acid may have been introduced into a progenitor and not into the cell under consideration. For example, a transgenic plant containing an exogenous nucleic acid can be the progeny of a cross between a stably transformed plant and a non-transgenic plant. Such progeny are considered to contain the exogenous nucleic acid.

"Expression" refers to the process of converting genetic information of a polynucleotide into RNA through transcription, which is catalyzed by an enzyme, RNA polymerase, and into protein, through translation of mRNA on ribosomes.

"Heterologous polypeptide" as used herein refers to a polypeptide that is not a naturally occurring polypeptide in a plant cell, e.g., a transgenic *Panicum virgatum* plant transformed with and expressing the coding sequence for a nitrogen transporter polypeptide from a *Zea mays* plant.

"Isolated nucleic acid" as used herein includes a naturally-occurring nucleic acid, provided one or both of the sequences immediately flanking that nucleic acid in its naturally-occurring genome is removed or absent. Thus, an isolated nucleic acid includes, without limitation, a nucleic acid that exists as a purified molecule or a nucleic acid molecule that is incorporated into a vector or a virus. A nucleic acid existing among hundreds to millions of other nucleic acids within, for example, cDNA libraries, genomic libraries, or gel slices containing a genomic DNA restriction digest, is not to be considered an isolated nucleic acid.

"Modulation" of the level of a cold tolerance refers to the change in the level of the indicated compound or constituent that is observed as a result of expression of, or transcription from, an exogenous nucleic acid in a plant cell. The change in level is measured relative to the corresponding level in control plants.

"Nucleic acid" and "polynucleotide" are used interchangeably herein, and refer to both RNA and DNA, including cDNA, genomic DNA, synthetic DNA, and DNA or RNA containing nucleic acid analogs. Polynucleotides can have any three-dimensional structure. A nucleic acid can be double-stranded or single-stranded (i.e., a sense strand or an antisense strand). Non-limiting examples of polynucleotides include genes, gene fragments, exons, introns, messenger RNA (mRNA), transfer RNA, ribosomal RNA, siRNA, micro-RNA, ribozymes, cDNA, recombinant polynucleotides, branched polynucleotides, nucleic acid probes and nucleic acid primers. A polynucleotide may contain unconventional or modified nucleotides.

"Operably linked" refers to the positioning of a regulatory region and a sequence to be transcribed in a nucleic acid so that the regulatory region is effective for regulating transcription or translation of the sequence. For example, to operably link a coding sequence and a regulatory region, the translation initiation site of the translational reading frame of the coding sequence is typically positioned between one and about fifty nucleotides downstream of the regulatory region. A regulatory region can, however, be positioned as much as about 5,000 nucleotides upstream of the translation initiation site, or about 2,000 nucleotides upstream of the transcription start site.

"Polypeptide" as used herein refers to a compound of two or more subunit amino acids, amino acid analogs, or other peptidomimetics, regardless of post-translational modification, e.g., phosphorylation or glycosylation. The subunits may be linked by peptide bonds or other bonds such as, for example, ester or ether bonds. Full-length polypeptides, truncated polypeptides, point mutants, insertion mutants, splice variants, chimeric proteins, and fragments thereof are encompassed by this definition.

"Progeny" includes descendants of a particular plant or plant line. Progeny of an instant plant include seeds formed on $F_1$, $F_2$, $F_3$, $F_4$, $F_5$, $F_6$ and subsequent generation plants, or seeds formed on $BC_1$, $BC_2$, $BC_3$, and subsequent generation plants, or seeds formed on $F_1BC_1$, $F_1BC_2$, $F_1BC_3$, and subsequent generation plants. The designation $F_1$ refers to the progeny of a cross between two parents that are genetically distinct. The designations $F_2$, $F_3$, $F_4$, $F_5$ and $F_6$ refer to subsequent generations of self- or sib-pollinated progeny of an $F_1$ plant.

"Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, introns, and combinations thereof. A regulatory region typically comprises at least a core (basal) promoter. A regulatory region also may include at least one control element, such as an enhancer sequence, an upstream element or an upstream activation region (UAR). For example, a suitable enhancer is a cis-regulatory element (−212 to −154) from the upstream region of the octopine synthase (ocs) gene. Fromm et al., *The Plant Cell*, 1:977-984 (1989).

"Up-regulation" refers to regulation that increases the level of an expression product (mRNA, polypeptide, or both) relative to basal or native states.

"Vector" refers to a replicon, such as a plasmid, phage, or cosmid, into which another DNA segment may be inserted so as to bring about the replication of the inserted segment. Generally, a vector is capable of replication when associated with the proper control elements. The term "vector" includes cloning and expression vectors, as well as viral vectors and integrating vectors. An "expression vector" is a vector that includes a regulatory region.

II. POLYPEPTIDES

Polypeptides described herein include cold tolerance-modulating polypeptides. Cold tolerance-modulating polypeptides can be effective to modulate cold tolerance levels when expressed in a plant or plant cell. Such polypeptides typically contain at least one domain indicative of cold tolerance-modulating polypeptides, as described in more detail herein. Cold tolerance-modulating polypeptides typically have an HMM bit score that is greater than 130, as described in more detail herein. In some embodiments, cold tolerance-modulating polypeptides have greater than 80% identity to SEQ ID NOs: 2, 20, 74, 93 or 112, as described in more detail herein.

A. Domains Indicative of Cold Tolerance-Modulating Polypeptides

A cold tolerance-modulating polypeptide can contain a B-box zinc finger domain. The B-box zinc finger domain is often found associated with CCT motif. SEQ ID NO: 20 sets forth the amino acid sequence of an *Arabidopsis* clone, identified herein as Ceres SEEDLINE ID no. ME04315 (SEQ ID NO: 20), that is predicted to encode a polypeptide containing a CCT motif and a B-box zinc finger domain. A B-box zinc finger domain is typically around 40 amino acids in length. This motif is generally associated with a finger. It is found, for example, in transcription factors, ribonucleoproteins and protooncoproteins. It has been shown to be essential but not sufficient to localize the PML protein in a punctate pattern in interphase nuclei. Among the 7 possible ligands for the zinc atom contained in a B-box, only 4 are used and bind one zinc atom in a Cys2-His2 tetrahedral arrangement. The NMR analysis reveals that the B-box structure comprises two beta-strands, two helical turns and three extended loop regions different from any other zinc binding motif. A CCT motif can be found in a number of plant proteins. It is rich in basic amino acids and has been called a CCT motif after Co, Col and Toc1. The CCT motif is about 45 amino acids long and contains a putative nuclear localization signal within the second half of the CCT motif. Toc1 mutants have been identified in this region. The CCT (CONSTANS, CO-like, and TOC1) domain is a highly conserved basic module of ~43 amino acids, which is found near the C-terminus of plant proteins. The CCT domain is often found in association with other domains, such as the B-box zinc finger, the GATA-type zinc finger, the ZIM motif or the response regulatory domain. The CCT domain contains a putative nuclear localization signal within the second half of the CCT motif and has been shown to be involved in nuclear localization and probably also has a role in protein-protein interaction.

In embodiments of the invention, a cold tolerance-modulating polypeptide can comprise a CCT motif having 80% or greater sequence identity to amino acid residues 285 to 329 of SEQ ID NO: 20, residues 291 to 335 of SEQ ID NO: 22, residues 235 to 279 of SEQ ID NO: 24, residues 217 to 261 of SEQ ID NO: 26, residues 311 to 355 of SEQ ID NO: 28, residues 285 to 329 of SEQ ID NO: 29, residues 281 to 325 of SEQ ID NO: 30, residues 302 to 346 of SEQ ID NO: 32, residues 289 to 333 of SEQ ID NO: 34, residues 295 to 339 of SEQ ID NO: 36, residues 261 to 305 of SEQ ID NO: 38, residues 284 to 328 of SEQ ID NO: 40, residues 288 to 332 of SEQ ID NO: 42, residues 261 to 305 of SEQ ID NO: 43, residues 239 to 283 of SEQ ID NO: 44, residues 294 to 338 of SEQ ID NO: 45, residues 279 to 323 of SEQ ID NO: 46, residues 261 to 305 of SEQ ID NO: 47, residues 239 to 283 of SEQ ID NO: 48, residues 294 to 338 of SEQ ID NO: 49, residues 261 to 305 of SEQ ID NO: 50, residues 298 to 342 of SEQ ID NO: 51, residues 241 to 285 of SEQ ID NO: 52, residues 268 to 312 of SEQ ID NO: 53, residues 245 to 289 of SEQ ID NO: 54, residues 238 to 282 of SEQ ID NO: 56, residues 245 to 289 of SEQ ID NO: 58, residues 279 to 323 of SEQ ID NO: 59, residues 236 to 280 of SEQ ID NO: 60, residues 250 to 294 of SEQ ID NO: 61, residues 322 to 366 of SEQ ID NO: 62, residues 297 to 341 of SEQ ID NO: 63, residues 348 to 392 of SEQ ID NO: 64, residues 312 to 356 of SEQ ID NO: 65, residues 340 to 384 of SEQ ID NO: 68, residues 307 to 351 of SEQ ID NO: 69, or residues 253 to 297 of SEQ ID NO: 71.

In embodiments of the invention, a cold tolerance-modulating polypeptide can comprise a B-box zinc finger domain having 80% or greater sequence identity to amino acid residues 56 to 103 of SEQ ID NO: 20, residues 62 to 109 of SEQ ID NO: 22, residues 64 to 106 of SEQ ID NO: 24, residues 34 to 81 of SEQ ID NO: 26, residues 63 to 110 of SEQ ID NO: 28, residues 56 to 103 of SEQ ID NO: 29, residues 56 to 103 of SEQ ID NO: 30, residues 60 to 107 of SEQ ID NO: 32, residues 56 to 103 of SEQ ID NO: 34, residues 51 to 98 of SEQ ID NO: 36, residues 70 to 112 of SEQ ID NO: 38, residues 51 to 98 of SEQ ID NO: 40, residues 52 to 99 of SEQ ID NO: 42, residues 72 to 114 of SEQ ID NO: 43, residues 62 to 104 of SEQ ID NO: 44, residues 50 to 97 of SEQ ID NO: 45, residues 55 to 102 of SEQ ID NO: 46, residues 72 to 114 of SEQ ID NO: 47, residues 62 to 104 of SEQ ID NO: 48, residues 50 to 97 of SEQ ID NO: 49, residues 27 to 71 of SEQ ID NO: 50, residues 60 to 107 of SEQ ID NO: 51, residues 1 to 48 of SEQ ID NO: 52, residues 1 to 48 of SEQ ID NO: 53, residues 1 to 48 of SEQ ID NO: 54, residues 62 to 104 of SEQ ID NO: 56, residues 64 to 106 of SEQ ID NO: 58, residues 1 to 48 of SEQ ID NO: 59, residues 61 to 103 of SEQ ID NO: 60, residues 70 to 112 of SEQ ID NO: 61, residues 52 to 99 of SEQ ID NO: 62, residues 51 to 98 of SEQ ID NO: 63, residues 77 to 119 of SEQ ID NO: 64, residues 59 to 106 of SEQ ID NO: 65, residues 59 to 106 of SEQ ID NO: 68, residues 34 to 66 of SEQ ID NO: 69, or residues 64 to 106 of SEQ ID NO: 71.

A cold tolerance-modulating polypeptide can contain a short-chain dehydrogenase domain. The motif is present in SEQ ID NO: 93, which sets forth the amino acid sequence of an *Arabidopsis* clone, identified herein as Ceres SEED-LINE ID no. ME17294 (SEQ ID NO: 93), that is predicted to encode a polypeptide containing a short-chain dehydrogenase domain. The short-chain dehydrogenases/reductases family (SDR) is a very large family of enzymes, most of which are known to be NAD- or NADP-dependent oxidoreductases. As the first member of this family to be characterized was *Drosophila* alcohol dehydrogenase, this family used to be called 'insect-type', or 'short-chain' alcohol dehydrogenases. Most members of this family are proteins of about 250 to 300 amino acid residues.

In embodiments of the invention, a cold tolerance-modulating polypeptide can comprise a short-chain dehydrogenase domain having 80% or greater identity to amino acid residues 38 to 173 of SEQ ID NO: 74, residues 37 to 174 of SEQ ID NO: 76, residues 23 to 160 of SEQ ID NO: 77, residues 7 to 168 of SEQ ID NO: 79, residues 43 to 179 of SEQ ID NO: 81, residues 49 to 188 of SEQ ID NO: 82, residues 48 to 187 of SEQ ID NO: 83, residues 37 to 172 of SEQ ID NO: 85, residues 35 to 170 of SEQ ID NO: 86, residues 20 to 160 of SEQ ID NO: 88, or residues 37 to 174 of SEQ ID NO: 90.

In some embodiments, a cold tolerance-modulating polypeptide is truncated at the amino- or carboxy-terminal end of a naturally occurring polypeptide. A truncated polypeptide may retain certain domains of the naturally occurring polypeptide while lacking others. Thus, length variants that are up to 5, 10, 15, 20, 25, 30, 35, 40, 45, 50, 55, 60, 65, 70, 75, 80, 85, 90, 95, 100, 105, 110, 115, 120, 125, 130, 135, 140, 145, 150, 155, 160, 165, or 170 amino acids shorter or longer typically exhibit the cold tolerance-modulating activity of a truncated polypeptide. In some embodiments, a truncated polypeptide is a dominant negative polypeptide. SEQ ID NO: 93 sets forth the amino sequence of a cold tolerance-modulating polypeptide that is truncated at the amino-terminal end relative to a naturally occurring polypeptide. Expression in a plant and/or plant tissue of such a truncated polypeptide confers a difference in the level of cold tolerance in a plant and/or tissue of the plant as compared to the corresponding level in tissue of a control plant.

B. Functional Homologs Identified by Reciprocal BLAST

In some embodiments, one or more functional homologs of a reference cold tolerance-modulating polypeptide defined by one or more of the Pfam descriptions indicated above are suitable for use as cold tolerance-modulating polypeptides. A functional homolog is a polypeptide that has sequence similarity to a reference polypeptide, and that carries out one or more of the biochemical or physiological function(s) of the reference polypeptide. A functional homolog and the reference polypeptide may be natural occurring polypeptides, and the sequence similarity may be due to convergent or divergent evolutionary events. As such, functional homologs are sometimes designated in the literature as homologs, or orthologs, or paralogs. Variants of a naturally occurring functional homolog, such as polypeptides encoded by mutants of a wild type coding sequence, may themselves be functional homologs. Functional homologs can also be created via site-directed mutagenesis of the coding sequence for a cold tolerance-modulating polypeptide, or by combining domains from the coding sequences for different naturally-occurring cold tolerance-modulating polypeptides ("domain swapping"). The term "functional homolog" is sometimes applied to the nucleic acid that encodes a functionally homologous polypeptide.

Functional homologs can be identified by analysis of nucleotide and polypeptide sequence alignments. For example, performing a query on a database of nucleotide or polypeptide sequences can identify homologs of cold tolerance-modulating polypeptides. Sequence analysis can involve BLAST, Reciprocal BLAST, or PSI-BLAST analysis of nonredundant databases using a cold tolerance-modulating polypeptide amino acid sequence as the reference sequence. Amino acid sequence is, in some instances, deduced from the nucleotide sequence. Those polypeptides in the database that have greater than 40% sequence identity are candidates for further evaluation for suitability as a cold tolerance-modulating polypeptide. Amino acid sequence similarity allows for conservative amino acid substitutions, such as substitution of one hydrophobic residue for another or substitution of one polar residue for another. If desired, manual inspection of such candidates can be carried out in order to narrow the number of candidates to be further evaluated. Manual inspection can be performed by selecting those candidates that appear to have domains present in cold tolerance-modulating polypeptides, e.g., conserved functional domains.

Conserved regions can be identified by locating a region within the primary amino acid sequence of a cold tolerance-modulating polypeptide that is a repeated sequence, forms some secondary structure (e.g., helices and beta sheets), establishes positively or negatively charged domains, or represents a protein motif or domain. See, e.g., the Pfam web site describing consensus sequences for a variety of protein motifs and domains on the World Wide Web at sanger.ac.uk/Software/Pfam/ and pfam.janelia.org/. A description of the information included at the Pfam database is described in Sonnhammer et al., *Nucl. Acids Res.*, 26:320-322 (1998); Sonnhammer et al., *Proteins*, 28:405-420 (1997); and Bateman et al., *Nucl. Acids Res.*, 27:260-262 (1999). Conserved regions also can be determined by aligning sequences of the same or related polypeptides from closely related species. Closely related species preferably are from the same family. In some embodiments, alignment of sequences from two different species is adequate.

Typically, polypeptides that exhibit at least about 40% amino acid sequence identity are useful to identify conserved regions. Conserved regions of related polypeptides exhibit at least 45% amino acid sequence identity (e.g., at least 50%, at least 60%, at least 70%, at least 80%, or at least 90% amino acid sequence identity). In some embodiments, a conserved region exhibits at least 92%, 94%, 96%, 98%, or 99% amino acid sequence identity.

Examples of amino acid sequences of functional homologs of the polypeptide set forth in SEQ ID NO: 2 are provided in FIG. 1 and in the Sequence Listing. Such exemplary functional homologs include Ceres CLONE ID no. 1897908 (SEQ ID NO:4), Ceres CLONE ID no. 1938030 (SEQ ID NO: 6), Ceres CLONE ID no. 1915941 (SEQ ID NO: 8), Ceres ANNOT ID no. 1461830 (SEQ ID NO: 10), Ceres ANNOT ID no. 1439985 (SEQ ID NO: 12), GI ID no. 15241794 (SEQ ID NO: 13), Ceres CLONE ID no. 1080942 (SEQ ID NO:15), and Ceres CLONE ID no. 1073190 (SEQ ID NO:17). In some cases, a functional homolog of SEQ ID NO: 2 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2.

Examples of amino acid sequences of functional homologs of the polypeptide set forth in SEQ ID NO: 20 are provided in FIG. 2 and in the Sequence Listing. Such exemplary functional homologs include Ceres CLONE ID no. 1842825 (SEQ ID NO: 22), Ceres CLONE ID no. 1834027 (SEQ ID NO: 24), Ceres CLONE ID no. 1837064 (SEQ ID NO: 26), Ceres ANNOT ID no. 1482536 (SEQ ID NO: 28), GI ID no. 18424009 (SEQ ID NO: 29), GI ID no. 9759262 (SEQ ID NO: 30), Ceres CLONE ID no. 463157 (SEQ ID NO: 32), Ceres CLONE ID no. 685991 (SEQ ID NO: 34), Ceres CLONE ID no. 702632 (SEQ ID NO: 36), Ceres CLONE ID no. 1559496 (SEQ ID NO: 38), Ceres CLONE ID no. 1674443 (SEQ ID NO: 40), Ceres CLONE ID no. 1828897 (SEQ ID NO: 42), GI ID no. 125540249 (SEQ ID NO: 43), GI ID no. 116310719 (SEQ ID NO: 44), GI ID no. 125556324 (SEQ ID NO: 45), GI ID no. 125538317 (SEQ ID NO: 46), GI ID no. 115447239 (SEQ ID NO: 47), GI ID no. 115459216 (SEQ ID NO: 48), GI ID no. 115469296 (SEQ ID NO: 49), GI ID no. 125582846 (SEQ ID NO: 50), GI ID no. 92875402 (SEQ ID NO: 51), GI ID no. 3341723 (SEQ ID NO: 52), GI ID no. 4091806 (SEQ ID NO: 53), GI ID no. 60459257 (SEQ ID NO: 54), Ceres CLONE ID no. 1756710 (SEQ ID NO: 56), Ceres CLONE ID no. 907473 (SEQ ID NO: 58), GI ID no. 4091804 (SEQ ID NO: 59), GI ID no. 21667487 (SEQ ID NO: 60), GI ID no. 21655154 (SEQ ID NO: 61), GI ID no. 45544883 (SEQ ID NO: 62), GI ID no. 21655166 (SEQ ID NO: 63), GI ID no. 10946337 (SEQ ID NO: 64), GI ID no. 90657642 (SEQ ID NO: 65), GI ID no. 45544887 (SEQ ID NO: 68), GI ID no. 47606678 (SEQ ID NO: 69), or Ceres CLONE ID no. 1755065 (SEQ ID NO: 71). In some cases, a functional homolog of SEQ ID NO: 20 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 20.

Examples of amino acid sequences of full length functional homologs of the truncated polypeptide set forth in SEQ ID NO: 93 are provided in FIG. 3 and in the Sequence Listing. Such exemplary functional homologs include Ceres CLONE ID no. 1844076 (SEQ ID NO: 74), Ceres CLONE ID no. 35974 (SEQ ID NO: 76), GI ID no. 10176876 (SEQ ID NO: 77), Ceres CLONE ID no. 473040 (SEQ ID NO: 79), Ceres CLONE ID no. 922223 (SEQ ID NO: 81), GI ID no. 125528967 (SEQ ID NO: 82), GI ID no. 125573200 (SEQ ID NO: 83), Ceres ANNOT ID no. 1527409 (SEQ ID NO: 85), GI ID no. 92871098 (SEQ ID NO: 86), Ceres CLONE ID no. 1831117 (SEQ ID NO: 88), and Ceres ANNOT ID no. 857222 (SEQ ID NO: 90). In some cases, a full length functional homolog of SEQ ID NO: 93 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 74, 76, 77, 79, 81, 82, 83, 85, 86, 88, 90, or 93.

Examples of amino acid sequences of functional homologs of the polypeptide set forth in SEQ ID NO: 93 are provided in FIG. 4 and in the Sequence Listing. Such exemplary functional homologs include Ceres ANNOT ID no. 857222 (SEQ ID NO: 110), Ceres CLONE ID no. 1831117 (SEQ ID NO: 95), GI ID no. 92871098 (SEQ ID NO: 96), Ceres CLONE ID no. 1844076 (SEQ ID NO: 98), Ceres CLONE ID no. 35974 (SEQ ID NO: 100), GI ID no. 110737329 (SEQ ID NO: 101), GI ID no. 10176876 (SEQ ID NO: 102), Ceres CLONE ID no. 473040 (SEQ ID NO: 104), Ceres CLONE ID no. 922223 (SEQ ID NO: 106), GI ID no. 125528967 (SEQ ID NO: 107), and GI ID no. 115442007 (SEQ ID NO: 108). In some cases, a functional homolog of SEQ ID NO: 93 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 93.

Figure 5:
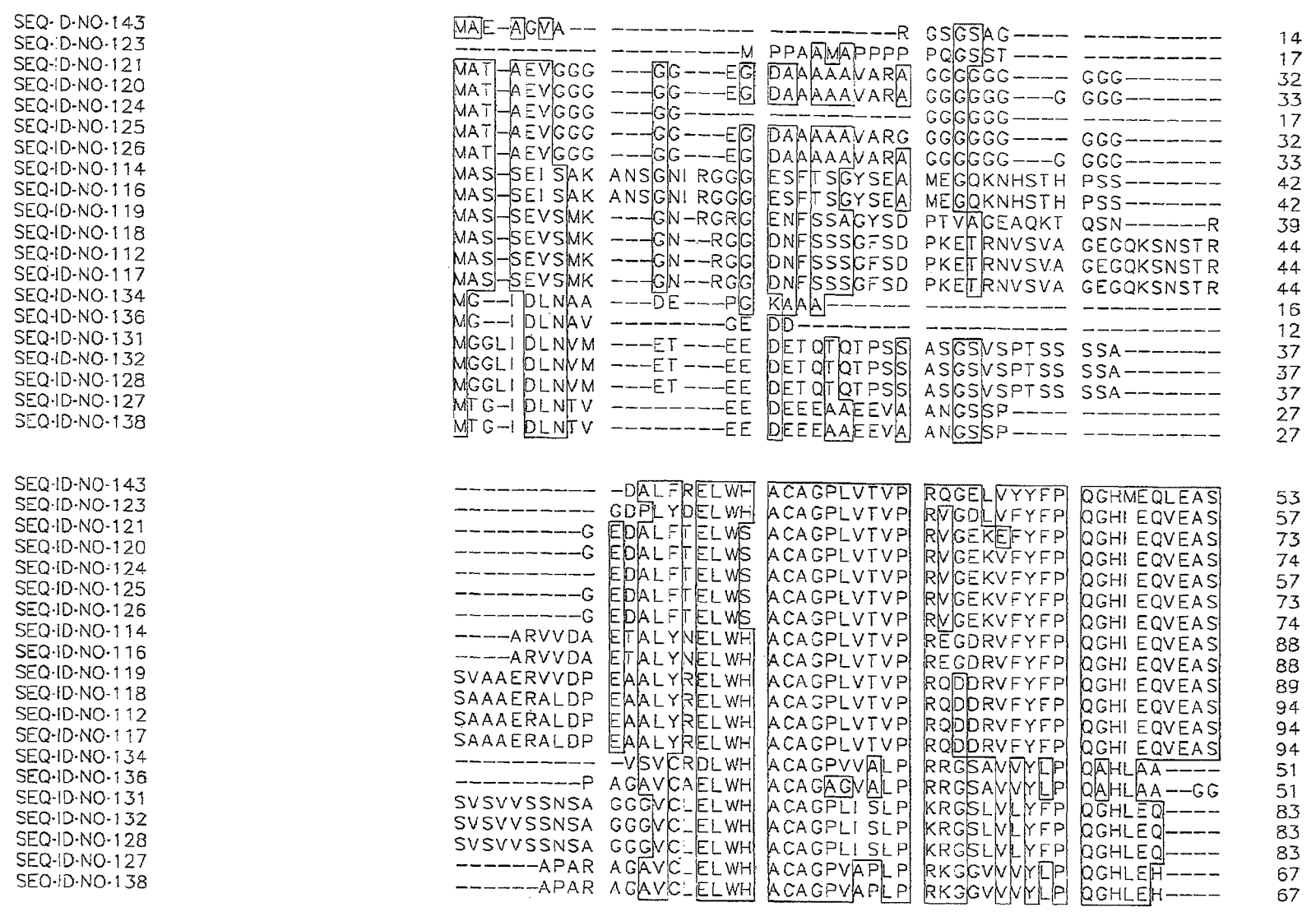
Figure 5:
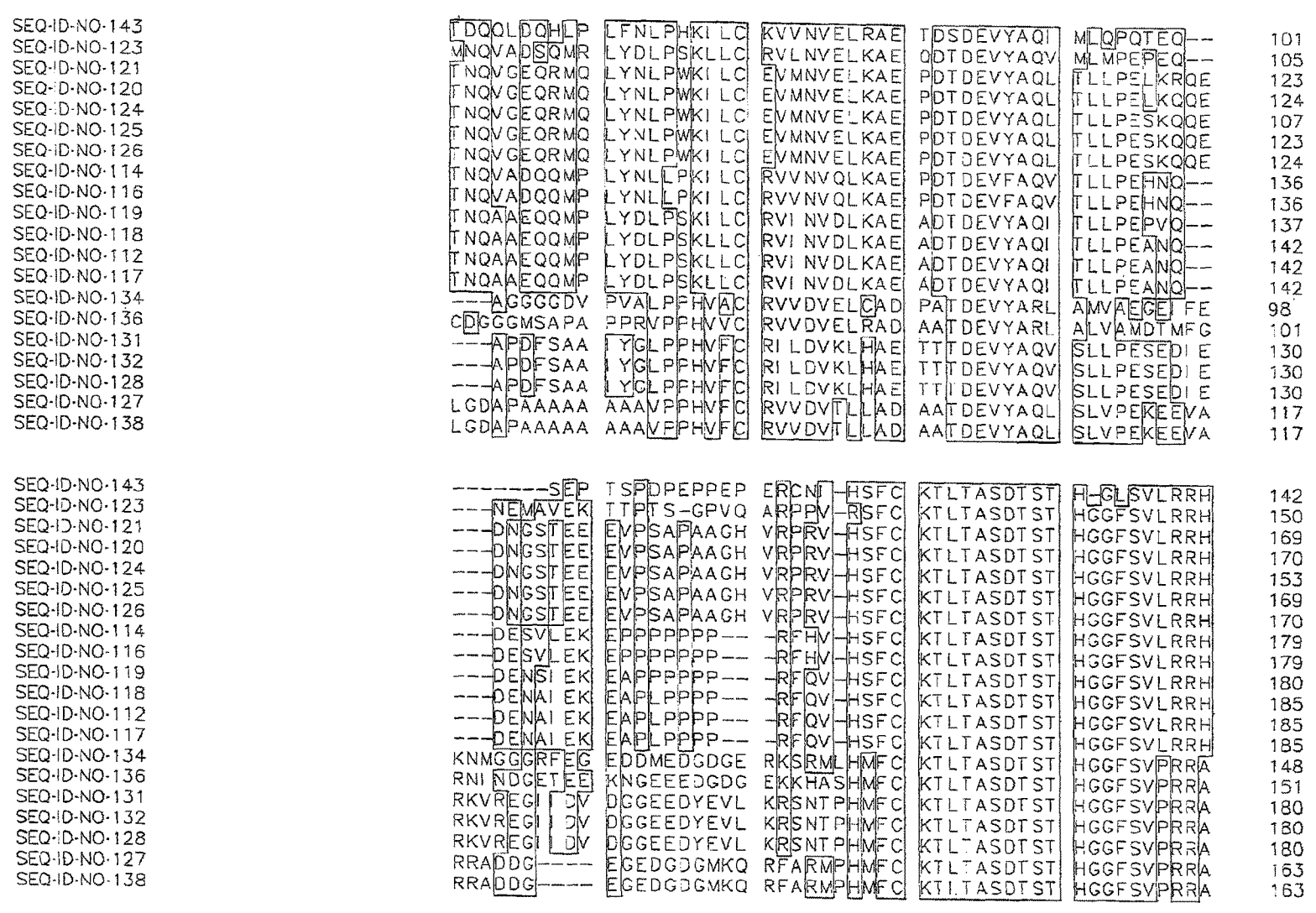
Figure 5:
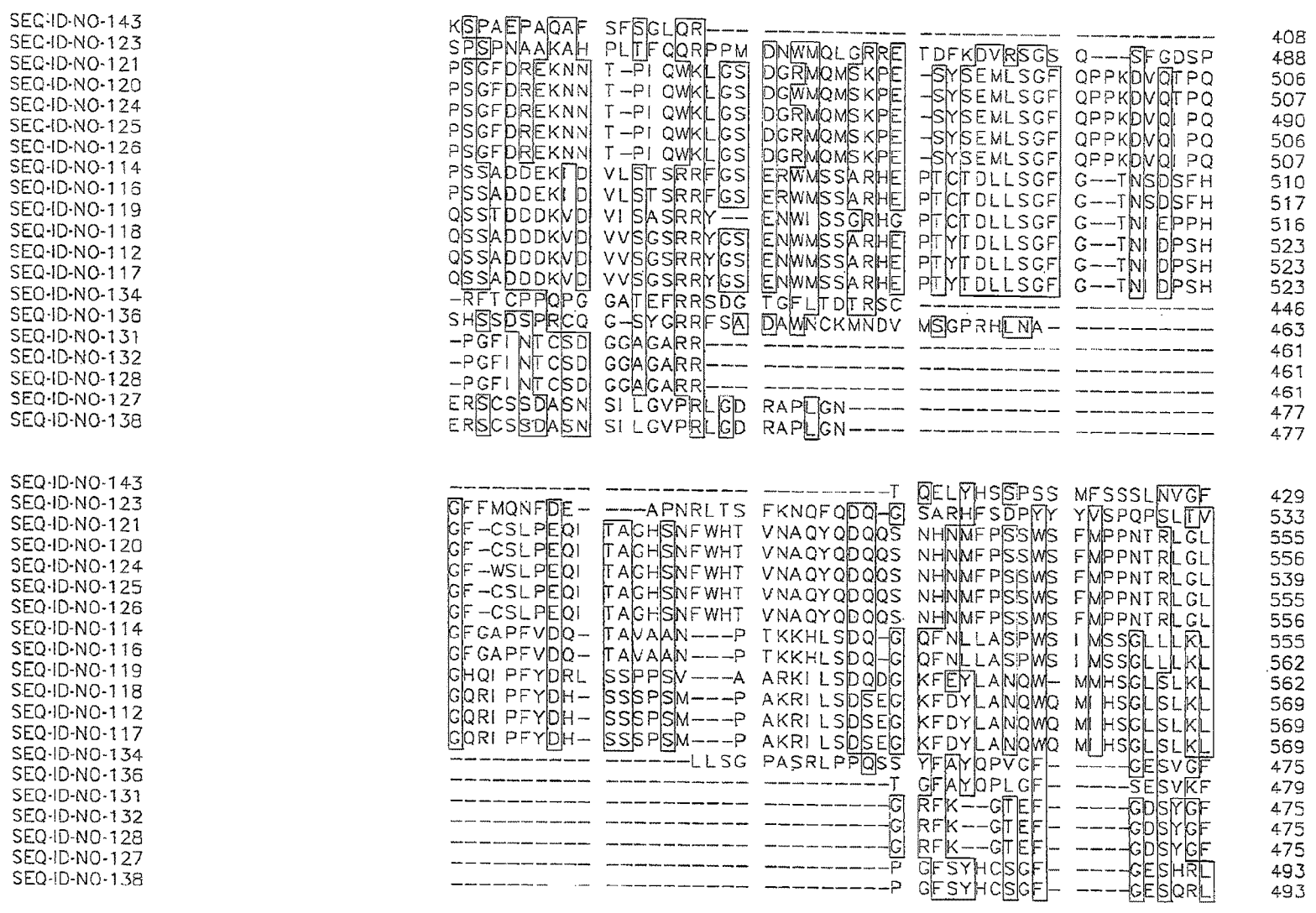
Figure 5:
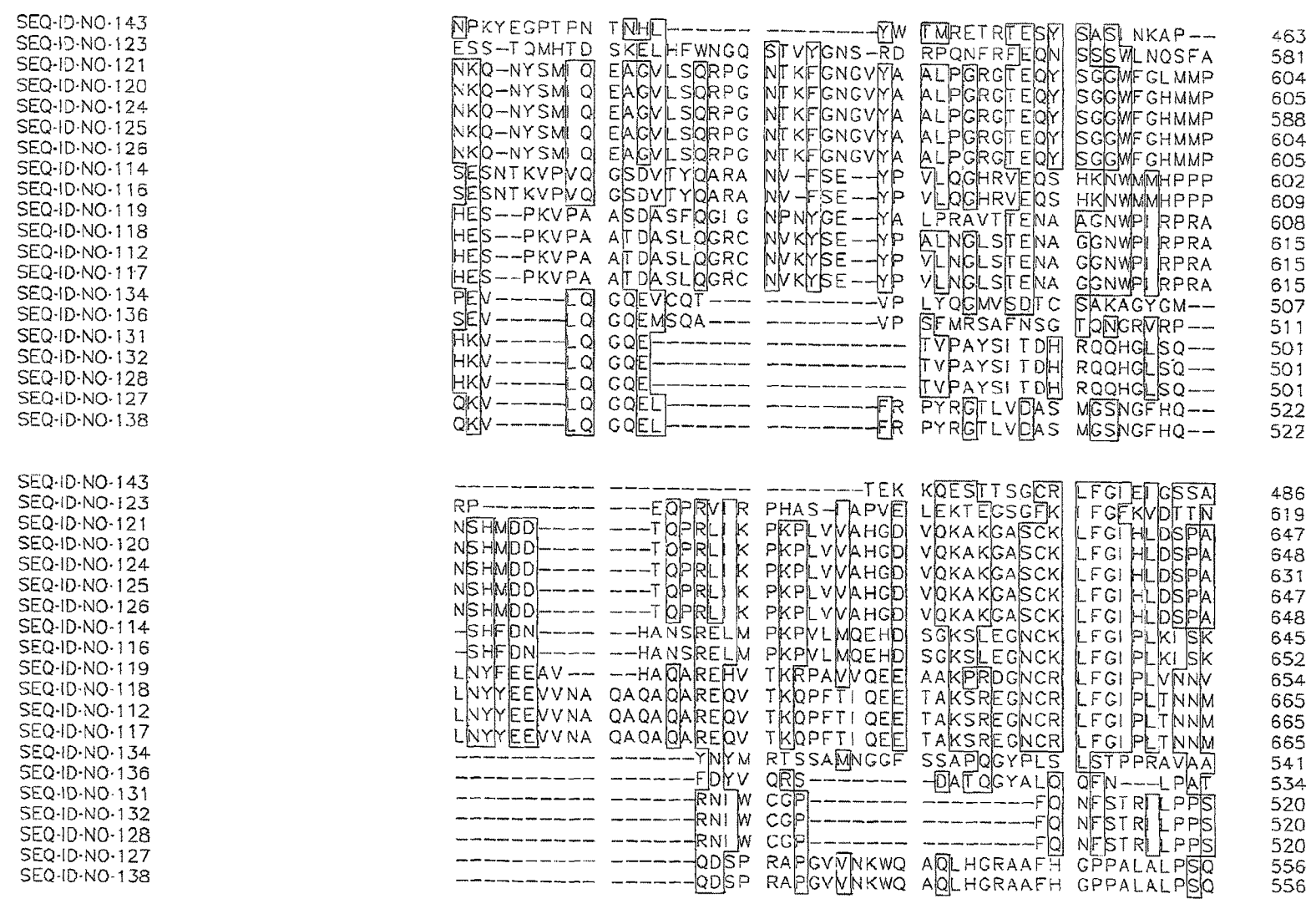
Figure 5:
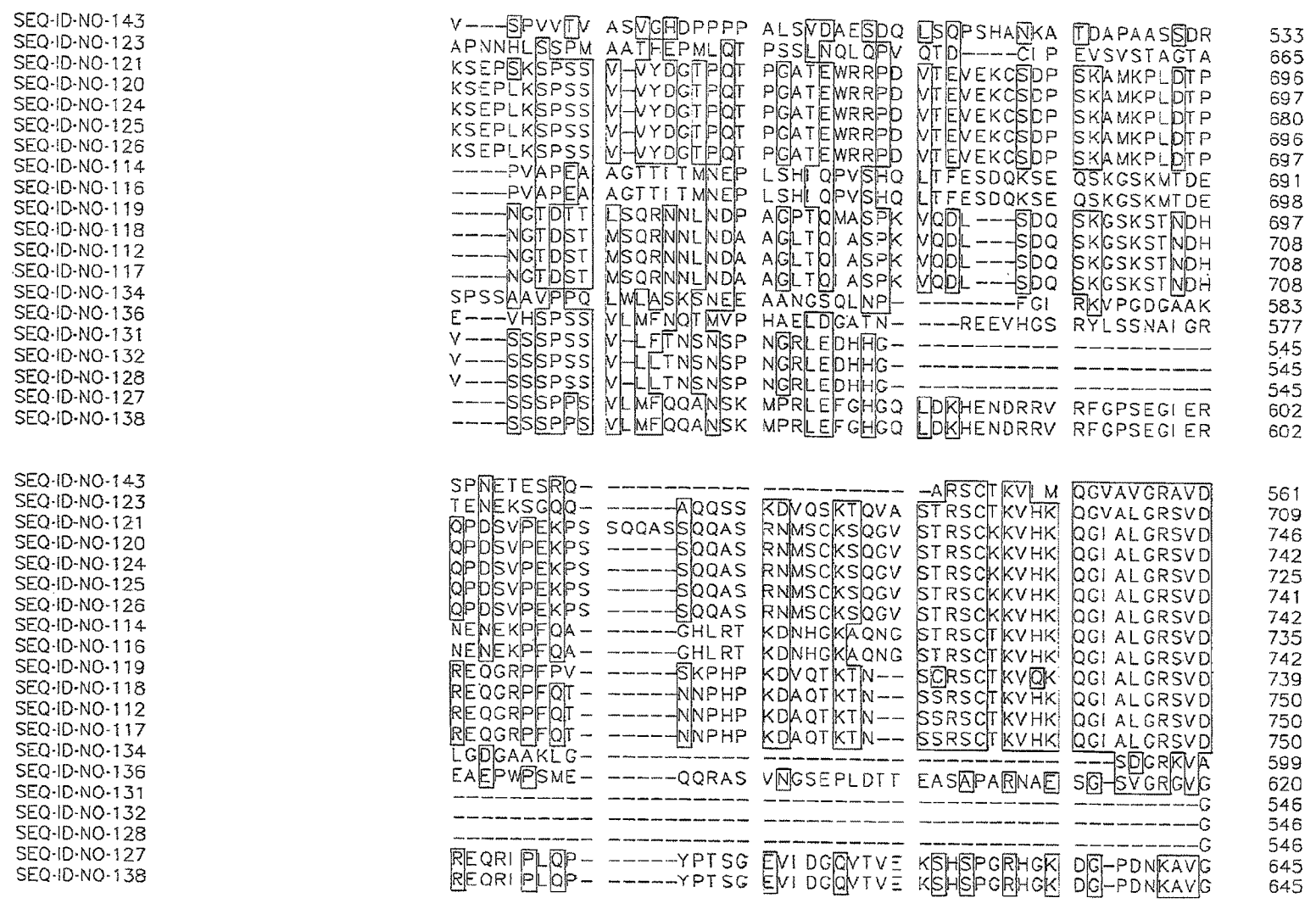
Figure 5:
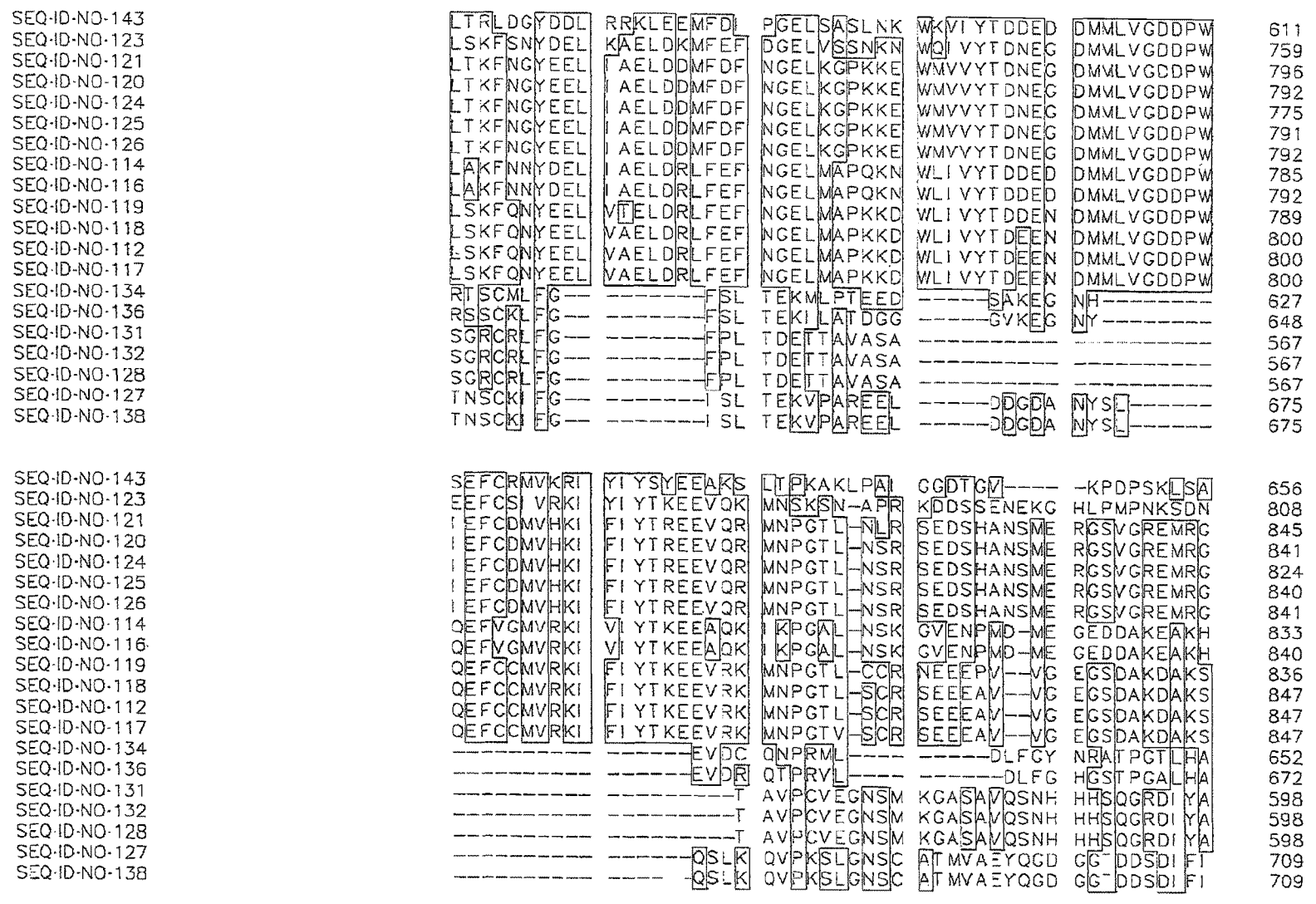

Examples of amino acid sequences of functional homologs of the polypeptide set forth in SEQ ID NO: 116 are provided in FIG. 5 and in the Sequence Listing. Such exemplary functional homologs include LOCUS ID no. AT5G62000 (SEQ ID NO: 112), Ceres ANNOT ID no. 1527370 (SEQ ID NO: 114), GI ID no. 62319853 (SEQ ID NO: 117), GI ID no. 62319903 (SEQ ID NO: 118), GI ID no. 47716275 (SEQ ID NO: 119), GI ID no. 125534572 (SEQ ID NO: 120), GI ID no. 26251300 (SEQ ID NO: 121), GI ID no. 125528952 (SEQ ID NO: 122), GI ID no. 115441981 (SEQ ID NO: 123), GI ID no. 23893346 (SEQ ID NO: 124), GI ID no. 115485689 (SEQ ID NO: 125), GI ID no. 108864435 (SEQ ID NO: 126), GI ID no. 50511471 (SEQ ID NO: 127), LOCUS ID no. At2g33860 (SEQ ID NO: 128), Ceres ANNOT ID no. 1536494 (SEQ ID NO: 130), GI ID no. 2245390 (SEQ ID NO: 131), GI ID no. 3228517 (SEQ ID NO: 132), Ceres CLONE ID no. 827306 (SEQ ID NO: 134), Ceres CLONE ID no. 1598488 (SEQ ID NO: 136), GI ID no. 125527740 (SEQ ID NO: 137), GI ID no. 125553314 (SEQ ID NO: 138), LOCUS ID no. At5g60450 (SEQ ID NO: 139), Ceres ANNOT ID no. 1515383 (SEQ ID NO: 141), and Ceres CLONE ID no. 462443 (SEQ ID NO: 143). In some cases, a functional homolog of SEQ ID NO: 116 has an amino acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the amino acid sequence set forth in SEQ ID NO: 116.

Examples of nucleic acid sequences of functional homologs of the tasiRNA encoding nucleic acid sequence set forth in SEQ ID NO: 111 are found in the Sequence Listing. Such exemplary functional homologs include 66, 67, 72, 73, 144, 145, 146, 147, 148, 149, 150, 151, 152, 153, 154, 155, and 156. In some cases, a functional homolog of SEQ ID NO: 111 has an nucleic acid sequence with at least 20% sequence identity, e.g., 25%, 30%, 35%, 40%, 45%, 50%, 52%, 56%, 59%, 61%, 65%, 70%, 75%, 80%, 85%, 90%, 95%, 97%, 98%, or 99% sequence identity, to the nucleic acid sequence set forth in SEQ ID NO: 111.

The identification of conserved regions in a cold tolerance-modulating polypeptide facilitates production of variants of cold tolerance-modulating polypeptides. Variants of cold tolerance-modulating polypeptides typically have 10 or fewer conservative amino acid substitutions within the primary amino acid sequence, e.g., 7 or fewer conservative amino acid substitutions, 5 or fewer conservative amino acid substitutions, or between 1 and 5 conservative substitutions. A useful variant polypeptide can be constructed based on one of the alignments set forth in FIG. 1, FIG. 2, FIG. 3, or FIG. 4 and/or homologs identified in the Sequence Listing. Such a polypeptide includes the conserved regions, arranged in the order depicted in the Figure from amino-terminal end to carboxy-terminal end. Such a polypeptide may also include zero, one, or more than one amino acid in positions marked by dashes. When no amino acids are present at positions marked by dashes, the length of such a polypeptide is the sum of the amino acid residues in all conserved regions. When amino acids are present at all positions marked by dashes, such a polypeptide has a length that is the sum of the amino acid residues in all conserved regions and all dashes.

C. Functional Homologs Identified by HMMER

In some embodiments, useful cold tolerance-modulating polypeptides include those that fit a Hidden Markov Model based on the polypeptides set forth in any one of FIGS. 1-4 or ARFs that are acted upon by tasiRNA (FIG. 5). A Hidden Markov Model (HMM) is a statistical model of a consensus sequence for a group of functional homologs. See, Durbin et al., *Biological Sequence Analysis: Probabilistic Models of Proteins and Nucleic Acids*, Cambridge University Press, Cambridge, UK (1998). An HMM is generated by the program HMMER 2.3.2 with default program parameters, using the sequences of the group of functional homologs as input. The multiple sequence alignment is generated by ProbCons (Do et al., Genome Res., 15(2):330-40 (2005)) version 1.11 using a set of default parameters: -c, - -consistency REPS of 2; -ir, - -iterative-refinement REPS of 100; -pre, - -pre-training REPS of 0. ProbCons is a public domain software program provided by Stanford University.

The default parameters for building an HMM (hmmbuild) are as follows: the default "architecture prior" (archpri) used by MAP architecture construction is 0.85, and the default cutoff threshold (idlevel) used to determine the effective sequence number is 0.62. HMMER 2.3.2 was released Oct. 3, 2003 under a GNU general public license, and is available from various sources on the World Wide Web such as hmmer.janelia.org; hmmer.wustl.edu; and fr.com/hmmer232/. Hmmbuild outputs the model as a text file.

The HMM for a group of functional homologs can be used to determine the likelihood that a candidate cold tolerance-modulating polypeptide sequence is a better fit to that particular HMM than to a null HMM generated using a group of sequences that are not structurally or functionally related. The likelihood that a candidate polypeptide sequence is a better fit to an HMM than to a null HMM is indicated by the HMM bit score, a number generated when the candidate sequence is fitted to the HMM profile using the HMMER hmmsearch program. The following default parameters are used when running hmmsearch: the default E-value cutoff (E) is 10.0, the default bit score cutoff (T) is negative infinity, the default number of sequences in a database (Z) is the real number of sequences in the database, the default E-value cutoff for the per-domain ranked hit list (domE) is infinity, and the default bit score cutoff for the per-domain ranked hit list (domT) is negative infinity. A high HMM bit score indicates a greater likelihood that the candidate sequence carries out one or more of the biochemical or physiological function(s) of the polypeptides used to generate the HMM. A high HMM bit score is at least 20, and often is higher. Slight variations in the HMM bit score of a particular sequence can occur due to factors such as the order in which sequences are processed for alignment by multiple sequence alignment algorithms such as the ProbCons program. Nevertheless, such HMM bit score variation is minor.

The cold tolerance-modulating polypeptides discussed below fit the indicated HMM with an HMM bit score greater than 20 (e.g., greater than 30, 40, 50, 60, 70, 80, 90, 100, 200, 300, 400, or 500). In some embodiments, the HMM bit score of a cold tolerance-modulating polypeptide discussed below is about 50%, 60%, 70%, 80%, 90%, or 95% of the HMM bit score of a functional homolog provided in the Sequence Listing of this application. In some embodiments, a cold tolerance-modulating polypeptide discussed below fits the indicated HMM with an HMM bit score greater than 20, and has a domain indicative of a cold tolerance-modulating polypeptide. In some embodiments, a cold tolerance-modulating polypeptide discussed below fits the indicated HMM with an HMM bit score greater than 20, and has 70% or greater sequence identity (e.g., 75%, 80%, 85%, 90%, 95%, or 100% sequence identity) to an amino acid sequence shown in any one of FIGS. 1-5.

Examples of polypeptides are shown in the Sequence Listing that have HMM bit scores greater than 130 when fitted to an HMM generated from the amino acid sequences set forth in FIG. 1 are identified in the Sequence Listing of this application. Such polypeptides include Ceres CLONE ID no. 1915941 (SEQ ID NO: 8), Ceres ANNOT ID no. 1461830 (SEQ ID NO: 10), Ceres CLONE ID no. 1080942 (SEQ ID NO: 15), and Ceres CLONE ID no. 1073190 (SEQ ID NO: 17).

Examples of polypeptides are shown in the Sequence Listing that have HMM bit scores greater than 185 when fitted to an HMM generated from the amino acid sequences set forth in FIG. 2 are identified in the Sequence Listing of this application. Such polypeptides include Ceres CLONE ID no. 1842825 (SEQ ID NO:22), Ceres ANNOT ID no. 1482536 (SEQ ID NO: 28), Ceres CLONE ID no. 463157 (SEQ ID NO: 32), Ceres CLONE ID no. 1674443 (SEQ ID NO: 40), GI ID no. 116310719 (SEQ ID NO: 44), Ceres CLONE ID no. 907473 (SEQ ID NO: 58), and Ceres CLONE ID no. 1755065 (SEQ ID NO:71).

Examples of polypeptides are shown in the Sequence Listing that have HMM bit scores greater than 655 when fitted to an HMM generated from the amino acid sequences set forth in FIG. 3 are identified in the Sequence Listing of this application. Such polypeptides include Ceres CLONE ID no. 473040 (SEQ ID NO: 79), Ceres CLONE ID no. 922223 (SEQ ID NO: 81), GI ID no. 125528967 (SEQ ID NO: 82), GI ID no. 125573200 (SEQ ID NO: 83), Ceres ANNOT ID no. 1527409 (SEQ ID NO: 85), GI ID no. 92871098 (SEQ ID NO: 86), Ceres CLONE ID no. 1831117 (SEQ ID NO: 88), and Ceres ANNOT ID no. 857222 (SEQ ID NO: 90).

Examples of polypeptides are shown in the Sequence Listing that have HMM bit scores greater than 315 when fitted to an HMM generated from the amino acid sequences set forth in FIG. 4 are identified in the Sequence Listing of this application. Such polypeptides include Ceres SEEDLINE ID no. ME17294 (SEQ ID NO: 93), Ceres CLONE ID no. 1831117 (SEQ ID NO: 95), Ceres CLONE ID no. 1844076 (SEQ ID NO: 98), Ceres CLONE ID no. 473040 (SEQ ID NO: 104), Ceres CLONE ID no. 922223 (SEQ ID NO: 106), and GI ID no. 125528967 (SEQ ID NO: 107).

Examples of polypeptides are shown in the Sequence Listing that have HMM bit scores greater than 790 when fitted to an HMM generated from the amino acid sequences set forth in FIG. 5 are identified in the Sequence Listing of this application. Such polypeptides include LOCUS ID no. AT5G62000 (SEQ ID NO: 112), Ceres ANNOT ID no. 1527370 (SEQ ID NO: 114), Ceres ANNOT ID no. 1473961 (SEQ ID NO: 116), GI ID no. 62319853 (SEQ ID NO: 117), GI ID no. 62319903 (SEQ ID NO:118), GI ID no. 47716275 (SEQ ID NO: 119), GI ID no. 125534572 (SEQ ID NO:120), GI ID no. 26251300(SEQ ID NO:121), GI ID no. 115441981 (SEQ ID NO:123), GI ID no. 23893346 (SEQ ID NO:124), GI ID no. 115485689 (SEQ ID NO:125), GI ID no. 108864435 (SEQ ID NO:126), GI ID no. 50511471 (SEQ ID NO:127), LOCUS ID no. At2g33860 (SEQ ID NO:128), GI ID no. 2245390 (SEQ ID NO:131), GI ID no. 3228517 (SEQ ID NO:132), Ceres CLONE ID no. 827306 (SEQ ID NO: 134), Ceres CLONE ID no. 1598488 (SEQ ID NO: 136), GI ID no. 125553314 (SEQ ID NO: 138), and Ceres CLONE ID no. 462443 (SEQ ID NO:143).

D. Percent Identity

In some embodiments, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to one of the amino acid sequences set forth in SEQ ID NOs: 2, 20, 93, and 74.

Polypeptides having such a percent sequence identity often have a domain indicative of a cold tolerance-modulating polypeptide and/or have an HMM bit score that is greater than 130, as discussed above. Amino acid sequences of cold tolerance-modulating polypeptides having at least 80% sequence identity to one of the amino acid sequences set forth in SEQ ID NOs: 2, 20, 93, and 74 are provided in FIGS. 1-4 and in the Sequence Listing.

"Percent sequence identity" refers to the degree of sequence identity between any given reference sequence, e.g., SEQ ID NO: 2, and a candidate cold tolerance-modulating sequence. A candidate sequence typically has a length that is from 80 percent to 200 percent of the length of the reference sequence, e.g., 82, 85, 87, 89, 90, 93, 95, 97, 99, 100, 105, 110, 115, 120, 130, 140, 150, 160, 170, 180, 190, or 200 percent of the length of the reference sequence. A percent identity for any candidate nucleic acid or polypeptide relative to a reference nucleic acid or polypeptide can be determined as follows. A reference sequence (e.g., a nucleic acid sequence or an amino acid sequence) is aligned to one or more candidate sequences using the computer program ClustalW (version 1.83, default parameters), which allows alignments of nucleic acid or polypeptide sequences to be carried out across their entire length (global alignment). Chenna et al., Nucleic Acids Res., 31(13):3497-500 (2003).

ClustalW calculates the best match between a reference and one or more candidate sequences, and aligns them so that identities, similarities and differences can be determined. Gaps of one or more residues can be inserted into a reference sequence, a candidate sequence, or both, to maximize sequence alignments. For fast pairwise alignment of nucleic acid sequences, the following default parameters are used: word size: 2; window size: 4; scoring method: percentage; number of top diagonals: 4; and gap penalty: 5. For multiple alignment of nucleic acid sequences, the following parameters are used: gap opening penalty: 10.0; gap extension penalty: 5.0; and weight transitions: yes. For fast pairwise alignment of protein sequences, the following parameters are used: word size: 1; window size: 5; scoring method: percentage; number of top diagonals: 5; gap penalty: 3. For multiple alignment of protein sequences, the following parameters are used: weight matrix: blosum; gap opening penalty: 10.0; gap extension penalty: 0.05; hydrophilic gaps: on; hydrophilic residues: Gly, Pro, Ser, Asn, Asp, Gln, Glu, Arg, and Lys; residue-specific gap penalties: on. The ClustalW output is a sequence alignment that reflects the relationship between sequences. ClustalW can be run, for example, at the Baylor College of Medicine Search Launcher site (searchlauncher.bcm.tmc.edu/multi-align/multi-align.html) and at the European Bioinformatics Institute site on the World Wide Web (ebi.ac.uk/clustalw).

To determine percent identity of a candidate nucleic acid or amino acid sequence to a reference sequence, the sequences are aligned using ClustalW, the number of identical matches in the alignment is divided by the length of the reference sequence, and the result is multiplied by 100. It is noted that the percent identity value can be rounded to the nearest tenth. For example, 78.11, 78.12, 78.13, and 78.14 are rounded down to 78.1, while 78.15, 78.16, 78.17, 78.18, and 78.19 are rounded up to 78.2.

In some cases, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 2. Amino acid sequences of polypeptides having greater than 45% sequence identity to the polypeptide set forth in SEQ ID NO: 2 are provided in FIG. 1 and in the Sequence Listing. Examples of such polypeptides include Ceres CLONE ID no. 1915941 (SEQ ID NO: 8), Ceres ANNOT ID no. 1461830 (SEQ ID NO: 10), Ceres CLONE ID no. 1080942 (SEQ ID NO: 15), and Ceres CLONE ID no. 1073190 (SEQ ID NO: 17).

In some cases, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 20. Amino acid sequences of polypeptides having greater than 45% sequence identity to the polypeptide set forth in SEQ ID NO: 20 are provided in FIG. 2 and in the Sequence Listing. Examples of such polypeptides include Ceres CLONE ID no. 1842825 (SEQ ID NO: 22), Ceres ANNOT ID no. 1482536 (SEQ ID NO: 28), Ceres CLONE ID no. 463157 (SEQ ID NO: 32), Ceres CLONE ID no. 1674443 (SEQ ID NO:40), GI ID no. 116310719 (SEQ ID NO: 44), Ceres CLONE ID no. 907473 (SEQ ID NO: 58), and Ceres CLONE ID no. 1755065 (SEQ ID NO: 71).

In some cases, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 93. Amino acid sequences of polypeptides having greater than 45% sequence identity to the polypeptide set forth in SEQ ID NO: 93 are provided in FIG. 3 and in the Sequence Listing. Examples of such polypeptides include Ceres CLONE ID no. 473040 (SEQ ID NO: 79), Ceres CLONE ID no. 922223 (SEQ ID NO: 81), GI ID no. 125528967(SEQ ID NO: 82), GI ID no. 125573200 (SEQ ID NO: 83), Ceres ANNOT ID no. 1527409 (SEQ ID NO: 85), GI ID no. 92871098 (SEQ ID NO: 86), Ceres CLONE ID no. 1831117 (SEQ ID NO: 88), and Ceres ANNOT ID no. 857222 (SEQ ID NO: 90).

In some cases, a cold tolerance-modulating polypeptide has an amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 93. Amino acid sequences of polypeptides having greater than 45% sequence identity to the polypeptide set forth in SEQ ID NO: 93 are provided in FIG. 4 and in the Sequence Listing. Examples of such polypeptides include Ceres CLONE ID no. 1831117 (SEQ ID NO: 95), Ceres CLONE ID no. 1844076 (SEQ ID NO: 98), Ceres CLONE ID no. 473040 (SEQ ID NO: 104), Ceres CLONE ID no. 922223 (SEQ ID NO: 106), and GI ID no. 125528967 (SEQ ID NO: 107).

In some cases, a cold tolerance-modulating tasiRNA acts upon an ARF amino acid sequence with at least 45% sequence identity, e.g., 50%, 52%, 56%, 59%, 61%, 65%, 70%, 75%, 80%, 85%, 90%, 95%, 97%, 98%, or 99% sequence identity, to the amino acid sequence set forth in SEQ ID NO: 116. Amino acid sequences of polypeptides having greater than 45% sequence identity to the polypeptide set forth in SEQ ID NO: 116 are provided in FIG. 5 and in the Sequence Listing. Examples of such polypeptides include LOCUS ID no. AT5G62000 (SEQ ID NO: 112), Ceres ANNOT ID no. 1527370 (SEQ ID NO: 114), GI ID no. 62319853 (SEQ ID NO: 117), GI ID no. 62319903 (SEQ ID NO:118), GI ID no. 47716275 (SEQ ID NO: 119), GI ID no. 125534572 (SEQ ID NO:120), GI ID no. 26251300 (SEQ ID NO:121), GI ID no. 115441981 (SEQ ID NO:123), GI ID no. 23893346 (SEQ ID NO:124), GI ID no. 115485689 (SEQ ID NO:125), GI ID no. 108864435 (SEQ ID NO:126), GI ID no. 50511471 (SEQ ID NO:127), LOCUS ID no. At2g33860 (SEQ ID NO:128), GI ID no. 2245390 (SEQ ID NO:131), GI ID no. 3228517 (SEQ ID NO:132), Ceres CLONE ID no. 827306 (SEQ ID NO: 134), Ceres CLONE ID no. 1598488 (SEQ ID NO: 136), GI ID no. 125553314 (SEQ ID NO: 138), and Ceres CLONE ID no. 462443 (SEQ ID NO:143).

E. Other Sequences

It should be appreciated that a cold tolerance-modulating polypeptide can include additional amino acids that are not involved in cold tolerance modulation, and thus such a polypeptide can be longer than would otherwise be the case. For example, a cold tolerance-modulating polypeptide can include a purification tag, a chloroplast transit peptide, a mitochondrial transit peptide, an amyloplast transit peptide, or a leader sequence added to the amino or carboxy terminus. In some embodiments, a cold tolerance-modulating polypeptide includes an amino acid sequence that functions as a reporter, e.g., a green fluorescent protein or yellow fluorescent protein.

III. NUCLEIC ACIDS

Nucleic acids described herein include nucleic acids that are effective to modulate cold tolerance levels when transcribed in a plant or plant cell. Such nucleic acids include, without limitation, those that encode a cold tolerance-modulating polypeptide and those that can be used to inhibit expression of a cold tolerance-modulating polypeptide via a nucleic acid based method.

A. Cold Tolerance-Modulating Nucleic Acids

Nucleic acids encoding cold tolerance-modulating polypeptides are described herein. Examples of such nucleic acids include SEQ ID NOs: 3, 5, 7, 9, 11, 14, 16, 18, 19, 21, 23, 25, 27, 31, 33, 35, 37, 39, 41, 55, 57, 70, 75, 78, 80, 84, 87, 89, 91, 92, 94, 97, 99, 103, 105, 109, 113, 115, 129, 133, 135, 140, and 142, as described in more detail below. A nucleic acid also can be a fragment that is at least 40% (e.g., at least 45, 50, 55, 60, 65, 70, 75, 80, 85, 90, 95, or 99%) of the length of the full-length nucleic acid set forth in SEQ ID NOs: 3, 5, 7, 9, 11, 14, 16, 18, 19, 21, 23, 25, 27, 31, 33, 35, 37, 39, 41, 55, 57, 70, 75, 78, 80, 84, 87, 89, 91, 92, 94, 97, 99, 103, 105, 109, 113, 115, 129, 133, 135, 140, and 142.

A cold tolerance-modulating nucleic acid can comprise the nucleotide sequence set forth in SEQ ID NO: 1. Alternatively, a cold tolerance-modulating nucleic acid can be a variant of the nucleic acid having the nucleotide sequence set forth in SEQ ID NO: 1. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 1.

A cold tolerance-modulating nucleic acid can comprise the nucleotide sequence set forth in SEQ ID NO: 19. Alternatively, a cold tolerance-modulating nucleic acid can be a variant of the nucleic acid having the nucleotide sequence set forth in SEQ ID NO: 19. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 19.

A cold tolerance-modulating nucleic acid can comprise the nucleotide sequence set forth in SEQ ID NO: 92. Alternatively, a cold tolerance-modulating nucleic acid can be a variant of the nucleic acid having the nucleotide sequence set forth in SEQ ID NO: 92. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 92.

A cold tolerance-modulating nucleic acid can comprise the nucleotide sequence set forth in SEQ ID NO: 97. Alternatively, a cold tolerance-modulating nucleic acid can be a variant of the nucleic acid having the nucleotide sequence set forth in SEQ ID NO: 97. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 97.

A cold tolerance-modulating nucleic acid can comprise the nucleotide sequence set forth in SEQ ID NO: 111. Alternatively, a cold tolerance-modulating nucleic acid can be a variant of the nucleic acid having the nucleotide sequence set forth in SEQ ID NO: 111. For example, a cold tolerance-modulating nucleic acid can have a nucleotide sequence with at least 80% sequence identity, e.g., 81%, 85%, 90%, 95%, 97%, 98%, or 99% sequence identity, to the nucleotide sequence set forth in SEQ ID NO: 111.

A cold tolerance-modulating sequence can be at least a fragment of a nucleotide sequence such as Ceres ANNOT ID no. 1473961 (SEQ ID NO: 116) or homologs thereof. For example, the cold tolerance-modulating nucleotide may be a tasiRNA. Such cold tolerance-modulating nucleotide sequences can act upon a protein that comprises an auxin response factor motif. This motif is present in SEQ ID NO: 112, which sets forth the amino acid sequence of an *Arabidopsis* clone, identified herein as LOCUS ID no. AT5G62000 (SEQ ID NO: 112), that is predicted to encode an polypeptide comprising an auxin response factor motif. In certain embodiments, the protein comprising an auxin response factor motif is an ARF protein. The ARFs are key regulators of auxin-modulated gene expression. There are multiple ARF proteins, some of which activate, while others repress transcription. ARF proteins bind to auxin-responsive cis-acting promoter elements (AuxREs) using an N-terminal DNA-binding domain. It is thought that Aux/IAA proteins activate transcription by modifying ARF activity through the C-terminal protein-protein interaction domains found in both Aux/IAA and ARF proteins.

A cold tolerance-modulating sequence can be at least a fragment of a nucleotide sequence such as Ceres ANNOT ID no. 1473961 (SEQ ID NO: 116) or homologs thereof. For example, the cold tolerance-modulating nucleotide may be a tasiRNA. Such cold tolerance-modulating nucleotide sequences can act upon a protein that comprises a B3 DNA binding domain. This domain is present in SEQ ID NO: 112, which sets forth the amino acid sequence of an *Arabidopsis* clone, identified herein as LOCUS ID no. AT5G62000 (SEQ ID NO: 112), that is predicted to encode an polypeptide comprising an B3 DNA binding domain. In certain embodiments, the protein comprising a B3 DNA binding domain is an ARF protein.

In some embodiments, a cold tolerance-modulating sequence is a tasiRNA sequence or a homolog thereof, such tasiRNA sequence being encoded by a nucleic acid sequence that comprises a domain having 80% or greater sequence identity to nucleic acid residues 305 to about 346 of SEQ ID NO: 111, residues 21 to about 62 of SEQ ID NO: 66, residues 20 to about 61 of SEQ ID NO: 67, residues 21 to about 62 of SEQ ID NO: 72, residues 21 to about 62 of SEQ ID NO: 73, residues 77 to about 118 of SEQ ID NO: 144, residues 292 to about 313 of SEQ ID NO: 145, residues 37 to about 78 of SEQ ID NO: 146, residues 56 to about 97 of SEQ ID NO: 147, residues 37 to about 78 of SEQ ID NO: 148, residues 45 to about 86 of SEQ ID NO: 149, residues 46 to about 98 of SEQ ID NO: 150, residues 476 to about 497 of SEQ ID NO: 151, residues 21 to about 62 of SEQ ID NO: 152, residues 21 to about 62 of SEQ ID NO: 153, residues 21 to about 62 of SEQ ID NO: 154, residues 21 to about 62 of SEQ ID NO: 155, or residues 21 to about 62 of SEQ ID NO: 156.

In some embodiments, a cold tolerance-modulating sequence is a nucleotide sequence or a homolog thereof, such as a tasiRNA sequence, wherein said nucleotide is encoded by a nucleic acid sequence that also comprises an miR390 recognition sequence having 80% or greater sequence identity to nucleic acid residues 109 to about 129 of SEQ ID NO: 66, residues 114 to about 135 of SEQ ID NO: 67, residues 119 to about 139 of SEQ ID NO: 72, residues 108 to about 128 of SEQ ID NO: 73, residues 234 to about 254 of SEQ ID NO: 144, residues 135 to about 176 of SEQ ID NO: 145, residues 173 to about 189 of SEQ ID NO: 147, residues 154 to about 170 of SEQ ID NO: 148, residues 134 to about 157 of SEQ ID NO: 149, residues 154 to about 198 of SEQ ID NO: 150, residues 319 to about 360 of SEQ ID NO: 151, residues 121 to about 141 of SEQ ID NO: 152, residues 120 to about 140 of SEQ ID NO: 153, residues 121 to about 141 of SEQ ID NO: 154, residues 121 to about 141 of SEQ ID NO: 155, residues 121 to about 141 of SEQ ID NO: 156, or residues 462 to about 483 of SEQ ID NO: 111. miR390 recognition sequences may guide in-phase processing of transcription (Allen et al. 2005).

In embodiments of the invention, a cold tolerance-modulating nucleotide, such as Ceres ANNOT ID no. 1473961 (SEQ ID NO: 116) or a homolog thereof, can act upon an polypeptide that comprises a B3 DNA binding domain having 80% or greater sequence identity to amino acid residues 163 to 268 of SEQ ID NO: 112, residues 157 to 262 of SEQ ID NO: 114, residues 157 to 262 of SEQ ID NO: 116, residues 163 to 268 of SEQ ID NO: 117, residues 163 to 268 of SEQ ID NO: 118, residues 158 to 263 of SEQ ID NO: 119, residues 148 to 253 of SEQ ID NO: 120, residues 147 to 252 of SEQ ID NO: 121, residues 123 to 228 of SEQ ID NO: 122, residues 128 to 233 of SEQ ID NO: 123, residues 131 to 236 of SEQ ID NO: 124, residues 147 to 252 of SEQ ID NO: 125, residues 148 to 253 of SEQ ID NO: 126, residues 141 to 246 of SEQ ID NO: 127, residues 158 to 263 of SEQ ID NO: 128, residues 142 to 247 of SEQ ID NO: 130, residues 158 to 263 of SEQ ID NO: 131, residues 158 to 263 of SEQ ID NO: 132, residues 126 to 231 of SEQ ID NO: 134, residues 129 to 234 of SEQ ID NO: 136, residues 114 to 219 of SEQ ID NO: 137, residues 141 to 246 of SEQ ID NO: 138, residues 176 to 281 of SEQ ID NO: 139, residues 152 to 257 of SEQ ID NO: 141, or residues 121 to 225 of SEQ ID NO: 143.

In embodiments of the invention, a cold tolerance-modulating tasiRNA sequence such as Ceres ANNOT ID no. 1473961 (SEQ ID NO: 116) can act upon an ARF polypeptide that comprises an auxin response factor motif having 80% or greater sequence identity to amino acid residues 290 to 372 of SEQ ID NO: 112, residues 284 to 366 of SEQ ID NO: 114, residues 284 to 366 of SEQ ID NO: 116, residues 290 to 372 of SEQ ID NO: 117, residues 290 to 372 of SEQ ID NO: 118, residues 285 to 367 of SEQ ID NO: 119, residues 275 to 357 of SEQ ID NO: 120, residues 274 to 356 of SEQ ID NO: 121, residues 250 to 331 of SEQ ID NO: 122, residues 255 to 336 of SEQ ID NO: 123, residues 258 to 340 of SEQ ID NO: 124, residues 274 to 356 of SEQ ID NO: 125, residues 275 to 357 of SEQ ID NO: 126, residues 268 to 349 of SEQ ID NO: 127, residues 285 to 367 of SEQ ID NO: 128, residues 269 to 351 of SEQ ID NO: 130, residues 285 to 367 of SEQ ID NO: 131, residues 285 to 367 of SEQ ID NO: 132, residues 253 to 334 of SEQ ID NO: 134, residues 256 to 337 of SEQ ID NO: 136, residues 241 to 322 of SEQ ID NO: 137, residues 268 to 349 of SEQ ID NO: 138, residues 302 to 384 of SEQ ID NO: 139, residues 279 to 361 of SEQ ID NO: 141, or residues 247 to 332 of SEQ ID NO: 143.

Isolated nucleic acid molecules can be produced by standard techniques. For example, polymerase chain reaction (PCR) techniques can be used to obtain an isolated nucleic acid containing a nucleotide sequence described herein. PCR can be used to amplify specific sequences from DNA as well as RNA, including sequences from total genomic DNA or total cellular RNA. Various PCR methods are described, for example, in PCR Primer: A Laboratory Manual, Dieffenbach and Dveksler, eds., Cold Spring Harbor Laboratory Press, 1995. Generally, sequence information from the ends of the region of interest or beyond is employed to design oligonucleotide primers that are identical or similar in sequence to opposite strands of the template to be amplified. Various PCR strategies also are available by which site-specific nucleotide sequence modifications can be introduced into a template nucleic acid. Isolated nucleic acids also can be chemically synthesized, either as a single nucleic acid molecule (e.g., using automated DNA synthesis in the 3' to 5' direction using phosphoramidite technology) or as a series of oligonucleotides. For example, one or more pairs of long oligonucleotides (e.g., >100 nucleotides) can be synthesized that contain the desired sequence, with each pair containing a short segment of complementarity (e.g., about 15 nucleotides) such that a duplex is formed when the oligonucleotide pair is annealed. DNA polymerase is used to extend the oligonucleotides, resulting in a single, double-stranded nucleic acid molecule per oligonucleotide pair, which then can be ligated into a vector. Isolated nucleic acids of the invention also can be obtained by mutagenesis of, e.g., a naturally occurring DNA.

B. Use of Nucleic Acids to Modulate Expression of Polypeptides i. Expression of a Cold Tolerance-Modulating Polypeptide A nucleic acid encoding one of the cold tolerance-modulating polypeptides described herein can be used to express the polypeptide in a plant species of interest, typically by transforming a plant cell with a nucleic acid having the coding sequence for the polypeptide operably linked in sense orientation to one or more regulatory regions. It will be appreciated that because of the degeneracy of the genetic code, a number of nucleic acids can encode a particular cold tolerance-modulating polypeptide; i.e., for many amino acids, there is more than one nucleotide triplet that serves as the codon for the amino acid. Thus, codons in the coding sequence for a given cold tolerance-modulating polypeptide can be modified such that optimal expression in a particular plant species is obtained, using appropriate codon bias tables for that species.

In some cases, expression of a cold tolerance-modulating polypeptide inhibits one or more functions of an endogenous polypeptide. For example, a nucleic acid that encodes a dominant negative polypeptide can be used to inhibit protein function. A dominant negative polypeptide typically is mutated or truncated relative to an endogenous wild type polypeptide, and its presence in a cell inhibits one or more functions of the wild type polypeptide in that cell, i.e., the dominant negative polypeptide is genetically dominant and confers a loss of function. The mechanism by which a dominant negative polypeptide confers such a phenotype can vary but often involves a protein-protein interaction or a protein-DNA interaction. For example, a dominant negative polypeptide can be an enzyme that is truncated relative to a native wild type enzyme, such that the truncated polypeptide retains domains involved in binding a first protein but lacks domains involved in binding a second protein. The truncated polypeptide is thus unable to properly modulate the activity of the second protein. See, e.g., US 2007/0056058. As another example, a point mutation that results in a non-conservative amino acid substitution in a catalytic domain can result in a dominant negative polypeptide. See, e.g., US 2005/032221. As another example, a dominant negative polypeptide can be a transcription factor that is truncated relative to a native wild type transcription factor, such that the truncated polypeptide retains the DNA binding domain(s) but lacks the activation domain(s). Such a truncated polypeptide can inhibit the wild type transcription factor from binding DNA, thereby inhibiting transcription activation.

ii. Inhibition of Expression of a Cold Tolerance-Modulating Polypeptide

Polynucleotides and recombinant constructs described herein can be used to inhibit expression of a cold tolerance-modulating polypeptide in a plant species of interest. See, e.g., Matzke and Birchler, *Nature Reviews Genetics* 6:24-35 (2005); Akashi et al., *Nature Reviews Mol. Cell Biology* 6:413-422 (2005); *Mittal, Nature Reviews Genetics* 5:355-365 (2004); Dorsett and Tuschl, *Nature Reviews Drug Discovery* 3: 318-329 (2004); and *Nature Reviews RNA interference collection*, October 2005 at nature.com/reviews/focus/mai. Typically, at least a fragment of a nucleic acid encoding cold tolerance-modulating polypeptides and/or its complement is expressed. A fragment is typically at least 20 nucleotides long, as needed for the methods noted below. A number of nucleic acid based methods, including antisense RNA, ribozyme directed RNA cleavage, post-transcriptional gene silencing (PTGS), e.g., RNA interference (RNAi), and transcriptional gene silencing (TGS) are known to inhibit gene expression in plants. Suitable polynucleotides include full-length nucleic acids encoding cold tolerance-modulating polypeptides or fragments of such full-length nucleic acids. In some embodiments, a complement of the full-length nucleic acid or a fragment thereof can be used. Typically, a fragment is at least 10 nucleotides, e.g., at least 12, 13, 14, 15, 16, 17, 18, 19, 20, 21, 22, 23, 24, 25, 26, 27, 30, 35, 40, 50, 80, 100, 200, 500 nucleotides or more. Generally, higher homology can be used to compensate for the use of a shorter sequence.

Antisense technology is one well-known method. In this method, a nucleic acid segment from a gene to be repressed is cloned and operably linked to a regulatory region and a transcription termination sequence so that the antisense strand of RNA is transcribed. The recombinant construct is then transformed into plants, as described herein, and the antisense strand of RNA is produced. The nucleic acid segment need not be the entire sequence of the gene to be repressed, but typically will be substantially complementary to at least a portion of the sense strand of the gene to be repressed. Generally, higher homology can be used to compensate for the use of a shorter sequence. Typically, a sequence of at least 30 nucleotides is used, e.g., at least 40, 50, 80, 100, 200, 500 nucleotides or more.

In another method, a nucleic acid can be transcribed into a ribozyme, or catalytic RNA, that affects expression of an mRNA. See, U.S. Pat. No. 6,423,885. Ribozymes can be designed to specifically pair with virtually any target RNA and cleave the phosphodiester backbone at a specific location, thereby functionally inactivating the target RNA. Heterologous nucleic acids can encode ribozymes designed to cleave particular mRNA transcripts, thus preventing expression of a polypeptide. Hammerhead ribozymes are useful for destroying particular mRNAs, although various ribozymes that cleave mRNA at site-specific recognition sequences can be used. Hammerhead ribozymes cleave mRNAs at locations dictated by flanking regions that form complementary base pairs with the target mRNA. The sole requirement is that the target RNA contains a 5'-UG-3' nucleotide sequence. The construction and production of hammerhead ribozymes is known in the art. See, for example, U.S. Pat. No. 5,254,678 and WO 02/46449 and references cited therein. Hammerhead ribozyme sequences can be embedded in a stable RNA such as a transfer RNA (tRNA) to increase cleavage efficiency in vivo. Perriman et al., *Proc. Natl. Acad. Sci. USA*, 92(13):6175-6179 (1995); de Feyter and Gaudron, Methods in Molecular Biology, Vol. 74, Chapter 43, "Expressing Ribozymes in Plants", Edited by Turner, P. C., Humana Press Inc., Totowa, NJ. RNA endoribonucleases which have been described, such as the one that occurs naturally in *Tetrahymena thermophile*, can be useful. See, for example, U.S. Pat. Nos. 4,987,071 and 6,423,885.

PTGS, e.g., RNAi, can also be used to inhibit the expression of a gene. For example, a construct can be prepared that includes a sequence that is transcribed into an RNA that can anneal to itself, e.g., a double stranded RNA having a stem-loop structure. In some embodiments, one strand of the stem portion of a double stranded RNA comprises a sequence that is similar or identical to the sense coding sequence or a fragment thereof of a cold tolerance-modulating polypeptide, and that is from about 10 nucleotides to about 2,500 nucleotides in length. The length of the sequence that is similar or identical to the sense coding sequence can be from 10 nucleotides to 500 nucleotides, from 15 nucleotides to 300 nucleotides, from 20 nucleotides to 100 nucleotides, or from 25 nucleotides to 100 nucleotides. The other strand of the stem portion of a double stranded RNA comprises a sequence that is similar or identical to the antisense strand or a fragment thereof of the coding sequence of the cold tolerance-modulating polypeptide, and can have a length that is shorter, the same as, or longer than the corresponding length of the sense sequence. In some cases, one strand of the stem portion of a double stranded RNA comprises a sequence that is similar or identical to the 3' or 5' untranslated region, or a fragment thereof, of an mRNA encoding a cold tolerance-modulating polypeptide, and the other strand of the stem portion of the double stranded RNA comprises a sequence that is similar or identical to the sequence that is complementary to the 3' or 5' untranslated region, respectively, or a fragment thereof, of the mRNA encoding the cold tolerance-modulating polypeptide. In other embodiments, one strand of the stem portion of a double stranded RNA comprises a sequence that is similar or identical to the sequence of an intron, or a fragment thereof, in the pre-mRNA encoding a cold tolerance-modulating polypeptide, and the other strand of the stem portion comprises a sequence that is similar or identical to the sequence that is complementary to the sequence of the intron, or a fragment thereof, in the pre-mRNA. The loop portion of a double stranded RNA can be from 3 nucleotides to 5,000 nucleotides, e.g., from 3 nucleotides to 25 nucleotides, from 15 nucleotides to 1,000 nucleotides, from 20 nucleotides to 500 nucleotides, or from 25 nucleotides to 200 nucleotides. The loop portion of the RNA can include an intron. A double stranded RNA can have zero, one, two, three, four, five, six, seven, eight, nine, ten, or more stem-loop structures. A construct including a sequence that is operably linked to a regulatory region and a transcription termination sequence, and that is transcribed into an RNA that can form a double stranded RNA, is transformed into plants as described herein. Methods for using RNAi to inhibit the expression of a gene are known to those of skill in the art. See, e.g., U.S. Pat. Nos. 5,034,323; 6,326,527; 6,452,067; 6,573,099; 6,753,139; and 6,777,588. See also WO 97/01952; WO 98/53083; WO 99/32619; WO 98/36083; and U.S. Patent Publications 20030175965, 20030175783, 20040214330, and 20030180945.

microRNA (miRNA) and tasiRNA, which are non-protein coding RNAs, can also be used to inhibit the expression of a gene. The gene targeted for inhibition may be an endogenous plant gene, a viral gene, a bacterial gene, a fungal gene, or an insect gene. miRNAs and tasiRNAs are regulatory agents consisting of about 19 to 25 ribonucleotides. miRNA are highly efficient at inhibiting the expression of endogenous genes and/or can guide in-phase processing of tasiRNA primary transcripts. tasiRNAs similarly inhibit gene expression by interacting with target mRNAs and guide cleavage by the same mechanism as do plant miRNAs, but differ from miRNAs in that they arise from double-stranded RNA, which may require RNA-dependent RNA polymerases.

For example, a tasiRNA can act upon an auxin responsive protein (ARF) (e.g., ARF3 or ARF4). In particular, inhibition of the expression of an ARF encoding gene (e.g., ARF3 or ARF4) may be obtained by interference by expression of a nucleic acid sequence encoding a tasiRNA. Transcription of a tasiRNA encoding nucleic acid sequence can be under the control of a promoter, such as, but not limited to, those promoters and regulatory regions described herein, or under promotional control of a tasiRNA coding sequence's own promoter. For such interference, the expression cassette is designed to express an RNA molecule that is modeled on an endogenous tasiRNA encoding sequence. The tasiRNA encoding sequence encodes an RNA that forms a hairpin structure containing a nucleotide sequence that is complementary to another endogenous gene (target sequence). For suppression of ARF protein expression, the nucleotide sequence is selected from an ARF transcript sequence and contains about 19 to 25 nucleotides of said ARF protein sequence in sense orientation and about 19 to 25 nucleotides of a corresponding antisense sequence that is complementary to the sense sequence. tasiRNA molecules are highly efficient at inhibiting the expression of endogenous genes. In *Arabidopsis*, a nuclear DCL enzyme is believed to be required for mature miRNA formation (Xie et al. (2004) PLoS Biol., 2:642-652, which is incorporated by reference herein) Inhibition of gene expression by miRNAs and tasiRNAs and methods for inhibition are known to those of skill in the art. See, for example, Javier, et al., (2003) Nature 425:257-263; Bartel (2004) Cell, 116:281-297; Kim (2005) Nature Rev. Mol. Cell Biol., 6:376-385; and Allen et al. (2005) Cell, 121:207-221, all of which are incorporated by reference herein.

Constructs containing regulatory regions operably linked to nucleic acid molecules in sense orientation can also be used to inhibit the expression of a gene. The transcription product can be similar or identical to the sense coding sequence, or a fragment thereof, of a cold tolerance-modulating polypeptide. The transcription product also can be unpolyadenylated, lack a 5' cap structure, or contain an unspliceable intron. Methods of inhibiting gene expression using a full-length cDNA as well as a partial cDNA sequence are known in the art. See, e.g., U.S. Pat. No. 5,231,020.

In some embodiments, a construct containing a nucleic acid having at least one strand that is a template for both sense and antisense sequences that are complementary to each other is used to inhibit the expression of a gene. The sense and antisense sequences can be part of a larger nucleic acid molecule or can be part of separate nucleic acid molecules having sequences that are not complementary. The sense or antisense sequence can be a sequence that is identical or complementary to the sequence of an mRNA, the 3' or 5' untranslated region of an mRNA, or an intron in a pre-mRNA encoding a cold tolerance-modulating polypeptide, or a fragment of such sequences. In some embodiments, the sense or antisense sequence is identical or complementary to a sequence of the regulatory region that drives transcription of the gene encoding a cold tolerance-modulating polypeptide. In each case, the sense sequence is the sequence that is complementary to the antisense sequence.

The sense and antisense sequences can be any length greater than about 10 nucleotides (e.g., 12, 13, 14, 15, 16, 17, 18, 19, 20, 21, 22, 23, 24, 25, 26, 27, 28, 29, 30, or more nucleotides). For example, an antisense sequence can be 21 or 22 nucleotides in length. Typically, the sense and antisense sequences range in length from about 15 nucleotides to about 30 nucleotides, e.g., from about 18 nucleotides to about 28 nucleotides, or from about 21 nucleotides to about 25 nucleotides.

In some embodiments, an antisense sequence is a sequence complementary to an mRNA sequence, or a fragment thereof, encoding a cold tolerance-modulating polypeptide described herein. The sense sequence complementary to the antisense sequence can be a sequence present within the mRNA of the cold tolerance-modulating polypeptide. Typically, sense and antisense sequences are designed to correspond to a 15-30 nucleotide sequence of a target mRNA such that the level of that target mRNA is reduced.

In some embodiments, a construct containing a nucleic acid having at least one strand that is a template for more than one sense sequence (e.g., 2, 3, 4, 5, 6, 7, 8, 9, 10 or more sense sequences) can be used to inhibit the expression of a gene. Likewise, a construct containing a nucleic acid having at least one strand that is a template for more than one antisense sequence (e.g., 2, 3, 4, 5, 6, 7, 8, 9, 10 or more antisense sequences) can be used to inhibit the expression of a gene. For example, a construct can contain a nucleic acid having at least one strand that is a template for two sense sequences and two antisense sequences. The multiple sense sequences can be identical or different, and the multiple antisense sequences can be identical or different. For example, a construct can have a nucleic acid having one strand that is a template for two identical sense sequences and two identical antisense sequences that are complementary to the two identical sense sequences. Alternatively, an isolated nucleic acid can have one strand that is a template for (1) two identical sense sequences 20 nucleotides in length, (2) one antisense sequence that is complementary to the two identical sense sequences 20 nucleotides in length, (3) a sense sequence 30 nucleotides in length, and (4) three identical antisense sequences that are complementary to the sense sequence 30 nucleotides in length. The constructs provided herein can be designed to have any arrangement of sense and antisense sequences. For example, two identical sense sequences can be followed by two identical antisense sequences or can be positioned between two identical antisense sequences.

A nucleic acid having at least one strand that is a template for one or more sense and/or antisense sequences can be operably linked to a regulatory region to drive transcription of an RNA molecule containing the sense and/or antisense sequence(s). In addition, such a nucleic acid can be operably linked to a transcription terminator sequence, such as the terminator of the nopaline synthase (nos) gene. In some cases, two regulatory regions can direct transcription of two transcripts: one from the top strand, and one from the bottom strand. See, for example, Yan et al., Plant Physiol., 141: 1508-1518 (2006). The two regulatory regions can be the same or different. The two transcripts can form double-stranded RNA molecules that induce degradation of the target RNA. In some cases, a nucleic acid can be positioned within a T-DNA or plant-derived transfer DNA (P-DNA) such that the left and right T-DNA border sequences, or the left and right border-like sequences of the P-DNA, flank or are on either side of the nucleic acid. See, US 2006/0265788. The nucleic acid sequence between the two regulatory regions can be from about 15 to about 300 nucleotides in length. In some embodiments, the nucleic acid sequence between the two regulatory regions is from about 15 to about 200 nucleotides in length, from about 15 to about 100 nucleotides in length, from about 15 to about 50 nucleotides in length, from about 18 to about 50 nucleotides in length, from about 18 to about 40 nucleotides in length, from about 18 to about 30 nucleotides in length, or from about 18 to about 25 nucleotides in length.

In some nucleic-acid based methods for inhibition of gene expression in plants, a suitable nucleic acid can be a nucleic acid analog. Nucleic acid analogs can be modified at the base moiety, sugar moiety, or phosphate backbone to improve, for example, stability, hybridization, or solubility of the nucleic acid. Modifications at the base moiety include deoxyuridine for deoxythymidine, and 5-methyl-2'-deoxycytidine and 5-bromo-2'-deoxycytidine for deoxycytidine. Modifications of the sugar moiety include modification of the 2' hydroxyl of the ribose sugar to form 2'-O-methyl or 2'-O-allyl sugars. The deoxyribose phosphate backbone can be modified to produce morpholino nucleic acids, in which each base moiety is linked to a six-membered morpholino ring, or peptide nucleic acids, in which the deoxyphosphate backbone is replaced by a pseudopeptide backbone and the four bases are retained. See, for example, Summerton and Weller, 1997, Antisense Nucleic Acid Drug Dev., 7:187-195; Hyrup et al., Bioorgan. Med. Chem., 4:5-23 (1996). In addition, the deoxyphosphate backbone can be replaced with, for example, a phosphorothioate or phosphorodithioate backbone, a phosphoroamidite, or an alkyl phosphotriester backbone.

C. Constructs/Vectors

Recombinant constructs provided herein can be used to transform plants or plant cells in order to modulate cold tolerance levels. A recombinant nucleic acid construct can comprise a nucleic acid encoding a cold tolerance-modulating polypeptide as described herein, operably linked to a regulatory region suitable for expressing the cold tolerance-modulating polypeptide in the plant or cell. Thus, a nucleic acid can comprise a coding sequence that encodes any of the cold tolerance-modulating polypeptides as set forth in SEQ ID NOs: 2, 20, 93, 74, or a homologs thereof. Examples of nucleic acids encoding cold tolerance-modulating polypeptides are set forth in SEQ ID NOs: 1, 19, 92, 97, or 111, and in FIGS. 1-4 and in the Sequence Listing. The cold tolerance-modulating polypeptide encoded by a recombinant nucleic acid can be a native cold tolerance-modulating polypeptide, or can be heterologous to the cell. In some cases, the recombinant construct contains a nucleic acid that inhibits expression of a cold tolerance-modulating polypeptide, operably linked to a regulatory region. Examples of suitable regulatory regions are described in the section entitled "Regulatory Regions."

Vectors containing recombinant nucleic acid constructs such as those described herein also are provided. Suitable vector backbones include, for example, those routinely used in the art such as plasmids, viruses, artificial chromosomes, BACs, YACs, or PACs. Suitable expression vectors include, without limitation, plasmids and viral vectors derived from, for example, bacteriophage, baculoviruses, and retroviruses. Numerous vectors and expression systems are commercially available from such corporations as Novagen (Madison, WI), Clontech (Palo Alto, CA), Stratagene (La Jolla, CA), and Invitrogen/Life Technologies (Carlsbad, CA).

The vectors provided herein also can include, for example, origins of replication, scaffold attachment regions (SARs), and/or markers. A marker gene can confer a selectable phenotype on a plant cell. For example, a marker can confer biocide resistance, such as resistance to an antibiotic (e.g., kanamycin, G418, bleomycin, or hygromycin), or an herbicide (e.g., glyphosate, chlorsulfuron or phosphinothricin). In addition, an expression vector can include a tag sequence designed to facilitate manipulation or detection (e.g., purification or localization) of the expressed polypeptide. Tag sequences, such as luciferase, β-glucuronidase (GUS), green fluorescent protein (GFP), glutathione S-transferase (GST), polyhistidine, c-myc, hemagglutinin, or Flag™ tag (Kodak, New Haven, CT) sequences typically are expressed as a fusion with the encoded polypeptide. Such tags can be inserted anywhere within the polypeptide, including at either the carboxyl or amino terminus.

D. Regulatory Regions

The choice of regulatory regions to be included in a recombinant construct depends upon several factors, including, but not limited to, efficiency, selectability, inducibility, desired expression level, and cell- or tissue-preferential expression. It is a routine matter for one of skill in the art to modulate the expression of a coding sequence by appropriately selecting and positioning regulatory regions relative to the coding sequence. Transcription of a nucleic acid can be modulated in a similar manner.

Some suitable regulatory regions initiate transcription only, or predominantly, in certain cell types. Methods for identifying and characterizing regulatory regions in plant genomic DNA are known, including, for example, those described in the following references: Jordano et al., *Plant Cell*, 1:855-866 (1989); Bustos et al., *Plant Cell*, 1:839-854 (1989); Green et al., *EMBO J.*, 7:4035-4044 (1988); Meier et al., *Plant Cell*, 3:309-316 (1991); and Zhang et al., *Plant Physiology*, 110:1069-1079 (1996).

Examples of various classes of regulatory regions are described below. Some of the regulatory regions indicated below as well as additional regulatory regions are described in more detail in U.S. patent application Ser. Nos. 60/505, 689; 60/518,075; 60/544,771; 60/558,869; 60/583,691; 60/619,181; 60/637,140; 60/757,544; 60/776,307; 10/957, 569; 11/058,689; 11/172,703; 11/208,308; 11/274,890; 60/583,609; 60/612,891; 11/097,589; 11/233,726; 11/408, 791; 11/414,142; 10/950,321; 11/360,017; PCT/US05/ 011105; PCT/US05/23639; PCT/US05/034308; PCT/US05/ 034343; and PCT/US06/038236; PCT/US06/040572; and PCT/US07/62762.

For example, the sequences of regulatory regions p326, YP0144, YP0190, p13879, YP0050, p32449, 21876, YP0158, YP0214, YP0380, PT0848, PT0633, YP0128, YP0275, PT0660, PT0683, PT0758, PT0613, PT0672, PT0688, PT0837, YP0092, PT0676, PT0708, YP0396, YP0007, YP0111, YP0103, YP0028, YP0121, YP0008, YP0039, YP0115, YP0119, YP0120, YP0374, YP0101, YP0102, YP0110, YP0117, YP0137, YP0285, YP0212, YP0097, YP0107, YP0088, YP0143, YP0156, PT0650, PT0695, PT0723, PT0838, PT0879, PT0740, PT0535, PT0668, PT0886, PT0585, YP0381, YP0337, PT0710, YP0356, YP0385, YP0384, YP0286, YP0377, PD1367, PT0863, PT0829, PT0665, PT0678, YP0086, YP0188, YP0263, PT0743 and YP0096 are set forth in the sequence listing of PCT/US06/040572; the sequence of regulatory region PT0625 is set forth in the sequence listing of PCT/ US05/034343; the sequences of regulatory regions PT0623, YP0388, YP0087, YP0093, YP0108, YP0022 and YP0080 are set forth in the sequence listing of U.S. patent application Ser. No. 11/172,703; the sequence of regulatory region PR0924 is set forth in the sequence listing of PCT/US07/ 62762; and the sequences of regulatory regions p530c10, pOsFIE2-2, pOsMEA, pOsYp102, and pOsYp285 are set forth in the sequence listing of PCT/US06/038236.

It will be appreciated that a regulatory region may meet criteria for one classification based on its activity in one plant species, and yet meet criteria for a different classification based on its activity in another plant species.

ii Broadly Expressing Promoters

A promoter can be said to be "broadly expressing" when it promotes transcription in many, but not necessarily all, plant tissues. For example, a broadly expressing promoter can promote transcription of an operably linked sequence in one or more of the shoot, shoot tip (apex), and leaves, but weakly or not at all in tissues such as roots or stems. As another example, a broadly expressing promoter can promote transcription of an operably linked sequence in one or more of the stem, shoot, shoot tip (apex), and leaves, but can promote transcription weakly or not at all in tissues such as reproductive tissues of flowers and developing seeds. Non-limiting examples of broadly expressing promoters that can be included in the nucleic acid constructs provided herein include the p326, YP0144, YP0190, p13879, YP0050, p32449, 21876, YP0158, YP0214, YP0380, PT0848, and PT0633 promoters. Additional examples include the cauliflower mosaic virus (CaMV) 35S promoter, the mannopine synthase (MAS) promoter, the 1' or 2' promoters derived from T-DNA of *Agrobacterium tumefaciens*, the figwort mosaic virus 34S promoter, actin promoters such as the rice actin promoter, and ubiquitin promoters such as the maize ubiquitin-1 promoter. In some cases, the CaMV 35S promoter is excluded from the category of broadly expressing promoters.

iii. Root Promoters

Root-active promoters confer transcription in root tissue, e.g., root endodermis, root epidermis, or root vascular tissues. In some embodiments, root-active promoters are root-preferential promoters, i.e., confer transcription only or predominantly in root tissue. Root-preferential promoters include the YP0128, YP0275, PT0625, PT0660, PT0683, and PT0758 promoters. Other root-preferential promoters include the PT0613, PT0672, PT0688, and PT0837 promoters, which drive transcription primarily in root tissue and to a lesser extent in ovules and/or seeds. Other examples of root-preferential promoters include the root-specific subdomains of the CaMV 35S promoter (Lam et al., *Proc. Natl. Acad. Sci. USA*, 86:7890-7894 (1989)), root cell specific promoters reported by Conkling et al., *Plant Physiol.*, 93:1203-1211 (1990), and the tobacco RD2 promoter.

iv. Maturing Endosperm Promoters

In some embodiments, promoters that drive transcription in maturing endosperm can be useful. Transcription from a maturing endosperm promoter typically begins after fertilization and occurs primarily in endosperm tissue during seed development and is typically highest during the cellularization phase. Most suitable are promoters that are active predominantly in maturing endosperm, although promoters that are also active in other tissues can sometimes be used. Non-limiting examples of maturing endosperm promoters that can be included in the nucleic acid constructs provided herein include the napin promoter, the Arcelin-5 promoter, the phaseolin promoter (Bustos et al., *Plant Cell*, 1(9):839-853 (1989)), the soybean trypsin inhibitor promoter (Riggs et al., *Plant Cell*, 1(6):609-621 (1989)), the ACP promoter (Baerson et al., *Plant Mol. Biol.*, 22(2):255-267 (1993)), the stearoyl-ACP desaturase promoter (Slocombe et al., *Plant Physiol.*, 104(4):167-176 (1994)), the soybean α' subunit of β-conglycinin promoter (Chen et al., *Proc. Natl. Acad. Sci. USA*, 83:8560-8564 (1986)), the oleosin promoter (Hong et al., *Plant Mol. Biol.*, 34(3):549-555 (1997)), and zein promoters, such as the 15 kD zein promoter, the 16 kD zein promoter, 19 kD zein promoter, 22 kD zein promoter and 27 kD zein promoter. Also suitable are the Osgt-1 promoter from the rice glutelin-1 gene (Zheng et al., *Mol. Cell Biol.*, 13:5829-5842 (1993)), the beta-amylase promoter, and the barley hordein promoter. Other maturing endosperm promoters include the YP0092, PT0676, and PT0708 promoters.

v. Ovary Tissue Promoters

Promoters that are active in ovary tissues such as the ovule wall and mesocarp can also be useful, e.g., a polygalacturonidase promoter, the banana TRX promoter, the melon actin promoter, YP0396, and PT0623. Examples of promoters that are active primarily in ovules include YP0007, YP0111, YP0092, YP0103, YP0028, YP0121, YP0008, YP0039, YP0115, YP0119, YP0120, and YP0374.

vi. Embryo Sac/Early Endosperm Promoters

To achieve expression in embryo sac/early endosperm, regulatory regions can be used that are active in polar nuclei and/or the central cell, or in precursors to polar nuclei, but not in egg cells or precursors to egg cells. Most suitable are promoters that drive expression only or predominantly in polar nuclei or precursors thereto and/or the central cell. A pattern of transcription that extends from polar nuclei into early endosperm development can also be found with embryo sac/early endosperm-preferential promoters, although transcription typically decreases significantly in later endosperm development during and after the cellularization phase. Expression in the zygote or developing embryo typically is not present with embryo sac/early endosperm promoters.

Promoters that may be suitable include those derived from the following genes: *Arabidopsis* viviparous-1 (see, GenBank No. U93215); *Arabidopsis* atmyc1 (see, Urao (1996) *Plant Mol. Biol.*, 32:571-57; Conceicao (1994) *Plant*, 5:493-505); *Arabidopsis* FIE (GenBank No. AF129516); *Arabidopsis* MEA; *Arabidopsis* FIS2 (GenBank No. AF096096); and FIE 1.1 (U.S. Pat. No. 6,906,244). Other promoters that may be suitable include those derived from the following genes: maize MAC1 (see, Sheridan (1996) *Genetics*, 142: 1009-1020); maize Cat3 (see, GenBank No. L05934; Abler (1993) *Plant Mol. Biol.*, 22:10131-1038). Other promoters include the following *Arabidopsis* promoters: YP0039, YP0101, YP0102, YP0110, YP0117, YP0119, YP0137, DME, YP0285, and YP0212. Other promoters that may be useful include the following rice promoters: p530c10, pOs-FIE2-2, pOsMEA, pOsYp102, and pOsYp285.

vii. Embryo Promoters

Regulatory regions that preferentially drive transcription in zygotic cells following fertilization can provide embryo-preferential expression. Most suitable are promoters that preferentially drive transcription in early stage embryos prior to the heart stage, but expression in late stage and maturing embryos is also suitable. Embryo-preferential promoters include the barley lipid transfer protein (Ltp1) promoter (*Plant Cell Rep* (2001) 20:647-654), YP0097, YP0107, YP0088, YP0143, YP0156, PT0650, PT0695, PT0723, PT0838, PT0879, and PT0740.

viii. Photosynthetic Tissue Promoters

Promoters active in photosynthetic tissue confer transcription in green tissues such as leaves and stems. Most suitable are promoters that drive expression only or predominantly in such tissues. Examples of such promoters include the ribulose-1,5-bisphosphate carboxylase (RbcS) promoters such as the RbcS promoter from eastern larch (*Larix laricina*), the pine cab6 promoter (Yamamoto et al., *Plant Cell Physiol.*, 35:773-778 (1994)), the Cab-1 promoter from wheat (Fejes et al., *Plant Mol. Biol.*, 15:921-932 (1990)), the CAB-1 promoter from spinach (Lubberstedt et al., *Plant Physiol.*, 104:997-1006 (1994)), the cab1R promoter from rice (Luan et al., *Plant Cell*, 4:971-981 (1992)), the pyruvate orthophosphate dikinase (PPDK) promoter from corn (Matsuoka et al., *Proc. Natl. Acad. Sci. USA*, 90:9586-9590 (1993)), the tobacco Lhcb1*2 promoter (Cerdan et al., *Plant Mol. Biol.*, 33:245-255 (1997)), the *Arabidopsis thaliana* SUC2 sucrose-H+ symporter promoter (Truernit et al., *Planta*, 196:564-570 (1995)), and thylakoid membrane protein promoters from spinach (psaD, psaF, psaE, PC, FNR, atpC, atpD, cab, rbcS). Other photosynthetic tissue promoters include PT0535, PT0668, PT0886, YP0144, YP0380 and PT0585.

ix. Vascular Tissue Promoters

Examples of promoters that have high or preferential activity in vascular bundles include YP0087, YP0093, YP0108, YP0022, and YP0080. Other vascular tissue-preferential promoters include the glycine-rich cell wall protein GRP 1.8 promoter (Keller and Baumgartner, *Plant Cell*, 3(10):1051-1061 (1991)), the *Commelina* yellow mottle virus (CoYMV) promoter (Medberry et al., *Plant Cell*, 4(2):185-192 (1992)), and the rice tungro bacilliform virus (RTBV) promoter (Dai et al., *Proc. Natl. Acad. Sci. USA*, 101(2):687-692 (2004)).

x. Inducible Promoters

Inducible promoters confer transcription in response to external stimuli such as chemical agents or environmental stimuli. For example, inducible promoters can confer transcription in response to hormones such as giberellic acid or ethylene, or in response to light or drought. Examples of drought-inducible promoters include YP0380, PT0848, YP0381, YP0337, PT0633, YP0374, PT0710, YP0356, YP0385, YP0396, YP0388, YP0384, PT0688, YP0286, YP0377, PD1367, and PD0901. Examples of nitrogen-inducible promoters include PT0863, PT0829, PT0665, and PT0886. Examples of shade-inducible promoters include PR0924 and PT0678. An example of a promoter induced by salt is rd29A (Kasuga et al. (1999) *Nature Biotech* 17: 287-291).

xi. Basal Promoters

A basal promoter is the minimal sequence necessary for assembly of a transcription complex required for transcription initiation. Basal promoters frequently include a "TATA box" element that may be located between about 15 and about 35 nucleotides upstream from the site of transcription initiation. Basal promoters also may include a "CCAAT box" element (typically the sequence CCAAT) and/or a GGGCG sequence, which can be located between about 40 and about 200 nucleotides, typically about 60 to about 120 nucleotides, upstream from the transcription start site.

xii. Other Promoters

Other classes of promoters include, but are not limited to, shoot-preferential, callus-preferential, trichome cell-preferential, guard cell-preferential such as PT0678, tuber-preferential, parenchyma cell-preferential, and senescence-preferential promoters. Promoters designated YP0086, YP0188, YP0263, PT0758, PT0743, PT0829, YP0119, and YP0096, as described in the above-referenced patent applications, may also be useful.

xiii. Other Regulatory Regions

A 5' untranslated region (UTR) can be included in nucleic acid constructs described herein. A 5' UTR is transcribed, but is not translated, and lies between the start site of the transcript and the translation initiation codon and may include the +1 nucleotide. A 3' UTR can be positioned between the translation termination codon and the end of the transcript. UTRs can have particular functions such as increasing mRNA stability or attenuating translation. Examples of 3' UTRs include, but are not limited to, polyadenylation signals and transcription termination sequences, e.g., a nopaline synthase termination sequence.

It will be understood that more than one regulatory region may be present in a recombinant polynucleotide, e.g., introns, enhancers, upstream activation regions, transcription terminators, and inducible elements. Thus, for example, more than one regulatory region can be operably linked to the sequence of a polynucleotide encoding a cold tolerance-modulating polypeptide.

Regulatory regions, such as promoters for endogenous genes, can be obtained by chemical synthesis or by subcloning from a genomic DNA that includes such a regulatory

IV. TRANSGENIC PLANTS AND PLANT CELLS

A. Transformation

The invention also features transgenic plant cells and plants comprising at least one recombinant nucleic acid construct described herein. A plant or plant cell can be transformed by having a construct integrated into its genome, i.e., can be stably transformed. Stably transformed cells typically retain the introduced nucleic acid with each cell division. A plant or plant cell can also be transiently transformed such that the construct is not integrated into its genome. Transiently transformed cells typically lose all or some portion of the introduced nucleic acid construct with each cell division such that the introduced nucleic acid cannot be detected in daughter cells after a sufficient number of cell divisions. Both transiently transformed and stably transformed transgenic plants and plant cells can be useful in the methods described herein.

Transgenic plant cells used in methods described herein can constitute part or all of a whole plant. Such plants can be grown in a manner suitable for the species under consideration, either in a growth chamber, a greenhouse, or in a field. Transgenic plants can be bred as desired for a particular purpose, e.g., to introduce a recombinant nucleic acid into other lines, to transfer a recombinant nucleic acid to other species, or for further selection of other desirable traits. Alternatively, transgenic plants can be propagated vegetatively for those species amenable to such techniques. As used herein, a transgenic plant also refers to progeny of an initial transgenic plant provided, as long as the progeny inherits the transgene. Seeds produced by a transgenic plant can be grown and then selfed (or outcrossed and selfed) to obtain seeds homozygous for the nucleic acid construct.

Transgenic plants can be grown in suspension culture, or tissue or organ culture. For the purposes of this invention, solid and/or liquid tissue culture techniques can be used. When using solid medium, transgenic plant cells can be placed directly onto the medium or can be placed onto a filter that is then placed in contact with the medium. When using liquid medium, transgenic plant cells can be placed onto a flotation device, e.g., a porous membrane that contacts the liquid medium. A solid medium can be, for example, Murashige and Skoog (MS) medium containing agar and a suitable concentration of an auxin, e.g., 2,4-dichlorophenoxyacetic acid (2,4-D), and a suitable concentration of a cytokinin, e.g., kinetin.

When transiently transformed plant cells are used, a reporter sequence encoding a reporter polypeptide having a reporter activity can be included in the transformation procedure and an assay for reporter activity or expression can be performed at a suitable time after transformation. A suitable time for conducting the assay typically is about 1-21 days after transformation, e.g., about 1-14 days, about 1-7 days, or about 1-3 days. The use of transient assays is particularly convenient for rapid analysis in different species, or to confirm expression of a heterologous cold tolerance-modulating polypeptide whose expression has not previously been confirmed in particular recipient cells.

Techniques for introducing nucleic acids into monocotyledonous and dicotyledonous plants are known in the art, and include, without limitation, Agrobacterium-mediated transformation, viral vector-mediated transformation, electroporation and particle gun transformation, e.g., U.S. Pat. Nos. 5,538,880; 5,204,253; 6,329,571 and 6,013,863. If a cell or cultured tissue is used as the recipient tissue for transformation, plants can be regenerated from transformed cultures if desired, by techniques known to those skilled in the art.

B. Screening/Selection

A population of transgenic plants can be screened and/or selected for those members of the population that have a trait or phenotype conferred by expression of the transgene. For example, a population of progeny of a single transformation event can be screened for those plants having a desired level of expression of a cold tolerance-modulating polypeptide or nucleic acid. Physical and biochemical methods can be used to identify expression levels. These include Southern analysis or PCR amplification for detection of a polynucleotide; Northern blots, 51 RNAse protection, primer-extension, or RT-PCR amplification for detecting RNA transcripts; enzymatic assays for detecting enzyme or ribozyme activity of polypeptides and polynucleotides; and protein gel electrophoresis, Western blots, immunoprecipitation, and enzyme-linked immunoassays to detect polypeptides. Other techniques such as in situ hybridization, enzyme staining, and immunostaining also can be used to detect the presence or expression of polypeptides and/or polynucleotides. Methods for performing all of the referenced techniques are known. As an alternative, a population of plants comprising independent transformation events can be screened for those plants having a desired trait, such as a modulated level of cold tolerance. Selection and/or screening can be carried out over one or more generations, and/or in more than one geographic location. In some cases, transgenic plants can be grown and selected under conditions which induce a desired phenotype or are otherwise necessary to produce a desired phenotype in a transgenic plant. In addition, selection and/or screening can be applied during a particular developmental stage in which the phenotype is expected to be exhibited by the plant. Selection and/or screening can be carried out to choose those transgenic plants having a statistically significant difference in a cold tolerance level relative to a control plant that lacks the transgene. Selected or screened transgenic plants have an altered phenotype as compared to a corresponding control plant, as described in the "Transgenic Plant Phenotypes" section herein.

C. Plant Species

The polynucleotides and vectors described herein can be used to transform a number of monocotyledonous and dicotyledonous plants and plant cell systems, including species from one of the following families: Acanthaceae, Alliaceae, Alstroemeriaceae, Amaryllidaceae, Apocynaceae, Arecaceae, Asteraceae, Berberidaceae, Bixaceae, Brassicaceae, Bromeliaceae, Cannabaceae, Caryophyllaceae, Cephalotaxaceae, Chenopodiaceae, Colchicaceae, Cucurbitaceae, Dioscoreaceae, Ephedraceae, Erythroxylaceae, Euphorbiaceae, Fabaceae, Lamiaceae, Linaceae, Lycopodiaceae, Malvaceae, Melanthiaceae, Musaceae, Myrtaceae, Nyssaceae, Papaveraceae, Pinaceae, Plantaginaceae, Poaceae, Rosaceae, Rubiaceae, Salicaceae, Sapindaceae, Solanaceae, Taxaceae, Theaceae, or Vitaceae.

Suitable species may include members of the genus *Abelmoschus, Abies, Acer, Agrostis, Allium, Alstroemeria, Ananas, Andrographis, Andropogon, Artemisia, Arundo, Atropa, Berberis, Beta, Bixa, Brassica, Calendula, Camellia, Camptotheca, Cannabis, Capsicum, Carthamus, Catharanthus, Cephalotaxus, Chrysanthemum, Cinchona, Citrullus, Coffea, Colchicum, Coleus, Cucumis, Cucurbita, Cynodon, Datura, Dianthus, Digitalis, Dioscorea, Elaeis, Ephedra, Erianthus, Erythroxylum, Eucalyptus, Festuca,*

*Fragaria, Galanthus, Glycine, Gossypium, Helianthus, Hevea, Hordeum, Hyoscyamus, Jatropha, Lactuca, Linum, Lolium, Lupinus, Lycopersicon, Lycopodium, Manihot, Medicago, Mentha, Miscanthus, Musa, Nicotiana, Oryza, Panicum, Papaver, Parthenium, Pennisetum, Petunia, Phalaris, Phleum, Pinus, Poa, Poinsettia, Populus, Rauwolfia, Ricinus, Rosa, Saccharum, Salix, Sanguinaria, Scopolia, Secale, Solanum, Sorghum, Spartina, Spinacea, Tanacetum, Taxus, Theobroma, Triticosecale, Triticum, Uniola, Veratrum, Vinca, Vitis*, and *Zea*.

Suitable species include *Panicum* spp., Sorghum spp., *Miscanthus* spp., *Saccharum* spp., *Erianthus* spp., *Populus* spp., *Andropogon gerardii* (big bluestem), *Pennisetum purpureum* (elephant grass), *Phalaris arundinacea* (reed canarygrass), *Cynodon dactylon* (bermudagrass), *Festuca arundinacea* (tall fescue), *Spartina pectinata* (prairie cordgrass), *Medicago sativa* (alfalfa), *Arundo donax* (giant reed), *Secale cereale* (rye), Salix spp. (willow), *Eucalyptus* spp. (*eucalyptus*), Triticosecale (*Triticum*—wheat X rye) and bamboo.

Suitable species also include *Helianthus annuus* (sunflower), Carthamus tinctorius (safflower), Jatropha curcas (jatropha), *Ricinus communis* (castor), *Elaeis guineensis* (palm), *Linum usitatissimum* (flax), and *Brassica juncea*.

Suitable species also include *Beta vulgaris* (sugarbeet), and *Manihot esculenta* (cassava).

Suitable species also include *Lycopersicon esculentum* (tomato), *Lactuca sativa* (lettuce), *Musa paradisiaca* (banana), *Solanum tuberosum* (potato), *Brassica oleracea* (broccoli, cauliflower, brusselsprouts), *Camellia sinensis* (tea), *Fragaria ananassa* (strawberry), *Theobroma cacao* (cocoa), *Coffea arabica* (coffee), *Vitis vinifera* (grape), *Ananas comosus* (pineapple), *Capsicum annum* (hot & sweet pepper), *Allium cepa* (onion), *Cucumis melo* (melon), *Cucumis sativus* (cucumber), *Cucurbita maxima* (squash), *Cucurbita moschata* (squash), *Spinacea oleracea* (spinach), *Citrullus lanatus* (watermelon), *Abelmoschus esculentus* (okra), and *Solanum melongena* (eggplant).

Suitable species also include *Papaver somniferum* (opium poppy), *Papaver orientale, Taxus baccata, Taxus brevifolia, Artemisia annua, Cannabis sativa, Camptotheca acuminate, Catharanthus roseus, Vinca rosea, Cinchona officinalis, Colchicum autumnale, Veratrum californica, Digitalis lanata, Digitalis purpurea, Dioscorea* spp., *Andrographis paniculata, Atropa belladonna, Datura stomonium, Berberis* spp., *Cephalotaxus* spp., *Ephedra sinica, Ephedra* spp., *Erythroxylum coca, Galanthus wornorii, Scopolia* spp., *Lycopodium serratum* (=*Huperzia serrata*), *Lycopodium* spp., *Rauwolfia serpentina, Rauwolfia* spp., *Sanguinaria canadensis, Hyoscyamus* spp., *Calendula officinalis, Chrysanthemum parthenium, Coleus forskohlii*, and *Tanacetum parthenium*.

Suitable species also include *Parthenium argentatum* (guayule), *Hevea* spp. (rubber), *Mentha spicata* (mint), *Mentha piperita* (mint), *Bixa orellana*, and *Alstroemeria* spp.

Suitable species also include *Rosa* spp. (rose), *Dianthus caryophyllus* (carnation), *Petunia* spp. (*petunia*) and *Poinsettia pulcherrima* (poinsettia).

Suitable species also include *Nicotiana tabacum* (tobacco), *Lupinus albus* (lupin), *Uniola paniculata* (oats), bentgrass (*Agrostis* spp.), *Populus tremuloides* (aspen), *Pinus* spp. (pine), *Abies* spp. (fir), *Acer* spp. (maple, *Hordeum vulgare* (barley), *Poa pratensis* (bluegrass), *Lolium* spp. (ryegrass) and *Phleum pratense* (timothy).

Thus, the methods and compositions can be used over a broad range of plant species, including species from the dicot genera *Brassica, Carthamus, Glycine, Gossypium, Helianthus, Jatropha, Parthenium, Populus*, and *Ricinus*; and the monocot genera *Elaeis, Festuca, Hordeum, Lolium, Oryza, Panicum, Pennisetum, Phleum, Poa, Saccharum, Secale, Sorghum, Triticosecale, Triticum*, and *Zea*. In some embodiments, a plant is a member of the species *Panicum virgatum* (switchgrass), *Sorghum bicolor* (sorghum, sudangrass), *Miscanthus giganteus* (miscanthus), *Saccharum* sp. (energycane), *Populus balsamifera* (poplar), *Zea mays* (corn), *Glycine max* (soybean), *Brassica napus* (canola), *Triticum aestivum* (wheat), *Gossypium hirsutum* (cotton), *Oryza sativa* (rice), *Helianthus annuus* (sunflower), *Medicago sativa* (alfalfa), *Beta vulgaris* (sugarbeet), or *Pennisetum glaucum* (pearl millet).

In certain embodiments, the polynucleotides and vectors described herein can be used to transform a number of monocotyledonous and dicotyledonous plants and plant cell systems, wherein such plants are hybrids of different species or varieties of a specific species (e.g., *Saccharum* sp. X *Miscanthus* sp.).

D. Transgenic Plant Phenotypes

In some embodiments, a plant in which expression of a cold tolerance-modulating polypeptide is modulated can have increased levels of cold tolerance and/or biomass in vegetative tissues. Cold tolerance can be measured by means well know to those of skill in the art, including, but not limited to, seedling survival, decreased photosynthesis and membrane damage (measured by electrolyte leakage), seedling area, yield, and or biomass. For example, a cold tolerance-modulating polypeptide or nucleic acid described herein can be expressed in a transgenic plant, resulting in increased levels of cold tolerance and/or biomass. The cold tolerance level can be increased by at least 2 percent, e.g., 2, 3, 4, 5, 6, 7, 8, 9, 10, 11, 12, 13, 14, 15, 16, 17, 18, 19, 20, 25, 30, 35, 40, 45, 50, 55, 60, 70, 80, 90, 100 or more than 100 percent, as compared to the cold tolerance level in a corresponding control plant that does not express the transgene. In some embodiments, a plant in which expression of a cold tolerance-modulating polypeptide or polynucleotide is modulated can have increased levels of biomass. The biomass level can be increased by at least 2 percent, e.g., 2, 3, 4, 5, 10, 15, 20, 25, 30, 35, 40, 50, 60, 70, 80, 90, 100, or more than 100 percent, as compared to the biomass level in a corresponding control plant that does not express the transgene. In some embodiments, differences can be measured for a plant in which expression of a cold tolerance-modulating polypeptide is modulated can be exposed to cold for one or more periods of time that may vary depending on climatic conditions. For example, for periods of about ½ hour, 1 hour, 3 hours, 6 hours, 12 hours, 1 day, 3 days, 5 days, 10 days, 1 month, 3 months, 6 months, 12 months, or the entire lifespan of such a plant.

Increases in cold tolerance in such plants can provide improved nutritional quantity and content in geographic locales where cold affects plants. Increases in cold tolerance in such plants can be useful in situations where plant parts such as, but not limited to, seeds, tubers, stems, leaves or roots are harvested for human or animal consumption.

Decrease in cold tolerance in such plants can be useful for species or varieties of plants that benefit from cold exposure. For example, cold sensitive plants might be able to undergo vernalization more easily. Decreases in cold tolerance in such plants can be useful in situations where plant parts such as, but not limited to, seeds, tubers, stems, leaves or roots are harvested for human or animal consumption.

Typically, a difference in the level of cold tolerance in a transgenic plant or cell relative to a control plant or cell is considered statistically significant at p<0.05 with an appropriate parametric or non-parametric statistic, e.g., Chi-square test, Student's t-test, Mann-Whitney test, or F-test. In some embodiments, a difference in the level of cold tolerance is statistically significant at p<0.01, p<0.005, or p<0.001. A statistically significant difference in, for example, the level of cold tolerance in a transgenic plant compared to the amount in cells of a control plant indicates that the recombinant nucleic acid present in the transgenic plant results in altered cold tolerance levels.

The phenotype of a transgenic plant is evaluated relative to a control plant. A plant is said "not to express" a polypeptide when the plant exhibits less than 10%, e.g., less than 9%, 8%, 7%, 6%, 5%, 4%, 3%, 2%, 1%, 0.5%, 0.1%, 0.01%, or 0.001%, of the amount of polypeptide or mRNA encoding the polypeptide exhibited by the plant of interest. Expression can be evaluated using methods including, for example, RT-PCR, Northern blots, Si RNAse protection, primer extensions, Western blots, protein gel electrophoresis, immunoprecipitation, enzyme-linked immunoassays, chip assays, and mass spectrometry. It should be noted that if a polypeptide is expressed under the control of a tissue-preferential or broadly expressing promoter, expression can be evaluated in the entire plant or in a selected tissue. Similarly, if a polypeptide is expressed at a particular time, e.g., at a particular time in development or upon induction, expression can be evaluated selectively at a desired time period.

V. PLANT BREEDING

Genetic polymorphisms are discrete allelic sequence differences in a population. Typically, an allele that is present at 1% or greater is considered to be a genetic polymorphism. The discovery that polypeptides disclosed herein can modulate cold tolerance content is useful in plant breeding, because genetic polymorphisms exhibiting a degree of linkage with loci for such polypeptides are more likely to be correlated with variation in a cold tolerance trait. For example, genetic polymorphisms linked to the loci for such polypeptides are more likely to be useful in marker-assisted breeding programs to create lines having a desired modulation in the cold tolerance trait.

Thus, one aspect of the invention includes methods of identifying whether one or more genetic polymorphisms are associated with variation in a cold tolerance trait. Such methods involve determining whether genetic polymorphisms in a given population exhibit linkage with the locus for one of the polypeptides depicted in FIGS. 1 to 4 and/or functional homologs thereof, such as, but not limited to those identified in the Sequence Listing of this application. The correlation is measured between variation in the cold tolerance trait in plants of the population and the presence of the genetic polymorphism(s) in plants of the population, thereby identifying whether or not the genetic polymorphism(s) are associated with variation for the trait. If the presence of a particular allele is statistically significantly correlated with a desired modulation in the cold tolerance trait, the allele is associated with variation for the trait and is useful as a marker for the trait. If, on the other hand, the presence of a particular allele is not significantly correlated with the desired modulation, the allele is not associated with variation for the trait and is not useful as a marker.

Such methods are applicable to populations containing the naturally occurring endogenous polypeptide rather than an exogenous nucleic acid encoding the polypeptide, i.e., populations that are not transgenic for the exogenous nucleic acid. It will be appreciated, however, that populations suitable for use in the methods may contain a transgene for another, different trait, e.g., herbicide resistance.

Genetic polymorphisms that are useful in such methods include simple sequence repeats (SSRs, or microsatellites), rapid amplification of polymorphic DNA (RAPDs), single nucleotide polymorphisms (SNPs), amplified fragment length polymorphisms (AFLPs) and restriction fragment length polymorphisms (RFLPs). SSR polymorphisms can be identified, for example, by making sequence specific probes and amplifying template DNA from individuals in the population of interest by PCR. If the probes flank an SSR in the population, PCR products of different sizes will be produced. See, e.g., U.S. Pat. No. 5,766,847. Alternatively, SSR polymorphisms can be identified by using PCR product(s) as a probe against Southern blots from different individuals in the population. See, U. H. Refseth et al., (1997) Electrophoresis 18: 1519. The identification of RFLPs is discussed, for example, in Alonso-Blanco et al. (Methods in Molecular Biology, vol. 82, "Arabidopsis Protocols", pp. 137-146, J. M. Martinez-Zapater and J. Salinas, eds., c. 1998 by Humana Press, Totowa, NJ); Burr ("Mapping Genes with Recombinant Inbreds", pp. 249-254, in Freeling, M. and V. Walbot (Ed.), The Maize Handbook, c. 1994 by Springer-Verlag New York, Inc.: New York, NY, USA; Berlin Germany; Burr et al. Genetics (1998) 118: 519; and Gardiner, J. et al., (1993) Genetics 134: 917). The identification of AFLPs is discussed, for example, in EP 0 534 858 and U.S. Pat. No. 5,878,215.

In some embodiments, the methods are directed to breeding a plant line. Such methods use genetic polymorphisms identified as described above in a marker assisted breeding program to facilitate the development of lines that have a desired alteration in the cold tolerance trait. Once a suitable genetic polymorphism is identified as being associated with variation for the trait, one or more individual plants are identified that possess the polymorphic allele correlated with the desired variation. Those plants are then used in a breeding program to combine the polymorphic allele with a plurality of other alleles at other loci that are correlated with the desired variation. Techniques suitable for use in a plant breeding program are known in the art and include, without limitation, backcrossing, mass selection, pedigree breeding, bulk selection, crossing to another population and recurrent selection. These techniques can be used alone or in combination with one or more other techniques in a breeding program. Thus, each identified plants is selfed or crossed a different plant to produce seed which is then germinated to form progeny plants. At least one such progeny plant is then selfed or crossed with a different plant to form a subsequent progeny generation. The breeding program can repeat the steps of selfing or outcrossing for an additional 0 to 5 generations as appropriate in order to achieve the desired uniformity and stability in the resulting plant line, which retains the polymorphic allele. In most breeding programs, analysis for the particular polymorphic allele will be carried out in each generation, although analysis can be carried out in alternate generations if desired.

In some cases, selection for other useful traits is also carried out, e.g., selection for fungal resistance or bacterial resistance. Selection for such other traits can be carried out before, during or after identification of individual plants that possess the desired polymorphic allele.

VI. ARTICLES OF MANUFACTURE

Transgenic plants provided herein have various uses in the agricultural and energy production industries. For example, transgenic plants described herein can be used to make animal feed and food products. Such plants, however, are often particularly useful as a feedstock for energy production.

Transgenic plants described herein often produce higher yields of grain and/or biomass per hectare, relative to control plants that lack the exogenous nucleic acid. In some embodiments, such transgenic plants provide equivalent or even increased yields of grain and/or biomass per hectare relative to control plants when grown under conditions of reduced inputs such as fertilizer and/or water. Thus, such transgenic plants can be used to provide yield stability at a lower input cost and/or under environmentally stressful conditions such as drought. In some embodiments, plants described herein have a composition that permits more efficient processing into free sugars, and subsequently ethanol, for energy production. In some embodiments, such plants provide higher yields of ethanol, butanol, other biofuel molecules, and/or sugar-derived co-products per kilogram of plant material, relative to control plants. Such processing efficiencies are believed to be derived from the chemical composition of the plant material. By providing higher yields at an equivalent or even decreased cost of production relative to control plants that do not have increased levels of cold tolerance, the transgenic plants described herein improve profitability for farmers and processors as well as decrease costs to consumers.

Seeds from transgenic plants described herein can be conditioned and bagged in packaging material by means known in the art to form an article of manufacture. Packaging material such as paper and cloth are well known in the art. A package of seed can have a label, e.g., a tag or label secured to the packaging material, a label printed on the packaging material, or a label inserted within the package, that describes the nature of the seeds therein.

The invention will be further described in the following examples, which do not limit the scope of the invention described in the claims.

VII. EXAMPLES

Example 1—Transgenic *Arabidopsis* Plants

The following symbols are used in the Examples with respect to *Arabidopsis* transformation: T1: first generation transformant; T2: second generation, progeny of self-pollinated T1 plants; T3: third generation, progeny of self-pollinated T2 plants; T4: fourth generation, progeny of self-pollinated T3 plants. Independent transformations are referred to as events.

The following is a list of nucleic acids that were isolated from *Arabidopsis thaliana* plants, Clone 2273, Clone 924103, and Clone 13209. The nucleic acids designated Clone 6639 and Clone 924103 were isolated from the species *Triticum aestivum*.

Each isolated nucleic acid described above was cloned into a Ti plasmid vector containing a phosphinothricin acetyltransferase gene which confers Finale™ resistance to transformed plants. A Ti plasmid vector useful for these constructs is CRS 338. Unless otherwise indicated, each Ceres Clone and/or Seedline derived from a Clone is in the sense orientation relative to either the 35S promoter in a Ti plasmid. Wild-type *Arabidopsis thaliana* ecotype Wassilewskija (Ws) plants were transformed separately with each construct. The transformations were performed essentially as described in Bechtold et al., C.R. Acad. Sci. Paris, 316:1194-1199 (1993).

Wild-type *Arabidopsis* Wassilewskija (Ws) plants were transformed with a Ti plasmid containing Clone 924103 in the sense orientation relative to the 326F promoter. The Ti plasmid vector used for this construct, CRS814, contains the Ceres-constructed, plant selectable marker gene phosphinothricin acetyltransferase (PAT) which confers herbicide resistance to transformed plants.

Wild-type *Arabidopsis* Wassilewskija (Ws) plants were transformed with a Ti plasmid containing clone 2273 in the sense orientation relative to the 32449 promoter.

Wild-type *Arabidopsis* Wassilewskija (Ws) plants were transformed with a Ti plasmid containing clone 13209 in the sense orientation relative to the 32449 promoter. The Ti plasmid vector used for this construct, CRS311, contains the Ceres-constructed, plant selectable marker gene phosphinothricin acetyltransferase (PAT) which confers herbicide resistance to transformed plants Transgenic *Arabidopsis* lines containing Clone 2273, Clone 6639, Clone 924103, or Clone 13209 were designated ME00327, ME04315, ME17294, or ME00572 respectively. The presence of each vector containing a nucleic acid described above in the respective transgenic *Arabidopsis* line transformed with the vector was confirmed by Finale™ resistance, PCR amplification from green leaf tissue extract, and/or sequencing of PCR products. As controls, wild-type *Arabidopsis* ecotype Ws plants were transformed with the empty vector—SR0059.

Example 2—Screening for Cold Tolerance in Transgenic Plants

How plants respond to stress in the environment dictates their ability to survive and reproduce. There are probably many mechanisms by which plants regulate the temperatures under which they will germinate (Lu and Hills, 2003). A number of polynucleotides that result in stress tolerance when over-expressed have been identified in model species such as *Arabidopsis*.

Over-expression of these polynucleotides could be useful for increasing low temperature, chilling or cold tolerance in crops. Assays described here focus on low temperature, chilling or cold tolerance in seedlings. The ability to germinate and grow under low temperature, chilling or cold, and wet conditions would allow a longer growing season and mitigate damage caused by unexpected low temperature, chilling or cold periods. If this trait is recapitulated in crops overexpressing these polynucleotides, the result could be very valuable in agriculture in many crops and environments and make a significant contribution to sustainable farming. Furthermore, low temperature, chilling or cold tolerance may be modulated by expressing these polynucleotides under the control of a low temperature, chilling or cold inducible promoter.

1. Cold Growth Superpool Screen

Plates of solidified agar MS medium are prepared for the screen as follows. One liter of medium is prepared by mixing 2.15 g of MS basal salt mixture (from Phytotech M524) and 7 g of agar (from EM Science, 1.01614.1000) in water, and adjusting the pH to 5.7 with a 10N KOH solution. After autoclaving, 45 ml of media are transferred under sterile conditions per 100 mm square×15 mm deep plate.

Individual superpool and control seeds are sterilized in a 30% bleach solution for 5 minutes. Seeds are then rinsed repeatedly with sterile water to eliminate all bleach solution. Seeds are plated using a COPAS™ robot (Union Biometrica, Holliston, Massachusetts) at a density of 72 seeds per plate. The plates are wrapped with vent tape and transferred to a dark 4° C. refrigerator for 3 days to promote uniform germination. The plates are then placed horizontally in a Conviron growth chamber set at 22° C., 16:8 hour light:dark cycle, 70% humidity with fluorescent lamps emitting a light intensity of ~100 μEinsteins. Normal growth is allowed to occur for 3-5 days. At end of 3-5 days of growth, images of the plates are scanned using an Epson perfection 4870 scanner. Then, cold-growth treatment is applied for 1-3 weeks. Accordingly, plates are transferred in a horizontal position to an 8° C. Conviron chamber under constant light at ~100 μEinsteins. After a defined number of days of cold-growth treatment, for example 7 or 14, the plates are scanned again. The WinRhizo software program (Regent Instruments Inc., Canada) is used to determine the area for each seedling from the scanned images.

Individual seedlings that perform better in the cold growth screen are identified by visual inspection for those showing obvious morphological differences and by statistical analysis of the seedling area data. DNA from these candidate seedlings is extracted and the transgene amplified using PCR. The PCR product is sequenced to determine the identity of the transgene and consequently the ME line from which the candidate is derived.

2. Cold Growth Assay

The cold growth assay is used to validate candidate misexpression (ME) lines obtained from screens for enhanced growth under cold conditions. This procedure allows a high-throughput methodology for assessing transgenic *Arabidopsis* candidates that have germinated at normal temperature (22° C.) and light (~100 to 200 μEinsteins) in a walk-in growth chamber on agar solidified MS medium before transfer to cold temperature. It relies on the ability to discriminate between seedlings that have become significantly larger during cold growth than controls by imaging the seedlings when they are transferred to the cold and then periodically thereafter under cold growth conditions.

Plate preparation for the cold growth assay and the growth conditions are the same as those described for the cold growth screen as described above. Seeds from independent transformation events for each ME line are bleach sterilized and then plated at a density of 40 seeds per plate (30 seeds from the event and 10 wild-type control seeds). After cold-growth treatment, the seedlings are then FINALE® treated to identify the plants carrying the ME vector.

Cold growth is characterized by statistical analysis as follows. The control population is the internal non-transgenic segregants for that particular event. When there are not enough internal non-transgenic segregants for an event, a pool of all non-transgenic segregants from all events associated with that ME line is used (i.e. when non-transgenics are less than five for the event or the event appears to be homozygous). Pooling is only done for events associated with the same ME line and within an experiment (an experiment is the set of plates with a common sow date). Thus in the final analysis, the pooled control population may be different for generations $T_2$ and $T_3$.

The WinRhizo software program (Regent Instruments Inc., Canada) is used to determine the area for each seedling. The change in area is calculated for a defined number of days of treatment. A one-tailed t-test is used to compare change in area and the mean size of the transgenic seedlings within an event to the internal non-transgenic segregants. Significance is assessed at an α-value of 0.05.

3. Cold Flux Assay

The cold flux growth assay is used to validate candidate misexpression (ME) lines obtained from screens for enhanced growth under fluctuating cold conditions. This procedure allows a high-throughput methodology for assessing transgenic *Arabidopsis* candidates that have germinated at normal temperature (22° C.) and light (~100 to 200 μEinsteins) in a walk-in growth chamber on agar solidified MS medium before transfer to cold temperature. It relies on the ability to discriminate between seedlings that have become significantly larger during growth under fluctuating cold conditions than controls by imaging the seedlings when they are transferred to the cold and then periodically thereafter under cold growth conditions.

Plate preparation for the cold growth assay and the growth conditions are the same as those described for the cold growth screen as described above. Seeds from independent transformation events for each ME line are bleach sterilized and then plated at a density of 61 seeds per plate (including both seeds from the event and wild-type control seeds). After cold flux-growth treatment, the seedlings are then FINALE®-treated to identify the plants carrying the ME vector.

Normal growth is allowed to occur for 3-5 days. At end of 3-5 days of growth, images of the plates are scanned using an Epson perfection 4870 scanner. After 3-5 days growth in normal conditions, the plates are transferred in a horizontal position to an 8° C. Conviron under constant light at ~100 μEinsteins. All transfers take place in the morning. Growth is allowed at 8° C. for 3-4 days. After 3-4 days growth at 8° C., plates are transferred to 1° C. Percival under constant light at ~70 μEinsteins. Growth is allowed at 1° C. for 3-4 days. 8° C./1° C. cycling is repeated for a total of 14 days. The plates are imaged using CF imager and Winrhizo scanner. Individual seedlings are selected which are significantly larger and/or exhibit increased photosynthetic efficiency (Fv/Fm). Plates are visually observed as well. DNA from these candidate seedlings is extracted and the transgene amplified using PCR. The PCR product is sequenced to determine the identity of the transgene and consequently the ME line from which the candidate is derived. These seedlings are then grown for progeny seed.

Cold flux growth is characterized by statistical analysis as follows. The control population is the internal non-transgenic segregants for that particular event. When there are not enough internal non-transgenic segregants for an event, a pool of all non-transgenic segregants from all events associated with that ME line is used (i.e. when non-transgenics are less than five for the event or the event appears to be homozygous). Pooling is only done for events associated with the same ME line and within an experiment (an experiment is the set of plates with a common sow date). Thus in the final analysis, the pooled control population may be different for generations T2 and T3.

The WinRhizo software program (Regent Instruments Inc., Canada) is used to determine the area for each seedling. The change in area is calculated for a defined number of days of treatment. A one-tailed t-test is used to compare change in area and the mean size of the transgenic seedlings within an event to the internal non-transgenic segregants. Significance is assessed at an α-value of 0.05.

Example 3—Results for ME00327 Events (SEQ ID NO:2)

Ectopic expression of clone 2273 (from *Arabidopsis thaliana*) under the control of the 32449 promoter in the ME00327 plants results in larger seedlings after 14 days fluctuation between 8° C. and 1° C.

The seedling area of transgenic plants within a seed line was compared to that of non-transgenic segregants within the same seed line after 14 days of growth at fluctuating temperatures of 8° C. and 1° C. Six events of ME00327 were analyzed as described in the cold flux assay (Example 2). Events -04 and -06 were significant in at least two generations at p<0.05 using a one-tailed t-test assuming unequal variance (Table 1). The transgenic plants were visibly larger than the controls.

Event -04 segregated 3:1 (R:S) for Finale™ resistance in the $T_2$ generation. Event -06 appears to segregate for two inserts (15:1) in the $T_2$ generation.

the same seed line after 10 days of growth at 8° C. Nine events of ME04315 were analyzed as described in the Cold Growth Assay described in Example 2 and showed significant tolerance under cold conditions in two generations. Three Events, -02, -03 and -06, were significant in both generations at p<0.05 using a one-tailed t-test assuming unequal variance (Table 2). '-99' signifies that seeds were pooled from several plants. Events -02 and -06 were from the T3 generation because T2 seed was not available.

TABLE 1 t-test comparison of seedling area between transgenic seedlings and control non-transgenic segregants after 14 days fluctuation between 8° C. and 1° C.

| Events | Event-Gen | Transgenic Avg | SE | N | Control Non-Transgenics[a] Avg | SE | N | t-test p-value |
|---|---|---|---|---|---|---|---|---|
| ME00327-04 | -04-T2 | 0.0383 | 0.0014 | 16 | 0.0297 | 0.0011 | 14 | 2.58E−05 |
| ME00327-04-02 | -04-T3 | 0.0490 | 0.0023 | 27 | 0.0410 | 0.0019 | 32 | 4.48E−03 |
| ME00327-04-03 | -04-T3 | 0.0522 | 0.0018 | 32 | 0.0378 | 0.0020 | 26 | 9.46E−07 |
| ME00327-04-04 | -04-T3 | 0.0497 | 0.0020 | 35 | 0.0364 | 0.0022 | 25 | 1.38E−05 |
| ME00327-06[c] | -06-T2 | 0.0314 | 0.0011 | 29 | 0.0272 | 0.0009 | 39 | 1.98E−03 |
| ME00327-06[bc] | -06-T2 | 0.0392 | 0.0012 | 54 | 0.0346 | 0.0008 | 194 | 8.17E−04 |
| ME00327-06-01 | -06-T3 | 0.0296 | 0.0015 | 41 | 0.0232 | 0.0016 | 17 | 2.47E−03 |
| ME00327-06-03 | -06-T3 | 0.0356 | 0.0015 | 42 | 0.0290 | 0.0019 | 15 | 4.44E−03 |

[a]Transgenic seedlings were compared to internal non-transgenic segregants within an event unless otherwise indicated.
[b]These events were sown twice. The first time was to identify ME00327 as a Hit. They were repeated the second time with the next generation to identify ME00327 as a Lead.
[c]These events did not segregate non-transgenic seedlings and were compared to pooled non-transgenics for the line.

Plants from Events -04 and -06 which are hemizygous or homozygous for clone 2273 do not show any negative phenotypes under standard conditions. Events -04 and -06 of ME00327 were tested for negative phenotypes compared to the empty vector control SR00559. The results showed no detectable reduction in germination rate, the plants appeared wild-type in all instances, and no statistical differences in days to flowering, rosette area 7 days post-bolting, or fertility (silique number and seed fill).

Example 4—Results for ME04315 Events (SEQ ID NO: 20)

Candidate ME04315 was identified by superpool screen described above in Example 2. Ectopic expression of Clone 6639 under the control of the 35S promoter in ME04315 plants results in early germination at 8° C. resulting in larger seedlings after 10 days at 8° C.

The seedling area of transgenic plants within a seed line was compared to that of non-transgenic segregants within Subsequently, next generation seeds for three of the events (T3 or T4 as needed) were evaluated under cold germination conditions.

The transgenic plants were visibly larger and lighter in color than the controls. Under cold conditions, seedlings typically become darker, presumably due to the accumulation of anthocyanin. The lighter color exhibited by ME04315 seedlings suggests a decrease in this stress response. ME04315 plants grown under standard conditions in soil did not appear different in color than controls.

Event -03 segregated 3:1 (R:S) for Finale™ resistance in the $T_2$ generation. Seed collected from individual, hemizygous plants was not available for Events -02 and -06. However, the $T_3$ generation seeds that were pooled from several $T_2$ plants segregated approximately 2:1 in a manner consistent with a single insert for Event -06 (only transgenic plants were pooled). Pooled $T_3$ generation seeds for Event -02 segregated 1:3.

TABLE 2

T-test comparison of seedling area between transgenic seedlings and control non-transgenic segregants after 10 days at 8° C.

| Events | Event-Gen | Transgenic Avg | SE | N | Control Non-Transgenics[a] Avg | SE | N | t-test p-value |
|---|---|---|---|---|---|---|---|---|
| ME04315-02-99[b] | 02-T3 | 0.0071 | 0.0013 | 10 | 0.0049 | 0.0007 | 24 | 7.50E−02 |
| ME04315-02-99 | 02-T3 | 0.0046 | 0.0007 | 16 | 0.0036 | 0.0002 | 50 | 7.92E−02 |
| ME04315-02-99-02[a] | 02-T4 | 0.0070 | 0.0002 | 61 | 0.0047 | 0.0002 | 213 | 6.66E−16 |
| ME04315-02-99-03 | 02-T4 | 0.0072 | 0.0002 | 45 | 0.0057 | 0.0007 | 3 | 2.08E−02 |
| ME04315-03[b] | 03-T2 | 0.0026 | 0.0002 | 18 | 0.0017 | 0.0003 | 7 | 0.0070 |
| ME04315-03 | 03-T2 | 0.0017 | 0.0001 | 35 | 0.0016 | 0.0001 | 19 | 0.2221 |
| ME04315-03-02 | 03-T3 | 0.0078 | 0.0005 | 12 | 0.0045 | 0.0011 | 7 | 6.69E−03 |
| ME04315-03-03 | 03-T3 | 0.0063 | 0.0003 | 45 | 0.0053 | 0.0004 | 24 | 0.0153 |

TABLE 2-continued

T-test comparison of seedling area between transgenic seedlings and control non-transgenic segregants after 10 days at 8° C.

| Events | Event-Gen | Transgenic | | | Control Non-Transgenics[a] | | | t-test |
|---|---|---|---|---|---|---|---|---|
| | | Avg | SE | N | Avg | SE | N | p-value |
| ME04315-06-99[b] | 06-T3 | 0.0034 | 0.0006 | 16 | 0.0023 | 0.0003 | 14 | 0.0499 |
| ME04315-06-99 | 06-T3 | 0.0029 | 0.0002 | 42 | 0.0021 | 0.0001 | 28 | 9.52E−04 |
| ME04315-06-99-02[a] | 06-T4 | 0.0072 | 0.0002 | 61 | 0.0047 | 0.0002 | 213 | 3.33E−16 |

[a]Transgenic seedlings were compared to non-transgenic segregants within a seed line except for the $T_4$ generation of Events -02 and -06. Since these seed lines were homozygous, they were compared to pooled non-transgenic segregants from another $T_4$ generation event that was grown in the same flat as the $T_4$ generation of Events -02 and -06.
[b]These events were sown twice. The first time was to identify ME04315 as a hit. They were repeated the second time with two generations to identify ME04315 as a Lead.

Plants from Events -02, -03 and -06 which are hemizygous or homozygous for Clone 6639 do not show any negative phenotypes under long-day conditions. The physical appearance of eight of the nine $T_1$ plants was identical to the controls. Event -06 was smaller and had fewer rosette leaves.

Events -02, -03 and -06 of ME04315 exhibited no statistically significant negative phenotypes compared to empty vector control SR00559. There was no detectable reduction in germination rate, the plants appeared wild-type in all instances, and there was no observable or statistical differences between experimentals and controls for days to flowering, rosette area 7 days post-bolting or fertility (silique number and seed fill).

Example 5—Results for ME17294 Events (SEQ ID NO:93) 5' Truncated

Nine events of ME17294 (Clone 924103 from *Triticum aestivum*) were analyzed as described in the cold germination assay (Example 2). In this study, the seedling area (a measure of germination timing and cotyledon expansion) of transgenic plants within a seed line was compared to that of non-transgenic segregants within the same seed line, except for the T3 generation of both events. These seed lines were homozygous for the transgene. For these seed lines, we used pooled non-transgenic segregants from another T3 generation event of ME17294 that were collected from plants grown in the same flat as the T3 generation of Events -08 and -09.

The two events, -08 and -09, were significant in two generations at p<0.05 using a one-tailed t-test assuming unequal variance (Table 3). The transgenic plants are visibly larger.

Events -08 and -09 segregated 3:1 (R:S) for Finale™ resistance in the $T_2$ generation. No $T_1$ phenotypes were reported for this line.

TABLE 3 t-test comparison of seedling area between transgenic seedlings and control non-transgenic segregants after 10 days at 8° C.

| Events | Event-Gen | Transgenic | | | Control Non-Transgenics[a] | | | t-test |
|---|---|---|---|---|---|---|---|---|
| | | Avg | SE | N | Avg | SE | N | p-value |
| ME17294-08[b] | 08-T2 | 0.0032 | 0.0003 | 24 | 0.0022 | 0.0002 | 9 | 2.57E−03 |
| ME17294-08 | 08-T2 | 0.0021 | 0.0001 | 41 | 0.0018 | 0.0001 | 10 | 4.52E−03 |
| ME17294-08-02[a] | 08-T3 | 0.0083 | 0.0003 | 48 | 0.0064 | 0.0002 | 234 | 3.05E−08 |
| ME17294-08-04 | 08-T3 | 0.0075 | 0.0003 | 54 | 0.0064 | 0.0002 | 234 | 9.19E−04 |
| ME17294-09[b] | 09-T2 | 0.0058 | 0.0003 | 22 | 0.0035 | 0.0002 | 9 | 1.02E−06 |
| ME17294-09 | 09-T2 | 0.0039 | 0.0002 | 41 | 0.0029 | 0.0002 | 16 | 4.59E−04 |
| ME17294-09-01[a] | 09-T3 | 0.0073 | 0.0003 | 46 | 0.0064 | 0.0002 | 234 | 5.53E−03 |
| ME17294-09-04[a] | 09-T3 | 0.0087 | 0.0003 | 63 | 0.0064 | 0.0002 | 234 | −9.10E−11 |

[a]Transgenic seedlings were compared to internal non-transgenic segregants within a seed line except for the $T_3$ generation of Events -08 and -09. Since these seed lines were homozygous, they were compared to pooled non-transgenic segregants from another $T_3$ generation event that was grown in the same flat as the $T_3$ generation of Events -08 and -09.
[b]These events were sown twice. The first time was to identify ME17294 as a Hit. They were repeated the second time with two generations to identify ME 17294 as a Lead.

Plants from Events -08 and -09 which are hemizygous or homozygous for clone 924103 do not show any negative phenotypes under standard conditions. Events -08 and -09 of ME17294 exhibited no statistically significant negative phenotypes compared to empty vector control SR00559. There was no detectable reduction in germination rate, the plants appeared wild-type in all instances, and there were no statistical differences between experimentals and controls for days to flowering, rosette area 7 days post-bolting, or fertility (silique number and seed fill).

Example 6—Results for ME00572 Events (SEQ ID NO:111) tasiRNA

Clone 13209, in ME00572 plants, is a trans-acting small interfering RNA (tasiRNA) that interacts with ARFs (Auxin Response Factors). A megapool containing superpools 9-12 was screened for seedlings that grew more vigorously than controls after transfer to fluctuating cold conditions according to Example 2. Seven candidates were chosen from this megapool. ME00572 was represented two times in this set.

Four events of ME00572 showed significant tolerance under cold fluctuating conditions in at least two generations. The seedling area of transgenic plants within a seed line was compared to that of non-transgenic segregants within the same seed line after 14 days of growth at fluctuating temperatures of 8° C. and 1° C. Five events of ME00572 were analyzed as described in the Cold Flux Assay described in Example 2. Events -01, -03, -04 and -05 were significant in at least two generations at p<0.05 using a one-tailed t-test assuming unequal variance (Table 4). The transgenic plants were visibly larger than the controls.

Events -01 and -05 segregated 3:1 (R:S) for Finale™ resistance in the T2 generation. Event -04 segregated 3:1 in the T3 generation. Event -03 segregated 1:1 in the T2 generation.

TABLE 4 t-test comparison of seedling area between transgenic seedlings and control non-transgenic segregants after 14 days fluctuation between 8° C. and 1° C.

| Events | Event-Gen | Transgenic Avg | SE | N | Control Non-Transgenics[a] Avg | SE | N | t-test p-value |
|---|---|---|---|---|---|---|---|---|
| ME00572-01 | -01-T2 | 0.0338 | 0.0293 | 26 | 0.0233 | 0.0010 | 4 | 0.155617 |
| ME00572-01[b] | -01-T2 | 0.0541 | 0.0021 | 45 | 0.0442 | 0.0030 | 13 | 4.92E−03 |
| ME00572-01-01 | -01-T3 | 0.0347 | 0.0017 | 40 | 0.0246 | 0.0014 | 14 | 1.53E−05 |
| ME00572-01-02[c] | -01-T3 | 0.0331 | 0.0013 | 59 | 0.0267 | 0.0005 | 294 | 2.35E−06 |
| ME00572-01-03[c] | -01-T3 | 0.0360 | 0.0010 | 59 | 0.0267 | 0.0005 | 294 | −9.39E−11 |
| ME00572-01-04 | -01-T3 | 0.0329 | 0.0013 | 46 | 0.0233 | 0.0018 | 14 | 3.19E−05 |
| ME00572-03 | -03-T2 | 0.0312 | 0.0016 | 11 | 0.0223 | 0.0013 | 19 | 9.71E−05 |
| ME00572-03[b] | -03-T2 | 0.0383 | 0.0024 | 24 | 0.0341 | 0.0023 | 25 | 1.04E−01 |
| ME00572-03-01 | -03-T3 | 0.0328 | 0.0014 | 30 | 0.0236 | 0.0008 | 28 | 1.42E−07 |
| ME00572-03-02 | -03-T3 | 0.0311 | 0.0010 | 26 | 0.0261 | 0.0015 | 33 | 3.81E−03 |
| ME00572-03-03 | -03-T3 | 0.0352 | 0.0011 | 28 | 0.0252 | 0.0009 | 32 | 1.39E−09 |
| ME00572-03-04 | -03-T3 | 0.0331 | 0.0019 | 23 | 0.0260 | 0.0014 | 35 | 1.97E−03 |
| ME00572-04-99 | -04-T3 | 0.0235 | 0.0009 | 23 | 0.0158 | 0.0020 | 7 | 6.98E−04 |
| ME00572-04-99[b] | -04-T3 | 0.0336 | 0.0012 | 31 | 0.0255 | 0.0010 | 29 | 2.01E−06 |
| ME00572-04-99-01[c] | -04-T4 | 0.0388 | 0.0014 | 57 | 0.0267 | 0.0005 | 294 | −9.39E−11 |
| ME00572-04-99-02 | -04-T4 | 0.0345 | 0.0011 | 41 | 0.0253 | 0.0018 | 19 | 3.93E−05 |
| ME00572-04-99-03[c] | -04-T4 | 0.0433 | 0.0012 | 60 | 0.0267 | 0.0005 | 294 | −3.33E−16 |
| ME00572-04-99-04 | -04-T4 | 0.0315 | 0.0010 | 44 | 0.0239 | 0.0012 | 16 | 3.22E−06 |
| ME00572-05 | -05-T2 | 0.0362 | 0.0020 | 19 | 0.0219 | 0.0020 | 10 | 1.13E−05 |
| ME00572-05-01[c] | -05-T3 | 0.0337 | 0.0011 | 57 | 0.0267 | 0.0005 | 294 | 6.21E−09 |
| ME00572-05-02 | -05-T3 | 0.0320 | 0.0014 | 39 | 0.0232 | 0.0020 | 17 | 3.59E−04 |
| ME00572-05-03[c] | -05-T3 | 0.0379 | 0.0011 | 59 | 0.0267 | 0.0005 | 294 | −9.39E−11 |
| ME00572-05-04 | -05-T3 | 0.0344 | 0.0020 | 37 | 0.0268 | 0.0022 | 19 | 7.26E−03 |

[a]Transgenic seedlings were compared to internal non-transgenic segregants within an event unless otherwise indicated.
[b]These events were sown twice. The first time was to identify ME00572 as a Hit. They were repeated the second time with the next generation to identify ME00572 as a Lead.
[c]These events did not segregate non-transgenic seedlings and were compared to pooled non-transgenics for the line.

Plants from Events -01, -03, -04 and -05 which are hemizygous or homozygous for clone 13209 do not show any negative phenotypes under standard conditions. Events -01, -03, -04 and -05 of ME00572 were tested for negative phenotypes compared to the empty vector control SR00559. There was no detectable reduction in germination rate, the plants appeared wild-type in all instances, and there was no statistical differences between experimentals and controls for days to flowering, rosette area 7 days post-bolting, and fertility (silique number and seed fill).

Example 7—Determination of Functional Homologs by Reciprocal BLAST

A candidate sequence was considered a functional homolog of a reference sequence if the candidate and reference sequences encoded proteins having a similar function and/or activity. A process known as Reciprocal BLAST (Rivera et al., Proc. Natl. Acad. Sci. USA, 95:6239-6244 (1998)) was used to identify potential functional homolog sequences from databases consisting of all available public and proprietary peptide sequences, including NR from NCBI and peptide translations from Ceres clones.

Before starting a Reciprocal BLAST process, a specific reference polypeptide was searched against all peptides from its source species using BLAST in order to identify polypeptides having BLAST sequence identity of 80% or greater to the reference polypeptide and an alignment length of 85% or greater along the shorter sequence in the alignment. The reference polypeptide and any of the aforementioned identified polypeptides were designated as a cluster.

The BLASTP version 2.0 program from Washington University at Saint Louis, Missouri, USA was used to determine BLAST sequence identity and E-value. The BLASTP version 2.0 program includes the following parameters: 1) an E-value cutoff of 1.0e-5; 2) a word size of 5; and 3) the -postsw option. The BLAST sequence identity was calculated based on the alignment of the first BLAST HSP (High-scoring Segment Pairs) of the identified potential functional homolog sequence with a specific reference polypeptide. The number of identically matched residues in the BLAST HSP alignment was divided by the HSP length, and then multiplied by 100 to get the BLAST sequence identity. The HSP length typically included gaps in the alignment, but in some cases gaps were excluded.

The main Reciprocal BLAST process consists of two rounds of BLAST searches; forward search and reverse search. In the forward search step, a reference polypeptide sequence, "polypeptide A," from source species SA was BLASTed against all protein sequences from a species of interest. Top hits were determined using an E-value cutoff of $10^{-5}$ and a sequence identity cutoff of 35%. Among the top hits, the sequence having the lowest E-value was designated as the best hit, and considered a potential functional homolog or ortholog. Any other top hit that had a sequence identity of 80% or greater to the best hit or to the original reference polypeptide was considered a potential functional homolog or ortholog as well. This process was repeated for all species of interest.

In the reverse search round, the top hits identified in the forward search from all species were BLASTed against all protein sequences from the source species SA. A top hit from the forward search that returned a polypeptide from the aforementioned cluster as its best hit was also considered as a potential functional homolog.

Functional homologs were identified by manual inspection of potential functional homolog sequences. Representative functional homologs for SEQ ID NO: 2, 20, 74, 93, and 116, are shown in FIGS. 1-5, respectively. Additional exemplary homologs are correlated to certain Figures in the Sequence Listing.

Example 8—Determination of Functional Homologs by Hidden Markov Models

Hidden Markov Models (HMMs) were generated by the program HMMER 2.3.2. To generate each HMM, the default HMMER 2.3.2 program parameters, configured for glocal alignments, were used.

An HMM was generated using the sequences shown in FIG. 1 as input. These sequences were fitted to the model and a representative HMM bit score for each sequence is shown in the Sequence Listing. Additional sequences were fitted to the model, and representative HMM bit scores for any such additional sequences are shown in the Sequence Listing. The results indicate that these additional sequences are functional homologs of SEQ ID NO: 2.

The procedure above was repeated and an HMM was generated for each group of sequences shown in FIGS. 2, 3, 4, and 5 using the sequences shown in each Figure as input for that HMM. A representative bit score for each sequence is shown in the Sequence Listing. Additional sequences were fitted to certain HMMs, and representative HMM bit scores for such additional sequences are shown in the Sequence Listing. The results indicate that these additional sequences are functional homologs of the sequences used to generate that HMM.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method of producing a plant and/or plant tissue, said method comprising producing a transgenic plant from a plant cell comprising an exogenous nucleic acid sequence, said exogenous nucleic acid sequence comprising a regulatory region operably linked to a nucleotide sequence encoding a polypeptide, wherein said polypeptide comprises an amino acid sequence that has 98% or greater sequence identity to the amino acid sequence of SEQ ID NO:93, and expressing the polypeptide in the transgenic plant, wherein the transgenic plant produced from said plant cell has an increased level of cold tolerance as compared to the corresponding level of cold tolerance of a control plant that does not comprise said exogenous nucleic acid sequence.

2. The method of claim 1, wherein the polypeptide comprises an amino acid sequence that has 99% or greater sequence identity to the amino acid sequence of SEQ ID NO:93.

3. The method of claim 1, wherein the polypeptide comprises the amino acid sequence of SEQ ID NO:93.

4. A method of increasing a level of cold tolerance in a plant, said method comprising introducing into a plant an exogenous nucleic acid sequence thereby producing a transgenic plant, said exogenous nucleic acid sequence comprising a regulatory region operably linked to a nucleotide sequence encoding a polypeptide, wherein said polypeptide comprises an amino acid sequence that has 98% or greater sequence identity to the amino acid sequence of SEQ ID NO:93, and expressing the polypeptide in the transgenic plant, wherein the transgenic plant has an increased level of cold tolerance as compared to the corresponding level of cold tolerance of a control plant that does not comprise said exogenous nucleic acid sequence.

5. The method of increasing the level of cold tolerance in a plant according to claim 4, wherein the polypeptide comprises an amino acid sequence that has 99% or greater sequence identity to the amino acid sequence of SEQ ID NO:93.

6. The method of claim 4, wherein the polypeptide comprises the amino acid sequence of SEQ ID NO:93.

* * * * *